United States Patent [19]
Geiwiz et al.

[11] Patent Number: 5,589,473
[45] Date of Patent: Dec. 31, 1996

[54] MONO- AND BICYCLIC DNA GYRASE INHIBITORS

[75] Inventors: Jürgen Geiwiz, Lörrach, Germany; Erwin Götschi, Reinach, Switzerland; Paul Hebeisen; Helmut Link, both of Basel, Switzerland; Thomas Lübbers, Lörrach, Germany

[73] Assignee: Hoffmann-La Roche Inc., Nutley, N.J.

[21] Appl. No.: 407,730

[22] Filed: Mar. 20, 1995

[30] Foreign Application Priority Data

Mar. 30, 1994 [EP] European Pat. Off. ............ 94104995
Feb. 7, 1995 [EP] European Pat. Off. ............ 95101595

[51] Int. Cl.$^6$ .................... C07D 291/08; A61K 31/395
[52] U.S. Cl. .................... 514/183; 540/455; 540/468; 540/452; 544/138; 544/316; 546/277; 546/269.1; 548/131; 548/110
[58] Field of Search .............. 540/455; 514/183

[56] References Cited

U.S. PATENT DOCUMENTS 5,294,609  3/1994  Arisawa et al. .................... 514/183

OTHER PUBLICATIONS

Kamiyama et al., Chemical Abstract 120:212154z (1994).
Goetschi et al, Chem. Abstract 121:124616 (1993).
The Merck Manual, 15th edition (1987), Berkow, M.D. editor, p. 46.

Goetschi, E., et al., *Pharmac. Ther.*, 60:367–380 (1993).

Kamiyama, Tsutomu, et al., *The Journal of Antibiotics*, 47(1): 37–45 (1993).

*Primary Examiner*—Philip I. Datlow
*Attorney, Agent, or Firm*—George W. Johnston; Alan P. Kass

[57] ABSTRACT

The present invention relates to a compound of the formula

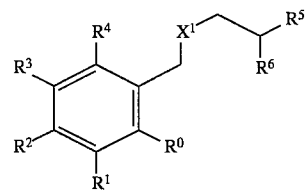

wherein
$X^1$, $R^1$, $R^2$, OP, $R^3$, $R^4$, $R^5$, $R^6$, and $R^0$ are as described herein, and their pharmaceutically acceptable salts thereof carrying an acidic and/or basic substituent.

The compound of formula I as well as their pharmaceutically acceptable salts inhibit DNA gyrase activity in bacteria and possess antibiotic, especially antibacterial activity against microorganisms and can be used in the control or prevention of infectious diseases.

37 Claims, No Drawings

MONO- AND BICYCLIC DNA GYRASE INHIBITORS

The present invention relates to compounds of the formula

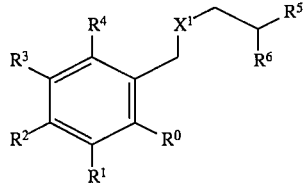

wherein $X^1$ is —S— or —SO—;

$R^1$ is hydrogen, halogen or optionally substituted lower alkyl, the optional substituent being halogen;

$R^2$ is hydrogen, hydroxy, amino, lower alkylamino, di-lower alkylamino, optionally substituted lower alkoxy or a group —OP;

OP is an easily hydrolyzable group;

$R^3$ is hydrogen, hydroxy, lower alkyl, halogen or a group —OP;

$R^4$ is halogen, hydroxy or a group —OP;

$R^5$ is hydrogen, cyano, optionally substituted esterified carboxy, optionally substituted amidated (thio)carboxy, optionally substituted alkyl, optionally substituted alkenyl or optionally substituted heterocycle;

$R^6$ is —$NR^7$—A , —N=B or optionally substituted heterocycle, in which $R^7$ is hydrogen or lower alkyl, A is optionally substituted iminoyl, optionally substituted (thio)acyl, optionally substituted esterified carboxy, optionally substituted amidated (thio)carboxy or optionally substituted heterocycle and B is optionally substituted alkylidene;

$R^0$ is cyano, optionally substituted esterified carboxy or optionally substituted heterocycle, or wherein $R^0$ and $R^6$ taken together represent a group —CO—O—Q—$X^2$—N($R^7$)—, wherein $R^7$ is as above, and $X^2$ is (thio)carbonyl or heterocycle, Q is —CH(RS)— or —CH($R^8$)—W—;

$R^8$ is hydrogen or optionally substituted lower alkyl, and

W is optionally substituted mono-, di-, tri-, tetra- or pentamethylene, provided that when W is monomethylene $X^2$ is other than (thio)carbonyl, or the pharmaceutically acceptable salts thereof carrying an acidic and/or basic substituent.

The invention includes compounds of the formula

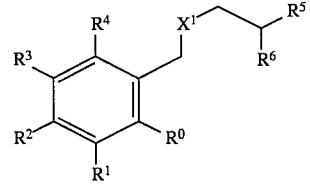

wherein the substituents are as previously described, $R^6$ and $R^0$ being taken separately, and compounds of the formula

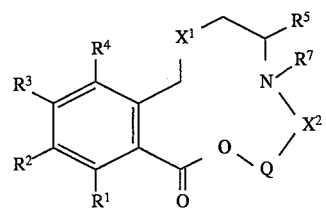

wherein the substituents are as previously described and $R^0$ and $R^6$ taken together represent a group —CO—O—Q—$X^2$—N($R^7$)—.

The compounds of formula I as well as their pharmaceutically acceptable salts inhibit DNA gyrase activity in bacteria and possess antibiotic, especially antibacterial activity against microorganisms and can be used in the control or prevention of infectious diseases in mammals, both human and non-human.

Objects of the present invention are the compounds of formula I and their pharmaceutically acceptable salts per se and for use as therapeutically active substances, the making of these compounds, medicaments containing these and the making of such medicaments, as well as the use of compounds of formula I and their pharmaceutically acceptable salts in the control or prevention of illnesses or in the improvement of health, especially in the control or prevention of infectious diseases. Objects of the present invention are also the compounds of formula XVIII, hereinbelow, per se and the making of these compounds.

Hereinabove and in the following, reference to the word "lower" such as in "lower alkyl", "lower alkoxy", "lower alkanoyl" etc. refers to hydrocarbon groups containing up to and including 6, preferably 1–3, in "lower alkenyl" and "lower alkynyl" preferably 2–4 and in "lower cycloalkyl" preferably 3–6 carbon atoms unless otherwise specified. Thus, e.g. "lower alkyl" in the following, alone or in combination with other groups such as in "lower alkylamino", "di-lower alkylamino", "aryl-lower alkyl" etc., is e.g. methyl, ethyl, tert-butyl, n-pentyl etc.; "lower alkoxy" has analogous meanings; "lower alkenyl" alone or in combination with other groups such as "lower cycloalkyl-lower alkenyl", "heterocycle-lower alkenyl" etc., is e.g. vinyl, 1- or 2-propenyl; "lower cycloalkyl" alone or in combination with other groups such as "lower cycloalkyl-lower alkenyl", "lower cycloalkyl-lower alkyl" etc. is e.g. cyclopropyl, cyclobutyl, cyclohexyl; "lower alkynyl" alone or in combination with other groups such as "lower cycloalkyl-lower alkynyl" is e.g. ethynyl, 1- or 2-propynyl; "lower alkanoyl" alone or in combination with other groups such as "lower alkanoyloxy" etc. is e.g. formyl, acetyl, propionyl, isobutyryl, pivaloyl etc.

Groups not specified by the word "lower", such as "alkyl", "alkoxy", "alkenyl", "acyl" and "alkanoyl", are intended to refer to groups containing up to and including 14 carbon atoms unless otherwise specified.

"(Thio)carboxy" refers to a carboxy group or a thiocarboxy group, i.e., a group —C(S)—OH.

"(Thio)acyl" refers to an acyl group or a thioacyl group.

"Acyl" alone or in combination with other groups such as in "acylamino", is preferably derived from a carboxylic acid and is thus e.g. lower alkanoyl, e.g. formyl, acetyl, propionyl, isobutyryl, pivaloyl; lower alkenoyl, e.g. crotonoyl, isocrotonoyl; lower cycloalkanoyl, e.g. cyclopropylcarbonyl; aroyl, e.g. benzoyl, o-carboxy-benzoyl, p-toluoyl, p-anisoyl, naphthoyl; heterocyclecarbonyl, e.g. furoyl, thenoyl. A special group of acyl comprises optionally N-mono- or N,N-dialkylated amino substituted acyl, such as the acyl residue of an α-amino acid, e.g. N,N-dimethylglycyl or L-alanyl. "Thioacyl" has analogous meanings.

"Halogen" alone or in combination with other groups such as in "halogen-lower alkyl" etc. refers to all four halogens, i.e. chlorine, bromine, iodine, fluorine, unless otherwise indicated.

The expressions "lower alkenylalkyl" and "lower alkynylalkyl" are employed to indicate that the double and triple bonds of these groups are not connected with the first carbon atom (such as in vinyl, ethynyl and 1-propynyl), but that these groups are limited to the less reactive groups having their unsaturation in 2-, 3- and further positions. It is understood that "lower alkenylalkyl" and "lower alkynylalkyl" refer to groups containing up to and including 5 carbon atoms, e.g. 2-propenyl, 2-butenyl, 3-butenyl, 2-methyl-2-propenyl, 2-propynyl, 2-butynyl, 3-butynyl, 2-methyl-2-propynyl.

"Heterocycle" alone or in combination with other groups such as in "heterocycle-lower alkyl" etc. refers, if not specified otherwise, to a 4 to 7 membered saturated or unsaturated heterocycle containing 1–4 nitrogen atoms and/or 1–2 sulfur or oxygen atoms, and if not specified otherwise, can be substituted by one or more groups selected from lower alkyl, lower alkoxy, lower acyl, halogen, hydroxy, oxo, optionally esterified or amidated carboxy, amino or a group OP. Examples for heterocycle are furyl, thienyl, thiazolyl, imidazolyl, oxazolyl, pyridyl, pyrimidinyl, pyrrolidinyl, morpholinyl, piperazinyl, 1-pyridinium, 1,2,4-oxadiazol-5-yl. The said heterocycle groups may be bound to a fused saturated or unsaturated 5 to 7 membered ring, which may contain 1–4 nitrogen atoms and/or a sulfur or oxygen atom to form e.g. a quinolinyl, quinoxalinyl, benzoxazolyl, benzthiazolyl, benzimidazolyl, indolyl, s-triazolo[1,5-a]pyrimidyl or pyrazolo[1,5-a]pyrimidinyl group.

Easily hydrolyzable groups —OP are groups which undergo hydrolytic cleavage under mild conditions, for example in the presence of suitable hydrolytic enzymes. In particular, OP represents an ester group, e.g. a lower alkanoyloxy group such as formyloxy, acetoxy, propionyloxy, isobutyryloxy, pivaloyloxy or a lower alkoxycarbonyloxy group such as methoxycarbonyloxy or ethoxycarbonyloxy. The group —OP can also be an ester group in which P represents the acyl residue of an optionally N-mono- or N,N-dialkylated amino acid, e.g. 4-aminomethylbenzoic acid, or an α-amino acid, such as glycine, alanine, phenylalanine, serine, tyrosine, proline, tryptophane, aspartic acid, glutamic acid, lysine, arginine or histidine, or of a peptide consisting of 2–4 α-amino acids, wherein any free amino function in aforesaid groups is optionally acylated with the residue of a lower alkanoic acid such as formyl or acetyl. Furthermore the group OP can be an ester of an organic dicarboxylic acid such as succinic acid, glutaric acid or adipic acid, or of an inorganic acid such as phosphoric acid or sulfuric acid.

$R^2$ in its meaning as substituted lower alkoxy is a lower alkoxy group defined as above which can be substituted by one or more groups selected from lower alkyl, lower alkoxy, lower acyl, halogen, hydroxy, oxo, amino or a group OP.

$R^5$ is hydrogen, cyano, optionally substituted esterified carboxy or optionally substituted amidated (thio)carboxy, optionally substituted alkyl, optionally substituted alkenyl or optionally substituted heterocycle. Exemplary of esterified carboxy and amidated (thio)carboxy groups $R^5$ are groups of the formula

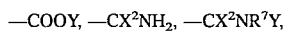

$-COOY, -CX^2NH_2, -CX^2NR^7Y,$ wherein $R^7$ and $X^2$ are as above and Y is alkyl, alkenylalkyl, alkynylalkyl, lower cycloalkyl, lower cycloalkyl-lower alkyl, lower cycloalkyl-lower alkenylalkyl, heterocycle, heterocycle-lower alkyl, heterocycle-lower alkenylalkyl, aryl, aryl-lower alkyl or aryl-lower alkenylalkyl or wherein the residue $-NR^7Y$ represents a 5 to 7 membered saturated N-heterocycle optionally containing a further N, O or S atom.

Thus, possible meanings for Y include alkyl, e.g. methyl, ethyl, isopropyl, tert-butyl, n-pentyl, n-decyl, etc., alkenylalkyl, e.g. 2-propenyl; alkynylalkyl, e.g. 2-propynyl, 3-butynyl; lower cycloalkyl, e.g. cyclopropyl, cyclobutyl, cyclopentyl, cyclohexyl; lower cycloalkyl-lower alkyl, e.g. cyclopropylmethyl, cyclopropylethyl; lower cycloalkyl-lower alkenylalkyl, e.g. cyclopropyl-2-propenyl; heterocycle, heterocycle-lower alkyl or heterocycle-lower alkenylalkyl, wherein the expression heterocycle is defined as above except that the kind of substituents for Y in these meanings shall not be limited to the aforementioned substituents possible for a heterocycle group. Examples for heterocycle are given above; examples for heterocycle-lower alkyl are, e.g. furfuryl, thenyl, 4-thiazolyl-methyl, 3-methyl-5-isoxazolyl-ethyl, 4-morpholinyl-methyl, 4-methyl-1-piperazinylmethyl, 1-pyridinium-methyl; examples for heterocycle-lower alkenylalkyl, e.g. 2-pyrrolyl-2-propenyl, 2-thienyl-2-propenyl. Further possible meanings for Y are aryl, e.g. phenyl, p-tolyl, o,m-dihydroxyphenyl, m,p-dihydroxyphenyl, p-methoxyphenyl (anisyl), m-methoxyphenyl, o,m-dimethoxyphenyl, 3,4,5-trimethoxyphenyl, p-trifluoromethyl-phenyl, naphthyl; aryl-lower alkyl, e.g. benzyl, phenethyl; or aryl-lower alkenylalkyl, e.g. phenyl-2-propenyl. The residue $-NR^7Y$ can also represent a 5 to 7 membered saturated N-heterocycle optionally containing a further N, O or S atom, e.g. pyrrolidino, piperidino, morpholino, thiomorpholino.

The above group Y can be further substituted, e.g. by halogen, i.e. fluorine, chlorine, bromine or iodine;
 by amino (such as in 2-amino-4-thiazolyl);
 by lower alkylamino, e.g. methylamino;
 by di-lower-alkylamino, e.g. dimethylamino;
 by lower cycloalkylamino, e.g. cyclopentylamino;
 by di-lower-cycloalkylamino, e.g. dicyclobutylamino;
 by heterocycleamino where the heterocycle moiety is defined as above, e.g. 4-pyridinyl-amino;
 by heterocycleoxy where the heterocycle moiety is defined as above, e.g. furyloxy or thienyloxy;
 by heterocyclethio where the heterocycle moiety is defined as above, e.g. furylthio, thienylthio or (2,5-dihydro-6-hydroxy-2-methyl-5-oxo-as-triazin-3-yl)thio;
 by a quaternary ammonium group such as tri-lower alkylammonium, e.g. trimethylammonium, 1-pyridinium, 1-lower-alkyl-morpholinium, e.g. 1-methyl-morpholinium, or 1-quinuclidinium (in such case the positive charge of the quaternary ammonium group is neutralized by a pharmaceutically acceptable anion such as those exemplified below under the acid addition salts of the compounds of formula I. The anion can also be the deprotonated moiety of a carboxy group present in the compound of formula I, in which the compound is present in the form of a zwitterion);
 by acylamino, e.g. acetamido, benzamido, p-toluoylamido or ethoxycarbonylamino;
 by amidino (optionally mono-, di- or tri-substituted by lower alkyl, viz. a group of the formula $-C(NRR')=NR''$ where R, R' and R'' are hydrogen or lower alkyl);
 by iminoyl (optionally mono or disubstituted by lower alkyl, viz. a group of the formula $-CR=NR'$, where R and R' are hydrogen or lower alkyl);
 by hydroxy;
 by a group OP wherein OP has the meaning given above;

by lower alkoxy, e.g. methoxy, ethoxy, optionally substituted by hydroxy or amino, e.g. 2-hydroxyethoxy;

by carbamoyloxy, optionally lower alkyl- or lower aryl-substituted, e.g. N-ethyl-carbamoyloxy or N-phenyl-carbamoyloxy;

by lower alkylthio, e.g. methylthio, ethylthio;
by lower cycloalkoxy, e.g. cyclopropoxy;
by lower cycloalkylthio, e.g. cyclopropylthio;
by lower alkenylalkoxy, e.g. 2-propenoxy;
by lower alkenylalkylthio, e.g. 2-propenylthio;
by aryloxy, e.g. phenoxy, p-tolyloxy, naphthyloxy;
by arylthio. e.g. phenylthio, p-tolylthio, naphthylthio;
by acyloxy, the acyl moiety of which is preferably derived from a carboxylic acid and is thus e.g. lower alkanoyl, e.g. formyl, acetyl, propionyl, isobutyryl, pivaloyl; lower alkenoyl, e.g. crotonoyl, isocrotonoyl; lower cycloalkanoyl, e.g. cyclopropylcarbonyl: aroyl, e.g. benzoyl, p-chlorbenzoyl, p-toluoyl, p-anisoyl, naphthoyl; heterocyclecarbonyl, e.g. furoyl, thenoyl;

by lower alkylsulfinyl or -sulfonyl, e.g. methylsulfinyl or -sulfonyl or ethylsulfinyl or -sulfonyl;

by lower alkenylalkylsulfinyl or -sulfonyl, e.g. 2-propenylsulfinyl or -sulfonyl;

by lower cycloalkylsulfinyl or -sulfonyl, e.g. cyclopropylsulfinyl or -sulfonyl;

by arylsulfinyl or- sulfonyl, e.g. phenylsulfinyl or -sulfonyl or p-tolylsulfinyl or -sulfonyl;

by heterocyclesulfinyl or -sulfonyl, e.g. furylsulfinyl or -sulfonyl or thienylsulfinyl or -sulfonyl;

by hydroxyimino or lower alkoxyimino, e.g. methoxyimino.

The above groups Y can further be substituted by carboxy which is optionally esterified or amidated, e.g. forming lower alkoxycarbonyl, carbamoyl or N-hydroxycarbamoyl (of which the last two may be N-substituted by lower alkyl or aryl).

Moreover, the above groups Y can be substituted by alkyl, e.g. methyl, ethyl, isopropyl or hexyl, with the further option that the said alkyl group can be itself substituted by one or several of the substituents foreseen as substituents for a group Y, but excluding alkyl from this further option; by lower cycloalkyl e.g. cyclopropyl, cyclobutyl, cyclohexyl; by lower alkenyl, e.g. vinyl, 2-propenyl; by aryl, e.g. phenyl, p-tolyl, p-methoxyphenyl, naphthyl; by arylalkyl, e.g. benzyl; by heterocycle where the heterocycle moiety is defined as above, e.g. 2-pyrrolidyl, 2-pyrrolyl, 2-thienyl, 4-acetyl-piperazinyl; by oxo, thioxo, cyano, nitro, azido, sulfamoyl or aminosulfonyl which may be substituted by lower alkyl or aryl, e.g. methylsulfamoyl, dimethylsulfamoyl, phenylsulfamoyl.

$R^5$ can also refer to an optionally substituted alkyl, alkenyl or heterocycle group where alkyl, alkenyl or heterocycle are defined as above, except that heterocycle is preferably a 5- or 6-membered heterocycle. Examples of unsubstituted alkyl, alkenyl or heterocycle groups $R^5$ are given above for these expressions. These groups can, however, also be substituted by 1 or more substituents as described above for the group Y and/or by 1–2 group(s) of the formula —(E)$_m$—Y in which Y has the meaning given above, E is —O—, —S—, —SO$_2$—, —COO—, —OCO—, —CONR$^7$—, —NR$^7$—, —NR$^7$—CO—, —NR$^7$SO$_2$—, —NR$^7$COO— or —NR$^7$CONR$^7$—, $R^7$ has the above meaning and m is zero or 1.

Consequently, substituted alkyl, alkenyl and heterocycle groups include groups such as
hydroxymethyl,
2-hydroxyethoxy,
fluoroethyl,
aminomethyl,
2-carboxyethyl,
4-fluoro-but-1-enyl,
2-ethoxycarbonyl-vinyl,
carbamoyloxymethyl,
[(phenylcarbamoyl)oxy]methyl,
methoxymethyl,
[(4-carbamoylphenyl)thio]methyl,
(ethoxycarbonyl)acetyl,
2-[(2-thiazolyl)carbamoyl]ethyl,
(dimethylamino)methyl,
4-aminomethyl-benzoyloxymethyl,
3-methyl- 1,2,4-oxadiazol-5-yl,
3-aminomethyl-oxadiazol-5-yl,
3-acetamidomethyl-oxadiazol-5-yl or
4-ethoxycarbonyl-thiazol-2-yl.

The above enumerated definition of Y including its further substitution possibilities is to be understood pragmatically such that apparently meaningless combinations such as "alkyl substituted alkyl", "alkenyl substituted alkenyl", "alkyl substituted alkenyl" etc. are intended to mean the abbreviated groups, i.e., the just stated expressions mean "alkyl", "alkenyl", and "alkenyl", respectively.

$R^6$ taken alone is optionally substituted heterocycle, —NR$^7$—A or —N=B, in which heterocycle and $R^7$ are as above, A is optionally substituted iminoyl, optionally substituted (thio)acyl, optionally substituted esterified carboxy, optionally substituted amidated (thio)carboxy or optionally substituted heterocycle and B is optionally substituted alkylidene.

A in its meaning as iminoyl, (thio)acyl, esterified carboxy or amidated (thio)carboxy can be a group of the formula
—CR$^7$=N—Y$^1$ (a: iminoyl)
—X$^2$—Y$^1$, (b: (thio)acyl)
—(CO)$_n$OY (c: esterified carboxy)
—X$^2$NR$^7$Y$^1$ (d: amidated (thio)carboxy)
wherein $R^7$ is hydrogen or lower alkyl, Y$^1$ is hydrogen or the group Y,
and X$^2$ and Y are as above.

A in its meaning as an optionally substituted heterocycle group is as defined above.

$R^6$ and A in their meaning as optionally substituted heterocycle can, however, also be substituted, e.g. by 1 or more substituents described above for the group Y and/or by 1–2 group(s) of the formula—(E)$_m$—Y in which E, m and Y have the meaning given above.

Optionally substituted alkylidene groups B are e.g. groups of the formulas
=CHY (e)
=C(Y)$_2$ (f)
=CR$^7$—NR$^7$Y$^1$ (g)
wherein R$^7$, Y and Y$^1$ are as above.

$R^0$ taken alone is cyano, optionally substituted esterified carboxy or optionally substituted heterocycle.

$R^0$ in its meaning as esterified carboxy is a group COOY$^2$ in which Y$^2$ is lower alkyl, lower alkenylalkyl, lower alkynylalkyl, lower cycloalkyl or lower cycloalkyl-lower alkyl. These groups possible for Y$^2$ have the meaning as above and can further be substituted in a similar way as described for the group Y, they can, however, not be 2,2,2-trichloroethyl or (R)-2-tert-butoxycarbonyl-1-methyl-ethyl.

$R^0$ in its meaning as heterocycle refers to a heterocycle group as defined above, in particular to an unsaturated 5- or 6-membered heterocycle containing 1–4 nitrogen atoms and/or a sulfur or oxygen atom. Examples for such heterocyclic groups are, e.g. 3-methyl-1,2,4-oxadiazol-5-yl, 4-methyl-thiazol-2-yl, imidazolyl, tetrazolyl or pyrimidinyl. These groups can, however, also be substituted, e.g. by 1 or more substituents selected from oxo, hydroxy, halogen, amino, optionally lower alkyl- or aryl-substituted carbamoyloxy, carboxy, N-hydroxy-carbamoyloxy and/or (a) group(s) of the formula —$(E)_m$—Y in which E, m and Y have the meaning given above.

$R^6$ and $R^0$ taken together represents a group —CO—O—Q—$X^2$—N($R^7$)—, wherein $R^7$ is hydrogen or lower alkyl, $X^2$ is (thio)carbonyl or heterocycle, $X^2$ in its meaning as heterocycle refers to heterocycles as defined above, preferably to 5- and 6-membered saturated or unsaturated heterocycles containing 1 to 3 heteroatoms selected from O, N, S. The connection to Q can be via a carbon or a nitrogen atom, and the connection to the group N($R^7$) is via a carbon atom. The substituents Q and N($R^7$) can be attached to a heterocyclic group $X^2$ in a 1,2- or a 1,3- or a 1,4-relation depending on the said heterocycle.

In addition to the compulsory substituents N($R^7$) and Q, $X^2$ in its meaning as heterocycle can be further substituted by 1 or 2 substituents as described above for the group Y, Q is —CH($R^8$)— or —CH($R^8$)—W— and $R^8$ is hydrogen or optionally substituted lower alkyl. Examples of unsubstituted lower alkyl groups are given above. $R^8$ in its meaning as a lower alkyl group can also be substituted in the same way as described for the group Y or a group of the formula $(E)_m$—Y in which E, m and Y have the meaning given above.

W is optionally substituted mono-, di-, tri-, tetra- or pentamethylene provided that when W is monomethylene $X^2$ is other than (thio)carbonyl which means that W in its meaning as a mono-, di-, tri-, tetra- or pentamethylene group can be substituted by 1–4 groups selected from substituents as defined above as possible for the group Y or by 1–4 lower alkyl groups which themselves can bear substituents as defined above as possible for the group Y or a group of the formula $(E)_m$—Y in which E, m and Y have the meaning given above.

Preferred meanings for various substituents are:
$X^1$: —S—;
$R^1$: Me, Br, Cl, hydrogen
$R^2$: Lower alkoxy or hydroxy;
$R^3$: Hydrogen;
$R^4$: Hydroxy or a group —OP;
$R^5$: Heterocycle, $C_1$–$C_5$ alkylamido, $C_1$–$C_5$ alkenylamido, cyano;
$R^6$: (Thio)acylamido, NH-heterocycle;
$R^7$: Hydrogen;
$R^8$: Hydrogen, hydroxymethyl;
$R^0$: —COOMe, CN;
Q: —CH($R^8$)—W—;
W: di-, tri- and tetramethylene for $X^2$=(thio)acyl and mono-, di- and trimethylene for $X^2$=heterocycle.

Particularly preferred meanings for various substituents are:
$X^1$: —S—;
$R^1$: Me, Br, Cl,
$R^2$: MeO;
$R^4$: Hydroxy;
$R^5$: 3-Methyl-1,2,4-oxadiazol-5-yl, allylamido, propylamido;
$R^6$: Thioacylamido, (thiophen-2-yl)-carbonylamido;
Q: —CH($R^8$)—W—;
W: di- and trimethylene for $X^2$=(thio)acyl and mono-, di- and trimethylene for $X^2$=heterocycle.

Preferred compounds of the invention include:
(4R,9S)-15-Hydroxy-9-acetoxymethyl-13-methoxy-12-methyl-11-oxo-6-thioxo-3,4,5,6,7,8,9,11-octahydro-1H-10,2,5-benzoxathiaazacyclo-tridecine-4-carboxylic acid methyl ester (4R,9S)-15-Hydroxy-9-hydroxymethyl-13-methoxy-12-methyl-11-oxo-6-thioxo-3,4,5,6,7,8,9,11-octahydro-1H-10,2,5-benzoxathiaazacyclo-tridecine-4-carboxylic acid cyclopentylamide (R)-16-Hydroxy-14-methoxy-13-methyl-12-oxo-6-thioxo-1,3,4,5,6,7,8,9,10,12-decahydro-11,2,5-benzoxathiaazacyclotetradecine-4-carboxylic acid methyl ester (R)-16-Hydroxy-14-methoxy-13omethyl-12-oxo-6-thioxo-1,3,4,5,6,7,8,9,10,12-decahydro-11,2,5-benzoxathiaazacyclotetradecine-4-carboxylic acid propylamide (R)-16-Hydroxy-14-methoxy-13-methyl-4-(3-methyl-1,2,4-oxadiazol-5-yl)-1,3,4,5,6,7,8,9,10,12-decahydro-11,2,5-benzoxathiaazacyclo-tetradecin-6,12-dione (R)-16-Hydroxy-14-methoxy-13-methyl-12-oxo-6-thioxo -1,3,4,5,6,7,8,9,10,12-decahydro-11,2,5-benzoxathiaazacyclotetradecine-4-carboxylic acid amide (R)-2-Bromo-5-hydroxy-3-methoxy-6-[2-(3-methyl-1,2,4-oxadiazol-5-yl)-2-thioacetylamino-ethylsulfanylmethyl]-benzoic acid methyl ester (R)-2-Chloro-5-hydroxy-3-methoxy-6-[2-(3-methyl-1,2,4-oxadiazol-5-yl)-2-thioacetylamino-ethylsulfanylmethyl]-benzoic acid methyl ester (R)-3-Hydroxy-5-methoxy-6-methyl-2-[2-(3-methyl-1,2,4-oxadiazol-5-yl)-2-acetylamino-ethylsulfanylmethyl]-benzonitrile (4R,9R)-9,16-Dihydroxy-14-methoxy-13-methyl-12-oxo-6-thioxo-1,3,4,5,6,7,8,9,10,12-decahydro-11,2,5-benzoxathiaazacyclotetradecine-4-carboxylic acid methyl ester (R)-6-[2-[4-(4-Amino-phenyl)-thiazol-2-ylamino ]-2-(3-methyl-1,2,4-oxadiazol-5-yl)-ethylsulfanylmethyl]-2-bromo-5-hydroxy-3-methoxy-benzoic acid methyl ester (R)-2-Bromo-5-hydroxy-3-methoxy-6-[2-[4-(methoxymethyl)-thiazol-2-ylamino]-2-(3-methyl-1,2,4-oxadiazol-5-yl)-ethylsulfanylmethyl]-benzoic acid methyl ester In particular the following compounds are preferred
(4R,9S)-15-Hydroxy-9-hydroxymethyl-13-methoxy-12-methyl-4-(3-methyl-1,2,4-oxadiazol-5-yl)-11-oxo-6-thioxo-3,4,5,6,7,8,9,11-octahydro-1H-10,2,5-benzoxathiaazacyclotridecine (R)-16-Hydroxy-14-methoxy-13-methyl-12-oxo-6-thioxo -1,3,4,5,6,7,8,9,10,12-decahydro-11,2,5-benzoxathiaazacyclotetradecine -4-carboxylic acid prop-2-ynylamide (R)-16-Hydroxy-14-methoxy-13-methyl-4-(3-methyl-1,2,4-oxadiazol-5-yl)-6-thioxo-1,3,4,5,6,7,8,9,10,12-decahydro-11,2,5-benzoxathiaazacyclotetradecin-12-one (R)-3-Hydroxy-5-methoxy-6-methyl-2-[2-(3-methyl-1,2,4-oxadiazol-5-yl)-2-thiophen-2-ylcarbothioylamino-ethylsulfanylmethyl]-benzoic acid methyl ester (4R)-N-[5-(16-Hydroxy-14-methoxy-13-methyl-12-oxo-6-thioxo -1,3,4,5,6,7,8,9,10,12-decahydro-11,2,5-benzoxathiaazacyclotetradecin-4-yl)-1,2,4-oxadiazol-3-ylmethyl]-acetamide (4R)-4-(3-Aminomethyl-1,2,4-oxadiazol-5-yl)-16-hydroxy-14-methoxy-13-methyl-6-thioxo-1,3,4,5,6,7,8,9,10,12-decahydro-11,2,5-benzoxathiaazacyclotetradecin-12-one hydrochloride (4R)-16-Hydroxy-4-[3-(isopropylamino)-methyl-1,2,4-oxadiazol-5-yl]-14-methoxy-13-methyl-6-thioxo-1,3,4,5,6,7,8,9,10,12-decahydro-11,2,5-benzoxathiaazacyclotetradecin-12-one hydrochloride.

Compounds of formula I carrying an acidic, e.g. carboxylic, substituent form pharmaceutically acceptable salts with bases. Examples of salts of compounds of formula I are the alkali metal salts, for example the sodium and potassium salts, the ammonium salts, the alkaline earth metal salts, for example calcium salts, the salts with organic bases, for example with amines such as diisopropylamine, benzylamine, dibenzylamine, triethanolamine, triethylamine, N,N-dibenzylethylenediamine, N-methylmorpholine, pyridine, piperazine, N-ethylpiperidine, N-methyl-D-glucamine and procaine or with amino acids such as arginine and lysine. Mono-, di-, tri-salts etc. can result depending on the number of acidic groups in the compounds of formula I.

Compounds of formula I which have a basic, e.g. amino, substituent also form acid addition salts with organic and inorganic acids. Examples of acid addition salts of compounds of formula I are salts with mineral acids, for example hydrohalic acids such as hydrochloric acid, hydrogen bromide and hydrogen iodide, sulfuric acid, nitric acid, phosphoric acid and the like, salts with organic sulphonic acids, for example with alkyl- and arylsulphonic acids such as ethanesulphonic acid, p-toluenesulphonic acid, benzenesulphonic acid and the like, as well as salts with organic carboxylic acids, for example with acetic acid, tartaric acid, maleic acid, citric acid, benzoic acid, salicylic acid, ascorbic acid and the like.

The invention also relates to compounds of the formula XVIII

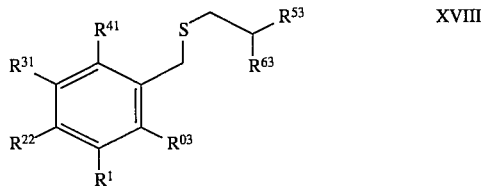

wherein $R^1$ is hydrogen, halogen, or optionally substituted lower alkyl, the optional substituent being halogen, $R^{o3}$ is cyano, optionally substituted esterified carboxy, optionally substituted heterocycle, nitro, $COOZ^1$, $CONH_2$, protected amino group, protected hydroxy group, or protected carboxy group; $R^{22}$ is hydrogen, hydroxy, amino, loweralkylamino, di-loweralkylamino, optionally substituted lower alkoxy, a group —OP, nitro, protected amino group, protected hydroxy group, or protected carboxy group; $R^{31}$ is hydrogen, hydroxy, lower alkyl, halogen, a group —OP, protected amino group, protected hydroxy group, or protected carboxy group; $R^{41}$ is halogen, hydroxy, a group —OP, protected amino group, protected hydroxy group, or protected carboxy group; $R^{53}$ is hydrogen, cyano, optionally substituted esterified carboxy, optionally substituted amidated (thio)carboxy, optionally substituted alkyl, optionally substituted alkenyl, optionally substituted heterocycle, $COOZ^1$, $CONH_2$, nitro, protected amino group, protected hydroxy group or protected carboxy group; $R^{63}$ is —$NR^7$—A, —N=B, optionally substituted heterocycle, in which $R^7$ is hydrogen or lower alkyl, A is optionally substituted imimethyl, optionally substituted (thio)acyl, optionally substituted esterified carboxy, optionally substituted amidated (thio)carboxy or optionally substituted heterocycle and B is optionally substituted alkylidene, nitro, —$NR^7Z^2$, protected amino group, protected hydroxy group, or protected carboxy group; —OP is an easily hydrolyzable group; $Z^1$ is hydrogen or a carboxy protected group; and $Z^2$ is hydroxy or amino protected group, the optionally substituted groups of $R^{o3}$, $R^{22}$, $R^{53}$, and $R^{63}$ additionally being optionally substituted by nitro and the optionally substituted groups of $R^{o3}$, $R^{22}$, $R^{31}$, $R^{41}$, $R^{53}$, and $R^{63}$ being optionally substituted by protected amino group, protected hydroxy group, or protected carboxy group.

The compounds of formula I and their pharmaceutically acceptable salts can be made in accordance with the invention by a process which comprises a) transforming the group $COOZ^1$ of a compound of the formula

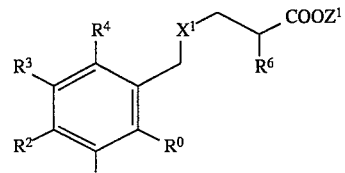

in which $R^0$–$R^4$, $R^6$ and $X^1$ are as above and $Z^1$ is hydrogen or a suitable carboxy protection group, into a group $R^5$, wherein $R^5$ is as above, with the option that any amino, hydroxy and/or carboxy group representing or being contained in $R^0$ and $R^2$–$R^6$ is protected during and deprotected after this process, or b) for the making of a compound of formula I in which at least one of the groups $R^0$, $R^2$, $R^5$ and $R^6$ represents or contains amino, reducing the nitro group(s) to amino in a compound of the formula

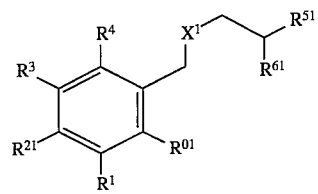

in which $R^1$, $R^3$, $R^4$ and $X^1$ are as above and $R^{01}$, $R^{21}$, $R^{51}$ and $R^{61}$ are as $R^0$, $R^2$, $R^5$ and $R^6$ above, except that at least one of these substituents represents or contains nitro, with the option that any amino, hydroxy and/or carboxy group representing or being contained in $R^{01}$, $R^{21}$, $R^3$, $R^4$, $R^{51}$ and $R^{61}$ is protected during and deprotected after this process, or c) for the making of a compound of formula I in which $X^1$ is —SO—, oxidizing a compound of formula I in which $X^1$ is —S— and $X^2$ is other than thiocarbonyl, with the option that any amino, hydroxy and/or carboxy group is protected during, and deprotected after this process, or, d) for the making of a compound of formula I, in which any of $R^0$, $R^2$–$R^6$ represents or contains (an) amino, hydroxy and/or carboxy group(s), cleaving off (a) protecting group(s) in a compound of the formula

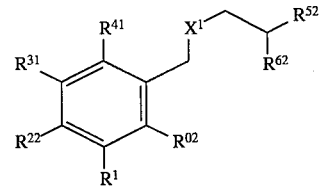

in which $R^1$ and $X^1$ are as above and $R^{02}$, $R^{22}$, $R^{31}$, $R^{41}$, $R^{52}$ and $R^{62}$ are as $R^0$, $R^2$, $R^3$, $R^4$, $R^5$ and $R^6$ above, except that any amino, hydroxy and/or carboxy group is protected, or e) for the making of a compound of formula IA, wherein $X^1$ is —S—, reacting a compound of the formula

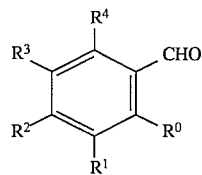

in which $R^0$–$R^4$ are as above, with a compound of the formula

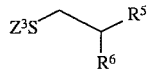

in which $R^5$ and $R^6$ are as above, and $Z^3$ is hydrogen or a suitable sulfur protecting group, in the presence of a suitable reducing agent, with the option that any amino, hydroxy and/or carboxy group representing or being contained in $R^0$ and $R^2$–$R^6$ is protected during and deprotected after this process, or f) for the making of a compound of formula IA, wherein $X^1$ is —S—, reacting a compound of the formula

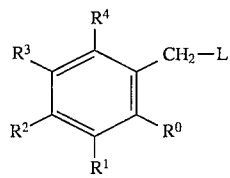

in which $R^0$–$R^4$ are as above, and L is OH or a suitable leaving group, with a compound of the formula

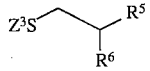

in which $R^5$, $R^6$ and $Z^3$ are as above, with the option that any amino, hydroxy and/or carboxy group representing or being contained in $R^0$ and $R^2$–$R^6$ is protected during and deprotected after this process, or g) for the making of a compound of formula IA, transforming the group $COOZ^1$ of a compound of the formula

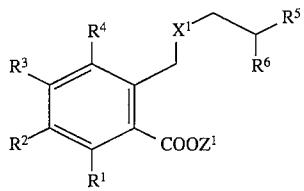

in which $R^1$–$R^6$, $X^1$ and $Z^1$ are as above, into a group $R^0$, wherein $R^0$ is as above, with the option that any amino, hydroxy and/or carboxy group representing or being contained in $R^0$ and $R^2$–$R^6$ is protected during and deprotected after this process, or h) for the making of a compound of formula IA, transforming the group $NR^7Z^2$ of a compound of the formula

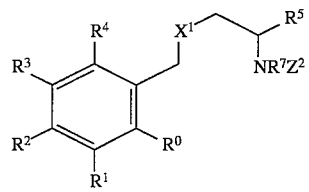

in which $R^0$–$R^5$, $R^7$, $X^1$ and $Z^2$ are as above, into a group $R^6$, wherein $R^6$ is as above, with the option that any amino, hydroxy and/or carboxy group representing or being contained in $R^0$ and $R^2$–$R^5$ is protected during and deprotected after this process, or i) for the making of a compound of formula IA, in which $R^6$ is a heterocycle or a group $NR^7A^1$, in which $A^1$ is acyl, esterified or amidated carboxy or heterocycle and $X^1$ is S, reacting a compound of the formula

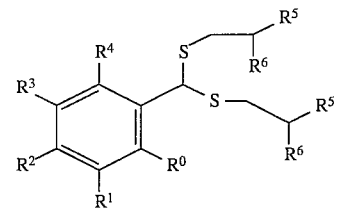

in which $R^0$–$R^5$ are as above and $R^6$ is a heterocycle or a group $NR^7A^1$, in which $R^7$ and $A^1$ are as above, with a suitable reducing agent, with the option that any amino, hydroxy and/or carboxy group representing or being contained in $R^0$, $R^2$–$R^6$ is protected during and deprotected after this process, or j) for the making of a compound of formula IA, in which $R^6$ is a group $NR^7A^1$, in which $R^7$ and $A^1$ are as above and $X^1$ is S, reacting a compound of the formula

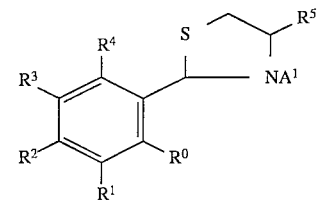

in which $R^0$–$R^5$ and $A^1$ are as above, with a suitable reducing agent, with the option that any amino, hydroxy and/or carboxy group representing or being contained in $R^0$, $R^2$–$R^5$ and $A^1$ is protected during and deprotected after this process, or k) for the making of a compound of formula IB cyclizing a carboxylic acid of the formula

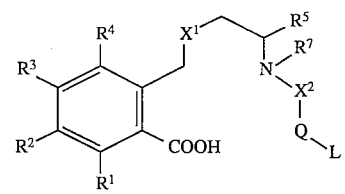

in which $R^1$–$R^5$, $R^7$, $X^1$, $X^2$ and Q are as above, and L is hydroxy or a suitable leaving group, with the option that any amino, hydroxy and/or carboxy group representing or being contained in $R^2$–$R^5$ and/or Q is protected during and deprotected after this process, or l) for the making of a compound of formula IB, wherein $X^2$ is (thio)carbonyl, cyclizing a (thio)carboxylic acid of the formula

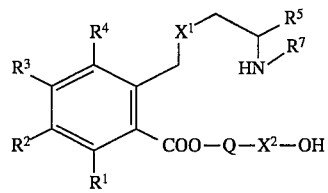

in which $R^1$–$R^5$, $R^7$, $X^1$ and Q are as above and $X^2$ is (thio)carbonyl, with the option that any amino, hydroxy and/or carboxy group representing or being contained in $R^2$–$R^5$ and/or Q, is protected during and deprotected after this process, or m) for the making of a compound of formula IB, wherein $X^1$ is —S—, cyclizing an aldehyde of the formula

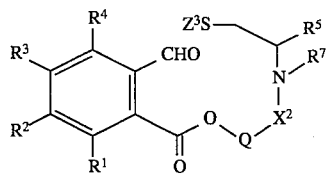

in which $R^1$–$R^5$, $R^7$, $X^2$, Q and $Z^3$ are as above, in the presence of a suitable reducing agent, with the option that any amino, hydroxy and/or carboxy group representing or being contained in $R^2$–$R^5$ and/or Q is protected during and deprotected after this process, or n) for the making of a compound of formula IB, in which $X^2$ is thiocarbonyl, reacting a corresponding compound of the formula

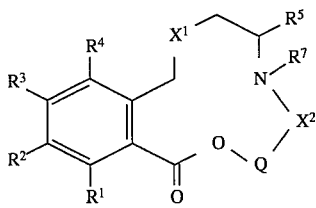

in which $X^2$ is carbonyl, with an agent yielding the corresponding thiocarbonyl derivative, with the option that any amino, hydroxy and/or carboxy group representing or being contained in $R^2$–$R^5$ and/or Q is protected during and deprotected after this process.

o) for the making of a pharmaceutically acceptable salt of a compound of formula I carrying an acidic and/or basic substituent, converting such compound of formula I into such salt.

The compounds of formula XVIII can be made in accordance with the invention by a process which comprises reacting a compound of the formula

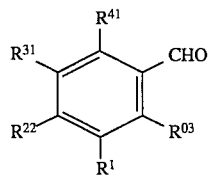

in which $R^{03}$, $R^1$, $R^{22}$, $R^{31}$ and $R^{41}$ are as above, with a compound of the formula

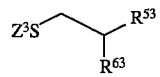

in which $R^{53}$, $R^{63}$ and $Z^3$ are as above, in the presence of a suitable reducing agent, with the option that any amino, hydroxy and/or carboxy group representing or being contained in $R^{03}$, $R^{22}$, $R^{31}$, $R^{41}$, $R^{53}$ and $R^{63}$ can be protected during this process.

Hereinabove and in the following $Z^1$, $Z^2$, $Z^3$ and $Z^4$ are hydrogen or a suitable carboxy, amino, thiol and a hydroxy-protecting group, respectively. In the following $Z^{11}$, $Z^{21}$, $Z^{31}$ and $Z^{41}$ represent specifically the corresponding protecting groups, i.e. $Z^{11}$, $Z^{21}$, $Z^{31}$ and $Z^{41}$ are a carboxy, amino, thiol and a hydroxy-protecting group, respectively. In the following examples for such protecting groups are described.

A suitable carboxy-protecting group ($Z^1/Z^{11}$) can be an ester form which can be easily converted into a free carboxyl group under mild conditions, the carboxy-protecting group being exemplified by, for example, tert-butyl, 4-nitrobenzyl, benzhydryl, allyl, 2,2,2-trichloroethyl, trialkylsilanyl such as tert-butyl-dimethylsilanyl, etc. For example, the following reagents and their corresponding compatible esters are utilized: 4-nitrobenzyl can be removed by hydrogenolysis in the presence of a catalyst such as palladium on charcoal at 0° C. to 40° C. in a solvent such as ethyl acetate or methanol; tert-butyl can be removed by reaction with trifluoroacetic acid, optionally in the presence of anisole at about 0° C. to room temperature with or without a co-solvent, such as dichlormethane; allyl can be removed by a palladium(0)catalyzed transallylation reaction in the presence of a tertiary amine such as N-methyl-morpholine (see for example J. Org. Chem. 1982, 47, 587); 2,2,2-trichloroethyl can be removed by reaction with zinc in a solvent such as aqueous acetic acid or a mixture of tetrahydrofuran and aqueous sodium dihydrogen phosphate; trialkylsilanyl can be cleaved off in a protic solvent such as methanol optionally in the presence of fluoride ions, e.g. by using ammonium fluoride.

The residues of in vivo easily cleavable esters may also be employed as carboxy-protecting groups. Examples of such esters, which can be of the conventional type, are the lower alkanoyloxyalkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester). These easily cleavable ester groups may be split off by treatment with an esterase such as pig liver esterase in aqueous solution in the presence of a co-solvent such as tetrahydrofuran or dimethylsulfoxide and at a temperature in the range of about 30° C. to 40° C.

Also conventional lower alkyl groups, e.g. methyl and ethyl, are useful as carboxy-protecting groups: they can be split off in the same manner as the lower alkanoyl and lower alkoxycarbonyl groups P described above. Thus, treatment with an inorganic base such as an alkali metal hydroxide or carbonate in a lower alkanol or tetrahydrofuran at about 0° C. to room temperature will remove these hydroxy and carboxy-protecting groups.

Suitable amino-protecting groups ($Z^2/Z^{21}$) are those employed in peptide chemistry, such as an alkoxycarbonyl group, e.g., tertbutoxy-carbonyl, etc., a substituted alkoxycarbonyl group, e.g., trichloroethoxycarbonyl, etc., a substituted arylmethoxycarbonyl group, e.g., 4-nitrobenzyloxycarbonyl, an alken-1-yl-methoxycarbonyl group, e.g. an allyloxycarbonyl, an arylmethyl group such as trityl or benzhydryl, a halogen-alkanoyl group such as chloroacetyl, bromoacetyl or trifluoroacetyl or a trialkylsilanyl group such as tert-butyl-dimethylsilanyl, etc.

Preferred amino-protecting groups are tert-butoxycarbonyl, trityl, allyloxycarbonyl and 2,2,2-trichloroethoxycarbonyl.

The amino-protecting groups may be cleaved off by acidic hydrolysis or alcoholysis (e.g. the tert-butoxycarbonyl or trityl group) or by basic hydrolysis (e.g. the trifluoroacetyl group). The chloroacetyl, bromoacetyl and iodoacetyl groups are cleaved off by treatment with thiourea. The 2,2,2-trichloroethoxycarbonyl group is cleaved off by reduction with zinc and an acid, an alken-1-yl-methoxycarbonyl group, e.g. an allyloxycarbonyl and a trialkylsilanyl group is cleaved off by heating with an alcohol such as ethanol optionally in the presence of a fluoride such as ammonium fluoride. Arylmethoxycarbonyl can be cleaved off by hydrogenolysis and allyloxycarbonyl is cleaved by palladium(O)catalyzed transallylation as described above for a 4-nitrobenzyl and an allyl ester, respectively.

Amino-protecting groups which are cleavable by acidic hydrolysis are preferably removed with the aid of a lower alkanecarboxylic acid which may be halogenated. In particular, formic acid or trifluoroacetic acid is used. The acid hydrolysis is generally carried out in a range of 0° C. to room temperature, although it can be carried out at a slightly higher or slightly lower temperature (e.g. at a temperature in the range of about −20° C. to +40° C.). Protecting groups which are cleavable under basic conditions are generally hydrolyzed with dilute aqueous alkali at 0° C. to +30° C. The chloroacetyl and bromoacetyl protecting groups can be cleaved off using thiourea in acidic, neutral or alkaline medium at about 0°–30° C. The 2,2,2-trichloroalkoxycarbonyl group is cleaved off by treatment with zinc and an acid, preferably aqueous acetic acid.

Suitable thiol-protecting groups ($Z^3/Z^{31}$) are those employed in peptide chemistry for the protection of the thiol function of cysteine such as trityl, 2,4,6-trimethoxybenzyl, or trialkylsilanyl e.g. trimethylsilanyl. Preferred thiol-protecting groups are those which are cleaved off under acidic conditions used in the making of compounds in accordance with process variants e) and m) such as trityl and 2,4,6-trimethoxybenzyl.

An alternative way for the protection of a thiol function represents the formation of a symmetrical or unsymmetrical disulfide. The reductive cleavage of 1 mole of such a disulfide releases 2 moles of the protected thiol in the case of the symmetrical, and 1 mole of the protected thiol in the case of the unsymmetrical disulfide. Examples for symmetrical disulfides are e.g. compounds $R^{63}(R^{53})CCH_2S\text{—}SCH_2C(R^{53})R^{63}$, viz. a compound XXXV as described below. Unsymmetrical disulfides are oxidized combinations of a thiol VI with an aryl or alkyl mercaptan, e.g. PhS-SCH$_2$C(R$^{53}$)R$^{63}$ or MeS-SCH$_2$C(R$^{53}$)R$^{63}$. Preferred are the symmetrical disulfides.

In a certain processes as e.g. in process variants e), f) or g), the deprotection of the thiol function can occur prior to its use, or optionally, except in case of unsymmetrical disulfides, the thiols can be generated concomitantly, i.e. in situ, by using reaction conditions suitable for the cleavage of the thiol-protecting group.

Trityl and 2,4,6-trimethoxybenzyl are easily cleavable under acidic conditions, e.g. in trifluoroacetic acid optionally in the presence of a mild reducing agent such as a trialkylsilane, e.g. triethylsilane, and of an inert co-solvent such as dichlormethane. Trialkylsilanyl is cleaved off under mild basic or acidic conditions, e.g. under the reaction conditions used in process variant f) described above.

The cleavage of a disulfide precursor can be accomplished with a suitable reducing agent such as a trialkylphospine, e.g. tributylphospine, in a solvent like trifluoroethanol at neutral or slightly basic conditions, e.g. by addition of sodium hydroxide or triethylamine, or, in the case of the in situ generation of the thiol VI in the course of a reaction in accordance with process variants e), f) or g), in a solvent or solvent mixture used for said process variants, but maintaining in the initial phase of these processes reaction conditions compatible with the disulfide cleavage reaction.

Possible hydroxy-protecting groups ($Z^4/Z^{41}$) are the easily cleavable groups P as defined above, e.g. lower alkanoyl and lower alkoxycarbonyl. They may be cleaved off by basic hydrolysis, e.g. by treatment with an inoganic base such as an alkali metal hydroxide or carbonate in a lower alkanol, e.g. methanol, or tetrahydrofuran and at a temperature in the range of about 0° C. to room temperature. Other hydroxy-protecting groups are those known per se, such as 4-nitrobenzyloxycarbonyl, allyloxycarbonyl or 2,2,2-trichloroethoxycarbonyl which can be cleaved off in an analogous manner as the 4-nitrobenzyl, allyl or 2,2,2-trichloroethyl carboxy-protecting groups described above; tert-butyl or trityl which can be removed by reaction with acid, e.g. trifluoroacidic acid, optionally in the presence of anisole; trialkylsilanyl, e.g. tert-butyl-dimethylsilanyl or dimethyl-(1,1,2-trimethylpropyl)-silanyl which can be cleaved off by treatment with fluoride as described above. Hydroxy groups may further be protected or masked as acetals or ketals, e.g. as tetrahydropyranyl ethers or methoxymethyl ethers. From these protection groups the hydroxy function can be liberated by acidic hydrolysis, e.g. with aqueous hydrochloric acid.

Besides the above mentioned easily cleavable hydroxy-protecting groups, phenolic hydroxy groups of the intermediates XV, XVI, XVIa, XX-XXII and XXX can also be protected as methyl ethers, i.e. the substituents $R^2$ or $R^{22}$ and/or $R^4$ or $R^{41}$ can also represent a methoxy group. In a later phase of the synthesis, e.g. after formation of the aidehyde XVI(a), these methoxy groups can optionally be cleaved off, e.g. using boron trichloride or boron tribromide in dichloromethane at a temperature between −80° C. and +20° C., and the free phenolic functions can be reprotected by protecting groups more suitable for cleavage in the final product, e.g. lower alkanoyl, lower alkoxycarbonyl or trialkylsilanyl.

The transformation of a group $COOZ^1$ in the starting compounds II into a group $R^5$ in accordance with variant a) of the process in accordance with the invention consists in particular of procedures known per se for the transformation of a carboxylic acid or a carboxylic acid derivative into cyano, optionally substituted esterified carboxy or optionally substituted amidated (thio)carboxy, optionally substituted alkyl, optionally substituted alkenyl or optionally substituted heterocycle.

In particular for the transformation of the group $COOZ^1$ into cyano, the $COOZ^1$ group is first transformed into a group $CONH_2$, e.g. by treating a group $COOCH_3$ with a solution of ammonia in methanol, and subsequently by dehydrating the $CONH_2$ group in a manner known per se, e.g. by reaction with thionyl chloride or trifluoroacetic anhydride and pyridine. This reaction is carried out in an inert solvent such as dioxane or tetrahydrofuran and the reaction temperature preferably lies in the range of about −20° C. to +20° C.

In particular for the transformation of the group $COOZ^1$ into esterified or amidated carboxy, the group $COOZ^1$ is estefified or amidated in a manner known per se with an agent yielding the corresponding ester or amide moiety. For example, esterification may be accomplished by treatment of the carboxylic acid of formula II, where $Z^1$ is hydrogen, or a reactive derivative thereof, such as the N-hydroxy-succinimide ester or a lower alkyl ester, e.g. a methyl ester with an alcohol of the formula Y—OH;

whereas amidation can be effected by an analogous treatment with an amine of the formula $NR^7Y$, where Y and $R^7$ are as above.

If the carboxylic acid of the formula II is reacted directly, i.e. without previous transformation into a reactive derivative, with an alcohol Y—OH or with an amine $NR^7Y$, a coupling agent such as a carbodiimide, e.g. dicyclohexylcarbodiimide, or a 1-lower alkyl-2-halopyridinium salt, e.g. 1-methyl-2-chloropyridinium iodide, should be used.

These esterification and amidation reactions are preferably carried out in an inert solvent such as dichloromethane, tetrahydrofuran or acetonitrile and at a temperature in the range of about −20° C. to +80° C.

The transesterification of a lower alkyl ester of formula II in which $Z^1$ is methyl or ethyl, can be achieved by reacting it with an alcohol of the formula Y—OH in the presence of a catalyst such as tetra-(lower alkoxy) orthotitanate, e.g. tetraisopropyl orthotitanate. This process can be optionally carded out in the presence of an inert co-solvent such as toluene, and the reaction temperature preferably lies in the range of about 60° C. to 150° C.

The amidation of a lower alkyl ester of formula II in which $Z^1$ is methyl or ethyl, can be achieved by reacting it with an amine of the formula $NR^7Y$ in a polar solvent such as methanol or dimethylsulfoxide at a reaction temperature of about −20° C. to 80° C.

In particular for the transformation of the group $COOZ^1$ in starting compounds II into thioamidated carboxy, the group $COOZ^1$ is first transformed into amidated carboxy as described above, followed by the transformation of this amidated carboxy into a thioamidated carboxy by methods known per se, e.g. by reaction with a thiation reagent such as phosphorus pentasulfide or, alternatively, with 2,4-bis-(4-methoxyphenyl)-2,4-dithioxo-1,3,2,4-dithiadiphosphetane (see Tetrahedron 37, 3635 (1981) in an inert solvent, e.g. toluene or benzene, at a reaction temperature of about 20° C. to 150° C.

In particular for the transformation of the group $COOZ^1$ in starting compounds II into alkenyl or alkyl, the group $COOZ^1$ in which $Z^1$ is methyl or ethyl, is reduced to a group $CH_2OH$ by reaction with a metal hydride, e.g. with sodium borohydride in methanol, and the $CH_2OH$ group can then be oxidized to a group CHO in a manner known per se (see e.g. Tetrahedron 34, 1651 (1978)), and the CHO group can then be reacted with an olefinating agent, e.g. a Wittig reagent of the formula $(C_6H_5)_3P=CH$-alkyl or $(C_6H_5)_3P=CH$-alkenyl, in which the groups "alkyl" and "alkenyl" are defined as above, except that they refer to groups which include not more then 13 carbon atoms, and in the case that the group $COOZ^1$ is to be transformed into alkyl, the resulting olefine can be hydrogenated, e.g. using hydrogen in the presence of a hydrogenation catalyst such as palladium on charcoal. Alternatively, the CHO group can be reacted with an organometallic reagent, e.g. with a Grignard reagent, such as propyl magnesium bromide or allyl magnesium bromide, which can be derived from a corresponding alkyl or alkenyl halide, to convert the group $COOZ^1$ into an alkyl or an alkenyl group, respectively.

In particular for the transformation of the group $COOZ^1$ in starting compounds II into heterocycle, the group $COOZ^1$ in which $Z^1$ is hydrogen or lower alkyl is subjected to procedures known per se for the preparation of heterocyles from carboxylic acids or from carboxylic acid derivatives (see e.g. A. R. Katritzky and Ch. W. Rees, Comprehensive Heterocyclic Chemistry Vol. 1–8, Pergamon Press).

In particular the preparation of compounds I, in which $R^5$ is hydrogen, is described hereinbelow in connection with How Sheet 1.

The reduction of nitro groups representing or being contained in $R^{01}$, $R^{21}$, $R^{51}$, and/or $R^{61}$ in starting compounds of formula III to amino according to variant b) of the process in accordance with the invention can be carried out in a manner known per se, e.g. by reaction with zinc, iron or tin in the presence of a mineral acid such as aqueous hydrochloric acid. The reaction is preferably carried out at a temperature in the range of about 0° C. to 50° C., optionally in the presence of a co-solvent such as tetrahydrofuran.

The oxidation of the starting compounds of formula I in which $X^1$ is —S— according to embodiment c) yields the oxidized analogs of formula I wherein $X^1$ is —SO— (sulfoxides). This oxidation is carried out by using an organic or inorganic oxidizing agent. Various compounds which readily deliver oxygen can be used as the oxidizing agent; for example, organic peroxides such as monosubstituted organic peroxides (e.g. $C_{1-4}$ alkyl- or alkanoylhydroperoxides such as tert-butylhydroperoxide), performic acid and peracetic acid, as well as phenyl-substituted derivatives of these hydroperoxides such as cumenehydroperoxide and perbenzoic acid. The phenyl substituent can, if desired, carry a further lower group (e.g. a lower alkyl or lower alkoxy group), a halogen atom or a carboxy group (e.g. 4-methylperbenzoic acid, 4-methoxy-perbenzoic acid, 3-chloroperbenzoic acid and mono-perphthalic acid). Various inorganic oxidizing agents can also be used as the oxidizing agent: for example, hydrogen peroxide, ozone, permanganates such as potassium or sodium permanganate, hypochlorites such as sodium, potassium or ammonium hypochlorite, peroxymonosulphuric and peroxydisulphuric acid. The use of 3-chloroperbenzoic acid is preferred. The oxidation is advantageously carried out in an inert solvent, for example, in an aprotic inert solvent such as tetrahydrofuran, dioxane, dichlormethane, chloroform, ethyl acetate or acetone or in a protic solvent such as water, a lower alkanol (e.g. methanol or ethanol) or a lower alkanecarboxylic acid which may be halogenated (e.g. formic acid, acetic acid or trifluoroacetic acid). The oxidation is generally carried out at a temperature in the range of −20° C. to +50° C. In order to obtain the corresponding sulfoxide, i.e. a compound of formula I in which $X^1$ stands for —SO—, with substantial exclusion of the corresponding sulfone it is preferable to use the oxidizing agent in equimolar amounts or in only slight excess in relation to the starting material.

According to variant d) of the process in accordance with the invention a starting compound of formula IV which is protected at any of amino, hydroxy and/or carboxy groups present is deprotected to yield a compound of formula I with free amino, hydroxy and/or carboxy groups.

Possible carboxy, amino, thiol- and hydroxy-protecting groups are described above in the definition of $Z^1$–$Z^4$ and thereinafter the methods for their cleavage.

The preparation of compounds of formula IA in accordance with variant e) of the process in accordance with the invention consists of the reaction of an aldehyde of the formula V with a compound of the formula VI in the presence of a reducing agent under acidic conditions. The reducing agent is selected as to be inert to the solvent used and unreactive towards the products. Preferred reducing agents are trialkylsilanes, e.g. triethylsilane or triisopropylsilane, and trialkylstannanes such as tri-n-butyltin hydride.

It is also possible to generate a thiol of the formula VI in situ by reduction of a corresponding disulfide $R^{63}(R^{53})CCH_2S-SCH_2C(R^{53})R^{63}$, viz. a compound XXXV, with an agent such as a trialkylphosphine, e.g. tributylphosphine, as described above. In the latter case, the pH of the reaction mixture has first to be kept neutral or optionally slightly basic by the addition of base, e.g. aqueous sodium hydroxide or triethylamine in order to allow the disulfide reduction, and subsequently, the acidic conditions necessary for the reaction between compounds V and VI are established by addition of the acids described above.

The acid can be selected from a wide variety of protic (Broensted) acids, e.g. methane sulfonic acid or trifluoroacetic acid, and aprotic (Lewis) acids, e.g. boron trifluoride in acetonitrile or boron trifluoride etherate in dichlormethane. They can be used in stochiometric amounts in the presence of an inert co-solvent, or in excess up to using them as the solvent. Preferred acids are trifluoroacetic acid used as the solvent itself or in a mixture with an inert solvent and boron trifluoride used in amounts of 1–5 equivalents in an inert solvent. Inert solvents in this process are e.g. dichloromethane, diethyl ether, tetrahydrofuran, acetonitrile, trifluoroethanol, or mixtures thereof. In the case that the thiol VI is generated in situ as described above, trifluoroethanol is a preferred (co-)solvent. The reaction temperature lies in the range of about $-20°$ C. to $+70°$ C., preferably in the range of about $-15°$ C. to $+30°$ C.

The preparation of compounds of formula IA in accordance with variant f) of the process in accordance with the invention consists of the reaction of a compound of the formula VII with a compound of the formula VI.

For L in compound VII=OH, the reaction between VII and VI is carried out under the reaction conditions described above (see variant e) except that no reducing agent is used.

If L in compound VII is a leaving group, the compound VII is reacted with a compound of the formula VI in which $Z^3$ is hydrogen. Preferred meanings for L are chlorine, bromine, iodine, or the residue of a sulfonic acid, e.g. methane sulfonyloxy or 4-toluene sulfonyloxy. The reaction is preferably effected in an inert organic solvent such as dichlormethane, ethyl acetate, N,N-dimethylformamide, dimethylsulfoxide, acetonitrile or ethanol in the presence of a weak non-nucleophilic organic base such as triethylamine or 4-methyl-morpholine, or in the presence of an inorganic base such as sodium or potassium carbonate. The reaction temperature preferably lies between $-60°$ C. and $+60°$ C., preferably between $0°$ C. and $+30°$ C.

It is also possible to generate a thiol of the formula VI in situ by reduction of a corresponding disulfide $R^{63}(R^{53})CCH_2S-SCH_2C(R^{53})R^{63}$, viz. a compound XXXV, with an agent such as a trialkylphosphine, e.g. tributylphosphine, as described above.

Compounds of the formula I, in which $R^5$ is hydrogen, can be prepared if the compound V or VII is reacted with a compound of the formula VI, in which $R^5$ is hydrogen. This process can be carried out using the corresponding procedures described above (variant e) and f)).

The transformation of a group $COOZ^1$ in starting compounds VIII into a group $R^0$ in accordance with variant g) of the process in accordance with the invention consists in particular of aforementioned procedures (see variant a)) known per se for the conversion of a carboxylic acid or a carboxylic acid derivative into a cyano, an optionally substituted esterified carboxy or a optionally substituted heterocyclic group.

The transformation of a group $NR^7Z^2$ in starting compounds IX into a group $R^6$, in which $R^6$ is —$NR^7$—A, —N=B or optionally substituted heterocycle, $R^7$ is hydrogen or lower alkyl, A is optionally substituted iminoyl, optionally substituted (thio)acyl, optionally substituted esterified carboxy, optionally substituted amidated (thio)carboxy or optionally substituted heterocycle and B is optionally substituted alkylidene, in accordance with variant h) of the process in accordance with the invention consists in particular of procedures known per se for the conversion of an amino group or an amino derivative into a optionally substituted iminoyl, (thio)acyl, esterified carboxy or amidated (thio)carboxy or a heterocycle derivative, an imino function, or a heterocyclic group.

In particular for the transformation into an iminoyl derivative, the group $NR^7Z^2$, wherein $Z^2$ is preferably hydrogen, is reacted with an iminoylating agent of the formula $L^1$—$CR^7$=N—$Y^1$, wherein $L^1$ is a leaving group, e.g. chlorine or lower alkoxy such as methoxy, and $R^7$ and $Y^1$ are as defined above. This reaction is carried out in an inert solvent such as dichloromethane or tetrahydrofuran and in the presence of a base such as triethylamine or pyridine. The reaction temperature preferably lies in the range of about $-20°$ C. to $+50°$ C.

Examples of such iminoylating agents are e.g. lower alkanimidic acid esters, e.g. methanimidic acid ethyl ester hydrochloride or lower alkanimidoyl chlorides, e.g. N-phenyl-ethanimidoyl chloride.

These agents can be prepared by methods known per se from compounds of the formula $O=CR^7$—N—$Y^1$, where $R^7$ and $Y^1$ are as above, by reacting the latter with a chlorinating agent such as phosphorus pentachloride or phosphorus oxychloride, or with an alkylating agent such as trimethyloxonium tetrafluoroborate.

In particular for the transformation into a (thio)acyl derivative, the group $NR^7Z^2$, wherein $Z^2$ is preferably hydrogen, is reacted with a (thio)acylating agent of the formula L-$(X^2)$n-$Y^1$ wherein L, $X^2$, n and $Y^1$ are as defined above.

Examples of acylating agents are carboxylic acids, e.g. acetic acid, benzoic acid, 2-thiophene-acetic acid, in which case the reaction is carried in the presence of a coupling agent such as a carbodiimide, e.g. dicyclohexyl-carbodiimide, or a lower alkyl-2-halopyridinium salt, e.g. 1-methyl-2-chloropyridinium iodide, in an inert solvent such as acetonitrile, dioxane or tetrahydrofuran.

It is also possible to use a reactive derivative of the said carboxylic acid, such as an acid halide, e.g. propionyl chloride or 2-thiophenecarbonyl chloride, an acid azide, e.g. 2-pyridine-carboxylic acid azide, a N-hydroxy-succinimide ester, e.g. N-acetyl glycine (N-hydroxy-succinimide) ester, or a mixed anhydride with another organic acid, e.g. trifluoroacetic acid or benzene sulfonic acid, or a reactive thiolester such as e.g. an S-(2-benzothiazolyl)thioester. In this case, the acylation of the amine is optionally performed in the presence of a base such as sodium bicarbonate, potassium carbonate, triethylamine, pyridine or N-methyl-morpholine in an inert solvent such as dichlormethane, chloroform, tetrahydrofuran, dioxane, acetonitrile or N,N-dimethylformamide. The reaction temperature can vary in a wide range between about $-50°$ C. and $+100°$ C., preferably between about $-20°$ C. and $+50°$ C.

In particular for the transformation of the group $NR^7Z^2$ into a thioacyl derivative, the group $NR^7Z^2$, wherein $Z^2$ is preferably hydrogen, is first acylated as described above, followed by the transformation of the resulting acylamido derivative into a thioacylamido derivative by methods known per see, e.g. by reaction with a thiation reagent (see variant a)). An alternative procedure for the preparation of thioacyl derivatives consists in the reaction of compounds of the formula IX, wherein $Z^2$ is preferably hydrogen, with thioacylating agents corresponding to those described in Bioorganic & Medicinal Chemistry Letters 3, 619 (1993), and using reaction conditions analogous to those described therein.

In particular for the transformation into an esterified carboxy derivative, the group $NR^7Z^2$, wherein $Z^2$ is preferably hydrogen, is reacted with a reactive derivative of a carboxylic or oxalylic acid derivative HO-(CO)$_n$OY, wherein n and Y are as defined above. Examples of reactive derivatives are acid chlorides, e.g. benzyl chloroformate or oxalylic acid mono ethyl ester chloride. These reactions are optionally performed in the presence of a base in an inert solvent as described above for the acylation using carboxylic acid halides.

In particular for the transformation into an amidated (thio)carboxy derivative, the group $NR^7Z^2$, wherein $Z^2$ is preferably hydrogen, is reacted with an iso(thio)cyanate $X^2$=C=N-$Y^1$, wherein $X^2$ and $Y^1$ are as above, e.g. phenyl isocyanate or 4-chlorophenyl isothiocyanate. The reaction is carried out in a solvent such as dichloromethane, chloroform, tetrahydrofuran, dioxane, acetonitrile or N,N-dimethylformamide or methanol. The reaction temperature can vary in a wide range between about −50° C. and +100° C., preferably between about −20° C. and +50° C.

For the transformation into an amidated thiocarboxy derivative, the group $NR^7Z^2$, wherein $Z^2$ is preferably hydrogen, is reacted first with a thiocarbonylating agent, e.g. 1,1'-thiocarbonyl-di-2(1H)-pyridon in an inert solvent such as dichlormethane, and the resulting isothiocyanate is then further reacted with an amine HN$R^7$Y1 wherein $R^7$ and $Y^1$ are as above, e.g. methylamine or 2-amino-thiazole, in a solvent such as chloroform, tetrahydrofuran, acetonitrile, N,N-dimethylformamide or methanol. The reaction temperature can vary in a wide range between about −50° C. and +100° C., preferably between about −20° C. and +50° C. According to a further alternative, an amidated thiocarboxy derivative can be obtained by subjecting an amidated carboxy derivative to methods known per se, e.g. to the reaction with a thiation reagent (see variant a)).

In particular for the transformation into an imino function, the group $NR^7Z^2$, wherein $Z^2$ is preferably hydrogen, is reacted with an oxo compound of the formula B=O, wherein B is as defined above, so as to obtain end products of formula IA where $R^6$ is the group —N=B. Compounds of formula B=O are e.g. aldehydes, e.g. compounds of the formula Y—CHO or ketones, e.g. compounds of the formula $Y_2$CO and the transformation can be carried out in a manner known per se, e.g. by reacting an aldehyde or a ketone corresponding to formula B=O with the amine of formula IX, wherein $Z^2$ is hydrogen, in an inert aprotic solvent, such as dichlormethane or toluene, and in the presence of an acidic catalyst such as p-toluenesulfonic acid and a water-binding agent such as molecular sieves or magnesium sulfate. This reaction is preferably carded out at a temperature in a range of about 0°–60° C.

In particular for the transformation into a heterocycle derivative $NR^7$-heterocycle, or into a heterocycle group, the group $NR^7Z^2$ is subjected to procedures known per se for the preparation of amino-substituted heterocycles or nitrogen containing heterocycles from amines or amino derivatives (see e.g. A. R. Katritzky and Ch. W. Rees, Comprehensive Heterocyclic Chemistry, Vol. 1–8, Pergamon Press).

The transformation of starting compounds X into compounds of formula IA in accordance with variant i) of the process in accordance with the invention can be carried out by subjecting compounds X to the reduction procedures described above for variant e).

The transformation of starting compounds XI into compounds of formula IA in accordance with variant j) of the process in accordance with the invention can be carried out by subjecting compounds XI to the reduction procedures described above for variant e).

The cyclization in accordance with variant k) of the process in accordance with the invention consists of an intramolecular esterification (lactonization) and utilizes starting materials of formula XII, in which L is hydroxy or a leaving group, and $X^1$, $X^2$, Q, $R^1$–$R^5$ and $R^5$ are as above, or reactive derivatives thereof.

For L=hydroxy, various procedures known per se can be used for the lactonization of the hydroxy-acid XII. A preferred method consists in using a di-lower alkyl azodicarboxylate, e.g. diethyl azodicarboxylate in combination with a triarylphosphine, e.g. triphenylphosphine in an aprotic organic solvent, such as benzene, toluene or dichlormethane. The reaction can be carried out at a temperature between about −10° C. and +80° C., preferably at about 0° C. to about +30° C. (see e.g. O. Mitsunobu, Synthesis 1, 1981).

According to an alternative procedure, a reactive derivative , viz. a compound corresponding to formula XII, in which the carboxy function has been converted into a reactive derivative, preferably into a reactive derivative with an N-heteroaromatic thiol, in particular 2-mercaptopyridine or a di-lower alkyl substituted 2-mercaptoimidazole such as 4-tert-butyl-N-isopropyl-2-mercaptoimidazole is prepared, which then in situ undergoes cyclization to a compound IB, in particular upon heating.

These N-heteroaromatic thiol esters can be prepared by reacting the disulfide corresponding to said thiol and triphenyl phosphine with the carboxylic acid of formula XII. The reaction proceeds in an aprotic organic solvent such as benzene, toluene, xylene or dichlormethane and at a temperature between −20° C. and +40° C., preferably at about 0° C. and +20° C. The reaction can proceed already under the said conditions. However, in general conversion is achieved to completion by heating the reaction mixture, preferably at reflux for about 0.1–20 hours.

Instead of the above N-heteroaromatic thiol ester an ester with a 1-lower alkyl-2-halopyridinium salt, preferably 1-methyl-2-chloropyridinium iodide, can be employed. For example, the starting compound of formula XII is reacted with e.g. 1-methyl-2-chloropyridinium iodide in the presence of a tertiary amine such as triethylamine in an aprotic organic solvent such as acetonitrile or dichlormethane at a temperature between room temperature and the boiling point of the reaction mixture, preferably the latter.

According to a further alternative the starting compound of formula XII is cyclized with the aid of a mixture of a carbodiimide (such as dicyclohexylcarbodiimide), 4-(dimethylamino)pyridine and an acid addition salt, e.g. the hydrochloride, of the latter. This reaction preferably proceeds in an inert, aprotic organic solvent such as tetrahydrofuran or, preferably, chloroform at a temperature between about room temperature and reflux temperature, preferably at the latter.

For L=leaving group as defined above, e.g. bromine, iodine or residue of sulfonic acid, e.g. methane sulfonyloxy, the cyclization of a starting compound XII is preferably effected in an inert organic solvent such as dichlormethane, ethyl acetate, N,N-dimethylformamide, dimethylsulfoxide, acetonitrile or ethanol in the presence of an inorganic base such as lithium hydroxide, potassium carbonate or cesium carbonate or of a weak non-nucleophilic organic base such as triethylamine, 4-methyl-morpholine or 1,1,3,3-tetramethylguanidine. The reaction temperature preferably lies between −60° C. and +60° C., preferably between 0° C. and 30° C.

The cyclization in accordance with variant 1) of the process in accordance with the invention consists of an intramolecular amidation and utilizes starting materials of formula XIII, in which $X^1$, Q, $R^1$–$R^5$ and $R^7$ are as above and $X^2$ is (thio)carbonyl, or reactive derivatives thereof.

The starting compounds of formula XIII themselves can be cyclized in the presence of carboxylic acid activators such as 1-lower alkyl-2-halopyridinium salts, e.g. 1-methyl-2-chloropyridinium iodide, dicyclohexylcarbodiimide or N-ethyl-5-phenyl-isoxazolium-3'-sulfonate, preferably in the presence of an organic base such as triethylamine or N-methyl-morpholine. The reaction is carried out in an aprotic organic solvent such as dichloromethane or acetonitrile and at a temperature between about 0° C. and the boiling point of the reaction mixture.

Reactive derivatives are compounds corresponding to formula XIII in which the carboxy function has been converted into a reactive derivative, using methods known per se, preferably into an acid halide, particularly the chloride; into a mixed acid anhydride, particularly with trifluoroacetic acid or p-toluenesulfonic acid, or into a reactive thiol ester, particularly a 2-pyridine thiol ester. These derivatives are obtained in a manner known per se by reacting the starting compound of formula XIII with an agent such as thionyl chloride, a reactive derivative of a corresponding acid, or with the disulfide corresponding to 2-pyridine thiol and triphenylphosphine in the above mentioned manner. The cyclization of the reactive derivatives of the carboxylic acids of formula XIII proceeds in an aprotic solvent such as toluene or dichlormethane and in the case of an acid halide or mixed acid anhydride, in the presence of an organic base such as triethylamine or pyridine, at a temperature between about −20° C. and 130° C., preferably in the range of about 0° C. and 110° C.

The cyclization in accordance with variant m) of the process in accordance with the invention consists of subjecting starting materials of formula XIV, in which $X^2$, $Z^3$, Q, $R^1$–$R^5$ and $R^7$ are as above, to the reduction procedures described above in variant e).

The preparation of a thiolactam of formula IB in which $X^2$ is thiocarbonyl in accordance with variant n) of the process in accordance with the invention can be carried out by reacting a lactam of the formula IBa with a thiation reagent according to the procedures described above.

The making of the pharmaceutically acceptable salts of the compounds of formula I in accordance with variant o) of the process in accordance with the invention can be carried out in a manner known per se; for example, by reacting a carboxylic acid of formula I with an equivalent amount of the desired base or, conversely, a free base of formula I with an equivalent amount of the desired organic or inorganic acid. The reaction is conveniently carried out in a solvent such as water or an organic solvent (e.g. ethanol, methanol, acetone and the like). The temperature at which the salt formation is carried out is not critical. The salt formation is generally carried out at room temperature, but it can be carried out at a temperature slightly above or below room temperature, for example in the range of 0° C. to +50° C. The acid addition salts can be converted into a free form by treatment with a base, such as a metal hydroxide, ammonia and the like, the base salts are converted into the free form by treatment with an acid such as hydrochloric acid and the like.

The starting compounds of formulas II–XIV can be prepared in accordance with the following Flow Sheets 1–5.

In Flow Sheets 1–5, $R^0$–$R^7$, $A^1$, L, Q, $X^2$, $Z^3$ and $Z^4$ are as above, $R^{03}$, $R^{22}$, $R^{31}$, $R^{41}$, $R^{53}$ and $R^{63}$ are as $R^0$, $R^2$, $R^3$, $R^4$, $R^5$ and $R^6$, respectively, except that $R^{03}$ and $R^{53}$ can also be COOZ$^1$ wherein $Z^1$ is as above or CONH$_2$, $R^{03}$, $R^{21}$, $R^{53}$ and $R^{63}$ can also be or contain nitro, $R^{63}$ can also be NR$^7$Z$^2$ wherein $Z^2$ is as above, and $R^{03}$, $R^{22}$, $R^{31}$, $R^{41}$, $R^{53}$ and $R^{63}$ can also be or contain a protected amino, hydroxy and/or carboxy group; $L^1$ is a leaving group, as defined above; $Z^{11}$, $Z^{21}$ and $Z^{41}$ are, respectively, a carboxy-, amino- and hydroxy-protection group, as defined above. A group $Z^5$ is meant to be hydrogen or either a carboxy protection group $Z^1$ or a hydroxy protection group $Z^4$, and a group $Z^{51}$ is meant to represent specifically the corresponding protection groups $Z^{11}$ or $Z^{41}$, depending on the character of the hydroxy function it is attached to. Thus in a compound containing the group —$X^2$—OZ$^5$ or —$X^2$—OZ$^{51}$, $Z^5$($Z^{51}$) is $Z^1$($Z^{11}$) for $X^2$=(thio)carbonyl or $Z^4$($Z^{41}$) for $X^2$=heterocycle, respectively. $X^2$ is preferably —CO—; end products with $X^2$=—CS— are preferably obtained as a final step as described above under o).

Compounds II–V and VII–XI can be made according to Flow Sheet 1 as follows (The formulas XVIII and XIX in Flow Sheet 1 comprise the starting compounds II–IV, VIII and IX, but do not include compounds Ia in accordance with the invention, i.e. at least one of $R^{03}$, $R^{22}$, $R^{31}$, $R^{41}$, $R^{53}$ and $R^{63}$ is not as $R^0$, $R^2$, $R^3$, $R^4$, $R^5$ and $R^6$, respectively):

Flow Sheet 1
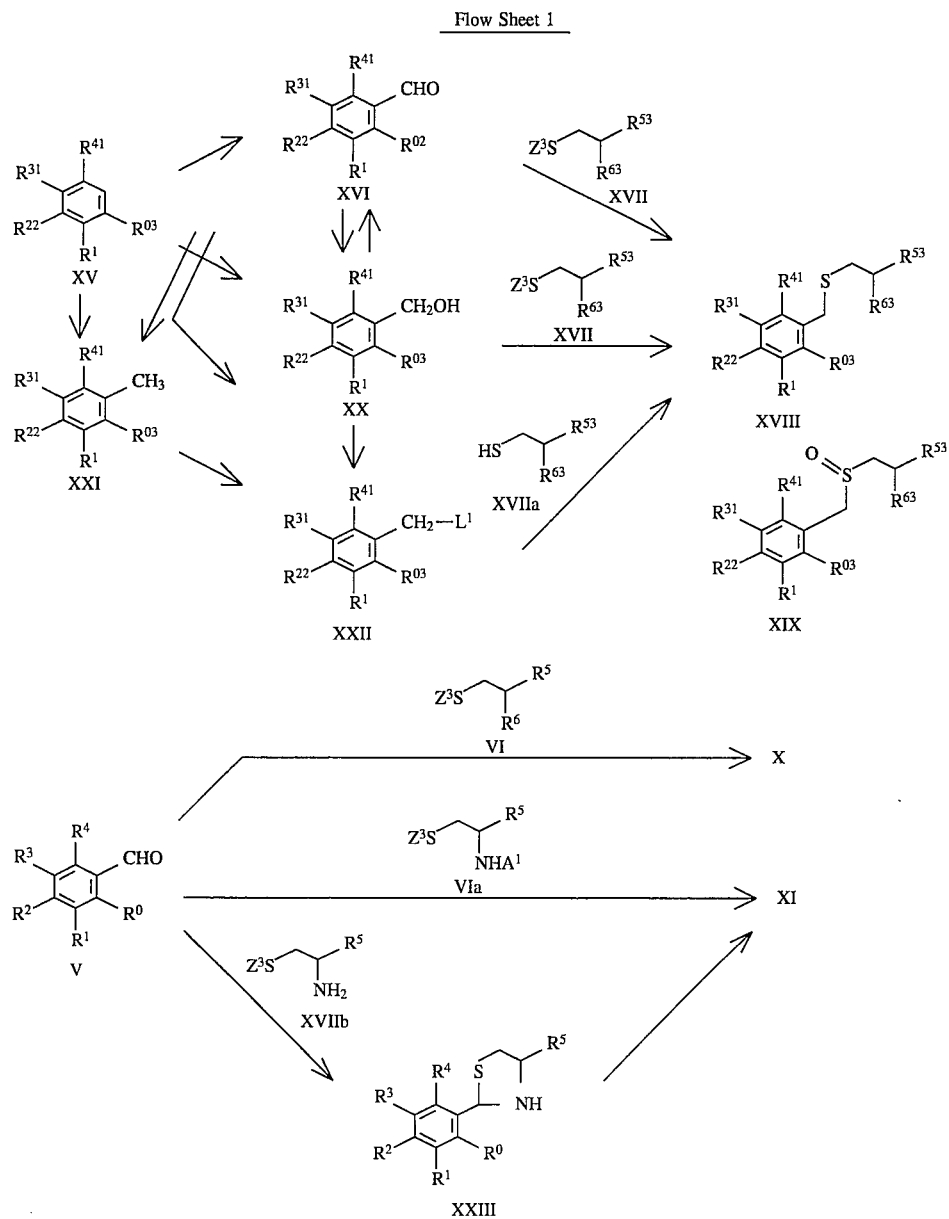
Compounds XII(a/b) and XIII(a/b) can be made according to Flow Sheet 2 as follows:

Flow Sheet 2
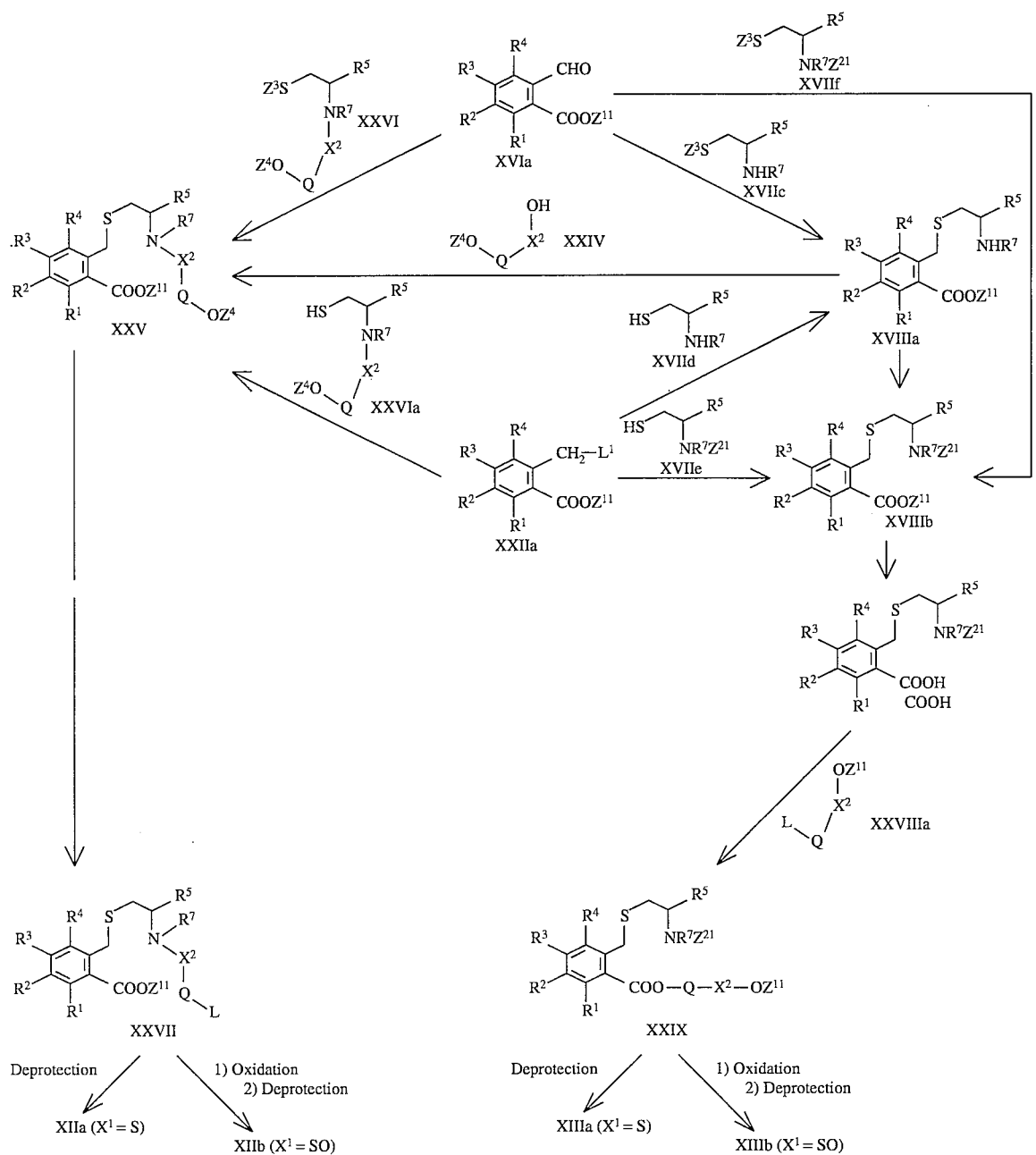
Compounds XIV can be made according to Flow Sheet 3 as follows:

Flow Sheet 3
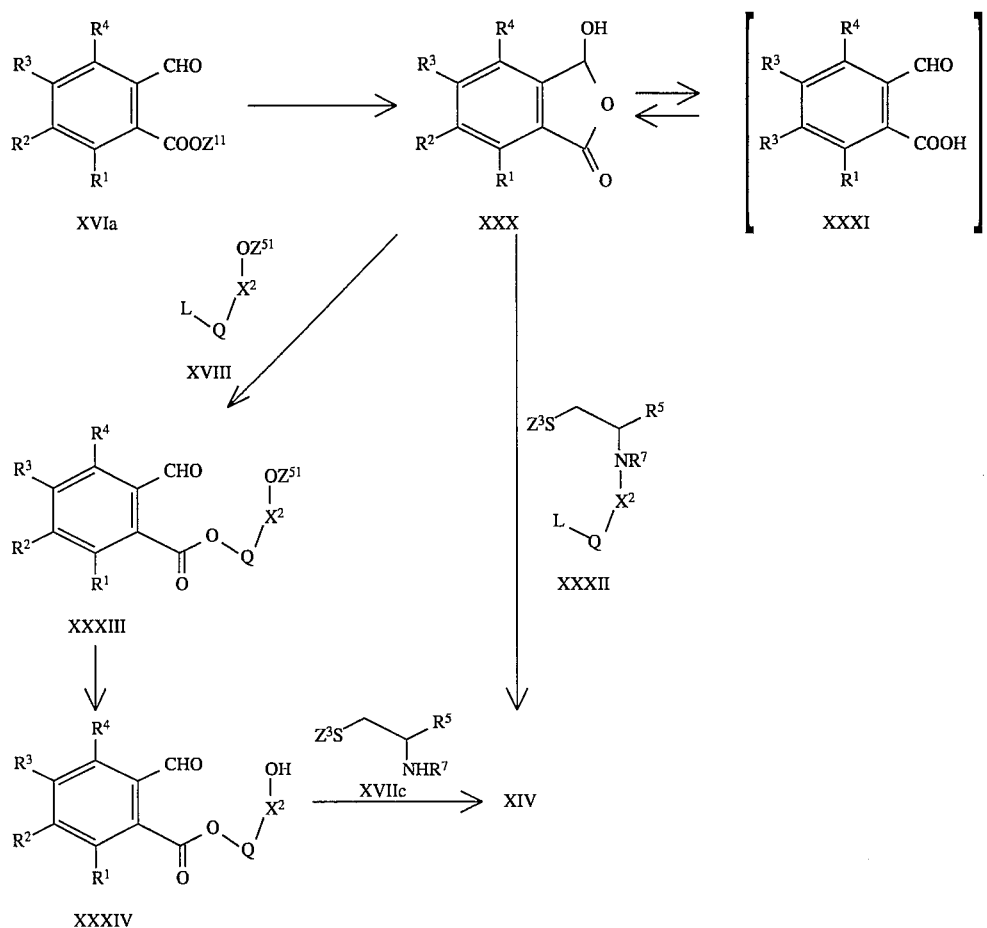
Starting compounds VI and the intermediates VIa and XVIIa–f can be made according to Flow Sheet 4 as follows (The formula XVII in Flow Sheet 4 comprises the starting compound VI):

Flow Sheet 4
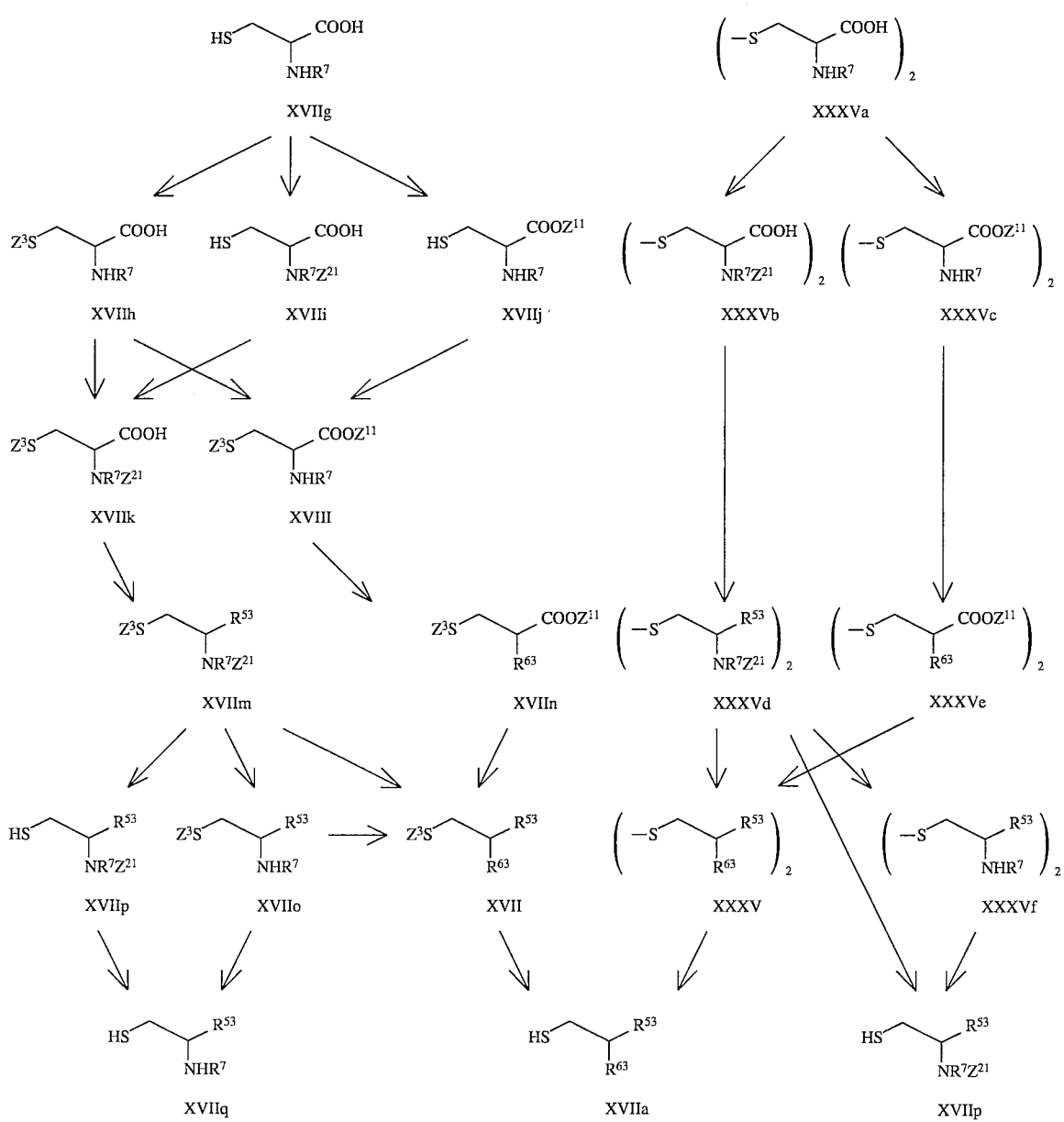
The making of intermediates XXIV, XXVI, XXVIa, XXVIII and XXXII can proceed according to Flow Sheet 5 as follows:

Flow Sheet 5

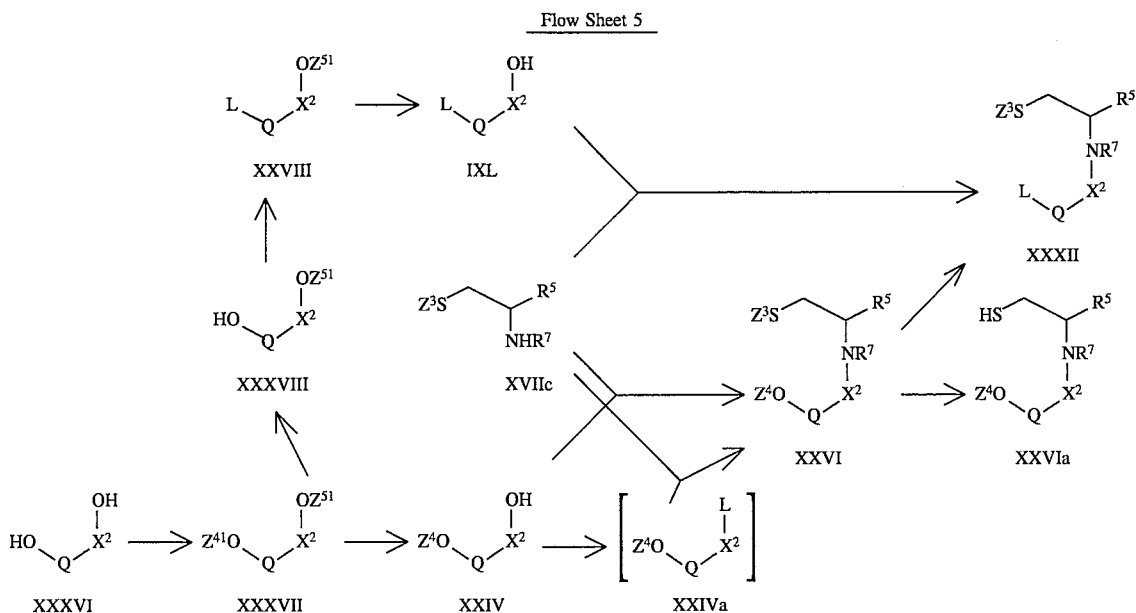

Reactions of Flow Sheet 1

Substituted benzene derivatives XV, e.g. derivatives of benzonitrile or benzoic acid, are formulated according to methods known per se, e.g. by the reaction with an agent formed between phosphoryl chloride and N-formyl-N-methyl-aniline or N,N-dimethylformamide (Vilsmeyer reagent) in an inert solvent such as dichloromethane or toluene at a reaction temperature between 0° C. and 150° C. to afford aldehydes of formula XVI.

In aldehydes of formula XVI substituents can be optionally converted into others, e.g. a group $R^{41}$=OMe can be cleaved as described above and the free phenol function can be reprotected with a suitable protecting group such as a tert-butyl-dimethylsilanyl group.

The making of starting compounds XVIII consists of reacting aldehydes XVI with optionally protected thiols XVII in the presence of a reducing agent in accordance with the reaction procedure described above (variant e)). $Z^3$ in its meaning as a protecting group comprises groups which will be cleaved under the acidic reaction conditions as outlined above.

By oxidizing thioethers of formula XVIII in the manner described above for process alternative c), e.g. by oxidizing with 3-chloroperbenzoic acid in dichloromethane, the corresponding sulfoxides XIX are obtained.

An alternative route for the preparation of XVIII, wherein $R^{o3}$ is not esterified carboxy, uses compounds of formula XX. Benzyl alcohols XX can be obtained either by hydroxymethylation of a compound XV, e.g. with formaldehyde in the presence of a base such as sodium hydroxide, in a polar solvent such as water, methanol or N,N-dimethylformamide.

Compounds XX can also be obtained by reduction of an aldehyde XVI with a suitable reducing agent, preferably a metal hydride such as sodium borohydride in a solvent such as tetrahydrofuran or methanol.

On the other hand, aldehydes of formula XVI can also be obtained by oxidation of benzylic alcohols XX using procedures known per se and also mentioned above in process variant a).

The conversion of an alcohols XX to thioethers of formula XVIII can be accomplished by reaction with compounds XVII using acidic reaction conditions as described for process variant f), e.g. by reaction in trifluoroacetic acid at 0° C. to 20° C.

According to a third alternative a benzene derivatives XV is first methylated to a toluene derivative XXI by methylation procedures known per se, i.e. either directly, e.g. by methylation of XV or a metal derivative thereof such as a lithium derivative, with a methylating agent such as methyl iodide, or by a two step procedure, e.g. by reaction of XV with formaldehyde and a secondary amine such as piperidine in aqueous acetic acid/acetic acetate solution (Mannich reaction) and subsequently subjecting the resulting piperidinyl-methyl derivative to hydrogenolytic reduction, e.g. with hydrogen in the presence of a catalyst such as palladium on charcoal and optionally in the presence of a base such as pyperidine, and using an alcohol, e.g. methanol as solvent.

An alternative route to toluene derivatives XXI consists in reducing aldehydes of formula XVI. A preferred method for this conversion is the catalytic hydrogenation, e.g. using hydrogen and palladium on charcoal in a solvent such as methanol or ethyl acetate.

Toluene derivatives XXI can be converted to reactive benzyl derivatives XXII wherein $L^1$ is a leaving group such as bromine. For example, benzyl bromides XXII ($L^1$=Br) are obtained by bromination, e.g. by reaction with N-bromosuccinimide in refluxing carbon tetrachloride in the presence of a radical starter such as α, α'-azo-isobutyronitrile or under irradiation with light, or alternatively by treatment with bromine in an inert solvent such as carbon tetrachloride under irradiation with light.

An alternative route to reactive benzyl derivatives XXII consists in converting the benzylic alcohol group in a compound XX to a leaving group $L^1$ by methods known per se, e.g. by reaction with methanesulfonyl chloride/pyridine, to a methanesulfonate XXII ($L^1$=OSO$_2$Me) or by reaction with triphenylphosphine-HBr to a benzyl bromide XXII ($L^1$=Br).

An alternative route to reactive benzyl intermediates XXII wherein L is Cl, Br or preferably J consists in reacting an aldehyde XVI with a suitable inorganic halide, e.g. sodium iodide or lithium bromide in the presence of a trialkylsilyl halide such as trimethylsilyl chloride and a suitable reducing agent, e.g. a silicon hydride such as 1,1,3,3-tetramethyldisiloxane. Polymethylhydrosiloxane in the presence of a suitable trialkylsilyl halide, e.g. trimethylsilyl iodide is also suitable for the preparation of intermediates where in L is halogen, e.g. iodine. This reactions can be performed in a manner known per se (see e.g. Can. J. Chem. 64. 2342 (1986)).

Benzyl derivatives of formula XXII can be condensed with thiols of formula XVIIa to yield thioethers of formula XVIII. The reaction is preferably effected in an inert organic solvent such as dichloromethane, ethyl acetate, N,N-dimethylformamide, dimethylsulfoxide, acetonitrile or ethanol in the presence of a weak non-nucleophilic organic base such as triethylamine, or in the presence of an inorganic base such as sodium or potassium carbonate. The reaction temperature preferably lies between −60° C. and +60° C., preferably between 0° C. and +30° C.

A starting compound X can be obtained by reaction of an aldehyde V with 2 or more equivalents of a thiol VI using standard reaction procedures for the formation of thioacetals from aldehydes, i.e. an acidic catalyst such as trifluoroacetic acid, boron trifluoride or zinc chloride in a solvent like dichloromethane or trifluoroacetic acid.

For the formation of starting compounds XI, an aldehyde V is reacted with a thiol VIa using similar reaction conditions as used for the formation of X, but using only 1 equivalent of VIa. When using an amine XVIIb instead of a compound VIa, a cyclic thio-aminal XXIII is formed which can subsequently be converted to a compound XI by acylation with a compound $A^1$-OH using procedures known per se for the acylation of amines, as described e.g. in process variant a).

Reactions of Flow Sheet 2

The making of the starting compounds XII(a and b) and XIII(a and b) can proceed according to Flow Sheet 2 as follows:

For the making of the starting compounds XIIa, an aldehyde of formula XVIa is reacted with an optionally protected thiol XVIIc in the presence of a reducing agent in an analogous manner as described for the conversion XVI to XVIII in accordance with the reaction procedure described above (variant e)), to yield an amine of formula XVIIIa.

An alternative route to prepare an amine XVIIIa consists in alkylating a thiol of formula XVIId with a compound of formula XXIIa, e.g. a benzyl bromide XXIIa ($L^1$=Br) using reaction conditions as described above for the conversion XXII to XXVIII.

Thioethers of formula XXV, wherein $X^2$ is (thio)carbonyl can be prepared by amidating an amine of formula XVIIIa with an optionally O-protected carboxylic (thio)acid XXIV, wherein $X^2$ is (thio)carbonyl in a manner commonly known and also described above in variant a). According to a particularly preferred method, compounds XVIIIa and XXIV, wherein $X^2$ is (thio)carbonyl are reacted with each other in the presence of a condensation agent such as N-(dimethylaminopropyl)-N'-ethyl-carbodiimide hydrochloride, preferably in an aprotic organic solvent, such as acetonitrile, dioxane or dichlormethane, and at a temperature between −20° C. and +20° C., preferably at −10° C. to +10° C. The amine of formula XVIIIa can be utilized as base or as salt with an inorganic or organic acid, e.g. as hydrochloride or trifluoroacetate; in the latter case an organic base such as N-methyl-morpholine needs to be added in the reaction, preferably in equimolar amount.

For the preparation of a thioether XXV wherein $X^2$ is heterocycle, a hydroxy derivative XXIV wherein $X^2$ is heterocycle, is first converted to a reactive intermediate $Z^4$O-Q-$X^2$-L (XXIVa) in which $X^2$ is heterocycle, L is a leaving group as defined above or in particular F and $Z^4$ and Q are as above, which is then reacted with an amine XVIIIa. Preferred groups L for heterocyclic intermediates XXIVa are F or $SO_3H$.

Two alternative routes to prepare thioethers of formula XXV consist in reacting (i) an aldehyde XVIa with an optionally protected thiol XXVI using the aforementioned procedure for the conversion of XVIa to XVIIIa, or (ii) a compound of formula XXIIa, e.g. a benzyl bromide XXIIa ($L^1$=Br), with a thiol of formula XXVIa using reaction conditions as described above for the conversion XXII to XVIII.

For the conversion of compounds of formula XXV to compounds XXVII, the group $OZ^4$ in its meaning as OH can optionally be converted to a leaving group, whereas $OZ^4$ in its meaning as a protected hydroxy group is cleaved off and the unmasked hydroxy group can optionally be converted to a leaving group. The cleavage of a group $OZ^4$, and the conversion of a hydroxy group to a leaving group can be accomplished as described above.

A starting compound of formula XIIa, where $X^1$ is —S—, is obtained by cleavage of the protecting group $Z^{11}$ in a thioether of formula XVII. This is carried out by methods described above.

By oxidizing a thioether of formula XXVII, wherein $X^2$ preferably is not (thio)carbonyl in the manner described above for process alternative c), e.g. by oxidizing with 3-chloroperbenzoic acid in dichlormethane and subsequently splitting off the protecting group $Z^{11}$ of the corresponding sulfoxide, starting compounds of formula XIIb, wherein $X^1$ is —SO—, are obtained.

For the making of the starting compounds XIIIa, wherein $X^2$ is (thio)carbonyl, an aldehyde of formula XVIa is reacted with an optionally S-protected thiol XVIIf in the presence of a reducing agent. This reaction proceeds in an analogous manner as described for the conversion XVI to XVIII in accordance with the reaction procedure described above (variant e)), to yield a compound of formula XVIIIb. Compounds XVIIIb can also be prepared by protecting the amino function of amines XVIIIa with a suitable amino-protecting group $Z^{21}$ using procedures described above. A further alternative to prepare amines XVIIIb consists of alkylating thiols of formula XVIIe with a compound of formula XXIIa, e.g. with a benzyl bromide XXIIa ($L^1$=Br) using reaction conditions as described above for the conversion XXII to XVIII.

Carboxylic acids XVIIIc can be obtained from intermediates XVIIIb by cleavage of the carboxy-protecting group with the appropriate procedure described above.

Esters of formula XXIX, wherein $X^2$ is (thio)carbonyl can be prepared by esterifying carboxylic acids XVIIIc with a compound of formula XXVIII, wherein $X^2$ is (thio)carbonyl in analogy to the methods described above for the intramolecular esterification reaction of process variant k). Exemplary for preferred methods are the reaction of a carboxylic acid XVIIIc (i) with an alcohol XXVIIIa (L=OH, $X^2$=(thio)carbonyl) in the presence of diethyl azodicarboxylate and triphenylphosphine in a solvent such as toluene or dichlormethane, or (ii) with an alkylating agent XXVIII (L=leaving group, $X^2$=(thio)carbonyl), e.g. a bromide XXVIIIa (L=Br) in the presence of a base such as 1,1,3,3-tetramethylguanidine in an inert solvent such as dimethyl sulfoxide.

A starting compounds of formula XIIIa where $X^1$ is —S— and $X^2$ is (thio)carbonyl, is obtained by cleavage off the protecting groups $Z^{11}$ and $Z^{21}$ in an ester of formula XXIX using methods described above.

By oxidizing a thioether of formula XXIX, wherein $X^2$ preferably is not (thio)carbonyl in the manner described above for process alternative c) and subsequently splitting off the protecting groups $Z^{11}$ and $Z^{21}$ of the corresponding sulfoxide, starting compounds of formula XIIIb, wherein $X^1$ is —SO—, are obtained.

Reactions of Flow Sheet 3

For the making of the starting compounds XIV, the carboxy-protection group of an aldehyde XVIa can be cleaved to afford a hydroxy-phtalide XXX which is the cyclic tautomer (pseudo acid) of a carboxylic acid XXXI. The pseudo acid XXX can be converted to the starting compound XIV by reaction with a compound XXXII according to the esterification methods mentioned above for the conversion XVIIIc to XXIX.

An alternative route for the making of a starting compound XIV consists in esterifying a pseudo acid XXX with a compound XXVIII using analogous procedures as cited above for the conversion of XVIIIc to XXIX, to afford XXXIII. The carboxy/hydroxy-protection group in a compound of formula XXXIII can be cleaved off as described above to afford an intermediate XXXIV which in case that $X^2$ is (thio)carbonyl, can then be amidated with an amine XVIIc according to methods commonly known and also described in process variant a), to afford XIV, wherein $X^2$ is (thio)carbonyl.

For the preparation of a starting compound XIV wherein $X^2$ is heterocycle, the group —$X^2$—OH in a compound XXXIV is first converted into a reactive group —$X^2$—L in analogy to the procedure described above for the reaction of XVIIIa with XXIV for the case that $X^2$ is heterocycle.

Reactions of Flow Sheet 4

The making of the starting compounds VI and of intermediates VIa and VIb is comprised in the making of compounds of formula XVII. The preparation of compounds XVII and of compounds of formula XVIIa-f which are used as intermediates (Flow Sheets 1 and 2), can proceed according to Flow Sheet 4 as follows:

Compounds of formula XVIIg can be protected at either of their free thiol, amino, or carboxy function, according to generally known protection techniques described above, to afford the intermediates XVIIh-j, respectively. Either the free carboxy or the free amino function in compounds XVIIh-j can further optionally be protected by a suitable protecting group to afford intermediates represented by the formulas XVIIk and XVIIl, respectively.

The conversion of intermediates XVIIk to intermediates of formula XVIIm (which comprises XVIIf) and of intermediates XVIII to intermediates of formula XVIIn consists of procedures described above in variant a) for the conversion of a group $COOZ^1$ to a group $R^5$, and for the conversion of a group $NR^7Z^2$ to a group $R^6$, respectively.

The preparation of intermediates of formula XVIIo (which comprises XVIIb) consists of cleavage off an amino-protecting group $Z^{21}$ in compounds of formula XVIIm by a suitable procedure as described above.

The preparation of intermediates XVII can be obtained by various routes, viz. by (i) converting in compounds XVIIn a group $COOZ^{11}$ to a group $R^{53}$ according to procedures described in process variant a) for the conversion of a group $COOZ^1$ to $R^5$, or (ii) converting in compounds XVIIm a group $NR^7Z^{21}$ to a group $R^{63}$ according to procedures described in process variant h) for the conversion of a group $NR^7Z^2$ to $R^6$, respectively.

The preparation of intermediates of formula XVIIa, XVIIq (which comprises XVIId) and XVIIp (which comprises XVIIe) consists in cleaving off a thiol-protecting- group ($Z^3$=protecting group) in compounds XVII, XVIIo and XVIIm by a suitable procedure as described above.

An alternative route to prepare thiol intermediates XVIIa and XVIIp starts from disulfides of formula XXXVa. Disulfides XXXVa can be protected in a first step at either their amino or their carboxy functions according to the protecting procedures described above to afford intermediates XXXVb and XXXVc.

The conversion of intermediates XXXVb to compounds of formula XXXVd, and of intermediates XXXVc to compounds of formula XXXVe involves procedures described above in process variant a) and h) for the conversion of a group $COOZ^1$ to $R^5$, and for the conversion of a group $NR^7Z^2$ to $R^6$, respectively.

The preparation of intermediates XXXV can proceed by two alternative routes, viz. by (i) converting in compounds XXXVe the groups $COOZ^{11}$ to the groups $R^{53}$, or (ii) converting in compounds XXXVd the groups $NR^7Z^{21}$ to the groups $R^{63}$, according to procedures described above.

The preparation of intermediates XXXVf consists in cleaving off amino- protecting groups $Z^{21}$ in compounds of formula XXXVd by a suitable procedure as described above.

The reductive cleavage of disulfides XXXV and XXXVd/f affords thiols of formula XVIIa and XVIIp, respectively. Procedures for this reaction are known per se. A preferred method consists in treating a disulfide with a reducing agent such as a trialkylphosphine, e.g. tributylphosphine, in a solvent like trifluoroethanol as neutral or slightly basic pH as outlined above.

Reactions of Flow Sheet 5

The preparation of intermediates of formula XXIV, XXVI, XXVIa, XXVIII (which comprises XXVIIIa) and XXXII (Flow Sheet 2, 3) can proceed according to Flow Sheet 5 as follows:

Fully protected compound XXXVII, which can be prepared by methods known per se, e.g. by stepwise protecting the hydroxy and in case that $X^2$ is (thio)carbonyl, the (thio)carboxy function(s) in compounds of formula XXXVI, wherein $X^2$ is (thio)carbonyl, can be selectively deprotected to afford either compounds of formula XXIV ($Z^4$=protecting group) or compounds of formula XXXVIII.

Compounds of formula XXIV, wherein $X^2$ is (thio)carbonyl can be amidated with an amines of formula XVIIc according to methods commonly known and also described above in process variants a) to afford compounds XXVI, wherein $X^2$ is (thio)carbonyl. For the preparation of a compound XXVI wherein $X^2$ is heterocycle, the group —$X^2$—OH in a compound XXIV is first converted into a leaving group XXIVa as described above for heterocyclic intermediates XXIV, and compound XXIVa is then reacted with an amine XVIIc as described above for the reaction of XVIIIa with XXIV. The preparation of compounds XXVIa consists in optionally cleaving off the thiol-protecting group $Z^3$ (if $Z^3$=protecting group) and optionally cleaving off a hydroxy-protecting group $Z^4$ (if $Z^4$=protecting group) using methods described above.

The conversion of intermediates XXVI to compounds of formula XXXII comprises optionally cleaving of the hydroxy-protecting group (if $Z^4$=protecting group) and transforming the unmasked hydroxy function into a leaving group L using procedures described above.

Intermediates XXVIII can be obtained by the analogous transformation of the hydroxy function in compounds XXXVIII into a leaving group L.

An alternative route for the preparation of compounds XXXII, wherein $X^2$ is (thio)carbonyl consists in deprotecting the (thio)carboxy function in compounds XXVIII, followed by amidating the resulting (thio)carboxylic acid IXL with an amine XVIIc using procedures described above for corresponding conversions.

The compounds of formula I as well as their corresponding pharmaceutically acceptable salts inhibit the DNA gyrase activity in bacteria and possess antibiotic, especially antibacterial activity against microorganisms.

A. Inhibition of DNA Gyrase Activity

The inhibition of DNA gyrase activity was measured using a DNA gyrase supercoiling assay according to R. Otter & N. Cozzarelli: Methods in Enzymology, Vol. 100, pp 171–180 (1983). DNA gyrase was isolated from *E. coli* H560, and relaxed pUC18 plasmid was used as substrate. The activities as regards inhibition of DNA gyrase activity, expressed as maximum non-effective concentration of the test compound (MNC in µg/ml) are compiled in the following Table 1:

TABLE 1

| End product from Example No. | MNC (µg/ml) |
|---|---|
| 11 | 0.02 |
| 14 | 0.2 |
| 16 | 0.01 |
| 23 | 0.01 |
| 26 | 0.04 |
| 27 | 0.01 |
| 32 | 0.01 |
| 33 | 0.01 |
| 69 | 0.04 |
| 71 | 0.5 |
| 92 | 0.04 |
| 97 | 0.4 |
| 111 | 0.1 |

B. Antibacterial Activity in vitro

In the following Table 2 there are compiled the minimum inhibitory concentrations (MIC; µg/ml) of some representative compounds of formula I against a series of pathogenic microorganisms.

The products in accordance with the invention can be used as medicaments, e.g. in the form of pharmaceutical preparations or compositions for enteral or parenteral application in the form of unit dosage. The unit dosage form can be administered, for example, perorally, e.g. in the form of tablets, coated tablets, dragees, hard and soft gelatin capsules, syrups, solutions, emulsions or suspensions, rectally, e.g. in the form of suppositories, or parenterally e.g. in the form of injection solutions.

The preparation of the pharmaceutical preparations or compositions can be effected in a manner which is familiar to any person skilled in the art by bringing the substances in accordance with the invention, optionally in combination with other therapeutically valuable substances, into a galenical administration form together with suitable, non-toxic, inert, therapeutically compatible solid or liquid carrier materials and, if desired, the usual pharmaceutical adjuvants.

As such carrier materials not only inorganic carrier materials are suitable, but also organic carrier materials. Thus, there can be used as carrier materials for tablets, coated tablets, dragees and hard gelatin capsules, for example, lactose, maize starch or derivatives thereof, talc, stearic acid or its salts. Suitable carriers for soft gelatin capsules are, for example, vegetable oils, waxes, fats and semi-solid and liquid polyols (depending on the nature of the active substance no carriers are, however, required in the case of soft gelatin capsules). Suitable carrier materials for the making of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example, natural or hardened oils, waxes, fats and semi-liquid or liquid polyols. The pharmaceutical preparations can also contain other therapeutically valuable substances.

As pharmaceutical adjuvants there come into consideration the usual preservatives, solubilizers, stabilizers, wetting agents, emulsifiers, sweeteners, colorants, flavorants, salts for varying the osmotic pressure, buffers, coating agents and antioxidants.

The pharmaceutical preparations or compositions can contain the substances in accordance with the invention in

TABLE 2

| | MIC (µg/ml) Compound of Example No. | | | | | | | | |
|---|---|---|---|---|---|---|---|---|---|
| Organism | 11 | 14 | 16 | 23 | 26 | 27 | 32 | 33 | 69 |
| *E. coli* B | >64 | 64 | >64 | 16 | >64 | 64 | >64 | 32 | >64 |
| *P. aeruginosa* 799/61 | 8 | 8 | 1 | 8 | 32 | 2 | 4 | 4 | >64 |
| *S. aureus* 25923 | 0.5 | 16 | 2 | 0.5 | 2 | 1 | 1 | 0.5 | 4 |
| *S. aureus* Smith | 0.5 | 8 | 0.5 | 0.25 | 0.5 | 0.5 | 0.5 | 0.25 | 2 |
| *S. epidermidis* 16-2 | 0.12 | 1 | 0.12 | 0.12 | 0.12 | 0.12 | 0.25 | 0.25 | 0.25 |
| *S. pyogenes* 15 | 2 | 4 | 2 | 2 | 4 | 4 | 2 | 1 | 2 |
| *S. faecalis* 6 | 2 | 4 | 1 | 1 | 2 | 0.5 | 2 | 0.5 | 2 |
| Organism | 71 | 92 | 97 | 130 | 132 | 142 | 171 | 175 | 180 |
| *E. coli* B | >64 | >64 | 64 | 32 | 64 | 64 | >64 | >64 | >64 |
| *P. aeruginosa* 799/61 | 64 | 64 | 64 | 64 | >64 | >64 | >64 | >64 | >64 |
| *S. aureus* 25923 | 2 | 4 | 16 | 0.5 | 4 | 2 | 8 | 4 | 2 |
| *S. aureus* Smith | 1 | 2 | 8 | 0.25 | 2 | 1 | 4 | 1 | 2 |
| *S. epidermidis* 16-2 | 0.5 | 1 | 1 | 0.12 | 0.5 | 0.12 | 1 | 1 | 1 |
| *S. pyogenes* 15 | 4 | 8 | 16 | 0.5 | 4 | 1 | 2 | 4 | 2 |
| *S. faecalis* 6 | 4 | 8 | 16 | 0.5 | 4 | 1 | 4 | 4 | 4 |

Agar dilution (Mueller-Hinton agar), Inoculum: $10^4$ CFU/spot amounts of about 25 mg to about 2000 mg, preferably from about 100 mg to about 1000 mg, per unit dosage form. For the prophylaxis and therapy of infectious diseases there comes into consideration for adults a daily dosage of about 0.05 g to about 4 g, especially about 0.1 g to about 2 g.

The following Examples are intended to illustrate the present invention in more detail, but are not intended to limit its scope in any manner.

EXAMPLE 1

To a solution of 268 mg of (4R)-13-[dimethyl-(1,1,2-trimethyl-propyl)-silanyloxy]-11-methoxy-10-methyl-4-(3-methyl-1,2,4-oxadiazol-5-yl)-3,4,5,6,7,9-hexahydro-1H-8,2,5-benzoxathiaazacycloundecine-6,9-dione in 10 ml of methanol were added 100 mg of ammonium fluoride, and the mixture was stirred for 30 min at room temperature. The mixture was diluted with 50 ml of ethyl acetate and washed with 30 ml of water and with 30 ml of brine. The organic layer was dried over sodium sulfate and the solvent was evaporated in vacuo. The residue was dissolved in ethyl acetate, then hexane was added, and the white solid was isolated by filtration to give 178 mg of (4R)-13-hydroxy-11-methoxy-10-methyl-4-(3-methyl-1,2,4-oxadiazol-5-yl)-3,4,5,6,7,9-hexahydro-1H-8,2,5-benzoxathiaazacycloundecine-6,9-dione as a white powder, m.p. 194°–196° C.

The starting material used above was prepared as follows:

(a) To a stirred solution of 504.4 g of 3,5-dihydroxy-2-methylbenzoic acid in 2 l of acetonitrile were added 0.5 l of dimethyl sulfate and 828 g of potassium carbonate. The mixture was heated to 54° C. when vigorous evolution of gas started. The mixture was cooled in an ice bath to keep the temperature below 70° C. Stirring was continued for 30 min at 70° C. and finally the mixture was heated at reflux for another 30 min. To the cooled mixture were added once more 0.5 l of dimethyl sulfate and 787 g of potassium carbonate and stirring was continued at reflux temperature for 1 h. After cooling to room temperature, the mixture was filtered and the unsoluble material was washed with 1.5 l of acetonitrile. The flitrate was concentrated in vacuo and the residual oil was distilled in vacuo to yield 601 g of 3,5-dimethoxy-2-methyl-benzoic acid methyl ester as a colorless oil, b.p. 102°–105° C. (0.06 mbar).

(b) To a solution of 340 ml of N,N-dimethylformamide in 1 l of dichloromethane were added slowly 404 ml of phosphoryl chloride. The solution was stirred for 1.5 h at room temperature, and then, a solution of 618 g of 3,5-dimethoxy-2-methylbenzoic acid methyl ester in 200 ml of dichloromethane was added within 10 min. The mixture was heated for 72 h at reflux temperature. After cooling, the mixture was slowly poured into 3 l of ice-water and subsequently extracted with 3.6 l of dichloromethane. The organic layer was washed with 2 l of saturated sodium carbonate solution and twice with 2 l of water. The organic layer was dried over sodium sulfate and the solvent was evaporated in vacuo. The solid residue was triturated in 3 l of ethyl acetate at 60° C., and after cooling, 1.5 l of hexane were added. The solid was isolated by filtration to yield 646 g of 2-formyl-3,5-dimethoxy-6-methylbenzoic acid methyl ester, m.p. 164°–165° C.

(c) To a suspension of 95.3 g of 2-formyl-3,5-dimethoxy-6-methylbenzoic acid methyl ester in 250 ml of dichloromethane were added 800 ml of a 1M solution of boron trichloride in dichloromethane over 40 min at a temperature of 5°–10° C. The mixture was allowed to warm to 20° C. within 30 min and stirring was continued at room temperature for 4 h. The clear solution was cooled to 5° C. and then poured into a mixture of 1.5 l of ice-water and 0.5 l of dichloromethane. The layers were separated and the aqueous phase was back-extracted with 0.4 l of dichloromethane. The organic layers were washed with water, dried over sodium sulfate and evaporated in vacuo. Crystallization of the residual material from ethyl acetate/hexane provided 77.3 g of 2-formyl-3-hydroxy-5-methoxy-6-methylbenzoic acid methyl ester as colorless crystals of m.p. 118°–119° C.

(d) A solution of 28 g of potassium hydroxide in 0.2 l of water was added to 44.8 g of 2-formyl-3-hydroxy-5-methoxy-6-methylbenzoic acid methyl ester. The mixture was warmed to 75° C. within 30 min and subsequently cooled to 5° C. Upon addition of 50 ml of 10N hydrochloric acid, a precipitate was formed immediately. The mixture was stirred at 0° C. for 30 min and then filtered. The solid material was washed with water and dried in vacuo. The crude product was triturated with 160 ml of hot ethyl acetate. The mixture was cooled and 0.9 l of hexane were added. The solid was isolated by filtration to yield 41.2 g of (RS)-3,4-dihydroxy-6-methoxy-7-methyl-1,3-dihydro-iso-benzofuran-1-one, m.p. >255° C. (dec.).

(e) To a solution of 42.0 g of (RS)-3,4-dihydroxy-6-methoxy-7-methyl-1,3-dihydro-isobenzofuran-1-one in 1 l of N,N-dimethylformamide were added 23.0 g of 1,1,3,3-tetramethylguanidine. The solution was stirred for 30 min and then, 48.4 g of allyl bromide were added and stirring was continued for 3 h. The mixture was evaporated in vacuo and the residue was dissolved in 0.7 l of ethyl acetate. The solution was washed with brine, dried over sodium sulfate, and the solvent was evaporated in vacuo. The solid residue was crystallized from tert-butyl methyl ether to give 37.3 g of 2-formyl-3-hydroxy-5-methoxy-6-methylbenzoic acid allyl ester as white crystals of m.p. 73°–74° C.

(f) To a solution of 75.1 g of 2-formyl-3-hydroxy-5-methoxy-6-methylbenzoic acid allyl ester in 0.6 l of N,N-dimethylformamide were added 81.0 g of dimethyl-(1,1,2-trimethyl-propyl)-chlorosilane and 45.5 g of triethylamine. The mixture was stirred for 4 h at rootn temperature and then evaporated in vacuo. The residue was taken up in 2 l of ethyl acetate, and the mixture was successively washed with 1N hydrochloric acid and with brine, and dried over sodium sulfate. The solvent was evaporated in vacuo and the residue was crystallized from hexane to give 108.8 g of 2-formyl-5-methoxy-6-methyl-3-[dimethyl-(1,1,2-trimethyl-propyl)silanyloxy]-benzoic acid allyl ester as white crystals of m.p. 81°–82° C.

(g) To a solution of 13.8 g of 2-formyl-5-methoxy-6-methyl-3-[dimethyl-(1,1,2-trimethyl-propyl)-silanyloxy]-benzoic acid allyl ester in 38 ml of trifiuoroacetic acid, cooled to 0° C., were added within 15 min a solution of 13.7 g of (R)-2-mercapto-1-(3-methyl-1,2,4-oxadiazol-5-yl)-ethylcarbamic acid tert-butyl ester and 6.2 g of triethylsilane in 38 ml of dichloromethane. The solution was kept at 0° C. for 18 h and then evaporated in vacuo. The residue was taken up in ethyl acetate and the solution was successively washed with water, saturated sodium carbonate solution and brine, and dried over sodium sulfate. The solvent was evaporated in vacuo and the residue was chromatographed on silica gel using ethyl acetate/hexane (1:3, v/v) as eluent to yield 14.1 g of (R)-2-[2-amino-2-(3-methyl-1,2,4-oxadiazol-5-yl)-ethylsulfanyl-methyl]-3-[dimethyl-(1,1,2-trimethyl-propyl)-silanyloxy]-5-methoxy-6-methylbenzoic acid allyl ester as a pale yellow oil.

$^1$H-NMR (250 MHz, CDCl$_3$): δ0.29(s,6H); 0.93(d,J=7 Hz,6H); 0.99(s,6H); 1.76 (m,1H); 1.80(broad s,2H); 2.09(s,3H); 2.38(s,3H); 2.80(dd,J=14 Hz and 8 Hz,1H); 2.96(dd, J=14 Hz and 5 Hz, 1H); 3.77(s,3H); 3.79(m,2H); 4.14(dd, J=8 Hz and 5 Hz,1H); 4.82(m,2H); 5.32(m,1H); 5.44(m, 1H); 6.06(m,1H); 6.39(s,1H) ppm.

(h) To a suspension of 1.07 g of (R)-2-[2-amino-2-(3-methyl-1,2,4-oxadiazol-5-yl)-ethylsulfanylmethyl]-3-[dimethyl-(1,1,2-trimethylpropyl)-silanyloxy]-5-methoxy-6-methylbenzoic acid allyl ester and 0.96 g of trityloxy-acetic acid in 15 ml of acetonitrile, cooled to 0° C., were added 0.58 g of N-(dimethylamino-propyl)-N'-ethyl-carbodiimide hydrochloride. The mixture was stirred at 0° C. for 4 h, then diluted with 30 ml of ethyl acetate, and washed successively with 0.5N hydrochloric acid, water, 5% sodium bicarbonate solution, and brine. The organic layer was dried over sodium sulfate and evaporated in vacuo. The residue was chromatographed on silica gel using ethyl acetate/hexane (1:1, v/v) as eluent to yield 1.42 g of (R)-3-[dimethyl-(1,1,2-trimethyl-propyl)silanyloxy]-5-methoxy-6-methyl-2-[2-(3-methyl-1,2,4-oxadiazol-5-yl)-2-(2-trityloxy-acetylamino]-ethylsulfanylmethyl]-benzoic acid allyl ester as a foam.

$^1$H-NMR (250 MHz,CDCl$_3$): δ0.26(s,3H); 0.27(s,3H); 0.90(d,J=7 Hz,6H); 0.95 (s,6H); 1.74 (m, 1H); 2.06(s,3H); 2,41(s,3H); 3.11(m,2H); 3.70(d,J=11 Hz,1H);3.75(d,J=11 Hz,1H); 3.77(s,3H); 3.79(s,2H); 4.77(m,2H); 5.23(5.35 (m,1H); 5.40(m,1H); 5.89–6.06(m,1H); 6.39(s,1H) 7.20–7.33(m,9H); 7.38–7.46 (m,6H); 7.64(d,J=7 Hz,1H) ppm.

(i) A solution of 1.26 g of the product of Example 1(h) in 15 ml of 80% aqueous acetic acid was heated to 60° C. for 40 min. The mixture was cooled and evaporated in vacuo, and the residue was chromatographed on silica gel using ethyl acetate/hexane (1:1, v/v) as eluent to yield 0.72 g of (R)-3-[dimethyl-(1,1,2-trimethyl-propyl)-silanyloxyl]-2-[(2-hydroxy-acetylamino)-2-(3-methyl-1,2,4-oxadiazol-5-yl)-ethylsulfanylmethyl]-5-methoxy-6-methyl-benzoic acid allyl ester as a colorless oil.

$^1$H-NMR (250 MHz,CDCl$_3$): δ0.27(s,3H); 0.30(s,3H); 0.94(d,J=7 Hz,6H); 0.98 (s,6H); 1.75 (m, 1H); 2.09(s,3H); 2,37(s,3H); 3.03(dd,J=14 Hz and 5 Hz,1H); 3.15(dd,J=14 Hz and 7 Hz,1H); 3.71(d,J=12 Hz,1H); 3.78(s,3H); 3.86(d, J=12 Hz,1H); 4.05(m,2H); 4.83(m,2H); 5.32(m,1H); 5.36(m,1H); 5.47(m,1 H); 6.03 (m,1 Hz); 6.39(s,1H) 7.25(d, J=3 Hz,1H) ppm.

(j) To a solution of 0.72 g of the product of Example 1(i) in 5 ml of ethyl acetate were added at 0° C. 10 mg of palladium(II)acetate and 0.037 ml of triethyl phosphite. The mixture was stirred for 5 min, then, 0.22 ml of morpholine were added and stirring was continued at 0° C. for 6 h. The mixture was diluted with 50 ml of ethyl acetate and washed with 1N hydrochloric acid and with brine. The organic layer was dried over sodium sulfate and evaporated in vacuo to yield 0.70 g of crude (R)-3[dimethyl-(1,1,2-tri-methyl-propyl)-silanyloxy]-2-[(2-hydroxyacetylamino)-2-(3-methyl-1,2,4-oxa-diazol-5-yl)-ethylsulfanylmethyl]-5-methoxy-6-methylbenzoic acid as an oil.

$^1$H-NMR (250 MHz,CDCl$_3$): δ0.27(s,3H); 0.29(s,3H); 0.93(d,J=7 Hz,6H); 0.98 (s,6H); 1.75 (m,1H); 2.14(s,3H); 2,37(s,3H); 3.05–3.24(m,2H); 3.77(s,3H); 3.83 (d,J=12 Hz,1H); 3.93(d,J=12 Hz,1H); 4.09(d,J=14 Hz, 1H); 4.29(d, J=14 Hz,1H); 5.35(m,1H); 6.39(s,1H); 7.79(d,J=8 Hz, 1H) ppm.

(k) To a solution of 0.70 g of the product of Example 1(j) and 0.63 g of tri-phenylphosphine in 30 ml of toluene, cooled to 0° C., were added 0.42 g of diethyl azodicarboxylate. The mixture was stirred for 15 min at 0° C. and for 6 h at room temperature, and then, the solvent was evaporated in vacuo. The residue was stirred with dichloromethane/hexane at 0° C. and the crystals formed were removed by filtration. The flitrate was evaporated in vacuo and the residue was chromatographed on silica gel using ethyl acetate/hexane (1:2, v/v) as ehent to yield 0.47 g (4R)-13-[dimethyl-(1,1,2-trimethyl-propyl)-silanyloxy]-11-methoxy-10-methyl-4-(3-methyl-1,2,4-oxadiazol-5-yl)-3,4,5,6,7,9-hexahydro-1H-8,2,5-benzoxathiaazacycloundecine-6,9-dione as an amorphous solid.

$^1$H-NMR (250 MHz,CDCl$_3$): δ0.28(s,3H); 0.32(s,3H); 0.94(d,J=7 Hz,6H); 1.00 (s,6H); 1.77 (m,1H); 2.13(s,3H); 2,35(s,3H); 2.94(dd,J=15 Hz and 6 Hz,1H); 3.26(d,J=12 Hz,1H) 3.55(dd,J=15 Hz and 2 Hz,1H); 3.78(s,3H); 4.47 (d,J=12 Hz,1H); 4.58(d,J=14 Hz,1H); 5.31(d,J=14 Hz,1H); 5.73(m,1H); 6.41(s,1H); 7.68 (d,J=9 Hz,1H) ppm.

(l) To a solution of 248 g Boc-L-cystine, 89 g of acetamidoxime and 2.9 g of 1-hydroxy-pyridin-2(1H)-one in 1 l of tetrahydrofuran was added at 0° C. over 30 min a solution of 250 g of dicyclohexylcarbodiimide in 0.8 l of tetrahydrofuran. The mixture was stirred for 16 h while the temperature was allowed to warm to 20° C. The mixture was cooled to 0° C. and the precipitate was removed by filtration. The filtrate was concentrated in vacuo to a volume of about 0.5, and then diluted again with 0.8 l of ethyl acetate. Upon addition of 1 l of water, a precipitate formed which was isolated by filtration, washed with 0.15 l of ethyl acetate and dried to afford 246.6 g of white crystals of m.p. 134°–136° C. This material was taken up in 0.8 l of toluene and the mixture was heated at reflux for 3 h, the water formed being removed continuously in a Dean-Stark trap. The mixture was cooled and 3 l of hexane were added. The precipitate formed was isolated to give 215.0 g of bis-[(R)-2-tert-butoxy-carbonylamino-2-(3-methyl-1,2,4-oxadiazol-5-yl)-ethyl] disulfide as white crystals, m.p. 130°–131° C.

(m) To a stirred solution of 30 g of the product of Example 1(l) in 50 ml of trifluoroethanol and 6 ml of water were added over 30 min 18.1 g of tributyl-phosphine, the temperature rising to 36° C. The pH of the solution was set to 8.0 by the addition of 0.36 g of triethylamine and stirring was continued for 2 h at room temperature. The solvent was evaporated in vacuo and the residue was chromatographed on silica gel using ethyl acetate/ hexane (1:3, v/v) as eluent to yield 24.1 g of (R)-2-mercapto-1-(3-methyl-1,2,4-oxadiazol-5-yl)-ethylcarbamic acid tertbutyl ester as a colorless oil.

$^1$H-NMR (250 MHz,CDCl$_3$): δ1.47(s,9H); 2.41(s,3H); 3.10(m,2H); 5.30(m,1H); 5.50(d broad,J=8 Hz,1H) ppm.

EXAMPLE 2

To a solution of 214 mg of (4R)-13-[dimethyl-(1,1,2-trimethyl-propyl)-silanyloxy]-11-methoxy-10-methyl-4-(3-methyl-1,2,4-oxadiazol-5-yl)-3,4,5,6,7,9-hexahydro-1H-8, 2,5-benzoxathiaazacycloundecine-6,9-dione in 6 ml of toluene were added 160 mg of 2,4-bis-(4-methoxyphenyl)-2,4-dithioxo-1,3,2,4-dithiaphosphetane and the mixture was heated to 80° C. for 30 min. The solvent was evaporated in vacuo, and the residue was chromatographed on silica gel using ethyl acetate/hexane (1:3, v/v) as eluent. The dimethyl-(1,1,2-trimethyl-propyl)-silanylated-product obtained was treated with ammonium fluoride in methanol in an analogous manner to the procedure described in Example 1 to yield, after crystallization from ethyl acetate/hexane, 114 mg of (4R)-13-hydroxy-11-methoxy-10-methyl-4-(3-methyl-1,2,4-oxadiazol-5-yl)-6-thioxo-3,4,5,6,7,9-hexahydro-1H-8,2,5-benzoxathiaazacyclo-undecine-9-one as a white solid, m.p. 162°–164° C.

EXAMPLE 3

A mixture of 35 mg of (4R,7R)-11,13-bis-(tert-butyl-dimethyl-silanyloxy)-7,10-dimethyl-6,9-dioxo-3,4,5,6,7,9-hexahydro-1H-8,2,5-benzoxathiaazacyclo-undecine-4-carboxylic acid methyl ester and 20 mg ammonium fluoride in 2 ml of methanol was stirred at room temperature for 1 h. The solvent was evaporated in vacuo and the residue was chromatographed on silica gel using ethyl acetate as eluent. The pure product was crystallized from dichloromethane to give 13 mg of (4R,7R)-11,13-dihydroxy-7,10-dimethyl-6,9-dioxo-3,4,5,6,7,9-hexahydro-1H-8,2,5-benzoxathiaazacycloundecine-4-carboxylic acid methyl ester as white crystals, m.p. 216°–218° C. (dec.).

The starting material used above was prepared as follows:

(a) A mixture of 1.53 g of 3,5-bis(tert-butyl-dimethylsilanyloxy)-2,6-di-methylbenzoic acid 4-nitrobenzyl ester and 0.50 g of N-bromosuccinimide in 27 ml of carbon tetrachloride was heated at reflux and with light irradiated for 1 h. The mixture was cooled in an ice bath and insoluble material was removed by filtration. The flitrate was evaporated in vacuo to provide 1.89 g of a pale yellow oil which contained 3,5-bis-(tert-butyl-dimethylsilanyloxy)-2-bromomethyl-6-methylbenzoic acid 4-nitrobenzyl ester.

(b) To a solution of 1.89 g of the product of Example 3(a) in 15 ml of dichloromethane—cooled to 0° C.—were added sequentially 1 g of (R)-3-mercapto-2-[2-(S)-trityloxy-propionylamino]-propionic acid methyl ester and 0.25 g of triethylamine. The mixture was stirred for 5 h, the temperature being allowed to rise to 20° C. The solvent was evaporated in vacuo and the residue was chromatographed on silica gel using ethyl acetate/hexane (1:1, v/v) as eluent to yield 0.89 g of 3,5-bis-(tert-butyl-dimethylsilanyloxy)-6-methyl-2-[(R)-2-[(S)-2-trityloxy-propionyl-amino]-2-methoxycarbonyl-ethylsulfanylmethyl]-benzoic acid 4-nitrobenzyl ester as a foam. This material was dissolved in 8 ml of methanol and 0.9 ml of trifluoroacetic acid and heated at reflux for 25 min. The solvents were evaporated in vacuo and the residue was chromatographed on silica gel using ethyl acetate/hexane (1:1, v/v) as eluent to yield 0.40 g of 3,5-bis-(tert-butyl-dimethylsilanyloxy)-2-[(R)2-[(S)-2-hydroxy-propionylamino)-2-methoxycarbonylethylsulfanylmethyl]-6-methylbenzoic acid 4-nitrobenzyl ester as a white solid.
$^1$H-NMR (400 MHz,DMSO-$d_6$): δ0.22(s,6H); 0.24(s,3H); 0.26(s,3H); 0.97(s,9H); 0.98(s,9H); 1.19(d,J=7 Hz,3H); 1.97(s,3H); 2.80–2.90(m,2H 3.59(s,3H); 3.67(s,2H); 3.95–4.05(m,1H); 4.42–4.50(m,1H); 5.48(s,2H); 5.67(d,J=5 Hz,1H); 6.64(s,1H); 7.75(d,J=9 Hz,2H); 7.92(d,J=8 Hz,2H); 8.27(d,J=9 Hz,2H) ppm.

(c) A mixture of 0.16 g of the product of Example 3(b) and 0.3 g of 5% palladium on charcoal in 20 ml of ethyl acetate was hydrogenated for 1 h at atmospheric pressure. The mixture was filtered and the filtrate was evaporated in vacuo. The residue was chromatographed on silica gel using ethyl acetate and ethyl acetate/acetic acid (98:2, v/v) as eluents, and the product-containing fractions were evaporated in vacuo to yield 110 mg of 3,5-bis-(tert-butyl-dimethylsilanyloxy)-2-[(R)-2-[(S)-2-hydroxy-propionylamino)-2-methoxycarbonyl-ethylsulfanylmethyl]-6-methylbenzoic acid as white foam.

(d) To a solution of the product of Example 3(c) and 136 mg of triphenyl-phosphine in 10 ml of dichloromethane, cooled to 0° C., were added 66 mg of diethyl azodicarboxylate. The mixture was stirred for 2 h at 0° C. The solvent was evaporated in vacuo and the residue was chromatographed on silica gel using ethyl acetate/hexane (1:3, v/v) as eluent to yield 73 mg of (4R,7R)-11,13-bis-(tert-butyl-dimethyl-silanyloxy)-7,10-dimethyl-6,9-dioxo-3,4,5,6,7,9-hexahydro-1H-8,2,5-benzoxathiaazacycloundecine-4-carboxylic acid methyl ester as a white foam.
$^1$H-NMR (400 MHz,CDCl$_3$): δ0.21(s,9H); 0.22(s,3H); 1.00(s,9H); 1.01(s,9H); 1.55(s,3H); 1.56(d,J=7 Hz,3H); 2.12(s,3H); 3.00–3.25(m,2H); broad, 1H); 3.74(s,3H); 4.20(d broad, 1H); 4,80–4.90(m,1H); 5.82(q,J=7 Hz,1H); 6.32(s,1H); 7.3(d broad,1H) ppm.

(e) To a solution of 38.6 g of (S)-2-hydroxy-propionic acid ethyl ester, 8.21 g of 4-dimethylamino-pyridine and 25.9 g of pyridine in 97 g of acetonitrile were added 92.0 g of triphenylchloromethane, and the mixture was heated at reflux for 16 h. The reaction mixture was cooled and partitioned between ethyl acetate and water. The organic layer was successively washed with 1M potassium hydrogensulfate solution, saturated potassium bicarbonate solution and brine, dried over magnesium sulfate and evaporated in vacuo. The residual oil was taken up in a solution of 22 g of sodium hydroxide in 200 ml of methanol, and the mixture was stirred for 16 h. The reaction mixture was filtered and the filtrate was diluted with 0.5 l of water. The resulting mixture was first concentrated in vacuo to a volume of about 0.5 l and then extracted with tert-butyl methyl ether and the organic phase was discarded. The pH of the aqueous phase was adjusted to 3 by the addition of 2N potassium hydrogensulfate solution and again extracted with tert-butyl methyl ether. The organic phase was washed with brine and dried over magnesium sulfate. The solvent was evaporated in vacuo and the residual oil was taken up in hexane to afford 56.0 g of (S)-2-trityloxy-propionic acid as off white crystals, m.p. 100°–106° C. Recrystallization from hexane/tert-butyl methyl ether afforded white crystals, m.p. 117.5°–119° C.

(f) To a suspension of 9.97 g of (S)-2-trityloxy-propionic acid, 5.60 g of L-cysteine methyl ester hydrochloride and 6.6 g of N-(3-dimethyl-aminopropyl)-N'-ethylcarbodiimide hydrochloride in 50 ml acetonitrile was added over 10 min a solution of 6.9 g of 4-methyl-morpholine in 50 ml of acetonitrile. The mixture was stirred at room temperature for 3 h and then partitioned between water and ethyl acetate. The organic layer was washed with brine, dried over magnesium sulfate and evaporated in vacuo. The residue was chromatographed on silica gel using ethyl acetate/hexane (1:2, v/v) as eluent to yield 2.30 g of (R)-3-mercapto-2-[(S)-2-methyl-3-trityloxy-propionylamino]-propionic acid methyl ester as amorphous solid.

$^1$H-NMR (250 MHz,DMSO-d$_6$): δ0.88(d,J=10 Hz,3H); 2.42(t,J=15 Hz,1H); 2.78 (dd,J=10 Hz and 15 Hz,2H); 3.66(s,3H); 4.01(q,J=10 Hz,1H); 4.20–4.30(m,1H); 7.25–7.50(m,16H); 7.82(d,J=16 Hz,1H) ppm.

EXAMPLE 4

A solution of 100 mg of the product of Example 3(d) and 100 mg of tetra-isopropyl-orthotitanate in 10 ml of ethanol was heated at reflux under argon for 16 h. The mixture was evaporated in vacuo to dryness and the residue was chromatographed on silica gel using ethyl acetate/hexane (1:3, v/v) as eluent to afford 70 mg of (4R,7R)-11,13-bis-(tert-butyl-dimethylsilanyloxy)-7,10-dimethyl-6,9-dioxo-3,4,5,6,7,9-hexahydro-1H-8,2,5-benzoxathiaazacyclo-undecine-4-carboxylic acid ethyl ester as white foam. This product was subjected in an analogous manner to the procedure described in Example 1 to yield (4R,7R)-11,13-dihydroxy-7,10-dimethyl-6,9-dioxo-3,4,5,6,7,9-hexa-hydro-1H-8,2,5-benzoxathiaazacycloundecine-4-carboxylic acid ethyl ester as a white solid.

$^1$H-NMR (250 MHz,DMSO-d$_6$): δ1.16(t,J=7 Hz,3H); 1.50(d,J=7 Hz,3H); 1.98 (s,3H); 2.80–2.90(m,1H); 3.10–3.20(m,1H); 3.25(d,J=12 Hz,1H); 4.08(q,J=7 Hz,2H); 4.25(d,J=12 Hz,1H); 4.66–4.79(m,1H); 5.25–5.36(m,1H); 6.48(s,1H); 7.60 (d,J=10 Hz,1H); 9.66(s,1H) ppm.

EXAMPLE 5

The product of Example 3(d) was subjected in an analogous manner to the procedures described in Example 2 to yield (4R,7R)-11,13-dihydroxy-7,10-dimethyl-9-oxo-6-thioxo-3,4,5,6,7,9-hexahydro-1H-8,2,5-benzoxathiaazacyclo-undecine-4-carboxylic acid methyl ester as a white foam.

$^1$H-NMR (250 MHz,DMSO-d$_6$): δ1.60(d,J=7 Hz,3H); 1.97(s,1H); 2.90–3.02 (m,2H); 3.18–3.30 (m,1H); 3.64(s, 3H); 4.25(d,J=12 Hz,1H); 5.35–5.45(m,1H); 5.77(q,J=7 Hz,1H); 4.47(s,1H); 9.56(d,J=10 Hz,1H); 9.67(s,2H) ppm.

EXAMPLE 6

(R)-15-(tert-Butyl-dimethylsilanyloxy)-13-methoxy-12-methyl-6,11-dioxo-3,4,5,6,7,8,9,11-octahydro-1H-10,2,5-benzoxathiaazacyclotridecine-4-carboxylic acid methyl ester was treated with ammonium fluoride in methanol in an analogous manner to the procedure described in Example 1 to yield (R)-15-hydroxy-13-methoxy-12-methyl-6,11-dioxo-3,4,5,6,7,8,9,11-octahydro-1H-10,2,5-benzoxathiaazacyclotridecine-4-carboxylic acid methyl ester as a white solid.

$^1$H-NMR (250 MHz,DMSO-d$_6$): δ1.91(s,3H) superimposed by 1.86–2.12(m,2H); 2.16–2.60(m,2H); 2.90(dd,J-14 Hz and 4 Hz,1H); 3.62(s,3H); 3.73(s,3H); 3.74 (d,J=12 Hz,1H); 3.88(d,J=12 Hz,1H); 4.14–4.38(m,2H); 4.42(m, 1H); 6.52(s,1H); 8.32(d,J=9 Hz,1H); 9.70(s,1H) ppm.

The starting material used above was prepared as follows:

(a) A mixture of 13.5 g of 3-(tert-butyl-dimethylsilanyloxy)-5-methoxy-2,6-dimethylbenzoic acid 4-nitrobenzyl ester and 5.34 g N-bromosuccinimide in 135 ml of carbon tetrachloride was heated at reflux and with light irradiation for 40 min. The mixture was cooled in an ice bath and insoluble material was removed by filtration. The filtrate was evaporated in vacuo to provide 18 g of an oil which contained 2-bromomethyl-3-(tert-butyl-dimethylsilanyloxy)-5-methoxy-6-methylbenzoic acid 4-nitrobenzyl ester.

(b) To a solution of 7.4 g of the product of Example 6(a) in 10 ml of dichloro-methane and 10 ml of acetonitrile were added 2.57 g of L-cysteine methyl ester hydrochloride. The mixture was cooled to 0° C. and 2.83 g of triethyl-amine were added. The mixture was stirred at 0° C. for 2 h, then diluted with 100 ml of ethyl acetate and washed successively with saturated sodium carbonate solution and brine. The organic layer was dried over sodium sulfate and evaporated in vacuo. The residue was chromatographed on silica gel using ethyl acetate/hexane (1:1, v/v) as eluent to yield 1.92 g of (R)-2-[2-amino-2-methoxycarbonylethyl-sulfanylmethyl]-3-(tert-butyl-dimethyl-silanyloxy)-5-methoxy-6-methylbenzoic acid 4-nitrobenzyl ester as a pale yellow oil.

$^1$H-NMR (250 MHz,CDCl$_3$): δ0.26(s,6H); 1.03(s,9H); 1.94(broad s,2H); 2.05 (s,3H); 2.64(dd,J=13 Hz and 8 Hz,1H); 2.85(dd,J=13 Hz and 4 Hz,1H); 3.52 (dd,J=8 Hz and 4 Hz,1H); 3.68(s,3H); 3.77(s,3H); 3.82(m,2H); 5.45(s, 2H); 6.40(s,1H); 7.65(d,J=8 Hz,1H); 8.24(d,J=8 Hz,1H) ppm.

(c) Operating in an analogous manner as described in Example 1(h), 1.74 g of the product of Example 6(b) were reacted with 1.56 g of 4-trityloxy-butyric acid. The mixture of the crude reaction product and of 150 mg of 4-toluene-sulfonic acid monohydrate in 60 ml of methanol was heated to 60° C. for 1 h. The solvent was evaporated in vacuo and the residue was chromatographed on silica gel using ethyl acetate/hexane (2:1, v/v) as eluent to yield 1.83 g of (R)-2-[2-(4-hydroxy-butyryl-amino)-2-methoxycarbonyl-ethylsulfanylmethyl]-3-(tert-butyl-dimethylsilanyloxy)-5-methoxy-6-methylbenzoic acid 4-nitrobenzyl ester as oil.

$^1$H-NMR (250 MHz,CDCl$_3$): δ0.24(s,3H); 0.27(s,3H); 1.02(s,9H); 1.73–1.87 (m,2H); 2.05(s,3H); 2.21–2.40(m, 2H); 2.73(broad s,1H); 2.81(dd,J=14 Hz and 4 Hz,1H); 3.06(dd,J=14 Hz and 5 Hz,1H); 3.61–3.71(m,2H); 3.68(s, 3H); 3.72 (d,J=12 Hz,1H); 3.78(s,3H); 3.90(d,J=12 Hz,1H); 4.73(m,1H); 5.41–5.53(AB-system, 2H); 6.39(s,1H); 6.45(d,J=8Hz,1H); 7.66(d,J=8 Hz,1H); 8.26 (d,J=8 Hz,1H) ppm.

(d) A mixture of 1.83 g of the product of Example 6(c) and 0.9 g of 5% palladium on charcoal in 55 ml of ethyl acetate was hydrogenated for 1 h at atmospheric pressure. The mixture was filtered and the filtrate was washed successively with 50 ml of 1N hydrochloric acid and with 100 ml of brine. The organic layer was dried over sodium sulfate and evaporated in vacuo to afford 1.47 g of crude (R)-2-[2-(4-hydroxy-butyrylamino)-2-methoxycarbonyl-ethylsulfanylmethyl]-3-(tert-butyl-dimethyl-silanyloxy)-5-methoxy-6-methylbenzoic acid as an amorphous solid.

($^1$H-NMR (250 MHz,CDCl$_3$): δ0.25(s,3H); 0.26(s,3H); 1.03(s,9H); 1.82–2.05 (m,2H); 2.15(s,3H); 2.50–2.59(m,2H); 2.89–3.05(m,2H); 3.65–3.90(m, 10H); 4.71(m,1H); 6.36(s,1H); 6.77(d,J=8Hz,1H) ppm.

(e) Operating in an analogs manner as described in Example 1(k), 1.47 g of the product of Example 6(d) were lactonized to yield 0.84 g of (R)-15-(tert-butyl-dimethylsilanyloxy)-13-methoxy-12-methyl-6,11-dioxo-3,4,5,6,7,8,9,11-octahydro-1H-10,2,5-benzoxathiaazacyclotridecine-4-carboxylic acid methyl ester as a white solid.

$^1$H-NMR (250 MHz,CDCl$_3$): δ0.24(s,3H); 0.26(s,3H); 1.02(s,9H); 2.00–2.53(m,4H); 2.08(s,3H); 2.65(dd,J=14 Hz and 8 Hz,1H); 2.89(dd,J=14 Hz and 4 Hz,1H); 3.64 (d,J=12 Hz,1H); 3.72(s,3H); 3.78(s,3H); 4.00(d,J=12 Hz,1H);

4.25–4.48(m,2H); 4.63(m,1H); 6.27(d,J=8 Hz,1H); 6.35(s, 1H) ppm.

(f) To a solution of 45 g of butane-1,4-diol in 0.25 l of pyridine, cooled to 0° C., were added 139.4 g of triphenylchloromethane and the mixture was stirred at room temperature for 26 h. The precipitate formed was removed by filtration and the filtrate was evaporated in vacuo. The residue was taken up in 0.5 l of ethyl acetate and the solution was washed successively with 200 ml portions of water, 1N hydrochloric acid, water, 5% sodium bicarbonate solution and brine. The organic layer was dried over sodium sulfate and evaporated in vacuo. Crystallization of the residual material from ethyl acetate/hexane afforded 69.0 g of 4-trityloxy-1-butanol as white crystals of m.p. 73°–74° C.

(g) To a solution of 43.9 g of oxalyl chloride in 0.52 l of dichloromethane, pre-cooled to −70° C., was added over 35 min a solution of 62.9 g of dimethylsulfoxide in 0.10 l of dichloromethane. The solution was stirred for 10 min at −70° C. Then, a solution of 76.5 g of 4-trityloxy-1-butanol in 0.3 l of dichloromethane was added over 35 min, the temperature being maintained at −65° to −70° C. Stirring was continued for another 20 min, and then, 92.9 g of triethylamine were added over 10 min at −60° to −70° C. The mixture was stirred for 20 min at −70° C., and then allowed to warm to 20° C. over 45 min. After the addition of 0.5 l of water, stirring was continued for 15 min. The layers were separated and the aqueous phase was extracted with 0.6 l of dichloromethane. The organic phase was washed with 0.6 l of water and dried over sodium sulfate, and the solvent was evaporated in vacuo. The residue was crystallized from hexane to yield 60.7 g of 4-trityloxy-butanal as white crystals of m.p. 62°–65° C.

(h) To a stirred mixture of 56.2 g of 4-trityloxy-butanal in 430 ml of acetone and 170 ml of water were added portionwise over 1.5 h 27.0 g of potassium permanganate, the temperature of the mixture being maintained at 20° to 25° C. Stirring was continued for 3 h, and then, the pH of the mixture was set to 5 by addition of 22 ml of 3N hydrochloric acid. Over 30 min, 300 ml of 38% sodium bisulfite solution were added dropwise at a reaction temperature of 20° to 30° C. The pH was lowered to 2 by addition of 80 ml of 3N hydrochloric acid, and subsequently the mixture was extracted with 1 l of ethyl acetate. The organic layer was washed with water, dried over sodium sulfate, and the solvent was evaporated in vacuo. The residue was crystallized from ethyl acetate/hexane to yield 46.0 g of 4-trityloxy-butyric acid as a white solid of m.p. 137°–140° C.

EXAMPLE 7

(R)-15-(tert-Butyl-dimethylsilanyloxy)-13-methoxy-12-methyl-6,11-dioxo-3,4,5,6,7,8,9,11-octahydro-1H-10,2,5-benzoxathiaazacyclo-tridecine-4-carboxylic acid methyl ester was subjected in an analogous manner to the procedures described in Example 2 to yield (R)-15-hydroxy-13-methoxy-12-methyl-11-oxo-6-thioxo-3,4,5,6,7,8,9,11-octahydro-1H-10,2,5-benzoxathiaaza-cyclotridecine-4-carboxylic acid methyl ester as a white solid.

$^1$H-NMR (250 MHz,DMSO-$d_6$): δ1.92(s,3H); 2.02–2.36(m,2H); 2.56–2.72(m,2H); 2.84–3.09(m,2H); 3.64(s,3H); 3.66(d,J=12 Hz,1H); 3.73(s,3H); 3.83(d,J=12 Hz,1H); 4.14–4.36(m,2H); 4.98(m,1H); 6.51(s,1H); 9.71(s, 1H); 10.27(d,J=8 Hz,1H) ppm.

EXAMPLE 8

A solution of 124 mg of (R)-15-hydroxy-13-methoxy-12-methyl-11-oxo-6-thioxo-3,4,5,6,7,8,9,11-octahydro-1H-10, 2,5-benzoxathiaazacyclo-tridecine-4-carboxylic acid methyl ester in a mixture of 1.5 ml of methanol and 1.5 ml of allylamine was heated to 50° C. for 2.5 h. The solution was evaporated in vacuo. The residue was chromatographed on silica gel using ethyl acetate/hexane (2:1, v/v) as eluent, and the purified product was crystallized from ethyl acetate/ hexane to afford 97 mg of (R)-15-hydroxy-13-methoxy-12-methyl-11-oxo-6-thioxo-3,4,5,6,7,8,9,11;octahydro-1 H-10, 2,5-benzoxathiaazacyclotridecine-4-carboxylic acid allylamide as a white solid.

$^1$H-NMR (250 MHz,DMSO-$d_6$): δ1.93(s,3H); 2.02–2.36(m,2H); 2.50–2.69(m,2H); 2.95(m,1H); 3.05(dd, J=14 Hz and 4 Hz, 1H); 3.59(d,J=12 Hz,1H); 3.60–3.76(m, 2H) superimposed by 3.73(s,3H); 3.96(d,J=12 Hz,1H); 4.20–4.37(m,2H); 5.00–5.22 (m,3H); 5.78(m,1H); 6.52(s, 1H); 8.24(t,J=7 Hz,1H); 9.71(s,1H); 10.17 (d,J=8 Hz,1H) ppm.

EXAMPLE 9

(4R,9S)-15-(tert-Butyl-dimethylsilanyloxy)-9-hydroxymethyl-13-methoxy-12-methyl-6,11-dioxo-3,4,5,6,7, 8,9,11-octahydro-1H-10,2,5-benzoxathiaazacyclotridecine-4-carboxylic acid methyl ester was subjected in an analogous manner to the procedure described in Example 1 to yield (4R,9S)-15-hydroxy-9-hydroxymethyl-13-methoxy-12-methyl-6,11-dioxo-3,4,5,6,7,8,9,11-octahydro-1H-10,2,5-benzoxathia-azacyclotridecine-4-carboxylic acid methyl ester as a white solid.

$^1$H-NMR (250 MHz,DMSO-$d_6$): δ1.92(s,3H); 2.18–2.30(m,1H); 2.35–2.50(m,1H); 2.60(dd,J=14 Hz and 11 Hz,1H); 3.02(dd,J=14 Hz and 4 Hz,1H); 3.44–3.58(m, 2H); 3.65(s,3H); 3.71(s,3H); 3.72(d,J=10 Hz,1H); 3.89(d,J= 10 Hz,1H); 4.62(m,1H); 4.88(broad t,1H); 5.25(m,1H); 6.49(s,1H); 8.29(d,J=9 Hz,1H); 9.65(s,1H) ppm.

The starting material used above was prepared as follows:

(a) Operating in an analogous manner as described in Example 1(h), 2.89 g of the product of Example 6(b) and 0.97 g of (R)-3-(2,2-dimethyl-1,3-dioxolan-4-yl)-propionic acid were reacted to yield 3.6 g of an oily product. A solution of 1.2 g of this oil and of 50 mg of toluene-4-sulfonic acid monohydrate in 5 ml of methanol was stirred for 30 min at room temperature. The solution was diluted with ethyl acetate and washed successively with 20 ml portions of saturated sodium bicarbonate solution and brine. The organic layer was dried over sodium sulfate and evaporated in vacuo and the residue was chromatographed on silica gel using ethyl acetate/hexane (2:1, v/v) as eluent to yield 0.45 g of 3-(tert-butyl-dimethylsilanyloxy)-2-[(R)-2-[(R)-4,5-dihydroxy-pentanoylamino]-2-methoxycarbonyl-ethylsulfanylmethyl]-5-methoxy-6-methylbenzoic acid 4-nitrobenzyl ester as a foam.

$^1$H-NMR (250 MHz,CDCl$_3$): δ0.26(s,3H); 0.27(s,3H); 1.02(s,9H); 1.64–1.86(m,2H); 2.06(s,3H); 2.21–2.45(m, 2H); 2.79(dd,J=14 Hz and 4 Hz,1H); 3.06(dd,J=14 Hz and 5 Hz,1H); 3.45(dd,J=11 Hz and 6 Hz,1H); 3.60(dd,J=11 Hz and 3 Hz,1H); 3.69 (s,3H); 3.69(d,J=12 Hz,1H); 3.78(s,3H); 3.88(d,J=12 Hz,1H); 4.71(m,1H); 5.41–5.54(m,2H); 6.39(s, 1H); 6.46(d,J=8 Hz,1H); 7.66(d,J=8 Hz,1H); 8.26(d,J=8 Hz,1H) ppm.

(b) The product of Example 9(a) was hydrogenated in an analogous manner as described in Example 6(d) and the resulting product was subjected in an analogous manner to the lactonization procedure described in Example 1(k) to yield after crystallization from ethyl acetate/hexane (4R,9S)-15-(tert-butyl-dimethylsilanyloxy)-9-hydroxymethyl-13-methoxy-12-methyl-6,11-dioxo-3,4,5,6,7,8,9,11-octahydro-1H-10,2,5-benzoxathiaazacyclotridecine-4-carboxylic acid methyl ester as white crystals, m.p. 133°–135° C.

(c) A mixture of 4.0 g of (R)-3-(2,2-dimethyl-1,3-dioxolan-4-yl)-acrylic acid ethyl ester and 0.4 g of 5% palladium on charcoal in 50 ml of ethyl acetate was hydrogenated for 1 h at atmospheric pressure. The mixture was filtered and the flitrate was evaporated in vacuo. The residual oil was subjected to bulb to bulb distillation to afford 2.9 g of (R)-3-(2,2-dimethyl-1,3-dioxolan-4-yl)-2-propionic acid ethyl ester as a colorless oil, b.p.~130° C. (0.1 mbar).

$^1$H-NMR (250 MHz,CDCl$_3$): δ1.26(t,J=7 Hz,3H); 1.35(s, 3H); 1.41(s,3H); 1.86 (m,2H); 2.42(m,2H); 3.55(dd,J=8 Hz and 7 Hz,1H); 4.02–4.20(m,4H) ppm.

(d) To a solution of 2.8 g of (R)-3-(2,2-dimethyl-1,3-dioxolan-4-yl)-2-propionic acid ethyl ester in 7 ml of methanol were added 0.59 g of potassium hydroxide and the mixture was heated to 40° C. for 1.5 h. The mixture was concentrated in vacuo to a volume of about 2 ml, subsequently diluted with ethyl acetate and extracted with water. The aqueous layer was acidified to pH 3 by the addition of 3N hydrochloric acid and then extracted with ethyl acetate. The organic layer was dried over sodium sulfate and evaporated in vacuo to yield 1.97 g of (R)-3-(2,2-dimethyl-1,3-dioxolan-4-yl)-propionic acid.

$^1$H-NMR (250 MHz,CDCl$_3$): δ1.35(s,3H); 1.41(s,3H); 1.90(m,2H); 2.51(m,2H); 3.57(dd,J=8 Hz and 6.5 Hz,1H); 4.06(m,1H); 4.14(m,1H) ppm.

EXAMPLE 10

(4R,9S)-9-Acetoxymethyl-15-(tert-butyl-dimethylsilanyloxy)-13-methoxy-12-methyl-6,11-dioxo-3,4,5,6,7,8,9,11-octahydro-1H-10,2,5-benzoxathiaazacyclotridecine-4-carboxylic acid methyl ester was subjected in an analogous manner to the procedure described in Example 1 to yield (4R,9S)-9-acetoxymethyl-15-hydroxy-13-methoxy-12-methyl-6,11-dioxo-3,4,5,6,7,8,9,11-octahydro-1H-10,2,5-benzoxathiaazacyclo-tridecine-4-carboxylic acid methyl ester as a white solid.

$^1$H-NMR (250 MHz,DMSO-d$_6$): δ1.84–2.12(m,2H) superimposed by 1.92(s,3H) and 2.01(s,3H); 2.22–2.50(m, 2H); 2.61(dd,J=14 Hz and 11 Hz 3.01(dd,J=14 Hz and 3 Hz,1H); 3.65(s,3H); 3.68(d,J=11 Hz,1H); 3.72(s,3H); 3.87(d,J=11 Hz,1H); 4.03(dd,J=13 Hz and 5 Hz, 1H); 4.34(dd,J=13 Hz and 3 Hz,1H); 4.60(m,1H); 5.48 (m,1H); 6.50(s,1H); 8.34(d,J=8 Hz,1H); 9.71(s,1H) ppm.

The starting material used above was prepared as follows:

(a) A solution of 61 mg of the product of Example 9(b) in 1 ml of acetic an-hydride and 0.05 ml of pyridine was heated to 60° C. for 2 h. The mixture was evaporated in vacuo and the residue was dissolved in ethyl acetate. The solution was washed successively with saturated sodium bicarbonate solution and brine. The organic layer was dried over sodium sulfate and evaporated in vacuo, and the residue was chromatographed on silica gel using ethyl acetate/dichloromethane (1:1, v/v) as eluent to yield 24 mg of (4R,9S)-9-acetoxymethyl-15-(tert-butyl-dimethyl-silanyloxy)-13-methoxy-12-methyl-6,11-dioxo-3,4,5,6,7,8,9,11-octahydro-1H-10,2,5-benzoxathiaazacyclotridecine-4-carboxylic acid methyl ester as an oil.

EXAMPLE 11

The product of Example 10(a) was subjected in an analogous manner to the procedures described in Example 2 to yield (4R,9S)-9-acetoxy-methyl-15-hydroxy-13-methoxy-12-methyl-11-oxo-6-thioxo-3,4,5,6,7,8,9,11-octahydro-1H-10,2,5-benzoxathiaazacyclotridecine-4-carboxylic acid methyl ester as a white solid.

$^1$H-NMR (250 MHz,DMSO-d$_6$): δ1.93(s,3H); 2.01(s,3H); 2.08–2.26(m,2H); 2.62–2.98(m,3H); 3.15(dd,J=14 Hz and 4 Hz,1H); 3.58(d,J=11 Hz,1H); 3.68(s,3H); 3.72 (s,3H); 3.84(d,J=11 Hz,1H); 4.07(dd,J=12 Hz and 6 Hz,1H); 4.38(dd,J=12 Hz and 4Hz,1H); 5.12(m,1H); 5.59(m,1H); 6.51(s,1H); 9.73(s,1H); 10.33(d,J=8 Hz,1H) ppm.

EXAMPLE 12

A mixture of 24 mg of the product of Example 11 and 8.3 mg of potassium carbonate in 0.5 ml of methanol was stirred at room temperature for 2 h. The mixture was diluted with ethyl acetate and washed successively with 1N hydrochloric acid and with water. The organic layer was dried over sodium sulfate, and the solvent was evaporated in vacuo. The residue was crystallized from ethyl acetate/hexane to yield 16 mg of (4R,9S)-15-hydroxy-9-hydroxymethyl-13-methoxy-12-methyl-11-oxo-6-thioxo-3,4,5,6,7,8,9,11-octahydro-1H-10,2,5-benzoxathiaazacyclotridecine-4-carboxylic acid methyl ester as a white solid.

$^1$H-NMR (250 MHz,DMSO-d$_6$): δ1.94(s,3H); 2.06–2.30(m,2H); 2.60–3.00(m,3H); 3.16(dd,J=14 Hz and 4 Hz,1H); 3.47–3.76(m,3H) superimposed by 3.66(s,3H) and by 3.72(s,3H); 3.84(d,J=11 Hz,1H); 4.92(m,1H); 5.11(m, 1H); 5.34(m,1H); 6.49 (s,1H); 9.67(s,1H); 10.26(d,J=8 Hz,1H) ppm.

EXAMPLE 13

A solution of 45 mg of the product of Example 12 in a mixture of 1 ml of methanol and 1 ml of prop-2-ynylamine was heated to 50° C. for 5 h. The mixture was evaporated in vacuo and the residual oil was chromatographed on silica gel using ethyl acetate/hexane (1:1, v/v) as eluent. The purified product was crystallized from ethyl acetate/hexane to yield 12 mg of (4R,9S)-15-hydroxy-9-hydroxymethyl-13-methoxy-12-methyl-11-oxo-6-thioxo-3,4,5,6,7,8,9,11-octahydro-1H-10,2,5-benzoxathiaazacyclotridecine-4-carboxylic acid prop-2-ynylamide as a white solid.

$^1$H-NMR (250 MHz,DMSO-d$_6$): δ1.93(s,3H); 2.10–2.27(m,2H); 2.55–2.80(m,2H); 2.84–3.00(m,1H); 3.08(dd,J=14 Hz and 4 Hz,1H); 3.15(t,J=1 Hz,1H); 3.48–3.59 (m,3H); 3.62(d,J=12 Hz,1H); 3.72(s,3H); 3.76–3.94(m,2H); 4.95(t,5 Hz,1H); 5.07 (m,1H); 5.43(m, 1H); 6.49(s,1H); 8.53(t,J=5 Hz,1H); 9.67(s,1H); 10.11 (d,J=8 Hz,1H) ppm.

EXAMPLE 14

By operating in an analogous manner as described in the previous example, but replacing prop-2-ynylamine by cyclopentylamine, there was obtained (4R,9S)-15-hydroxy-9-hydroxymethyl-13-methoxy-12-methyl-11-oxo-6-thioxo-3,4,5,6,7,8,9,11-octahydro-1H-10,2,5-benzoxathiaazacyclotridecine-4-carboxylic acid cyclopentylamide as a white solid.

¹H-NMR (250 MHz,DMSO-d₆): δ1.30–2.26(m,10H) superimposed by 1.93(s,3H); 2.68(dd,J=14 Hz and 12 Hz,1H); 2.85–2.96(m,1H); 3.02(dd,J=14 Hz and 4 Hz,1H); 3.53(m,2H); 3.59(d,J=11 Hz,1H); 3.71(s,3H); 3.85(d,J=11 Hz,1H); 3.93(m,1H); 4.94 (t,J=5 Hz,1H); 5.03(m,1H); 5.43(m,1H); 6.49(s,1H); 8.06(d,J=7 Hz,1H); 9.71(s,1H); 10.36(d,J=8 Hz,1H) ppm.

EXAMPLE 15

A mixture of 240 mg of (4R,9S)-15-(tert-butyl-dimethylsilanyloxy)-13-methoxy-12-methyl-4-(3-methyl-1,2,4-oxadiazol-5-yl)-9-(trityloxy-methyl)-3,4,5,6,7,8,9,11-octahydro-1H-10,2,5-benzoxathiaazacyclo-tridecine-6,11-dione and 24 mg of p-toluenesulfonic acid monohydrate in 5 ml of methanol was heated to 50° C. for 20 min. The solvent was evaporated in vacuo and the residue was chromatographed on silica gel using ethyl acetate/hexane (2:1, v/v) as eluent to yield 40 mg of the (tert-butyl-dimethylsilanylated)-product which was treated with ammonium fluoride in methanol in an analogous manner to the procedure described in Example 1 to yield 26 mg of (4R,9S)-15-hydroxy-9-hydroxymethyl-13-methoxy-12-methyl-4-(3-methyl-1,2,4-oxadiazol-5-yl)-3,4,5,6,7,8,9,11-octahydro-1H-10,2,5-benzoxathiaazacyclotridecine-6,11-dione as a white solid.

¹H-NMR (250 MHz,DMSO-d₆): δ1.84–2.48(m,4H) superimposed by 1.93(s,3H) and 2.33(s,3H); 2.82(dd,J=14 Hz and 11 Hz,1H); 3.19(dd,J=14 Hz and 4 Hz,1H); 3.54(m,2H); 3.72(s,3H); 3.74(d,J=12 Hz,1H); 3.96(d,J=12 Hz,1H); 4.94 (t,J=5.5 Hz,1H); 5.24–5.42(m,2H); 6.50(s,1H): 6.61(d, J=9 Hz,1H): 9.70(s,1H) ppm.

The starting material used above was prepared as follows:

(a) By operating in an analogous manner, the product of Example 1(g) was reacted with (R)-3-(2,2-dimethyl-1,3-dioxolan-4-yl)-propionic acid as described in Example 1(h) and the resulting product was treated with toluene-4-sulfonic acid monohydrate in methanol as described in Example 9(a) to yield 3-(tert-butyl-dimethylsilanyloxy)-2-[(R)-2-[(R)-4,5-dihydroxy-pentanoylamino]-2-(3-methyl-1,2,4-oxadiazol-5-yl)ethylsulfanylmethyl]-5-methoxy-6-methyl-benzoic acid 4-nitrobenzyl ester as an amorphous solid.

¹H-NMR (250 MHz,CDCl₃): δ0.26(s,3H); 0.31(s,3H); 0.94(d,J=7 Hz,6H); 0.98 (s,6H); 1.64–1.86(m,3H); 2.10(s,3H); 2.17–2.53(m,2H) superimposed by 2.36 (s,3H); 2.84(dd,J=14 Hz and 4 Hz,1H); 3.26(dd,J=14 Hz and 5 Hz,1H); 3.40–3.77(m,4H); 3.79(s,3H); 3.91(d,J=12 Hz,1H); 4.84(m,2H); 5.30–5.49(m,3H); 6.07(s,1H); 6.39(s,1H); 6.81(d,J=8 Hz,1H) ppm.

(b) A mixture of 1.3 g of the product of Example 15(a) and 0.61 g of triphenylchloromethane in 4 ml of pyridine was stirred at room temperature for 20 h. The mixture was evaporated in vacuo. The residue was taken up in 100 ml of ethyl acetate and the solution was washed successively with 30 ml of 1N hydrochloric acid and with 60 ml of brine. The organic layer was dried over sodium sulfate and evaporated in vacuo. The residue was chromatographed on silica gel using ethyl acetate/hexane (1:1, v/v) as eluent to yield 1.15 g of 3-(tert-butyl-dimethylsilanyloxy)-2-[(R)-2-[(R)-4-hydroxy-5-trityloxy-pentanoylamino]-2-(3-methyl-1,2,4-oxadiazol-5-yl)-ethylsulfanylmethyl]-5-methoxy-6-methylbenzoic acid 4-nitrobenzyl ester as an amorphous foam.

¹H-NMR (250 MHz,CDCl₃): δ0.25(s,3H); 0.29(s,3H); 0.94(d,J=7 Hz,6H); 0.98 (s,6H); 1.60–1.88(m,3H); 2.08(s,3H); 2.17–2.46(m,2H) superimposed by 2.34 (s,3H); 2.84(dd,J=14 Hz and 5 Hz,1H); 3.11(m,2H); 3.23(dd,J=14 Hz and 6 Hz,1H); 3.64(d,J=12 Hz,1H); 3.75(s,3H); 3.81(m,1H); 3.88(d,J=12 Hz,1H); 4.82(m,2H); 5.27–5.47(m,3H); 6.02(m,1H); 6.37(s,1H); 6.68(d,J=8 Hz,1H); 7.19–7.36(m,9H); 7.40–7.47(m,6H) ppm.

(c) The product of Example 15(b) was subjected sequentially and in an analogous manner to the procedures described in Example 1(j) and 1(k) to yield (4R,9S)-15-(tert-butyl-dimethylsilanyloxy)-13-methoxy-12-methyl-4-(3-methyl-1,2,4-oxadiazol-5-yl)-9-(trityloxymethyl)-3,4,5,6,7,8,9,11-octahydro-1H-10,2,5-benzoxathiaazacyclotridecine-6,11-dione as an amorphous foam.

¹H-NMR (250 MHz,CDCl₃): δ0.26(s,3H); 0.28(s,3H); 0.92(d,J=7 Hz,6H); 0.97 (s,6H); 1.76(m,1H); 1.99(s,3H); 2.25(m,2H); 2.36(s,3H); 2.43(m,2H); 2.82(dd,J=14 Hz and 10 Hz,1H); 3.18(dd,J=14 Hz and 4 Hz,1H); 3.38(dd,J=10 Hz and 5 Hz,1H); 3.49(dd,J=10 Hz and 4 Hz,1H); 3.74(d,J=11 Hz,1H); 3.75(s,3H); 4.03 (d,J=11 Hz,1H); 5.34(m,1H); 5.43(m,1H); 6.32(d,J=8 Hz,1H); 6.37(s,1H); 7.18–7.36(m, 9H); 7.40–7.47 (m,6H) ppm.

EXAMPLE 16

To a solution of 159 mg of the product of Example 15(c) in 3 ml of toluene were added 116 mg of 2,4-bis-(4-methoxyphenyl)-2,4-dithioxo-1,3,2,4-dithia-phosphetane and the mixture was heated to 80° C. for 40 min. The solvent was evaporated in vacuo and the residue was subjected in an analogous manner to the procedures described in Example 15 to yield (4R,9S)-15-hydroxy-9-hydroxymethyl-13-methoxy-12-methyl-4(3-methyl-1,2,4-oxadiazol-5-yl)-6-thioxo-3,4,5,6,7,8,9,11-octahydro-1H-10,2,5-benzoxathiaazacyclotridecine-11-one as a white solid.

¹H-NMR (250 MHz,DMSO-d₆): δ1.94(s,3H); 2.14–2.28(m,1H); 2.34(s,3H); 2.64–2.80(m,1H); 2.85–3.02(m,2H); 3.30–3.40(m,1H); 3.57(m,1H); 3.66(d,J=10 Hz,1H); 3.72(s,3H); 3.94(d,J=10 Hz,1H); 4.97(t,J=5 Hz,1H); 5.41(m,1H); 5.94(m,1H); 6.50 (s,1H); 9.71(s,1H); 10.55(d,J=8 Hz,1H) ppm.

EXAMPLE 17

(R)-14,16-bis-(tert-Butyl-dimethylsilanyloxy)-13-methyl-6,12-dioxo-1,3,4,5,6,7,8,9,10,12-decahydro-11,2,5-benzoxathiaazacyclotetradecine-4-carboxylic acid methyl ester was treated with ammonium fluoride in methanol in an analogous manner to the procedure described in Example 1 to yield, after crystallization from ethyl acetate/hexane, (R)-14,16-dihydroxy-13-methyl-6,12-dioxo-1,3,4,5,6,7,8,9,10,12-decahydro-1,2,5-benzoxathiaazacyclotetradecine-4-carboxylic acid methyl ester as a white solid.

¹H-NMR (250 MHz,DMSO-d₆): δ1.58–1.90(m,4H) superimposed by 1.87(s,3H); 2.32–2.50(m,2H); 2.67(dd,J=14 Hz and 12 Hz,1H); 3.02(dd,J=14 Hz and 4 Hz,1H); 3.61(d,J=11 Hz,1H); 3.64(s,3H); 3.75(d,J=11 Hz,1H); 3.98–4.12(m,1H); 4.32–4.53(m,2H); 6.44(s,1H); 8.32(d,J=8 Hz,1H); 9.50(s,2H) ppm.

The starting material used above was prepared as follows:

(a) The product of Example 3(a) and (R)-3-mercapto-2-[5-trityloxypentanoylamino)]-propionic acid methyl ester were reacted in an analogous manner to the procedure described in Example 3(b) and the resulting product was subjected in analogous manner to a sequence of procedures described in Example 1(i) and 6(d,e) to yield (R)-14,16-bis-(tert-butyl-dimethylsilanyloxy)-13-methyl-6,12-dioxo-1,3,4,5,6,7,8,9,10,12-decahydro-11,2,5-benzoxathiaazacyclotetradecine-4-carboxylic acid methyl ester as an amorphous foam.

¹H-NMR (250 MHz,CDCl₃): δ0.21(s,6H); 0.23(s,3H); 0.24(s,3H); 1.00(s,9H); 1.02(s,9H); 1.74–2.00(m,6H); 2.06(s,3H); 2.23–2.37(m,1H); 2.45–2.59(m,1H); 2.96(d,J=5 Hz,2H); 3.65(d,J=11 Hz,1H); 3.73(s,3H); 3.92(d,J=11 Hz,1H); 4.52(m,2H); 4.69(m,1H); 6.33(s,1H); 6.53(d,J=8 Hz,1H) ppm.

(b) Pentane-1,5-diol was subjected in an analogous manner to the sequence of procedures described in Example 6(f,g,h) to give 5-trityloxypentanoic acid as white crystals of m.p. 146°–148° C.;

c) A suspension of 10.3 g of L-cysteine methyl ester hydrochloride and 21.6 g of 5-trityloxy-pentanoic acid in a mixture of 120 ml of acetonitrile and 80 ml of dichloromethane was treated at 0° C. with 6.1 g of 4-methylmorpholine. To the stirred solution was added dropwise at 10° C. over 20 min a solution of 12.4 g of dicyclohexylcarbodiimide in 120 ml of acetonitrile. The reaction mixture was stirred for 5 h at 0° C. The precipitate formed was filtered off and the filtrate was evaporated in vacuo. The oily residue was dissolved in 200 ml of ethyl acetate and the solution was washed consecutively with 0.5N hydrochloric acid, water, 5% aqueous sodium bicarbonate solution and brine. The organic layer was dried over sodium sulfate and evaporated in vacuo. The crude product was chromatographed on silica gel using ethyl acetate/dichloromethane/hexane(1:1:2, v/v/v) as eluent to give (R)-3-mercapto-2-[5-trityloxy-pentanoylamino)]-propionic acid methyl ester as an oil.

¹H-NMR (250 MHz,CDCl₃): δ1.30(t,J=8 Hz,1H); 1.58–1.84(m,4H); 2.22(t,J=6 Hz,1H); 3.00(dd,J=8 Hz and 4 Hz,2H); 3.08(t,J=6 Hz,2H); 3.78(s,3H); 4.88(m,1H); 6.29(d, J=9 Hz,1H); 7.19–7.36(m,9H); 7.42–7.48(m,6H) ppm.

EXAMPLE 18

The product of Example 17(a) was subjected in an analogous manner to the procedures described in Example 2 to yield (R)-14,16-dihydroxy-13-methyl-12-oxo-6-thioxo-1,3,4,5,6,7,8,9,10,12-decahydro-11,2,5-benzoxathiaazacyclotetradecine-4-carboxylic acid methyl ester as a white solid.

¹H-NMR (250 MHz,DMSO-d₆): δ1.60–1.78(m,2H); 1.81–1.96(m,2H) superimposed by 1.87(s,3H); 2.55–2.69(m,1H); 2.80–2.98(m,2H); 3.16(dd,J=14 Hz and 4 Hz,1H); 3.59(d,J=10 Hz,1H); 3.66(s,3H); 3.78(d,J=10 Hz,1H); 3.93(m,1H); 4.94(t,J=5 Hz,1H); 5.03(m,1H); 5.43(m,1H); 6.49(s,1H); 8.06(d,J=7 Hz,1H); 9.71(s,1H); 10.36 (d,J=8 Hz,1H) ppm.

EXAMPLE 19

(R)-16-(tert-Butyl-dimethylsilanyloxy)-14-methoxy-6,12-dioxo-1,3,4,5,6,7,8,9,10,12-decahydro-11,2,5-benzoxathiaazacyclotetradecine-4-carboxylic acid methyl ester was subjected in an analogous manner to the procedure described in Example 1 to yield (R)-16-hydroxy-14-methoxy-6,12-dioxo-1,3,4,5,6,7,8,9,10,12-decahydro-11,2,5-benzoxathiaazacyclotetradecine-4-carboxylic acid methyl ester as a white solid.

¹H-NMR (250 MHz,DMSO-d₆): δ1.58–1.86(m,4H); 1.98(m,1H); 2.39(m,1H); 2.63 (dd,J=13 Hz and 10 Hz,1H); 2.99(dd,J=13 Hz and 4 Hz,1H); 3.63(s,3H); 3.71(s,3H); 3.90(d,J=11 Hz,1H); 4.07(d,J=11 Hz,1H); 4.11(m,1H); 4,40(m,1H); 4.45(m,1H); 6.54(d,J=2.5 Hz,1H); 6.58(d,J=2.5 Hz,1H); 8.27(d,J=7 Hz,1H); 10.01(s,1H) ppm.

The starting material used above was prepared as follows:

(a) 2-Bromomethyl-3-(tert-butyl-dimethylsilanyloxy)-5-methoxybenzoic acid 4-nitrobenzyl ester and (R)-3-mercapto-2-[5-trityloxy-pentanoylamino)]-propionic acid methyl ester were reacted in an analogous manner to the procedure described in Example 3(b), and the resulting product was subjected in analogous manner to a sequence of procedures described in Example 1(i) and 6(d,e) to yield (R)-16-(tert-butyl-dimethylsilanyloxy)-14-methoxy-6,12-dioxo-1,3,4,5,6,7,8,9,10,12-decahydro-11,2,5-benzoxathiaazacyclotetradecine-4-carboxylic acid methyl ester as an amorphous foam.

¹H-NMR (400 MHz,CDCl₃): δ0.26(s,6H); 1.03(s,9H); 1.80–1.97(m,4H); 2.33(m,1H); 2.55(m,1H); 2.91(dd,J=13 Hz and 6 Hz,1H); 3.04(dd,J=13 Hz and 5 Hz,1H); 3.74(s, 3H); 3.79(s,3H); 4.06(d,J=11 Hz,1H); 4.16(d,J=11 Hz,1H); 4.44(m,1); 4.53(m,1H); 4.68(m,1H); 6.46–6.52(m,2H); 6.89(d,J=2 Hz,1H) ppm.

EXAMPLE 20

The product of Example 19(a) was subjected in an analogous manner to the procedures described in Example 2 to yield (R)-16-hydroxy-14-methoxy-12-oxo-6-thioxo-1,3,4,5,6,7,8,9,10,1-decahydro-11,2,5-benzoxathiaazacyclotetradecine-4-carboxylic acid methyl ester as a white solid.

¹H-NMR (400 MHz,DMSO-d₆): δ1.70(m,2H); 1.89(m,2H); 2.58–2.68(m,1H); 2.84–2.97(m,2H); 3.14(dd,J=14 Hz and 4 Hz,1H); 3.66(s,3H); 3.70(s,3H); 3.90(d,J=11 Hz,1H); 4.02(d,J=11 Hz,1H); 4.10(m,1H); 4.49(m,1H); 5.04(m,1H); 6.54 (d,J=2.5 Hz,1H); 6.58(d,J=2.5 Hz,1H); 10.04(s,1H); 10.22(d,J=8 Hz,1H) ppm.

EXAMPLE 21

To a solution of 51 mg of the product of Example 19(a) in a mixture of 0.5 ml of tetrahydrofuran and 0.5 ml of methanol, cooled to 0° C., was added a solution of 38 mg of sodium borohydride in 0.5 ml of methanol. The solution was stirred at 0° C. for 30 min, and then poured into ice-cold 1N hydrochloric acid. The mixture was extracted with ethyl acetate and the organic layer was washed with brine and dried over sodium sulfate. The solvent was evaporated in vacuo and the residue was treated with ammonium fluoride in methanol in an analogous manner to the procedure described in Example 1. The crude product was chromatographed on RP-8 silica gel (LiChroprep(R)RP-8;Merck) using 30% aqueous acetonitrile as eluent. The product-containing fractions were combined and lyophilized to give (R)-16-hydroxy-4-hydroxymethyl-14-methoxy-1,3,4,5,6,7,8,9,10,12-decahydro-11,2,5-benzoxathiaazacyclotetradecin-6,12-dione as a white powder.

¹H-NMR (250 MHz,DMSO-d₆): δ1.54–1.96(m,5H); 2.32(dd,J=13 Hz and 9 Hz,1H); 2.82(dd,J=13 Hz and 3 Hz,1H); 3.18–3.40(m,2H); 3.70(s,3H); 3.71–3.87(m,2H); 3.95(d,J=11 Hz,1H); 4.05–4.15(m,1H); 4.44–4.56(m,1H); 4.73(t,J=5 Hz,1H); 6.55(d,J=2 Hz,1H); 6.59(d,J=2 Hz,1H); 7.57(d,J=8 Hz,1H); 9.95(s,1H) ppm.

EXAMPLE 22

(R)-16-( tert-Butyl-dimethylsilanyloxy)-14-methoxy-13-methyl-6,12-dioxo-1,3,4,5,6,7,8,9,10,12-decahydro-11,2,5-benzoxathiaazacyclo-tetradecine-4-carboxylic acid methyl ester was subjected in an analogous manner to the procedure described in Example 1 to yield (R)-16-hydroxy-14-methoxy-13-methyl-6,12-dioxo-1,3,4,5,6,7,8,9,10,12-decahydro-11,2,5-benzoxathiaazacyclotetradecine-4-carboxylic acid methyl ester as a white solid.

$^1$H-NMR (250 MHz,DMSO-d$_6$): δ1.60–2.03(m,5H) superimposed by 1.90(s,3H); 2.34–2.48(m,1H); 2.68(dd,J= 13 Hz and 10 Hz,1H); 3.04(dd,J=13 Hz and 4 Hz,1H); 3.64(s,3H); 3.65(d,J=11 Hz,1H); 3.69(s,3H); 3.75(d,J=11 Hz,1H); 4.06(m,1H); 4.36(m,1H); 4.46(m,1H); 6.51(s,1H); 8.33(d,J=8 Hz,1H); 9.73(s,1H) ppm.

The starting material used above was prepared as follows:

(a) By operating in an analogous manner as described in Example 1(h), the product of Example 6(b) was reacted with 5-trityloxy-pentanoic acid and the resulting product was subjected in an analogous manner to a sequence of procedures described in Example 1(i) and 6(d,e) to yield (R)-16-(tert-butyl-dimethylsilanyloxy)-14-methoxy-13-methyl-6,12-dioxo-1,3,4,5,6,7,8,9,10, 12-decahydro-11,2,5-benzoxathiaazacyclotetradecine-4-carboxylic acid methyl ester as an amorphous foam.

$^1$H-NMR (250 MHz,CDCl$_3$): δ0.26(s,6H); 1.03(s,9H); 1.60–2.06(m,5H) superimposed by 1.93(s,3H); 2.34–2.49(m,1H); 2.69(dd,J=14 Hz and 11 Hz,1H); 3.02(dd, J=14 Hz and 4 Hz,1H); 3.63(s,3H); 3.70(d,J=11 Hz,1H); 3.72(s,3H); 3.80(d,J=11 Hz,1H); 4.09(m,1H); 4.40(m,1H); 4.54(m,1H); 6.42(s,1H); 8.37(d,J=8 Hz,1H) ppm.

EXAMPLE 23

The product of Example 22(a) was subjected in an analogous manner to the procedures described in Example 2 to yield (R)-16-hydroxy-14-methoxy-13-methyl-12-oxo-6-thioxo-1,3,4,5,6,7,8,9,10,12-decahydro-1,2,5-benzoxathiaazacyclotetradecine-4-carboxylic acid methyl ester as a white solid.

$^1$H-NMR (250 MHz,DMSO-d$_6$): δ1.60–2.00(m,4H) superimposed by 1.90(s,3H); 2.60(m,1H); 2.80–2.98(m, 2H); 3.16(dd,J=14 Hz and 4 Hz,1H); 3.62(d,J=10 Hz,1H); 3.66(s,3H); 3.73(m,1H); 3.81(d,J=10 Hz,1H); 4.07(m,1H); 4.49(m,1H); 4.91(m,1H); 6.51(s,1H); 9.76(s,1H); 10.28(d, J=7 Hz,1H) ppm.

EXAMPLE 24

(R)-16(tert-Butyl-dimethylsilanyloxy)-14-methoxy-13-methyl-12-oxo-6-thioxo-1,3,4,5,6,7,8,9,10,12-decahydro-11,2,5-benzoxathiaaza-cyclotetradecine-4-carboxylic acid allylamide was subjected in an analogous manner to the procedure described in Example 1 to yield (R)1.6-hydroxy-14-methoxy-13-methyl-12-oxo-6-thioxo-1,3,4,5,6,7,8,9,10, 12-decahydro-11,2,5-benzoxathiaazacyclotetradecine-carboxylic acid allylamide as a white solid.

$^1$H-NMR (250 MHz,DMSO-d$_6$): δ1.60–2.04(m,4H) superimposed by 1.70(s,3H); 2.56(m,1H); 2.79(dd,J=14 Hz and 12 Hz,1H); 2.94(m,1H); 3.16(dd,J=14 Hz and 4 Hz,1H); 3.60(d,J=10 Hz,1H); 3,63–3.79(m,2H) superimposed by 3.72(s,3H); 3.81(d,J=10 Hz,1H); 4.10(m,1H); 4.50(m,1H); 4.91(m,1H); 5.05(dd,J=10 Hz and 2 Hz,1H);.5.19(dd,J=18 Hz and 2 Hz,1H); 5.77(m,1H); 6.50(s,1H); 8.2(t,J=6 Hz,1H); 9.73(s,1H); 10.10(d,J=8 Hz,1H) ppm.

The starting material used above was prepared as follows:

(a) A solution of 263 mg of the product of Example 22(a) in a mixture of 2.5 ml of methanol and 2.5 ml of allylamine was heated to 50° C. for 5 h. The solution was evaporated in vacuo. The residue was chromatographed on silica gel using ethyl acetate/hexane (1:2, v/v) as eluent and the purified product was crystallized from ethyl acetate/hexane to afford 188 mg of (R)-16-(tert-butyl-dimethylsilanyloxy)-14-methoxy-13-methyl-6,12-dioxo-1,3,4,5,6,7,8,9,10,12-decahydro-11,2, 5-benzoxathiaazacyclotetradecine-4-carboxylic acid allylamide as a white solid.

$^1$H-NMR (250 MHz,CDCl$_3$): δ1.60–1.96(m,4H); 2.08(s, 3H); 2.30(m,1H); 2.51(m,1H); 2.77(dd,J=14 Hz and 10 Hz,1H); 3.01(dd,J=14 Hz and 4 Hz,1H); 3.42(d,J=11 Hz,1H); 3.78(s,3H); 3.82(m,1H); 3.99(d,J=11 Hz,1H); 4.21–4.40(m,1H); 4.71(m,1H); 5.03–5.10(m,2H); 5.78(m, 1H); 6.26(d,J=8 Hz,1H); 6.37(s,1H); 6.75(t,J=6 Hz,1H) ppm (b) The product of Example 24(a) was treated with 2,4-bis-(4-methoxy-phenyl)-2,4-dithioxo-1,3,2,4-dithiaphosphetane in an analogous manner to the procedure described in Example 2 and the crude product was chromatographed on silica gel using ethyl acetate/hexane (1:2, v/v) as eluent to yield (R)-16-(tert-butyl-dimethylsilanyloxy)-14-methoxy-13-methyl-12-oxo-6-thioxo-1,3,4,5,6,7,8,9,10,12-decahydro-11,2,5-benzoxa-thiaazacyclotetradecine-4-carboxylic acid allylamide as the major product, and (R)-16-(tert-butyl-dimethylsilanyloxy)-14-methoxy-13-methyl-6,12-dioxo-1,3,4,5,6,7,8,9,10,12-decahydro-11,2,5-benzoxa-thiaazacyclotetradecine-4-carbothioic acid allyl-amide as the minor product.

EXAMPLE 25

(R)-16-(tert-Butyl-dimethylsilanyloxy)-14-methoxy-13-methyl-6,12-dioxo-1,3,4,5,6,7,8,9,10,12-decahydro-11,2,5-benzoxathiaazacyclo-tetradecine-4-carbothioic acid allylamide was subjected in an analogous manner to the procedure described in Example 1 to yield (R)-16-hydroxy-14-methoxy-13-methyl-6,12-dioxo-1,3,4,5,6,7,8,9,10,12-decahydro-11,2,5-benzoxathiaazacyclotetradecine-4-carbothioic acid allylamide as a white solid.

$^1$H-NMR (250 MHz,DMSO-d$_6$): δ inter alia 1.70(s,3H); 3.73(s,3H); 5.10–5.25 (m,2H); 5.72–5.95(m,1H); 6.50(s, 1H); 8.20(d,J=8 Hz,1H); 9.71(s,1H); 10.22(m,1H) ppm.

EXAMPLE 26

A solution of 43 mg of the product of Example 23 in a mixture of 0.5 ml of methanol and 0.5 ml of propylamine was heated to 50° C. for 6 h. The solution was evaporated in vacuo, the residue was dissolved in ethyl acetate and the solution was washed with 1N hydrochloric acid and water. The organic layer was dried over sodium sulfate and evaporated in vacuo, the residue was chromatographed on silica gel using ethyl acetate/hexane (1:2, v/v) as eluent, and the purified product was crystallized from ethyl acetate/hexane to afford 22 mg of (R)-16-hydroxy-14-methoxy-13-methyl-12-oxo-6-thioxo-1,3,4,5,6,7,8,9,10,12-decahydro-11,2,5-benzoxathiaazacyclotetradecine-4-carboxylic acid propylamide as a white solid.

$^1$H-NMR (250 MHz,DMSO-d$_6$): δ0.84(t,J=8 Hz,3H); 1.41(m,2H); 1.63–2.02(m,4H) superimposed by 1.90(s,3H); 2.55(m,1H); 2.76(dd,J=14 Hz and 12 Hz,1H); 2.92 (m,1H); 3.01(dt,J=8 Hz and 8 Hz,2H); 3.11(dd,J=14 Hz and 4 Hz,1H); 3.60 (d,J=10 Hz,1H); 3.72(s,3H); 3.81(d,J=10 Hz,1H); 4.10(m,1H); 4.49(m,1H); 4.85(m,1H); 6.51(s,1H); 8.08(t,J=6 Hz,1H); 9.73(s,1H); 10.08(d,J=8 Hz,1H) ppm.

EXAMPLE 27

A solution of 43 mg of the product of Example 23 in a mixture of 0.5 ml of methanol and 0.5 ml of prop-2-ynylamine was heated to 50° C. for 8 h. The solution was evaporated in vacuo, the residue was dissolved in ethyl acetate, and the solution was washed with 1N hydrochloric acid and water. The organic layer was dried over sodium sulfate and evaporated in vacuo and the residue was chromatographed on silica gel using ethyl acetate/hexane (1:2, v/v) as eluent. The purified product was crystallized from ethyl acetate/hexane to afford 22 mg (R)-16-hydroxy-14-methoxy-13-methyl-12-oxo-6-thioxo-1,3,4,5,6,7,8,9,10,12-decahydro-11,2,5-benzoxathiaazacyclotetradecine-4-carboxylic acid prop-2-ynylamide as a white solid.

$^1$H-NMR (250 MHz,DMSO-d$_6$): δ1.60–2.00(m,4H) superimposed by 1.90(s,3H); 2.56(m,1H); 2.74(dd,J:14 Hz and 11 Hz,1H); 2.92(m,1H); 3.10(dd,J:14 Hz and 4 Hz,1H); 3.14(t,J=1 Hz,1H); 3.57(d,J=10 Hz,1H); 3.72(s,3H); 3.80(d, J=10 Hz,1H); 3.86(m,2H); 4.07(m,1H); 4.51(m,1H); 4.90(m,1H); 6.51(s,1H); 8.57(t,J=5 Hz,1H); 9.73(s,1H); 10.11(d,J=7 Hz,1H) ppm.

EXAMPLE 28

A solution of 43 mg of the product of Example 23 in a mixture of 0.5 ml of methnol and 0.5 ml of 3-aminopropanol was heated to 50° C. for 20 min. The mixture was diluted with ethyl acetate and washed with 1N hydrochloric acid and water. The organic layer was dried over sodium sulfate and evaporated in vacuo and the solid residue was recrystallized from ethyl acetate/hexane to afford 12 mg (R)-16-hydroxy-14-methoxy-3-methyl-12-oxo-6-thioxo-1, 3,4,5,6,7,8,9,10,12-decahydro-11,2,5-benzoxathiaazacyclotetradecine-4-carboxylic acid 3-hydroxy-propylamide as a white solid.

$^1$H-NMR (250 MHz,DMSO-d$_6$): δ1.55(m,2H); 1.60–2.00(m,4H) superimposed by 1.90(s,3H); 2.54(m,1H); 2.74(dd,J=14 Hz and 11 Hz,1H); 2.92(m,1H); 3.04–3.16 (m,3H); 3.40(m,2H); 3.60(d,J=11 Hz,1H); 3.75(s,3H); 3.80(d,J=11 Hz,1H); 4.12 (m,1H); 4.41(t,J=5 Hz,1H); 4.50(m,1H); 4.85(m,1H); 6.50(s,1H); 8.07(t,J=5 Hz,1H); 9.73(s,1H); 10.08(d,J=8 Hz,1H) ppm.

EXAMPLE 29

A solution of 20 mg of (4R,9R)-16-(tert-butyl-dimethyl-silanyloxy)-ethoxycarbonyloxy-14-methoxy-13-methyl-6, 12-dioxo-1,3,4,5,6,7,8,9,10,12-decahydro-11,2,5-benzoxathiaazacyclotetradecine-4-carboxylic acid methyl ester was subjected in an analogous manner to the procedure described in Example 1. The crude product was dissolved in 0.5 ml of a 0.6M solution of sodium methoxide in methanol. The solution was stirred at 0° C. for 7 min whereupon 2 ml of 1N hydrochloric acid were added. The mixture was extracted with ethyl acetate and the organic layer was washed with water, dried over sodium sulfate and evaporated in vacuo. The residue was crystallized from ethyl acetate/hexane to afford 5 mg of (4R,9R)-9,16-dihydroxy-14-methoxy-13-methyl-6,12-dioxo-1,3,4,5,6,7,8,9,10,12-decahydro-11,2,5-benzoxa-thiaazacyclotetradecine-4-4-carboxylic acid methyl ester as a white solid.

$^1$H-NMR (250MHz,DMSO-d6): δ inter alia 1.60(m,2H); 1.88–2.06(m,2H) super-imposed by 1.91(s,3H); 2.60(dd,J= 14 Hz and 12 Hz,1H); 3.08(dd,J=14 Hz and 4 Hz,1H); 3.64(s,3H); 3,72(s,3H); 3.76(d,J=10 Hz,1); 3.91(d,J=10 Hz,1H); 4.00–4.40(m,2H); 4.25–4.50(m,2H); 5.06(d,J=5 Hz,1H); 6.51(s,1H); 8.32(d,J=8 Hz,1H); 9.73(s,1H) ppm.

The starting material used above was prepared as follows:

(a) The product of Example 6(a) and (R)-3-(2,2-dimethyl-1,3-dioxolan-4-yl)-propionic acid were reacted in an analogous manner to the procedure described in Example 6(b), and the resulting product was subjected in an analogous manner to a sequence of procedures described in Example 9(a) and 15(b) to yield 3-(tert-butyl-dimethylsilanyloxy)-2-[(R)-2-[(R)-4-hydroxy-5-trityloxy-pentanoylamino]-2-methoxycarbonylethyl-sulfanylmethyl]-5-methoxy-6-methylbenzoic acid 4-nitrobenzyl ester as an amorphous foam.

$^1$H-NMR (250MHz,CDCl$_3$): δ inter alia 0.24 (s,3H); 0.26(s,3H); 1.02(s,9H); 1.64(m,1H); 1.76(m,1H); 2.04(s, 3H); 2.28(m,2H); 2.78(dd,1H); 3.00(dd,1H); 3.67(s,3H), 3.72(d,J=12 Hz,1H); 3.75(s,3H); 3.86(d,J=12 Hz,1H); 5.44(m,2H); 6.37(s,1H); 6.40(d,J=8 Hz,1H); 7.20–7.33(m, 9H); 7.38–7.45(m,6H); 7.62(d,J=8 Hz,1H) 8.22(d,J=8 Hz,1H) ppm.

(b) To a solution of 281 mg of the product of Example 29(a) in 0.7 ml of pyridine were added at 0° C. 260 mg of ethyl chloroformate. The mixture was stirred at room temperature for 18 h. After the addition of 50 mg of ethyl chloroformate, the mixture was stirred for another h and than evaporated in vacuo. The residue was taken up in 3 ml of 80% aqueous acetic acid and the mixture was heated to 60° C. for 1.5 h. The mixture was evaporated in vacuo and the residue was chromatographed on silica gel using ethyl acetate/hexane (2:1, v/v) as eluent to yield 146 mg of 3-(tert-butyl-dimethylsilanyloxy)-2-[(R)-2-[(R)-4-ethoxycarbonyloxy-5-hydroxy-pentanoylamino]-2-methoxycarbonyl-ethyl-sulfanylmethyl]-5-methoxy-6-methylbenzoic acid 4-nitrobenzyl ester as an amorphous foam.

$^1$H-NMR (250MHz,CDCl$_3$): δ0.24(s,3H); 0.27(s,3H); 1.02(s,9H); 1.30(t,7 Hz,3H); 1.60(broad s,1H); 1.98(m,2H); 2.05(s,3H); 2.28(m,2H); 2.80 (dd,J=14 Hz and 4 Hz,1H); 3.01(dd,J=14 Hz and 5 Hz,1H); 3.60–3.80(m,2H) superimposed by 3.68(s,3H), 3.71(d,J=12 Hz,1H) ,and 3.73(s,3H); 3.86(d,J=12 Hz,1H); 4.19(q,J=7 Hz,2H); 4.65–4.80(m,2H); 5.46(m,2H); 6.36(d,J=8 Hz,1H); 6.39(s,1H); 7.67(d,J=9 Hz,1H); 8.25(d,J=9 Hz,1H) ppm.

(c) The product of Example 29(b) was hydrogenated in an analogous manner as described in Example 6(d) and the resulting product was subjected in an analogous manner to the lactonization procedure described in Example 1(k) to yield after crystallization from ethyl acetate/hexane (4R,9R)-16-(tert-butyl-dimethylsilanyloxy)-9-ethoxycarbonyloxy-14-methoxy-13-methyl-6,12-dioxo-1,3,4,5,6,7,8,9,10,12-decahydro-11,2,5-benzoxathiaazacyclotetradecine-4-4-carboxylic acid methyl ester as a white solid.

$^1$H-NMR (250MHz,CDCl$_3$): δ0.24(s,3H); 0.26(s,3H); 1.03(s,9H); 1.31(t,J=7 Hz,3H); 2.07(s,3H); 2.14(m,2H); 2.39(m,1H); 2.54(m,1H); 2.93(dd,J=14 Hz and 6 Hz,1H); 3.05(dd,J=14 Hz and 5 Hz,1H); 3.60(d,J=11 Hz,1H); 3.73(s, 3H); 3.77 (s,3H); 3.98(d,J=11 Hz,1H); 4.21(q,J=7 Hz,1H); 4.46(dd,J=12 Hz and 5 Hz,1H); 4.67(dd,J=12 Hz and 5 Hz,1H); 4.79(m,1H); 5.02(m,1H); 6.37(s,1H); 6.57 (d,J=8 Hz,1H) ppm.

EXAMPLE 30

The product of Example 29(c) was subjected in an analogous manner to the procedure described in Example 8 to yield (4R,9R)-9,16-dihydroxy-14-methoxy-13-methyl-6,12-dioxo-1,3,4,5,6,7,8,9,10,12 -decahydro-11,2,5-benzoxathiaazacyclotetradecine-4-4-carboxylic acid allylamide as a white solid.

$^1$H-NMR (250MHz,DMSO-d$_6$): δ inter alia 1.91(s,3H); 3.04(dd,J=14 Hz and 4 Hz, 1H); 3.58(d,J=10 Hz,1H); 3.73(s, 3H); 3.78(d,J=10 Hz,1H); 4.36(m,1H); 4.98–5.16(m,2H);

5.51(m,1H);, 6.51(s,1H); 8.07(d,J=8 Hz,1H); 8.14(t,J=6 Hz,1H); 9.70(s,1H) ppm.

EXAMPLE 31

(4R,9R)-16-(tert-Butyl-dimethylsilanyloxy)-9-ethoxycarbonyloxy-14-methoxy-13-methyl-12-oxo-6-thioxo-1,3,4,5,6,7,8,9,10,12-decahydro-11,2,5-benzoxathiaazacyclotetradecine-4-4-carboxylic acid methyl ester was subjected in an analogous manner to the procedure described in Example 1 to yield (4R,9R)-9-ethoxycarbonyloxy-16-hydroxy-14-methoxy-13-methyl-12-oxo-6-thioxo-1,3,4,5,6,7,8,9,10,12-decahydro-11,2,5-benzoxathiaazacyclotetradecine-4-4-carboxylic acid methyl ester as white solid.

$^1$H-NMR (250MHz,DMSO-d$_6$): δ inter alia 1.19(tJ=7 Hz,3H); 1.70(s,3H); 2.00(m,1H); 2.16(m,1H); 2.72(m,1H); 2.83(dd,J=14 Hz and 11 Hz,1H); 2.93(m,1H); 3.21(dd,J=14 Hz and 4 Hz,1H); 3.64(d,J=10 Hz,1H); 3.66(s,3H); 3.73(s, 3H); 3.81(d,J=10 Hz,1H); 4.09(q,J=7 Hz,2H); 4.33(dd,J=12 Hz and 5 Hz,1H); 4.54 (dd,J=12 Hz and 4 Hz,1H); 4.80–5.04(m,2H); 6.53(s,1H); 9.82(s,1H); 10.46 (d,J=7 Hz,1H) ppm.

The starting material used above was prepared as follows:

a) The product of Example 24(c) was treated with 2,4-bis-(4-methoxy-phenyl)-2,4-dithioxo-1,3,2,4-dithiaphosphetane in an analogous manner to the procedure described in Example 2, and the crude product was chromatographed on silica gel using ethyl acetate/hexane (1:2, v/v) as eluent to yield (4R,9R)-16-(tert-butyl-dimethylsilanyloxy)-9-ethoxy-carbonyloxy-14-methoxy-13-methyl-12-oxo-6-thioxo -1,3,4,5,6,7,8,9,10,12-decahydro-11,2,5-benzoxathiaazacyclotetradecine-4-carboxylic acid methyl ester as an amorphous foam.

$^1$H-NMR (250MHz,CDCl$_3$): δ0.24(S,3H); 1.04(s,9H); 1.31(t,J:6 Hz,3H); 2.06(s,3H); 2.14(m, 1H); 2.31(m,1H); 3.04(m,2H); 3.04(dd,J=14 Hz and 5 Hz,1H); 3.28(dd,J=14 Hz and 4 Hz,1H); 3.52(d,J=11 Hz,1H); 3.76(s,3H); 3.77 (s,3H); 4.00(d,J=11 Hz,1H); 4.21(q,J=6 Hz,1H); 4.35(dd,J= 11 Hz and 5 Hz,1H); 4.83(dd,J:11 Hz and 6 Hz,1H); 5.02(m,1H); 5.41(m,1H); 6.37(s,1H); 8.38 (d,J=8 Hz,1H) ppm.

EXAMPLE 32

A solution of 46 mg of the product of Example 31(a) in 1.2 ml of a 0.6M solution of sodium methoxide in methanol was stirred at 0° C. for 40 min, whereupon 2 ml of 1N hydrochloric acid were added. The mixture was extracted with ethyl acetate and the organic layer was washed with water, dried over sodium sulfate and evaporated in vacuo. The residue was chromatographed on silica gel using ethyl acetate/hexane (2:1, v/v) as eluent to yield after crystallization from ethyl acetate/hexane 10 mg of(4R,9R)-9,16-dihydroxy-14-methoxy-13-methyl-12-oxo-6-thioxo-1,3,4,5,6,7,8,9,10,12-decahydro-11,2,5-benzoxathiaazacyclotetradecine-4-carboxylic acid methyl ester as a white solid.

$^1$H-NMR (250 MHz,DMSO-d$_6$): δ inter alia 1.91(s,3H); 3.25(dd,J=14 Hz and 4 Hz,1H); 3.65(d,J=10 Hz,1H); 3.66(s, 3H); 3.73(s,3H); 3.80(d,J=10 Hz,1H); 4.29 (m,1H); 6.51(s, 1H); 9.76(s,1H); 10.34(d,J=7 Hz,1H) ppm.

EXAMPLE 33

(R)-16-(tert-Butyl-dimethylsilanyloxy)-14-methoxy-13-methyl-4-(3-methyl-1,2,4-oxadiazol-5-yl)-1,3,4,5,6,7,8,9,10,12-decahydro-11,2,5-benzoxathiaazacyclotetradecine-6,12-dione was subjected in an analogous manner to the procedure described in Example 1 to yield (R)-6-hydroxy-14-methoxy-13-methyl-4-(3-methyl-1,2,4-oxadiazol-5-yl)-1,3,4,5,6,7,8,9,10,12-decahydro-11,2,5-benzoxathiaazacyclotetradecine-6,12-dione as a white solid. $^1$H-NMR (250 MHz,DMSO-d$_6$): δ 1.71(m,2H); 1.86(m,2H); 1.91(s,3H); 2.02 (m,1H); 2.33(s,3H); 2.39(m,1H); 2.87(dd,J=13 Hz and 11 Hz,1H); 3.23(dd,J=14 Hz and 4 Hz,1H); 3.70(d,J=11 Hz,1H); 3.73(s,3H); 3.85(d,J=11 Hz,1H); 4.07(m,1H); 4.54 (m,1H); 5.16(m,1H); 6.52(s,1H); 8.65(d,J=8 Hz,1H); 9.75(s, 1H) ppm.

The starting material used above was prepared as follows:

(a) To a solution of 15 g of 2-formyl-3-hydroxy -5-methoxy-6-methylbenzoic acid allyl ester in 0.12 l of N,N-dimethylformamide were added 13.8 g of tert-butyl-dimethylchlorosilane and 12.0 g of triethylamine. The mixture was stirred for 3 h at room temperature and then evaporated in vacuo. The residue was taken up in 0.4 l of ethyl acetate and the solution was washed successively with 1N hydrochloric acid, water and brine. The organic layer was dried over sodium sulfate. The solvent was evaporated in vacuo and the solid residue was recrystallized from hexane to give 20.5 g of 2-formyl-3-(tert-butyl-dimethylsilanyloxy)-5-methoxy-6-methylbenzoic acid allyl ester as white crystals of m.p. 94°–95° C.

(b) The product of Example 1(m) and 2-formyl-3-(tert-butyl-dimethylsilanyloxy)-5-methoxy-6-methylbenzoic acid allyl ester were subjected in an analogous manner to the procedure described in Example 1(g) to yield (R)-2-[2-amino-2-(3-methyl-1,2,4-oxadiazol-5-yl)-ethylsulfanylmethyl]-3-(tert-butyl -dimethylsilanyloxy)-5-methoxy-6-methyl-benzoic acid allyl ester as a pale yellow oil.

$^1$H-NMR (250 MHz,CDCl$_3$): δ inter alia 0.23(s,3H); 0.24(s,3H); 1.01(s,9H); 2.07 (s,3H); 2.38(s,3H); 3.52(d,J=11 Hz,1H); 3.82–3.94(m,1H) superimposed by 3.88 (s,3H) and 3.90(s,2H); 4.05(d, J=11 Hz,1H); 4.47(dd,J=12 Hz and 10 Hz,1H); 4.60(dd,J=12 Hz and 5 Hz, 1H); 6.12(m,1H); 6.37(s,1H) ppm.

(c) The product of Example 33(b) was acylated with 5-trityloxypentanoic acid in an analogous manner as described in Example 1(hl), and the resulting product was subjected in an analogous manner to a sequence of procedures described in Example 1(i,j,k) to yield (R)-16-(tert-butyl-dimethylsilanyioxy)-14-methoxy-13-methyl-4-(3-methyl-1,2,4-oxadiazol-5-yl)-1,3,4,5,6,7,8,9,10,12-decahydro-11,2,5-benzoxathiaazacyclotetradecine-6,12-dione as an amorphous solid.

$^1$H-NMR (250 MHz,CDCl$_3$)δ 0.24(s,6H); 1.01(s,9H); 1.76–2.00(m,4H); (s,3H); 2.35(m,1H); 2.36(s,3H); 2.60(m, 1H); 3.01(dd,J=14 Hz and 6 Hz,1H); 3.11(dd,J=14 Hz and 5 Hz,1H); 3.69(d, J=12 Hz,1H); 3.78(s,3H); 3.98(d,J=12 Hz, 1H); 4.54(m,2H); 5.35(m,1H); 6.36(s,1H) 6.64(d,J=8 Hz,1H) ppm.

EXAMPLE 34

The product of Example 33(c) was subjected in an analogous manner to the procedures described in Example 2 to yield (R)-16-hydroxy-14-methoxy-13-methyl-4-(3-methyl-1,2,4-oxadiazol-5-yl)-6-thioxo-1,3,4,5,6,7,8,9,1 0,12-decahydro-11,2,5-benzoxathiaazacyclotetradecin-12-one as a white solid.

$^1$H-NMR (250 MHz,CDCl$_3$): δ 1.73(m, 2H); 1.91(s,3H); 1.95(m,2H); 2.34(s,3H); 2.64(m,1H); 2.88(m,1H); 3.02(dd,

J=13 Hz and 11 Hz,1H); 3.33(dd,J=13 Hz and 4 Hz,1H); 3.71(d,J=10 Hz,1H); 3.73(s,3H); 3.89(d,J=10 Hz,1H); 4.08(m,1H); 4.54(m,1H); 5.75(m,1H); 6.52(s,1H); 9.78(s, 1H); 10.60(d,J=8 Hz,1H) ppm.

EXAMPLE 35

(R)-17-(tert-Butyl-dimethylsilanyloxy)-15-methoxy-14-methyl-6,13-dioxo-3,4,5,6,7,8,9,10,11,13-decahydro-1H-12,2,5-benzoxathiaazacyclopentadecine-4-carboxylic acid methyl ester was subjected in an analogous manner to the procedure described in Example 1 to yield (R)-17-hydroxy-15-methoxy-14-methyl-6,13-dioxo-3,4,5,6,7,8,9,10,11,13-decahydro-1H-12,2,5-benzoxathiaazacyclopentadecine-4-carboxylic acid methyl ester as a white solid.

$^1$H-NMR (250 MHz,DMSO-$d_6$): δ 1.32–1.80(m,6H); 1.90(s,3H); 2.12(m,2H); 2:66(dd,J=14 Hz and 11 Hz,1H); 3.08(dd,J=14 Hz and 4 Hz,1H); 3.63(m,2H); 3.64(s,3H); 3.73(s,3H); 4.12(m,1H); 4.33(m,1H); 4.47(m,1H); 6.52(s, 1H); 8.30 (d,J=8 Hz,1H); 9.74(s,1H) ppm.

The starting material used above was prepared as follows:

(a) The product of Example 6(*a*) and 6-hydroxy-hexanoic acid were reacted in an analogous manner to the procedure described in Example 1(*h*) and the resulting product was subjected in an analogous manner to a sequence of procedures described in Example 1(*i*) and 6(*d,e*) to yield (R)-17-(tert-butyl-dimethylsilanyloxy)-15-methoxy-14-methyl-6,13-dioxo-3,4,5,6,7,8,9,10,11,13-decahydro-1H-12,2,5-benzoxathiaazacyclopentadecine-4-carboxylic acid methyl ester as an amorphous foam.

$^1$H-NMR (250 MHz,CDCl$_3$): δ inter alia 0.23(s,3H); 0.28(s,3H); 1.04(s,9H); 1.22–1.39(m,2H); 1.49–1.85(m, 2H); 2.05(s,3H); 2.11–2.37(m,2H); 2.85(dd,J=13 Hz and 5 Hz,1H); 3.07(dd,J=13 Hz and 4 Hz,1H); 3.71(d,J=12 Hz,1H); 3.76(s,3H); 3.92 (d,J=12 Hz,1H); 4.80(m,1H); 6.24(d,J=8 Hz,1H); 6.34(s,1H) ppm.

EXAMPLE 36

The product of Example 35(*a*) was subjected in an analogous manner to the procedures described in Example 2 to yield (R)-17-hydroxy-15-methoxy-14-methyl-13-oxo-6-thioxo -3,4,5,6,7,8,9,10,11,13-decahydro-1H-12,2,5-benzoxathiaazacyclopentadecine-4-carboxylic acid methyl ester as a white solid.

$^1$H-NMR (250 MHz,DMSO-$d_6$): δ 1.28–1.84(m,6H); 1.89(s,3H); 2.52–2.73(m,2H); 2.85(dd,J=14 Hz and 11 Hz,1H); 3.20(dd,J=14 Hz and 4 Hz,1H); 3.59(d,J=11 Hz,1H); 3.67(d,J=11 Hz, 1H); 3.68(s,3H); 3.73(s,3H); 4.18(m,1H); 4.27(m,1H); 5.25(m,1H); 6.52(s,1H); 9.76(s, 1H); 10.31(d,J=8 Hz,1H) ppm.

EXAMPLE 37

The product of Example 36 was subjected in an analogous manner to the procedures described in Example 8 to yield (R)-17-hydroxy-15-methoxy-14-methyl-13-oxo-6-thioxo -3,4,5,6,7,8,9,10,11,13-decahydro-1H-12,2,5-benzoxathiaazacyclopentadecine-4-carboxylic acid allylamide.

$^1$H-NMR (250 MHz,DMSO-$d_6$): δ 1.93(s, 3H); 2.02–2.36(m,2H); 2.50–2.69(m,2H); 2.95(m,1H); 3.05(dd, J=14 Hz and 4 Hz,1H); 3.59(d,J=12 Hz,1H); 3.62–3.76(m, 2H) superimposed by 3.73(s,3H); 3.96(d,J=12 Hz,1H); 4.20–4.37(m,2H); 5.00–5.22 (m,3H); 5.78(m,1H); 6.52(s, 1H); 8.24(t,J=5 Hz,1H); 9.71(s,1H); 10.17(d,J=8 Hz,1H) ppm.

EXAMPLE 38

(R)-18-(tert-Butyl-dimethylsilanyloxy)-16-methoxy-15-methyl-6,14-dioxo-1,3,4,5,6,7,8,9,10,11,12,14-dodecahydro-13,2,5-benzoxathiaazacyclohexadecine-4-carboxylic acid methyl ester was subjected in an analogous manner to the procedures described in Example 2 to yield (R)-18-hydroxy-16-methoxy-15-methyl-14-oxo-6-thioxo-1,3,4,5,6,7, 8,9,10,11,12,14-dodecahydro-13,2,5-benzoxathiaazacyclohexadecine-4-carboxylic acid methyl ester as a white solid.

$^1$H-NMR (250 MHz,DMSO-$d_6$): δ inter alia 1.14–1.42(m, 4H); 1.46–1.76(m,4H); 1.93(s,3H); 2.71(m,1H); 2.90(dd,J= 14 Hz and 11 Hz,1H); 3.10(dd,J=14 Hz and 3 Hz,1H); 3.66(s,3H); 3.67(d,J=11 Hz,1H); 3.73(s,3H); 3.82(d,J=11 Hz, 1H); 4.04 (m,1H); 4.34(m,1H); 5.13(m,1H); 6.52(s,1H); 9.75(s,1H); 10.18(d,J=7 Hz,1H) ppm.

The starting material used above was prepared as follows:

(a) Heptane-1,7-diol was subjected in an analogous manner to the sequence of procedures described in Example 6(*f,g,h*) to give 7-trityloxy-heptanoic acid as a colorless oil.

$^1$H-NMR (250 MHz,CDCl$_3$): δ 1.20–1.45(m,4H); 1.51–1.68(m,4H); 2.32(t,J=7 Hz, 2H); 3.04(t,J=6 Hz,2H); 7.18–7.34(m,9H); 7.38–7.48(m,6H) ppm.

(b) The product of Example 6(*a*) and 7-trityioxy-heptanoic acid were reacted in an analogous manner to the procedure described in Example 1(*h*) and the resulting product was subjected in an analogous manner to a sequence of procedures described in Example 1(*i*) and 6(*d,e*) to yield (R)-18-(tert-butyl-dimethylsilanyloxy)-16-methoxy-15-methyl-6,14-dioxo-1,3,4,5,6,7,8,9,10, 11,12,14-dodecahydro -13,2,5-benzoxathiaazacyciohexadecine-4-carboxyl acid methyl ester as an amorphous foam.

$^1$H-NMR (250 MHz,CDCl$_3$): δ 0.24(s.3H); 0.26(s,3H); 1.03(s,9H); 1.25–1.35(m,4H); 1.40–1.55(m,2H) 1.70–1.90(m,2H); 2.07(s,3H); 2.11–2.35(m,2H); 2.88(dd, 1H); 3.12(dd,1H); 3.76(s,3H); 3.77(s,3H); 3.81(m,2H); 4.41(m,1H); 4.80(m,1H); 6.16(d,J=8 Hz,1H); 6.34(s,1H) ppm.

EXAMPLE 39

(R)-2-[2-Acetylamino-2-(3-methyl-1,2,4-oxadiazol-5-yl)-ethyl-sulfanyl-methyl]-3-(tert-butyl-dimethylsilanyloxy)-5-methoxy-6-methylbenzoic acid methyl ester was subjected in an analogous manner to the procedure described in Example 1 to yield (R)-2-[2-acetylamino-2-(3-methyl-1, 2,4-oxadiazol-5-yl)-ethylsulfanylmethyl]-3-hydroxy-5-methoxy-6-methylbenzoic acid methyl ester as a white solid.

$^1$H-NMR (250 MHz,DMSO-$d_6$): δ 1.93(s, 3H); 2.33(s, 3H); 2.75–3.03(m,2H); 3.55–3.75(m,2H); 3.73(s,3H); 3.79(s, 3H); 5.20–5.32(m,1H); 6.53(s,1H); 8.66(d,1H) ppm.

The starting material used above was prepared as follows:

(a) A mixture of 10.0 g of tert-butyl-dimethyl-chlorosilane and 10.0 g of sodium iodide in 50 ml of acetonitrile was stirred at room temperature for 1 h. The mixture was cooled to 0° C. and 14.0 g of 2-formyl-3-hydroxy-5-methoxy-6-methylbenzoic acid methyl ester were added at once followed by dropwise addition of 6.7 g of triethylamine over 15 min. The mixture was allowed to warm to room temperature and stirred for 2 h. The reaction mixture was partitioned between water and ethyl acetate. The organic layer was washed successively with 2N potassium hydrogensulfate, saturated sodium bicarbonate and brine, dried over magnesium sulfate and evaporated in vacuo. The solid residue was recrystallized from ethyl acetate/hexane to give 13.0 g of 3-(tert-butyl-dimethylsilanyloxy)-2-formyl-5-methoxy -6-methyl-benzoic acid methyl ester as white crystals, m.p: 125°–131° C.

(b) To a stirred solution of 10.0 g of the product of Example 39(a) in 30 ml of trifluoroacetic acid and 50 ml of dichloromethane was added at 0° C. a solution of 11.5 g of the product of Example 1(m) and 5.16 g triethylsilane in 50 ml of dichloromethane, and stirring was continued at 0° C. for 16 h. The solvent was evaporated in vacuo and the residue was chromatographed on silica gel using ethyl acetate/hexane (1:1, v/v) and ethyl acetate/hexane/methanol (10:10:1, v/v/v) as eluents to yield 8.67 g of (R)-2-[2-amino-2-(3-methyl-1,2,4-oxadiazol-5-yl)-ethylsulfanylmethyl]-3-(tert-butyl-dimethylsilanyloxy)-5-methoxy-6-methyl-benzoic acid methyl ester as a pale yellow oil.

$^1$H-NMR (250 MHz,CDCl$_3$): δ 0.26(s,3H); 0.27(s,3H); 1.02(s,9H); 2.06(s, 3H); 2.37(s,3H); 3.00–3.29(m,2H); 3.65–3.85(m,2H); 3.77(s,3H); 3.93(s,3H); 4.35 (m,1H); 5.45(s broad,ca. 2H); 6.42(s,1H) ppm.

(c) To a solution of 65 mg of the product of Example 39(b) in 2 ml of acetonitrile were added at 0° C. 11 mg of acetic acid and 39 mg of N-(3-dimethylamino-propyl)-N'-ethyl -carbodiimide hydrochloride. The mixture was stirred for 1 h at 0° C. and then partitioned between water and ethyl acetate. The organic layer was washed with water and brine, dried over magnesium sulfate and evaporated in vacuo to afford 71 mg of (R)-2-[2-acetyl-amino-2-(3-methyl-1,2,4-oxadiazol-5-yl)-ethylsulfanylmethyl]-3-(tert-butyl-dimethylsilanyloxy)-5-methoxy-6-methylbenzoic acid methyl ester as white foam.

EXAMPLE 40

The product of Example 39(c) was subjected in an analogous manner to the procedures described in Example 2 to yield (R)-3-hydroxy-5-methoxy-6-methyl-2-[2-(3-methyl-1,2,4-oxadiazol-5-yl)-2-thioacetyl-amino -ethylsulfanylmethyl]-benzoic acid methyl ester as a white solid.

$^1$H-NMR (250 MHz,CDCl$_3$): δ 2.07(s,3H); 2.40(s,3H); 2.61(s,3H); 3.05–3.21 (m,2H); 3.68–3.87(m,2H); 3.80(s, 3H); 3.94(s,3H); 6.15–6.25(m,1H); 6.47(s,1H); 8.18(d,1H) ppm.

EXAMPLE 41–63

By reacting the product of Example 39(b) with the mixed anhydride of acetic and formic acid, or with chloroacetyl chloride, propionyl chloride, 2-methyl-propionyl chloride, cyclopropionyl chloride, benzoyl chloride, furan-2-carbonyl chloride, thiophene-2-carbonyl chloride, 5-methyl-thiophene-2-carbonyl chloride, or thiophen-2ylacetyl chloride, respectively, in an inert solvent, e.g. dichloromethane, in the presence of triethylamine, or with pyridine-2-carboxylic acid azide, pyridine-3-carboxylic acid azide or pyridine-4-carboxylic acid azide, respectively, in the presence of in an inert solvent, e.g. in dichloromethane, in the presence of 4-dimethylamino-pyridine, and subsequently either directly cleaving of the silanyl protecting group as described in Example 1, or subjecting the products of the acylation reaction in an analogous manner to the procedures described in Example 2, the following compounds were prepared:

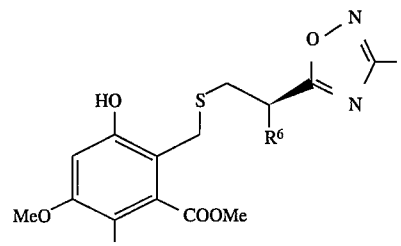

| Example No | R$^6$ | $^1$H-NMR (250 MHz) (solvent) δ, inter alia, ppm. |
|---|---|---|
| 41 | NHCHO | (DMSO-d$_6$) 1.93(s, 3H); 2.33(s, 3H); 2.84–3.07(m, 2H); 3.55–3.75(m, 2H); 3.73(s, 3H); 3.79(s, 3H); 5.29–5.43(m, 1H); 6.53(s, 1H); 8.13(s, 1H); 8.88(d, 1H); 9.83(s, 1H) |
| 42 | NHCOCH$_2$Cl | (DMSO-d$_6$) 1.92(s, 3H); 2.34(s, 3H); 2.85–3.10(m, 2H); 3.56–3.75(m, 2H); 3.73(s, 3H); 3.79(s, 3H); 4.16(s, 2H); 5.25–5.37(m, 1H); 6.53(s, 1H); 9.04(d, 1H); 9.84(s, 1H) |
| 43 | NHCOCH$_2$CH$_3$ | (CDCl$_3$) 1.18(t, 3H); 2.06(s, 3H); 2.28(q, 2H); 2.39(s, 3H); 2.82–3.10(m, 2H); 3.65–3.95(m, 2H); 3.78(s, 3H); 3.92(s, 3H); 5.55–5.65(m, 1H); 6.49(s, 1H); 6.50(d, 1H) |
| 44 | NHCSCH$_2$CH$_3$ | (DMSO-d$_6$) 119(t, 3H); 192(s, 3H); 2.34(s, 3H); 2.62(q, 2H); 3.00–3.10(m, 2H); 3.56–3.77(m, 2H); 3.73(s, 3H); 3.79(s, 3H); 5.93–6.06(m, 1H); 6.53(s, 1H); 9.85(s, 1H); 10.54(d, 1H) |
| 45 | NHCOCH(CH$_3$)$_2$ | (DMSO-d$_6$) 0.97–1.05(m, 6H); 1.93(s, 3H); 2.33(s, 3H); 2.35–2.54(m, 1H); 2.80–3.05(m, 2H); 3.55–3.75(m, 2H); 3.73(s, 3H); 3.79(s, 3H); 5.20–5.30(m, 1H); 6.53(s, 1H); 8.50(d, 1H); 9.82(s, 1H) |
| 46 | NHCSCH(CH$_3$)$_2$ | (DMSO-d$_6$) 1.09–1.20(m, 6H); 1.92(s, 3H); 2.34(s, 3H); 2.85–3.02(m, 1H); 3.03–3.12(m, 2H); 3.56–3.80(m, 2H); 3.72(s, 3H); 3.79(s, 3H); 6.02(q, 1H); 6.53(s, 1H); 9.84(s, 1H); 10.44(d, 1H) |
| 47 | NHCO—◁ | (DMSO-d$_6$) 0.65–0.80(m, 4H); 1.54–1.67(m, 1H); 1.93(s, 3H); 2.33(s, 3H); 2.82–3.02(m, 2H); 3.56–3.75(m, 2H); 3.73(s, 3H); 5.22–5.36(q, 1H); 6.53(s, 1H); 8.86(d, 1H); 9.82(s, 1H) |
| 48 | NHCS—◁ | (DMSO-d$_6$) 0.85–1.15(m, 4H); 1.92(s, 3H); 2.10–2.25(m, 1H); 2.34(s, 3H); 3.00–3.10(m, 2H); 3.60–3.78(m, 2H); 3.73(s, 3H); 3.79(s, 3H); 6.00–6.10(m, 1H); 6.53(s, 1H); 9.85(s, 1H); 10.71(d, 1H) |

67
-continued

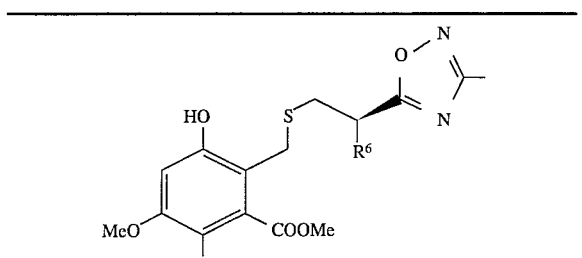

| Example No | R⁶ | ¹H-NMR (250 MHz) (solvent) δ, inter alia, ppm. |
|---|---|---|
| 49 | NHCO—phenyl | (DMSO-d₆) 1.92(s, 3H); 2.34(s, 3H); 3.00–3.20(m, 2H); 3.60–3.85(m, 2H); 3.73(s, 3H); 3.76(s, 3H); 5.42–5.56(m, 1H); 6.53(s, 1H); 7.45–7.63(m, 3H); 7.86–7.96(m, 2H); 9.14(d, 1H); 9.84(s, 1H) |
| 50 | NHCS—phenyl | (DMSO-d₆) 1.93(s, 3H); 2.35(s, 3H); 3.10–3.25(m, 2H); 3.60–3.88(m, 2H); 3.73(s, 3H); 3.78(s, 3H); 6.10–6.24(m, 1H); 6.54(s, 1H); 7.40–7.60(m, 3H); 7.75–7.85(m, 2H); 9.87(s, 1H); 10.77(d, 1H) |
| 51 | NHCO—furyl(O) | (DMSO-d₆) 1.93(s, 3H); 2.33(s, 3H); 2.96–3.20(m, 2H); 3.60–3.80(m, 2H); 3.73(s, 3H); 3.77(s, 3H); 5.40–5.55(m, 1H); 6.53(s, 1H); 6.63–6.71(m, 1H); 7.16–7.24(m, 1H); 7.88–7.94(m, 1H); 9.05(d, 1H); 9.84(s, 1H) |
| 52 | NHCS—furyl(O) | (DMSO-d₆) 1.92(s, 3H); 2.33(s, 3H); 3.11–3.25(m, 2H); 3.56–3.86(m, 2H); 3.73(s, 3H); 3.76(s, 3H); 6.20–6.30(m, 1H); 6.53(s, 1H); 6.68–6.75(m, 1H); 7.30–7.37(m, 1H); 7.95–8.02(m, 1H); 9.85(s, 1H); 10.59(d, 1H) |
| 53 | NHCO—thienyl(S) | (DMSO-d₆) 1.92(s, 3H); 2.34(s, 3H); 2.95–3.16(m, 2H); 3.60–3.80(m, 2H); 3.73(s, 3H); 3.76(s, 3H); 5.40–5.50(m, 1H); 6.53(s, 1H); 7.16–7.22(m, 1H); 7.80–7.88(m, 2H); 9.17(d, 1H); 9.64(s, 1H) |
| 54 | NHCS—thienyl(S) | (DMSO-d₆) 1.92(s, 3H); 2.35(s, 3H); 3.10–3.20(m, 2H); 3.60–3.85(m, 2H); 3.73(s, 3H); 3.77(s, 3H); 6.10–6.25(m, 1H); 6.53(s, 1H); 7.18–7.25(m, 1H); 7.76–7.90(m, 2H); 9.86(s, 1H); 10.56(d, 1H) |
| 55 | NHCS—methylthienyl | (DMSO-d₆) 1.92(s, 3H); 2.34(s, 3H); 2.45(s, 3H); 2.80–3.22(m, 2H); 3.58–3.85(m, 2H); 3.73(s, 3H); 3.77(s, 3H); 6.07–6.23(m, 1H); 6.53(s, 1H); 6.88–6.96(m, 1H); 7.60–7.66(m, 1H); 9.86(s, 1H); 10.42(d, 1H) |

68
-continued

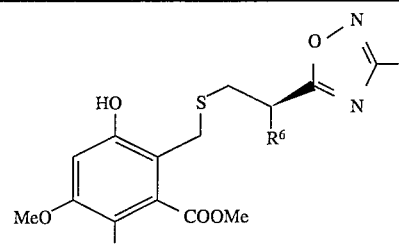

| Example No | R⁶ | ¹H-NMR (250 MHz) (solvent) δ, inter alia, ppm. |
|---|---|---|
| 56 | NHCOCH₂—thienyl(S) | (DMSO-d₆) 1.92(s, 3H); 2.33(s, 3H); 2.84–3.05(m, 2H); 3.54–3.75(m, 2H); 3.73(s, 5H); 3.77(s, 3H); 5.21–5.34(m, 1H); 6.53(s, 1H); 6.88–7.00(m, 2H); 7.33–7.40(m, 1H); 8.94(d, 1H); 9.83(s, 1H) |
| 57 | NHCSCH₂—thienyl(S) | (DMSO-d₆) 1.92(s, 3H); 2.34(s, 3H); 3.00–3.10(m, 2H); 3.52–3.76(m, 2H); 3.73(s, 3H); 3.77(s, 3H); 4.16(s, 2H); 5.86–6.00(m, 1H); 6.53(s, 1H); 6.90–7.00(m, 2H); 7.35–7.41(m, 1H); 9.84(s, 1H); 10.92(d, 1H) |
| 58 | NHCO—pyridyl(2) | (CDCl₃) 2.06(s, 3H); 2.43(s, 3H); 2.96–3.23(m, 2H); 3.75–4.02(m, 2H); 3.78(s, 3H); 3.91(s, 3H); 5.76–5.87(m, 1H); 6.50(s, 1H); 7.03(s, 1H); 7.44–7.54(m, 1H); 7.85–7.95(m, 1H); 8.20–8.26(m, 1H); 8.60–8.65(m, 1H); 8.80(d, 1H) |
| 59 | NHCS—pyridyl(2) | (CDCl₃) 2.05(s, 3H); 2.44(s, 3H); 3.19–3.37(m, 2H); 3.78(s, 3H); 3.81(s, 2H); 3.91(s, 3H); 6.34–6.48(m, 3H); 7.45–7.55(m, 1H); 7.82–7.92(m, 1H); 8.53–8.60(m, 1H); 8.65(d, 1H); 10.74(d, 1H) |
| 60 | NHCO—pyridyl(3) | (CDCl₃) 2.02(s, 3H); 2.40(s, 3H); 3.01–3.25(m, 2H); 3.67–3.94(m, 2H); 3.75(s, 3H); 3.90(s, 3H); 5.72–5.84(m, 1H); 6.44(s, 1H); 6.94–7.00(m, 1H); 7.40–7.50(m, 2H); 8.16–8.24(m, 1H); 8.74–8.81(m, 1H); 9.08–9.13(m, 1H) |
| 61 | NHCS—pyridyl(3) | (CDCl₃) 2.01(s, 3H); 2.44(s, 3H); 3.15–3.36(m, 2H); 3.67–3.84(m, 2H); 3.77(s, 3H); 3.86(s, 3H); 6.26–6.47(m, 3H); 7.32–7.42(m, 1H); 8.13–8.21(m, 1H); 8.66–8.85(m, 2H); 9.00–9.05(m, 1H) |
| 62 | NHCO—pyridyl(4) | (CDCl₃) 2.02(s, 3H); 2.41(s, 3H); 3.00–3.25(m, 2H); 3.69–3.94(m, 2H); 3.75(s, 3H); 3.89(s, 3H); 5.69–5.80(m, 1H); 6.47(s, 1H); 7.49(d, 1H); 7.71–7.78(m, 2H); 8.73–8.81(m, 2H) |

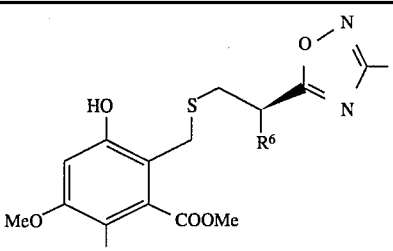

| Example No | R⁶ | ¹H-NMR (250 MHz) (solvent) δ, inter alia, ppm. |
|---|---|---|
| 63 | NHCS—[pyridyl] | (CDCl₃) 2.02(s, 3H); 2.41(s, 3H); 3.08–3.31(m, 2H); 3.70–3.96(m, 2H); 3.73(s, 3H); 3.86(s, 3H); 6.16–6.28(m, 1H); 6.41(s, 1H); 7.64–7.72(m, 2H); 8.50–8.61(m, 2H); 9.25(d, 1H) |

EXAMPLE 64–66

By reacting the product of Example 39(b) with pyridin-2-yl isocyanate, pyridin-3-yl isocyanate or pyridin-4-yl isocyanate, respectively, in refluxing dioxane, and subsequently cleaving of the silanyl protection group in an analogous manner to the procedure described in Example 1, the following compounds were prepared:

| Example No | R⁶ | ¹H-NMR (250 MHz, CDCl₃) δ, inter alia, ppm. |
|---|---|---|
| 64 | NHCONH—[2-pyridyl] | 2.04(s, 3H); 2.42(s, 3H); 2.96–3.23(m, 2H); 3.74(s, 3H); 3.76–4.02(m, 2H); 3.90(s, 3H); 5.64–5.77(m, 1H); 6.46(s, 1H); 6.77–6.85(m, 1H); 6.87–6.97(m, 1H); 7.52(s broad, 1H); 7.56–7.66(m, 1H); 7.94(s, 1H); 8.18–8.24(m, 1H) |
| 65 | NHCONH—[3-pyridyl] | 2.03(s, 3H); 2.37(s, 3H); 2.91–3.17(m, 2H); 3.75–4.05(m, 2H); 3.73(s, 3H); 3.99(s, 3H); 5.35–5.47(m, 1H); 6.47(s, 1H); 6.56(d, 1H); 7.33–7.42(m, 2H); 8.34–8.42(m, 2H) |
| 66 | NHCONH—[4-pyridyl] | 2.03(s, 3H); 2.37(s, 3H); 2.91–3.17(m, 2H); 3.75–4.05(m, 2H); 3.73(s, 3H); 3.99(s, 3H); 5.35–5.47(m, 1H); 6.47(s, 1H); 6.56(d, 1H); 7.33–7.42(m, 2H); 8.34–8.42(m, 2H) |

EXAMPLE 67

To a solution of 110 mg of the product of Example 39(c) in 2 ml of dichloromethane were added at 0° C. 120 mg of triphenylphosphine, 62.5 mg of diethyl azodicarboxylate and 79 mg of trimethylsilyl azide. The mixture was stirred at 0° C. for 1 h, and then another 120 mg of triphenylphosphine, 62.5 mg of diethyl azodicarboxylate and 79 mg of trimethylsilyl azide were added and stirring was continued for another 2 h at 0° C. The solvents were evaporated and the residue was chromatographed on silica gel using ethyl acetate/hexane (1:2, v/v) as eluent. The pure product was subjected in an analogous manner to the procedure described in Example 1 to yield 7 mg of (R) 3-hydroxy-5-methoxy-6-methyl-2-[2-(3-methyl-1,2,4-oxadiazol-5-yl)-2-[5-methyl-(1,2,3,4-tetrazol-1-yl)]-ethylsulfanylmethyl]-benzoic acid methyl ester as a white foam.

¹H-NMR (250 MHz, CDCl₃): δ 2.05(s, 3H); 2.41(s, 3H); 2.56(s, 3H); 3.41–3.79 (m, 4H); 3.81(s, 3H); 3.89(s, 3H); 5.80–5.91(m, 1H); 6.15(s, 1H); 6.52(s, 1H) ppm.

EXAMPLE 68

A suspension of 1.23 g of the product of Example 19(a) in 30 ml of saturated methanolic ammonia was stirred at room temperature for 12 h. The reaction mixture was evaporated in vacuo and the residue was crystallized from ethyl acetate/hexane to yield 0.75 g of (R)-16-hydroxy-14-methoxy-13-methyl-6,12-dioxo-1,3,4,5,6,7,8,9,10,12-decahydro-11,2,5-benzoxathiaazacyclotetradecine-4-carboxylic acid amide as a white solid.

¹H-NMR (250 MHz, DMSO-d₆): δ 1.56–1.75(m, 2H); 1.77–2.00(m, 2H) superimposed by 1.90(s, 3H); 2.40–2.65(m, 3H); 3.02(dd, J=14 Hz and 4 Hz, 1H); 3.61 (d, J=11 Hz, 1H); 3.72(s, 3H); 3.80(d, J=11 Hz, 1H); 4.05(m, 1H); 4.29(m, 1H); 4.55 (m, 1H); 6.50(s, 1H); 7.07(s, 1H); 7,41(s, 1H); 7.98(d, J=8 Hz, 1H); 9.70(s, 1H) ppm.

EXAMPLE 69

The product of Example 20 was subjected in an analogous manner to the procedure described in Example 68 to yield (R)-16-hydroxy-14-methoxy-13-methyl-12-oxo-6-thioxo-1,3,4,5,6,7,8,9,10,12-decahydro-11,2,5-benzoxathiaazacyclotetradeeine-4-carboxylic acid amide as a white solid.

¹H-NMR (250 MHz, DMSO-d₆): δ 1.58–1.80(m, 2H); 1.85–2.04(m, 2H) super-imposed by 1.90(s, 3H); 2.56(m, 1H); 11 Hz, 1H); 2.94(m, 1H); 3.18(dd, J=13 Hz and 4 Hz, 1H); 3.59(d, J=11 Hz, 1H); 3.72(s, 3H); 3.80(d, J=11 Hz, 1H); 4.09(m, 1H); 4.52(m, 1H); 4.86(m, 1H); 6.51(s, 1H); 7.17(s, 1H); 7,55(s, 1H); 9.73(s, 1H); 10.00(d, J=7 Hz, 1H) ppm.

EXAMPLE 70

(R)-2-[2-Acetylamino-2-(3-methyl-1,2,4-oxadiazol-5-yl)-ethylsulfanyl-methyl]-6-bromo-3-(tert-butyl-dimethylsilanyloxy)-5-methoxy-benzoic acid methyl ester was subjected in an analogous manner to the procedure described in Example 1 to yield (R)-2-[2-acetylamino-2-(3-methyl-1,2,4-oxadiazol-5-yl)-ethylsulfanylmethyl]-6-bromo-3-hydroxy-5-methoxy-benzoic acid methyl ester as an amorphous foam.

¹H-NMR (250 MHz, DMSO-d₆): δ 1.88(s, 3H); 2.33(s, 3H); 2.95(m, 2H); 3.57(d, J=14 Hz, 1H); 3.66(d, J=14 Hz, 1H); 3.79(s, 3H); 3.82(s, 3H); 5.26(m, 1H); 6.64(s, 1H); 8.66(d, J= 7.5 Hz, 1H); 10.40(broad signal, 1H) ppm.

The starting material used above was prepared as follows:

(a) To a solution of 23.5 g of 3-hydroxy-5-methoxy-2-methylbenzoic acid methyl ester in 1.3 l of chloroform was added over 1 h at −50° to −60° C. a solution of 19.2 g of bromine in 0.2 l of chloroform. Stirring was continued for 2.5 h at −40° C. and for 2 h at 0° C. The reaction mixture was evaporated in vacuo at 0° C.; the residue was dissolved in a mixture of toluene/ethanol (1:1, v/v) and the solvent was again evaporated in vacuo. This procedure Was repeated twice with toluene/ethanol (1:1, v/v), and finally once with toluene. The residue was chromatographed on silica gel using ethyl acetate as eluent and the pure product was crystallized from ethyl acetate to yield 28 g of 2-bromo-3-methoxy-5-hydroxy-6-methylbenzoic acid methyl ester as white crystals, m.p. 105°–110° C.

(b) 2-Bromo-3-methoxy-5-hydroxy-6-methylbenzoic acid methyl ester was subjected in analogous manner to a sequence of procedures described in Example 33(a) and 6(a) to yield 6-bromo-2-bromomethyl-3-(tert-butyl-dimethylsilanyloxy)-5-methoxybenzoic acid methyl ester as a yellow oil.

$^1$H-NMR (250 MHz, CDCl$_3$): δ 0.32(s,6H); 1.06(s,9H); 3.85(s,3H); 3.99(s,3H); 4.47(s,2H); 6.43(s,1H) ppm.

(c) 6-Bromo-2-bromomethyl-3-(tert-butyl-dimethylsilanyloxy)-5-methoxy-benzoic acid methyl ester and (R)-N-[2-mercapto-1-(3-methyl-1,2,4-oxadiazol-5-yl)-ethyl]-acetamide were subjected in an analogous manner to the procedure described in Example 6(b) to yield (R)-2-[2-acetylamino-2-(3-methyl-1,2,4-oxadiazol-5-yl)-ethylsulfanylmethyl]-6-bromo-3-(tert-butyl-dimethyl-silanyloxy)-5-methoxybenzoic acid methyl ester as a pale yellow oil.

$^1$H-NMR (250 MHz, CDCl$_3$): δ 0.26(s,3H); 0.29(s,3H); 1.02(s,9H); 1.99(s,3H); 2.38(s,3H); 2.90(dd,J=14 Hz and J=4 Hz,1H); 3.23(dd,J=14 Hz and J=4 Hz,1H); 3.56(d,J=14 Hz,1H); 3.81(d,J=14 Hz, 1H); 3.85(s,3H); 3.97(s,3H); 5.48(m,1H); 6.44(s,1H); 6.58(d,J=8 Hz,1H) ppm.

(d) By proceeding in an analogous manner as described in Example 1(l,m), but replacing Boc-L-cystine by N,N'-diacetyl-L-cystine, there was obtained (R)-N-[2-mercapto-1-(3-methyl-1,2,4-oxadiazol-5-yl)-ethyl]-acetamide as an oil.

$^1$H-NMR (250 MHz, CDCl$_3$): δ 1.37–1.48 (m,1H); 2.12(s, 3H); 2.42(s,3H); 2.96–3.29(m,2H); 5.54–5.67(m,1H); 6.50(d broad,j=8 Hz,1H) ppm.

EXAMPLE 71

The product of Example 70(c) was subjected in an analogous manner to the procedures described in Example 2 to yield (R) -2-bromo-5-hydroxy-3-methoxy-6-[2-(3-methyl-1,2,4-oxadiazol-5-yl)-2-thioacetylamino -ethylsulfanylmethyl]-benzoic acid methyl ester as an amorphous solid.

$^1$H-NMR (250 MHz, CDCl$_3$): δ 2.42(s,3H); 2.62(s,3H); 3.16(m,2H); 3.70 (d,J=14 Hz,1H); 3.80(d,J=14 Hz,1H); 3.87(s,3H); 3.98(s,3H); 6.24(m,1H); 6.54(s,1H); 8.08(d,J=8 Hz,1H) ppm.

EXAMPLE 72

(R)-2-[2-Amino-2-(3-methyl-1,2,4-oxadiazol-5-yl)-ethylsulfanylmethyl]-6-bromo-3-(tert-butyl-dimethylsilanyloxy)-5-methoxy-benzoic acid methyl ester and thiophene-2-carboxylic acid were subjected in an analogous manner to the procedure described in Example 1(h) to yield after crystallization from diethyl ether/hexane (R)-2-bromo-5-hydroxy-3-methoxy-6-[2-(3-methyl-1,2,4-oxadiazol-5-yl)-2-thiophen-2-ylcarbonylamino-ethylsulfanylmethyl ]-benzoic acid methyl ester as white crystals, m.p. 108° C.

$^1$H-NMR (250 MHz, CDCl$_3$): δ 2.40(s,3H); 3.05(dd,J=14 Hz and 7 Hz,1H); 3.20(dd,J=14 Hz and 5 Hz,1H); 3.71(d, J=14 Hz,1H); 3.81(s,3H); 3.91 (d,J=14 Hz,1H); 3.95(s,3H); 5.77(m,1H); 6.53(s,1H); 6.98(d,J=8 Hz,1H); 7.11(dd,1H); 7.47(s,1H); 7.56(dd,1H); 7.64(dd,1H) ppm.

The starting material used above was prepared as follows:

(a) The product of Example 70(b) and the product of Example 1(m) were subjected in an analogous manner to the procedure described in Example 6(b) to yield (R)-2-bromo-6-[2-tert-butoxycarbonylamino-2-(3-methyl-1,2,4-oxadiazol-5-yl)-ethylsulfanylmethyl]-5-(tert-butyl-dimethylsilanyloxy)-3-methoxy-benzoic acid methyl ester as a colorless oil.

$^1$H-NMR (250 MHz, CDCl$_3$): δ 0.28(s,6H); 1.02(s,9H); 1.44(s,9H); 2.39(s, 3H); 3.05(m,2H); 3.60(d,J=14 Hz,1H); 3.69(d,J=14 Hz,1H); 3.84(s,3H); 3.96 (s,3H); 5.15(broad s,1H); 5.42(d,1H); 6.44(s,1H) ppm.

(b) A solution of 1.30 g of the product of Example 72(a) in 20 ml of trifluoro-acetic acid was stirred at 0° C. for 2 h. The solution was evaporated in vacuo and the residue was taken up in diethyl ether. The solution was washed successively with saturated sodium bicarbonate solution and brine, dried over sodium sulfate, and the solvent was evaporated in vacuo to yield 1.1 g of (R)-2-[2-amino-2-(3-methyl-1,2,4-oxadiazol-5-yl)-ethylsulfanylmethyl]-6-bromo-3-(tert-butyl-dimethyl-silanyloxy)-5-methoxy-benzoic acid methyl ester as a pale yellow oil.

$^1$H-NMR (250 MHz, CDCl$_3$): δ 0.28(s,6H); 1.02(s,9H); 2.39(s,3H); 2.89 (dd,J=14 Hz and 4 Hz,1H); 3.07(dd,J=14 Hz and J=4 Hz,1H); 3.71(s,2H); 3.85(s,3H); 3.95(s,3H); 4.24(m,1H); 6.45(s,1H) ppm.

EXAMPLES 73–76

By reacting the product of Example 72(b) with thiophene-2-carboxylic acid, thiophene-3-carboxylic acid, 2-aminothiazole-4-carboxylic acid, and thiazole-2-carboxylic acid, respectively, in an analogous manner as described in Example 1(h), and by subsequently either directly cleaving of the silanyl protecting group as described in Example 1, or reacting the products of the acylation reaction with 2,4-bis-(4-methoxyphenyl)-2,4-dithioxo-1,3,2,4-dithiaphosphetane and subsequent cleavage of the silanyl protecting group in an analogous manner as described in Example 2, the following compounds were prepared:

| Example No | R$^6$ | $^1$H-NMR (250 MHz, CDCl$_3$) δ, inter alia, ppm |
|---|---|---|
| 73 | NHCS-(thiophen-2-yl) | 2.43(s, 3H); 3.24(dd, 1H); 3.35(dd, 1H); 3.69(d, 1H); 3.81(d, 1H); 3.83(s, 3H); 3.95(s, 3H); 6.35(m, 1H); 6.47(s, 1H); 6.66(s, 1H); 7.11(dd, 1H); 7.55(m, 2H); 8.29(d, 1H) |

73
-continued

![structure: HO, MeO, Br, COOMe benzene with S-CH2-CH(R6)-oxadiazole]

| Example No | R⁶ | ¹H-NMR (250 MHz, CDCl₃) δ, inter alia, ppm |
|---|---|---|
| 74 | NHCO—[thiophene] | 2.40(s, 3H); 3.03(dd, 1H); 3.20(dd, 1H); 3.73(d, 1H); 3.81(s, 3H); 3.92(d, 1H); 3.94(s, 3H); 3.79(ddd, 1H); 6.52(s, 1H); 6.97(d, 1H); 7.37(dd, 1H); 7.44(dd, 1H); 7.53(s, 1H); 7.99(dd, 1H) |
| 75 | NHCS—[thiophene] | 2.41(s, 3H); 3.23(dd, 1H); 3.34(dd, 1H); 3.70(d, 1H); 3.78(d, 1H); 3.81(s, 3H); 3.93(s, 3H); 6.36(ddd, 1H); 6.46(s, 1H); 7.33(dd, 1H); 7.54(dd, 1H); 7.96(dd, 1H); 8.39(d, 1H) |
| 76 | NHCO—[aminothiazole] NH₂ | 2.42(s, 3H); 2.99(dd, 1H); 3.14(dd, 1H); 3.75(d, 1H); 3.84(s, 3H); 3.96(s, 3H); 3.98(d, 1H); 5.10(broad, 2H); 5.76(ddd, 1H); 6.54(s, 1H); 7.43(s, 1H); 7.87(d, 1H) |
| 77 | NHCO—[thiazole N] | 2.05(s, 3H); 2.42(s, 3H); 3.07(dd, 1H); 3.17(dd, 1H); 3.77(d, 1H); 3.85(s, 3H); 3.89(d, 1H); 3.97(s, 3H); 5.75(m, 1H); 6.53(s, 1H); 7.65(d, 1H); 7.93(d, 1H); 8.10(d, 1H) |

EXAMPLE 78

A solution of 40 mg of (R)-2-bromo-5-(tert-butyl -dimethyl-silanyloxy)-6-[2-isothiocyanato-2-(3-methyl-1,2,4-oxadiazol-5-yl)ethylsulfanylmethyl]-3-methoxybenzoic acid methyl ester in 4 ml of tetrahydrofuran was saturated at −3° C. with dry ammonia. The solution was stirred for 30 min at room temperature and then evaporated in vacuo to yield (R)-2-bromo-5-(tert-butyl-dimethylsilanyloxy) -3-methoxy-6-[2-(3-methyl-1,2,4-oxadiazol-5-yl)-2-thioureido-ethylsulfanylmethyl]-benzoic acid methyl ester. This material was subjected in an analogous manner to the procedure described in Example 1 to afford 20 mg of (R)-2-bromo-5-hydroxy-3-methoxy-2-[2-(3-methyl-1,2,4-oxadiazol-5-yl)-6-thioureido-ethylsulfanylmethyl ]-benzoic acid methyl ester as a white solid.

¹H-NMR (250 MHz,CDCl₃): δ 2.38(s,3H); 3.04(dd,J=14 Hz and J=6 Hz,1H); 3.17(dd,J=14 Hz and J=6 Hz,1H); 3.67(d,J=14 Hz,1H); 3.85(s,3H); 3.88 (d,J=14 Hz,1H); 3.99(s,3H); 6.05(broad s,1H); 6.25(s,2H); 6.53(s,1H); 7.40(d,J=8 Hz,1H) ppm.

The starting material used above was prepared as follows:
(a) To a solution of 0.88 g of the product of Example 72(b) in 40 ml of dichloromethane, cooled to 0° C., were added 0.37 g of 1,1'-thiocarbonyl-di-pyridin-2(1H)-one. The mixture was stirred at room temperature for 15 min and then evaporated in vacuo. The residue was chromatographed on silica gel using ethyl acetate as eluent to yield 0.90 g of (R)-2-bromo-5-(tert-butyl-dimethylsilanyloxy)-6-[2-isothiocyanato-2-(3-methyl-1,2,4-oxadiazol-5-yl)-ethylsulfanylmethyl]-3-methoxy-benzoic acid methyl ester as a colorless oil.

¹H-NMR (250 MHz,CDCl₃): δ 0.29(s,3H); 0.30(s,3H); 1.02(s,9H); 2.42(s,3H); 3.11(dd,J=14 Hz and 7 Hz,1H); 3.21(dd,J=14 Hz and 6 Hz,1H); 3.74(s,2H); 3.86(s,3H); 3.96(s,3H); 4.98(t,J=5 Hz,1H) 6.47(s,1H) ppm.

EXAMPLES 79–86

By operating in an analogous manner, the product of Example 78(a) was subjected to the procedure described in Example 78, but using acetonitrile or a mixture of acetonitrile and N,N-dimethylformamide as solvent, and replacing ammonia by methylamine, 4-methoxy-aniline, 2-aminothiazole, 1-amino-1,3,4 -triazole, 5-amino-uracile, 2-dimethylamino-ethylamine, 2-(pyrrolidine-1-yl) ethylamine or 2-(morpholin-4-yl)-ethylamine, respectively, and subsequent cleavage of the silanyl prot,ecting groups in an analogous manner as described in Exampie 1, the following compounds were prepared:

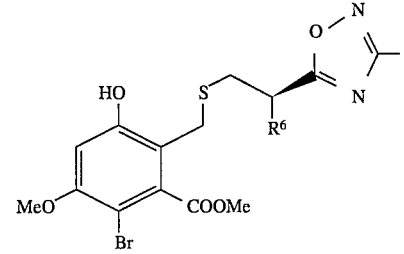

| Example No | R⁶ | ¹H-NMR (250 MHz) (solvent) δ, inter alia, ppm |
|---|---|---|
| 79 | NHCSNHMe | (CDCl₃) 2.37(s, 3H); 3.01(dd, 1H); 3.03(d, 3H); 3.19(dd, 1H); 3.67(d, 1H); 3.86(s, 3H); 3.95(d, 1H); 3.98(s, 3H); 6.19(broad, 1H); 6.39(broad, 1H); 6.52(s, 1H) |
| 80 | NHCSNH—[phenyl]—OMe | (CDCl₃) 2.39(s, 3H); 2.99(dd, 1H); 3.17(dd, 1H); 3.83(s, 3H); 3.85(s, 3H); 3.94(s, 3H); 6.3(ddd, 1H); 6.52(s, 1H); 6.60(d, 1H); 6.95(d, 2H); 7.23(d, 2H); 7.77(s, 1H) |

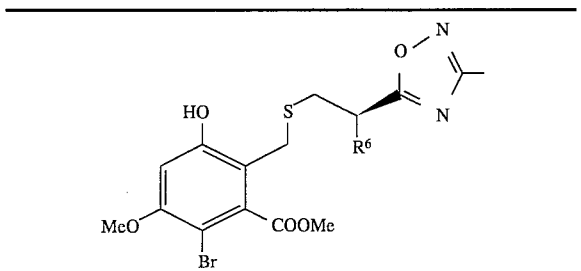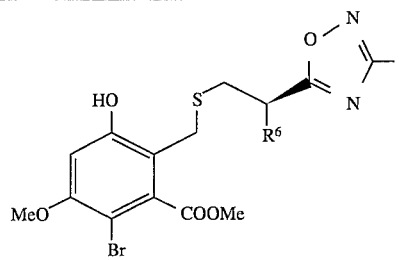

| Example No | R⁶ | ¹H-NMR (250 MHz) (solvent) δ, inter alia, ppm |
|---|---|---|
| 81 | NHCSNH—(thiazole) | (CDCl₃) 2.42(s, 3H); 3.23(2xdd, 2H); 3.82(s, 3H); 3.96(s, 3H); 6.25(broad, 1H); 6.51(s, 1H); 6.87(d, 1H); 7.36(d, 1H); 11.32(broad, 1H) |
| 82 | NHCSNH—N(triazole) | (DMSO-d₆) 2.34(s, 3H); 3.07(t, 2H); 3.58(d, 1H); 3.74(d, 1H); 3.79(s, 3H); 3.84(s, 3H); 5.94(broad, 1H); 6.64(s, 1H); 8.62(broad, 1H); 11.05(broad, 1H) |
| 83 | NHCSNH—(uracil) | (DMSO-d₆) 2.34(s, 3H); 3.05(t, 2H); 3.57(d, 1H); 3.70(d, 1H); 3.79(s, 3H); 3.83(s, 3H); 5.95(m, 1H); 6.63(s, 1H); 6.95(broad, 1H); 7.05(s, 1H); 9.05(s, 1H) |
| 84 | NHCSNH–CH₂CH₂–N(CH₃)₂ | (CDCl₃) 2.37(s, 3H); 2.40(2, 6H); 2.68(m, 2H); 3.07(d, 2H); 3.72(d, 1H); 3.85(s, 3H); 3.92(d, 1H); 3.94(s, 3H); H); 6.40(s, 1H) |
| 85 | NHCSNH–CH₂CH₂–N(pyrrolidine) | (CDCl₃) 2.18(m, 4H); 2.35(s, 3H); 3.05(dd, 1H); 3.35(dd, 1H); 3.79(s, 4H); 3.86(s, 3H); 3.94(s, 3H); 4.32(broad, 1H); 6.23(broad, 1H); 6.85(s, 1H); 7.46(broad, 1H); 8.12(broad, 1H) |
| 86 | NHCSNH–CH₂CH₂–N(morpholine) | (CDCl₃) 2.38(s, 3H); 2.94(t, 2H); 3.20(broad s, 2H); 3.84(s, 3H); 3.96(s, 3H); 6.23(broad, 1H); 6.57(s, 1H); |

EXAMPLE 87

To a solution of 324 mg of the product of Example 72(b) in 20 ml of methanol were added 102 mg of 4-chloro-phenyl isothiocyanate. The mixture was stirred at room temperature 16 h and then evaporated in vacuo. The residue was subjected in an analogous manner to the procedure described in Example 1 to yield (R)-2-bromo-6-[2-[3-(4-chloro-phenyl)-thioureido]-2-(3-methyl-1,2,4-oxadiazol-5-yl)-ethylsulfanylmethyl]-5-hydroxy-3-methoxy-benzoic acid methyl ester as a white solid.

¹H-NMR (250 MHz,CDCl₃): δ 2.39(s,3H); 3.06(dd,J=14 Hz and 6 Hz,1H); 3.18 (dd,J=14 Hz and 5 Hz,1H); 3.69(d, J=14 Hz,1H); 3.80(d,J=14 Hz,1H); 3.86(s,3H); 3.95(s,3H); 6.26(m,1H); 6.52(s,1H); 6.82(s,1H); 6.84(d,J=8 Hz,1H); 7.27(d,J=8 Hz, 2H); 7.40(d,J=8 Hz,2H); 7.96(s,1H) ppm.

EXAMPLE 88

By operating in an analogous manner as described in Example 87, but replacing 4-chloro-phenyl isothiocyanate by 4-pyridin-4-ylamino-phenyl isothiocyanate, there was obtained (R)-2-bromo-5-hydroxy-3-methoxy-6-[2-(3-methyl-1,2,4-oxadiazol-5-yl)-2-[3-(4-pyridin-4-ylamino-phenyl)-thioureido]-ethylsulfanylmethyl]-benzoic acid methyl ester as a foam.

¹H-NMR (250 MHz,DMSO-d₆): δ 2.36(s, 3H); 3.16(m, 2H); 3.60(d,J=12 Hz,1H); 3.76(d,J=12 Hz, 1H); 3.80(s,3H); 3.85(s,3H); 4.39(m,1H); 6.10(m,1H); 6.64(s,1H); 6.89(d, J=6 Hz,2H); 7.20(d,J=8 Hz,2H); 7.43(d,J=8 Hz,2H); 8.20(d, J=6 Hz,2H); 8.31(d,J=8 Hz,1H); 8.89(s,1H); 9.90(s,1H) ppm.

The starting material used above was prepared as follows:
(a) To a solution of 13.4 g of N-(4-pyridinyl)-1,4-diamino-benzene in 400 ml of pyridine were added 36.2 g of triethylamine and 50 ml of carbon disulfide. The mixture was stirred at room temperature for 15 min. Upon the addition of 1 l of diethyl ether, a precipitate was formed which was isolated by filtration to afford 27 g of a white solid of m.p. 120°–124° C. To a suspension of 10.86 g of this material in 3 l of dichloromethane were added 3.27 g of triethylamine and 3.42 g of ethyl chloroformate and the mixture was stirred at room temperature for 3 h. The precipitate was filtered off and the filtrate was washed with saturated sodium bicarbonate solution. The organic layer was dried over sodium sulfate and evaporated in vacuo. The residue was chromatographed on silica gel using dichloromethane/methanol (1:1, v/v) as eluent to give after crystallization from dichloromethane/methanol 2.8 g of 4-pyridin-4-ylamino -phenyl isothiocyanate as yellow crystals, m.p. 195°–196° C.

EXAMPLE 89

By operating in an analogous manner as described in Example 87, but replacing 4-chloro-phenyl isothiocyanate by 4-(4-acetyl-piperazin-1-yl)-phenyl isothiocyanate, there was obtained (R)-2-[2-[3-[4-(4-acetyl-piperazin-1-yl)-phenyl]-thioureido]-2-(3-methyl-1,2,4-oxadiazol-5-yl)-ethylsulfanylmethyl]-6-bromo-3-hydroxy-5-methoxybenzoic acid methyl ester as a white solid.

$^1$H-NMR (250 MHz,CDCl$_3$): δ 2.16(s,3H); 2.38(s,3H); 3.00(dd,J=15 Hz and 7 Hz,1H); 3.19(dd,J=15 Hz and 5 H,1H); 3.20(m,2H); 3.64(m,2H); 3.75(m,4H); 3.77(m,2H); 3.85(s,3H); 3.94(s,3H); 6.31(m,1H); 6.55(1H); 6.66(d,J=8 Hz,1H); 6.93(d,J=8 Hz,2H); 7.19(d,J=8 Hz,2H); 7.84(s,1H) ppm.

The starting material used above was prepared as follows:

(a) By operating in an analogous manner as described in Example 88(*a*), but replacing N-(4-pyridinyl)-1,4-diamino-benzene by 1-acetyl-4-(4-amino-phenyl) -piperazine, there was obtained after crystallization from diethyl ether/hexane 4-(4-acetyl -piperazin-1-yl)-phenyl isothiocyanate as white crystals, m.p. 98°–100° C.

EXAMPLE 90

By operating in an analogous manner, 2-bromo-5-(tert-butyl-dimethylsilanyloxy)-3-methoxy-6-methyl-benzoic acid ethyl ester was subjected to the procedure described in Example 3(*a*). The resulting dibromo compound was reacted with the product of Example 1(*m*) as described in Example 6(*b*). The resulting product was subjected to the procedure described in Example 72(*b*) to afford an amino compound which was acylated with thiophene-2-carboxylic acid using the procedure described in Example 1(*h*), and the resulting product was finally treated with ammonium fluoride in methanol in an analogous manner to the procedure described in Example 1 to yield (R)-2-bromo-5-hydroxy-3-methoxy-6-[2-(3-methyl-1,2,4-oxadiazol- 5-yl)-2-(thiophen-2-ylcarbonylamino)-ethylsulfanylmethyl ]-benzoic acid ethyl ester as an amorphous solid.

MS m/z: (M–H)$^-$=554.2/556.2

The starting material used above was prepared as follows:

(a) A suspension of 23 g 2-bromo-5-hydroxy-3-methoxy-6-methyl-benzoic acid methyl ester in 200 ml of 3N sodium hydroxide was stirred at 70° C. for 85 h. The cooled solution was washed with diethyl ether and acidified to pH 1 by the addition of 3N hydrochloric acid. The aqueous layer was extracted with diethyl ether and the organic phase was washed with brine, dried over sodium sulfate and evaporated in vacuo. The residue was recrystallized from diethyl ether/pentane to yield 21 g of 2-bromo-5-hydroxy-3-methoxy-6-methyl-benzoic acid as white crystals, m.p.79°–80° C.

(b) To a solution of 12.0 g of 2-bromo-5-hydroxy-3-methoxy-6-methyl-benzoic acid in 700 ml of acetonitrile were added at –5° C. 27.7 g of tert-butyldimethylchlorosilane and 18.5 g of triethylamine. The mixture was stirred for 30 min at –5° C. and for 16 h at 20° C. The solvent was evaporated in vacuo and the solid residue was washed with water and dried in vacuo. A solution of this material in 200 ml of ethanol was heated for 8 h to 80° C. The solvent was evaporated in vacuo and the residue was recrystallized from pentane to yield 12.0 g of 2-bromo-5-(tert-butyl-dimethylsilanyloxy)-3-methoxy-6-methyl-benzoic acid as white crystals, m.p. 120°–125° C.

(c) To 5 ml of thionyl chloride were added at –20° C. 100 mg of 2-bromo-5-(tert-butyl -dimethylsilanyloxy)-3-methoxy-6-methyl-benzoic acid. The mixture was stirred for 1 h at –20° C. and for 16 h at 20° C. and then evaporated in vacuo. The residue was dissolved in 10 ml of ethanol and the solution was stirred at 20° C. for 24 h. The solvents were evaporated in vacuo and the residual oil was chromatographed on silica gel using ethyl acetate/hexane (1:1, v/v) as eluent to yield 105 mg of 2-bromo-5-(tert-butyl -dimethylsilanyloxy)-3-methoxy-6-methyl-benzoic acid ethyl ester as colorless oil.

$^1$H-NMR (250 MHz,CDCl$_3$): δ 0.23(s, 6H); 1.01(s,9H); 1.40(t,3H); 2.10(s,3H); 3.82(s,3H); 4.43(q,2H); 6.41(s,1H) ppm.

EXAMPLE 91

(R)-2-[2-Acetylamino-2-(3-methyl-1,2, 4-oxadiazol-5-yl)-ethylsulfanyl-methyl]-3-(tert-butyl -dimethylsilanyloxy)-6-chloro-5-methoxy-benzoic acid methyl ester was subjected in an analogous manner to the procedure described in Example 1 to yield (R)-2-[2-acetylamino-2-(3-methyl-1, 2,4-oxadiazol-5-yl)-ethylsulfanylmethyl]-6-chloro-3-hydroxy-5-methoxy-benzoic acid methyl ester as a yellow solid.

$^1$H-NMR (250 MHz,CDCl$_3$): δ 2.08(s,3H); 2.39(s,3H); 2.89(dd,J=14 Hz and 4 Hz,1H); 3.05(dd,J=14 Hz and 4 Hz,1H); 3.71(d,J=14 Hz,1H); 3.82 (d,J=14 Hz,1H); 3.84(s, 3H); 3.95(s,3H); 5.60(m,1H); 6.51(d,J=8 Hz,1H); 6.57(s, 1H) ppm.

The starting material used above was prepared as follows:

(a) To a solution of 60 mg of 3-hydroxy-5-methoxy-2-methyl-benzoic acid methyl ester in 5 ml of N,N-dimethylformamide was added over 10 min a solution of 40 mg of N-chlorosuccinimide in 2 ml of N,N-dimethylformamide. The mixture was stirred at room temperature for 20 h and then evaporated in vacuo. The residue was chromatographed on silica gel using dichloromethane/methanol (50:1, v/v) as eluent to give after crystallization from dichloromethane/methanol 57 mg of 2-chloro-5-hydroxy-3-methoxy-6-methyl -benzoic acid methyl ester as white crystals, m.p. 92° C.

(b) 2-Chloro-5-hydroxy-3-methoxy-6-methyl -benzoic acid methyl ester was subjected in analogous manner to a sequence of procedures described in Example 33(*a*) and 6(*a*) to yield 2-bromomethyl-6-chloro-3-(tert-butyl-dimethylsilanyloxy)-5-methoxybenzoic acid methyl ester which was reacted with (R)-N-[2-mercapto-1-(3-methyl-1,2,4-oxadiazol-5-yl)-ethyl]-acetamide in an analogous manner to the procedure described in Example 6(*b*) to yield (R)-2-[2-acetylamino-2-(3-methyl-1,2,4-oxadiazol-5-yl)-ethylsulfanylmethyl]-3-(tert-butyl-dimethylsilanyloxy)-6-chloro-5-methoxy-benzoic acid methyl ester as a pale yellow oil.

$^1$H-NMR (250 MHz,CDCl$_3$): δ 0.26(s,3H); 0.29(s,3H); 1.02(s,9H); 2.00(s,3H); 2.38(s,3H); 2.87(dd,J=14 and 5 Hz,1H); 3.22(dd,J=14 and 4 Hz,1H); 3.58(d,J=14 Hz,1H); 3.82(d,J=14 Hz,1H); 3.86(s,3H); 3.97 (s,3H); 5.47(m,1H); 6.46(s,1H); 6.58(d,J=8 Hz,1H) ppm.

EXAMPLE 92

The product of Example 91(b) was subjected in an analogous manner to the procedures described in Example 2 to yield (R)-2-chloro-5-hydroxy-3-methoxy-6-[2-(3-methyl-1,2,4-oxadiazol-5-yl)-2-thio-acetylamino -ethylsulfanylmethyl]-benzoic acid methyl ester as a white solid.

$^1$H-NMR (250 MHz,CDCl$_3$): δ 2.41(s,3H); 2.62(s,3H); 3.15(m,2H); 3.69 (d,J=14 Hz,1H); 3.81(d,J=14 Hz,1H); 3.88(s,3H); 3.98(s,3H); 6.23(m,1H); 6.56(s,1H); 8.15(d,J=8 Hz,1H) ppm.

EXAMPLE 93

By operating in an analogous manner, 2-fluoro-3-methoxy-6-methyl-5-[dimethyl-(1,1,2-trimethyl -propyl)-silanyloxy]-benzoic acid methyl ester was subjected to a sequence of procedures described in Example 90 to yield (R)-2-fluoro-5-hydroxy-3-methoxy-6-[2-(3-methyl-1,2,4-oxadiazol-5-yl)-2-thiophen-2-ylcarbonylamino-ethylsulfanylmethyl ]-benzoic acid methyl ester as an amorphous solid.

MS m/z: (M–H)$^-$=480.3

The starting material used above was prepared as follows:

(a) To a solution of 2.0 g of 3,5-dihydroxybenzoic acid methyl ester in 70 ml of acetonitrile were added at 0° C. 4.2 g of N-fluoro-N-chloro-methyl-triethylenediamine bis-tetrafluoroborate. The mixture was stirred for 1 h at 0° C. and then for 18 h at 20° C. The mixture was evaporated in vacuo and the residue Was partitioned between ethyl acetate and brine. The organic layer was dried over sodium sulfate and evaporated in vacuo to yield 2.0 g of crude 2-fluoro -3,5-dihydroxybenzoic acid methyl ester as a red oil (MS m/z: M$^+$=186). This material was subjected in an analogous manner to a sequence of procedures described in Example 1(a,b,c, and f) to yield 5-[dimethyl-(1,1,2-trimethyl-propyl)-silanyloxy]-2-fluoro-6-formyl-3-methoxy-benzoic acid methyl ester as a colorless oil.

$^1$H-NMR (250 MHz,CDCl$_3$): δ 0.18(s, 6H); 0.80(d,6H); 0.85(s,6H); 1.60(m,1H); 3.78(s,3H); 3.83(s,3H); 6.29(d, 1H); 10,07(d,1H) ppm.

(b) To a solution of 1.3 g of 2-fluoro-6-formyl -3-methoxy-5-[dimethyl-(1,1,2-trimethyl-propyl)-silanyloxy]-benzoic acid methyl ester in 4 ml of trifluoroacetic acid, cooled to 0° C., was added over 10 min a solution of 0.6 g of triethylsilane in 4 ml of dichloromethane. The solution was kept at 0° C. for 18 h and then evaporated in vacuo. The residue was taken up in ethyl acetate and the solution was successively washed with water, saturated sodium carbonate solution and brine, and dried over sodium sulfate. The solvent was evaporated in vacuo and the residue was chromatographed on silica gel using ethyl acetate/hexane (1:3, v/v) as eluent to yield 1.1 g of 2-fluoro-3-methoxy-6-methyl-5-[dimethyl -(1,1,2-trimethyl-propyl)-silanyloxy]-benzoic acid methyl ester as colorless oil.

$^1$H-NMR (250 MHz,CDCl$_3$): δ 0.23(s,3H); 0.94(d,6H); 0.98(s,6H); 1.75(m,1H); 2.10(s,3H); 3.83(s,3H); 3.93(s,3H); 6.46(d,1H) ppm.

EXAMPLE 94

By operating in an analogous manner, 2-chloro-6-methyl -3-methoxy-5-[dimethyl-(1,1,2-trimethyl-propyl) -silanyloxy]-benzoic acid methyl ester was subjected to a sequence of procedures described in Example 90 to yield (R)-2-chloro-5-hydroxy-3-methoxy-6-[2-(3-methyl-1,2,4-oxadiazol-5-yl)-2-thiophen-2-ylcarbonylaminoethylsulfanylmethyl]-benzoic acid methyl ester as an amorphous solid.

MS m/z: (M–H)$^-$=496.2

The starting material used above was prepared as follows:

(a) The product of Example 91(a) was subjected in an analogous manner to the procedure described in Example 1(f) to yield 2-chloro-6-methyl-3-methoxy-5-[dimethyl-(1,1,2-trimethyl -propyl)silanyloxy]-benzoic acid methyl ester as colorless oil.

$^1$H-NMR (250 MHz,CDCl$_3$): δ 0.25(s,6H); 0.94(d,6H); 0.98(s,6H); 1.76(m,1H); 2.07(s,3H); 3.83(s,3H); 3.94(s,3H); 6.44(s,1H) ppm.

EXAMPLE 95

2-Hydroxy-4-methoxy-5-methyl-6-(3-methyl-1,2,4-oxadiazol-5-yl)-benzaldehyde and (R)-N-[2-mercapto-1-(3-methyl-1,2,4-oxadiazol-5-yl) -ethyl]-acetamide were subjected in an analogous manner to the procedure described in Example 1(g) to yield (R)-N-[2-[6-hydroxy-4-methoxy-3-methyl-2-(3-methyl -1,2,4-oxadiazol-5-yl)benzylsulfanyl]-1-(3-methyl-1,2,4-oxadiazol-5-yl)-ethyl]-acetamide as an oil.

$^1$H-NMR (250 MHz,CDCl$_3$): δ 1.98(s,3H); 2.06(s,3H); 2.39(s,3H); 2.52(s,3H); 2.87(dd,J=14 Hz and 7 Hz,1H); 2.96(dd,J=14 Hz and 6 Hz,1H); 3.66 (d,J=14 Hz,1H); 3.82(s, 3H); 3.88(d,J=14 Hz,1H); 5.60(m,1H); 6.49(d,J=8 Hz,1H); 6.60(s,1H) ppm.

The starting material used above was prepared as follows:

(a) 3,5-Dimethoxy-2-methyl-benzoic acid and acetamidoxime were subjected in an analogous manner to the procedures described in Example 1(l) to yield after crystallization from dichloromethane/ethanol 3,5-dimethoxy-2-methyl-1-(3-methyl-1,2,4-oxadiazol-5-yl)-benzene as pale yellow crystals, m.p. 70° C.

(b) To a solution of 4.06 g of N-methyl-formanilide in 10 ml of dichloro-methane were added 4.6 g of phosphoryl chloride. The solution was stirred for 1.5 h at room temperature, and then, a solution of 4.68 g of 3,5-dimethoxy-2-methyl-1-(3-methyl-1,2,4-oxadiazol-5-yl)-benzene in 10 ml of dichloromethane was added. The mixture was heated for 72 h at reflux temperature. After cooling, the mixture was poured into ice-water and subsequently extracted with dichloromethane. The organic layer was washed with saturated sodium carbonate solution and water. The organic layer was dried over sodium sulfate and the solvent was evaporated in vacuo. The solid residue was crystallized from dichloromethane to yield 4.0 g of 2-formyl-3,5-dimethoxy-6-(3-methyl-1,2,4-oxadiazol-5-yl)-benzene as white crystals, m.p. 182°–183° C.

(c) To a solution of 4 g of the product of Example 95(b) in 50 ml of dichloromethane, cooled to –20° C., were added 4.2 g of boron tribromide. The solution was stirred for 6 h at 0° C. followed by 3 h at room temperature. The mixture was poured into ice-water and subsequently extracted with dichloromethane. The organic layer was washed with brine, dried over sodium sulfate, and the solvent was evaporated in vacuo. The residue was chromatographed on silica gel using ethyl acetate/hexane (1:1, v/v) as eluent to yield after crystallization from ethyl acetate/hexane 2.9 g of 2-hydroxy-4-methoxy-5-methyl-6-(3-methyl-1,2,4-oxadiazol-5-yl)-benzaldehyde as white crystals, m.p. 135°–136° C.

EXAMPLE 96

By operating in an analogous manner, 108 mg of the product of Example 95 were subjected to a sequence of procedures described in Example 33(a) and Example 2 to yield 28 mg of (R)-N-[2-[6-hydroxy-4-methoxy-3-methyl-2-(3-methyl-1,2,4-oxadiazol-5-yl)-benzylsulfanyl]-1-(3-methyl-1,2,4-oxadiazol-5-yl)-ethyl]-thioacetamide as a white solid.

$^1$H-NMR (250 MHz,CDCl$_3$): δ 1.98(s,3H); 2.40(s,3H); 2.54(s,3H); 2.59(s,3H); 3.12(m,2H); 3.66(d,J=14 Hz,1H); 3.77(d,J=14 Hz,1H); 3.83(s,3H); 6.17(m,1H); 6.58(s,1H); 8.16(d,J=8 Hz,1H) ppm.

EXAMPLE 97

To a solution of 8 mg of (R)-2-[2-acetylamino-2-(3-methyl-1,2,4-oxadiazol-5-yl)-]-3-[(tert-butyl-dimethylsilanyloxy)-5-methoxy-6-methyl -ethylsulfanylmethyl]-benzoic acid amide in 3 ml of dichloromethane, cooled to 0° C., was added a solution of 3.3 mg of triethylamine and 3.2 mg of trichloroacetyl chloride in 0.5 ml of dichloromethane. The solution was stirred for 15 min at room temperature. Water was added and the mixture was extracted with dichloromethane. The organic layer was washed successively with 5% sodium hydroxide solution, 5% aqueous sulfuric acid and brine, and dried over sodium sulfate. The solvent was evaporated in vacuo and the residue was subjected in an analogous manner to the procedure described in Example 1 to yield 5 mg of crude (R)-N-[2-(2-cyano-6-hydroxy-4-methoxy-3-methyl -benzylsulfanyl]-1-(3-methyl-1,2,4-oxadiazol-5 -yl)-ethyl]-acetamide as a yellow solid.

$^1$H-NMR (250 MHz,CDCl$_3$): δ 2.12(s,3H); 2.33(s,3H); 2.42(s,3H); 2.92 (dd,J=14 Hz and 6 Hz,1H); 3.11(dd,J=14 Hz and 6 Hz,1H); 3.81(s,3H); 5.66(m,1H); 6.47(d,J=8 Hz,1H); 6.61(s,1H) ppm.

The starting material used above was prepared as follows:

(a) By operating in an analogous manner, the product of Example 33(a) and (R)-N-[2-mercapto-1-(3-methyl-1,2,4-oxadiazol-5-yl)ethyl]-acetamide were subjected to the procedure described in Example 1(g), and the resulting product was subjected in an analogous manner to the procedure described in Example 1(j) to yield (R)-2-[2-acetylamino-2-(3-methyl-1,2,4-oxadiazol-5-yl)-ethylsulfanylmethyl]-3-[(tert-butyl-dimethylsilanyloxy)-5-methoxy-6-methyl -benzoic acid as a foam.

$^1$H-NMR (250 MHz,CDCl$_3$): δ 0.24(s,3H); 0.27(s,3H); 1.01(s,3H); 2.02(s,3H); 2.17(s,3H); 2.37(s,3H); 3.06(m,2H); 3.73(d,J=12 Hz,1H); 3.78(s,3H); 4.01(d,J=12 Hz,1H); 5.21(m,1H); 6.39(s,1H); 6.70(d,J=8 Hz,1H) ppm.

(b) To a solution of 100 mg of the product of Example 97(a) in 7 ml of acetonitrile were added 16 mg of triethylamine and 59 mg of 1-hydroxy-benzotriazole. The solution was stirred for 1.5 h and then evaporated in vacuo. The residue was partitioned between ethyl acetate and water, the organic layer was dried over sodium sulfate o and evaporated in vacuo to yield 105 mg of (R)-2-[2-acetylamino-2-( 3-methyl-1,2,4-oxadiazol-5-yl)-ethylsulfanylmethyl]-3-[(tert-butyl-dimethylsilanyloxy)-5-methoxy-6-methyl-benzoic acid benzotriazol-1-yl ester as a yellow foam.

$^1$H-NMR (250 MHz,CDCl$_3$): δ 0.30(s,3H); 0.32(s,3H); 1.06(s,9H); 2.00(s,3H); 2.27(s,3H); 2.44(s,3H); 3.12(dd,J= 14 Hz and 5 Hz,1H); 3.28(dd,J=14 Hz and Hz,1H); 3.85(s, 3H); 3.90(d,J=13 Hz,1H); 4.02(d,J=13 Hz,1H); 5.50(m,1H); 6.55(s,1H); 6.93(d,J=8 Hz,1H); 7.40–7.70(m,3H); 8.13(d, J=8 Hz,1H) ppm.

(c) A solution of 75 mg of the product of Example 97(b) in 15 ml of tetrahydrofuran was saturated at 0° C. with dry ammonia. The solution was stirred for 3 h at 0° C. and then evaporated in vacuo. The residue was partitioned between diethyl ether and water, the organic layer was dried over sodium sulfate and evaporated in vacuo, and the crude product was chromatographed on silica gel using dichloromethane/methanol (20:1 v/v) as eluent to yield 25 mg of (R)-2-[2-acetylamino-2-(3-methyl-1,2,4-oxadiazol-5-yl) -ethylsulfanylmethyl]-3-[(tert-butyl-dimethylsilanyloxy)-5-methoxy-6-methyl-benzoic acid amide as a yellow foam.

$^1$H-NMR (250 MHz,CDCl$_3$): δ 0.24(s,3H); 0.27(s,3H); 1.01(s,9H); 1.98(s,3H); 2.17(s,3H); 2.36(s,3H); 3.13(m,1H); 3.66(d,J=14 Hz,1H); 3.77(s,3H); 3.93 (d,J=14 Hz,1H); 5.25(m,1H); 5.98(broad s,1H); 6.29(broad s,1H); 6.37(s, 1H); 6.75(d,J=8 Hz,1H) ppm.

EXAMPLE 98

By operating in an analogous manner, the product of Example 33(b) was reacted with thiophene-2-carboxylic acid as described in Example 1(h) and the resulting product was subjected in analogous manner to a sequence of procedures described in Examples 1(j), 97(b,c) and 97, to yield (R)-N-[2-(2-cyano-6-hydroxy-4-methoxy-3-methyl-benzylsulfanyl]-1-(3-methyl-1,2,4-oxadiazol-5-thiophene -carboxamide as a white solid.

MS m/e: (M–H)$^-$=443.6

EXAMPLE 99

(R)-3-(tert-Butyl-dimethylsilanyloxy)-5-methoxy-6-methyl-2-[2-(3-methyl-1,2,4-oxadiazol-5-yl)-2-thioacetylamino-ethylsulfanylmethyl]-benzoic acid 2-methoxy-ethyl ester was subjected in an analogous manner to the procedure described in Example 1 to yield (R)-3-hydroxy-5-methoxy-6-methyl-2-[2-(3-methyl-1,2,4-oxadiazol-5-yl)-2-thioacetylamino-ethylsulfanylmethyl]-benzoic acid 2-methoxy-ethyl ester as a colorless oil.

$^1$H-NMR (250 MHz,CDCl$_3$): δ 2.08(s,3H); 2.37(s,3H); 2.54(s,3H); 3.07 (dd,J=14 Hz and 7 Hz,1H); 3.17(dd,J=14 Hz and 6 Hz,1H); 3.39(s,3H); 3.65–3.78(m,5H); 3.85–3, 97(m,2H); 4.50(m,2H); 6.12(m,1H); 6.49(broad s,2H) ppm.

The starting material used above was prepared as follows:

(a) A mixture of 100 mg of the product of Example 97(b), 36 mg of 2-methoxy-ethanol, 54 mg of triphenylphosphine and 41 mg of diethyl azodi-carboxylate in 10 ml of tetrahydrofuran was stirred for 20 h at room temperature. The solvent was evaporated in vacuo and the residue was chromatographed on silica gel using ethyl acetate/hexane (4:1, v/v) as eluent to yield 58 mg of (R)-3-(tert-butyl-dimethylsilanyloxy)-5-methoxy-6-methyl-2-[2-(3-methyl-1,2,4-oxadiazol-5-yl)-2 -thioacetylamino-ethylsulfanylmethyl]-benzoic acid 2-methoxy-ethyl ester as a yellow oil.

$^1$H-NMR (250 MHz,CDCl$_3$): δ 0.23(s,3H); 0.28(s,3H); 1.02(s,9H); 1.92(s,3H); 2.10(s,3H); 2.36(s,3H); 2.78(dd,J= 14 Hz and 5 Hz,1H); 3.28(dd,J=14 Hz and 6 Hz,1H); 3.38(s, 3H); 3.64(d,J=14 Hz,1H); 3.72(m,2H); 3.78(s,3H); 3.94 (d,J=14 Hz,1H); 4.49(m,2H); 5.40(m,1H); 6.36(s,1H); 6.78(d,J=8 Hz,1H) ppm.

EXAMPLES 100–107

By operating in an analogous manner, the product of Example 23 was subjected to the procedure described in Example 26, but replacing propylamine by 5-amino-pentanol, 2-(2-amino -ethoxy)-ethanol, (S)-2-amino-propan-1-ol, (R)-2-amino-3-methyl-butan-1-ol, 2-(dimethylamino)-ethylamine, 2-pyrrolidin-1-yl -ethylamine, N-isopropyl-ethane-1,2-diamine, 4-amino-1-(dimethylamino)-but-2-yne, respectively, the following compounds were prepared:

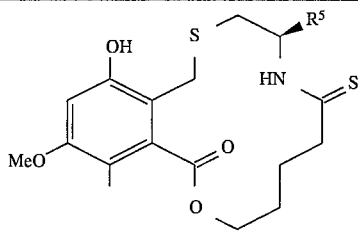

| Example No | R⁵ | Mass spectrum: m/e |
|---|---|---|
| 100 | CONH(CH₂)₅OH | $(M + H)^+ = 499.4$ |
| 101 | CONH(CH₂)₂O(CH₂)₂OH | $(M - H)^- = 499.4$ |
| 102 | CONH-CH(CH₂OH)- | $(M - H)^- = 497.3$ |
| 103 | CONH-CH(CH₂OH)-CH(CH₃)₂ | $(M - H)^- = 469.5$ |
| 104 | CONH-CH₂CH₂-N(CH₃)- | $(M + H)^+ = 484.5$ |
| 105 | CONH-CH₂CH₂-(pyrrolidinyl) | $(M - H)^- = 508.4$ |
| 106 | CONH-CH₂CH₂-NH-CH(CH₃)₂ | $(M + H)^+ = 498.4$ |
| 107 | CONH—CH₂—≡—CH₂—N< | $(M + H)^+ = 508.0$ |

EXAMPLES 108 AND 109

By operating in an analogous manner, the product of Example 22 was subjected to the procedure described in Example 26, but replacing propylamine by 2-(N,N-diiso-propylamino)-ethylamine or 2-pyridin-2-yl-ethylamine, respectively, the following compounds were prepared:

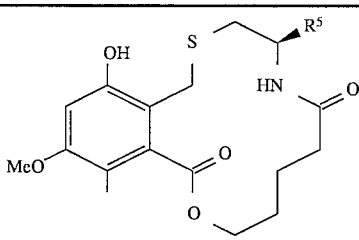

| Example No | R⁵ | Mass spectrum: m/z |
|---|---|---|
| 108 | CONH(CH₂)₂—N[CH(CH₃)₂]₂ | $(M + H)^+ = 522.4$ |
| 109 | CONH-CH₂CH₂-(2-pyridyl) | $(M - H)^- = 500.3$ |

EXAMPLES 110 AND 111

To a solution of 110 mg of the product of Example 33(c) in 4 ml of dichloromethane were added at 0° C. 63 mg of 55% 3-chloro-perbenzoic acid. The solution was stirred at 0° C. for 30 minutes, then diluted with dichloromethane, washed successively with saturated sodium bicarbonate solution and brine, dried over sodium sulfate and evaporated in vacuo. The residual oil was treated with ammonium fluoride in methanol in an analogous manner to the procedure described in Example 1 to yield, after chromatographic separation on silica gel using dichloromethane/methanol (50:1, v/v) as eluent, (2R,4R )-16-hydroxy-14-methoxy-13-methyl -4-(3-methyl-1,2,4-oxadiazol-5-yl)-2-oxo -1,3,4,5,6,7,8,9,10,12-decahydro-11,2,5-benzoxathiaazacyclotetradecin-6,12-dione (Example 110) and (2S,4R)-16-hydroxy-14-methoxy-13-methyl-4-(3-methyl-1,2,4-oxadiazol-5-yl)- 2-oxo-1,3,4,5,6,7,8,9,10,12-decahydro-11,2,5-benzoxathi-aazacyclotetradecin-6,12-dione (Example 111) as white solids.

MS m/z: $(M-H)^- = 432.3$

EXAMPLE 112

2-Chloro-5-[dimethyl-(1,1,2-trimethyl-propyl) -silanyloxy]-6-iodomethyl-3-methoxy-benzoic acid allyl ester was reacted with the product of Example 1(m) in an analogous manner to the procedure described in Example 6(b), the resulting product was acylated with 5-trityloxy-pentanoic acid in an analogous manner as described in Example 1(*h*), and the resulting product was subjected in an analogous manner to a sequence of procedures described in Examples 1(*i,j,k*) and in Example 1 to yield (R)-13-chloro-16-hydroxy-14-methoxy -6,12-dioxo-1,3,4,5,6,7,8,9,10,12-decahydro-11,2,5-benzoxathiaazacyclotetradecine-4-carboxylic acid methyl ester as a white solid.

MS m/z: (M–H)⁻=430.3 and 432.3 (2:1)

The starting material used above was prepared as follows:
(a) 2-Chloro-6-formyl-3,5-dimethoxy-benzoic acid methyl ester was subjected in an analogous manner to a sequence of procedures described in Examples 1(*c, d, e, f*) to yield 2-chloro -5-[dimethyl-( 1,1,2-trimethyl-propyl)-silanyloxy]-6-formyl-3-methoxy benzoic acid allyl ester as a white solid, m.p. 97° C.

(b) To a solution of 3.3 g of 2-chloro-5-[dimethyl-(1,1,2-trimethyl-propyl)-silanyloxy]-6-formyl-3-methoxy-benzoic acid allyl ester in 4 ml of acetonitrile were added 1.8 g of sodium iodide and 1.6 ml of trimethyl-chlorosilane. A white precipitate occurred. The mixture was stirred for 5 min at 20° C. The suspension was cooled to 0° C. and 1.48 ml of tetramethyldisiloxane were added. The mixture was stirred for hours at 0° C. and then partitioned between 20 ml of ethyl acetate and 20 ml of water. The aqueous phase was extracted twice with 20 ml of ethyl acetate. The organic layer was dried over sodium sulfate and the solvent was evaporated in vacuo. The residue was chromatographed on silica gel using diethyl ether/hexane (3:1, v/v) as eluent to afford 3.39 g of 2-chloro-5-[dimethyl-(1,1,2-trimethyl-propyl)-silanyloxy]-6-iodomethyl-3-methoxy-benzoic acid allyl ester as a colorless oil.

¹H-NMR (250 MHz,CDCl₃): δ 0.36(s,6H); 0.95(s,3H): 0.98(s,3H); 1.04(s,6H); 1.62(sept,1H), 3.84(s,3H); 4.39(s, 2H); 4.90–4.92(m,2H); 5.30–5.36(m,1H); 5.50–5.53(m, 1H); 6.05–6.20(1H,m); 8.43(s,1H) ppm.

EXAMPLE 113

(R)-13-Chloro-14-methoxy-16-[dimethyl-(1,1,2 -trimethyl-propyl)-silanyloxy]-6,12-dioxo-1,3,4,5,6,7,8,9, 10,12-decahydro-11,2,5-benzoxathiaazacyclotetradecine-4-carboxylic acid methyl ester was subjected in an analogous manner to the procedures described in Example 2 to yield (R)-13-chloro-16-hydroxy-14-methoxy-12-oxo-6-thioxo-1, 3,4,5,6,7,8,9,10,12-decahydro-11,2,5-benzoxathiaazacyclotetradecine-4-carboxylic acid methyl ester as a white solid.

MS m/z: (M–H)⁻=446.3 and 448.3 (2:1)

EXAMPLE 114

2-Bromo-6-formyl-3,5-dimethoxy-benzoic acid methyl ester was subjected in an analogous manner to a sequence of procedures described in Examples 1(*c, d, e, f*), 112(*b*) and 112 to yield (R)-13-bromo-16-hydroxy-14-methoxy-6,12-dioxo-1,3,4,5,6,7,8,9,10,12-decahydro-11,2, 5-benzoxathiaazacyclotetradecine-4-carboxylic acid methyl ester as a white solid.

MS m/z: (M–H)⁻=474.1 and 476.1 (1:1)

EXAMPLE 115

To a solution of 60 mg of the product of Example 68 in 1.2 ml of dioxane were added at 0° C. 36 mg of pyridine and 95 mg of trifluoroacetic acid anhydride. The mixture was allowed to warm to 20° C. within 5 min and stirring was continued for 15 min at 20° C. Ethyl acetate was added and the mixture Was washed successively with 1N hydrochloric acid, 5% sodium carbonate solution and brine. The organic layer was dried over sodium sulfate and the solvent was evaporated in vacuo. The solid residue was purified by chromatography on silica gel using hexane/ethyl acetate (1:2, v/v) as eluent, to yield 21 mg of (R)-4-cyano-16-hydroxy-14-methoxy-13-methyl-1,3,4,5,6,7,8,9,10,12-decahydro-11,2,5-benzoxathiaazacyclotetradecin-6,12-dione as a white solid.

MS m/z: (M+H)⁺=379.4

EXAMPLE 116

A solution of 12 mg of (R)-16-[dimethyl-(1,1,2-trimethyl-propyl)-silanyloxy]-14-methoxy-13-methyl-6,12-dioxo-1,3, 4,5,6,7,8,9,10,12-decahydro-11,2,5-benzoxathiaazacyclotetradecine-4-thiocarboxylic acid amide and 8 mg of 3-bromo-2-oxopropionic acid ethyl ester in 0.5 ml of tetrahydrofuran was stirred at 20° C. for 20 h. The solvent was evaporated in vacuo and the residue was subjected in an analogous manner to the procedure described in Example 1 to yield, after chromatographic purification using hexane/ethyl acetate (1:1, v/v) as eluent, 4 mg of (R)-4-(4-ethoxy-carbonyl-thiazol-2-yl)-16-hydroxy-14-methoxy-13-methyl-1,3,4,5,6,7,8,9,10,12-decahydro-11,2,5-benzoxathiaazacyclotetradecin-6,12-dione as a white solid.

MS m/z: (M–H)⁻=507.2

The starting material used above was prepared as follows:
(a) The product of Example 68 was subjected in an analogous manner to the procedure described in Example 1(*f*) and the resulting (R)-16-[dimethyl-(1,1, 2-trimethyl-propyl)-silanyloxy]-14-methoxy -13-methyl-6,12-dioxo-1,3,4,5,6,7,8,9,10,12-decahydro -11,2, 5-benzoxathiaazacyclotetradecine-4-carboxylic acid amide was reacted in toluene with an equimolar amount of 2,4-bis-(4-methoxyphenyl)-2,4-dithioxo-1,3,2,4-dithiaphosphetane at 60° C. for 30 min. The solvent was evaporated in vacuo, and the residue was chromatographed on silica gel using ethyl acetate/hexane (1:2, v/v) as eluent, to yield (R)-16-[dimethyl-(1,1,2-trimethyl-propyl)-silanyloxy]-14-methoxy-13-methyl-6,12-dioxo-1,3,4,5,6,7,8,9,10,12-decahydro-11,2,5-benzoxathiaazacyclotetradecine-4-thiocarboxylic acid amide as a white foam.

EXAMPLE 117

By operating in an analogous manner, the product of Example 117(*a*) was subjected to the procedure described in Example 1 to yield (4R,7S)-15-hydroxy-13-methoxy-12-methyl -4-[3-methyl-1,2,4-oxadiazol-5-yl]-6,11 -dioxo-3,4, 5,6,7,8,9,11-octahydro-1H-10,2,5-benzoxathiaazacyclotridecin-7-yl]-carbamic acid 1,1-dimethylethyl ester as a white solid.

MS m/z: (M–H)⁻=535.2

The starting material used above was prepared as follows:
(a) By operating in an analogous manner, the product of Example 1(*g*) was reacted with Boc-L-homoserine as described in the procedure of Example 1(*h*), and the resulting product was subjected to a sequence of procedures described in Example 1(*j, k*) to yield (4R,7S)-15-[dimethyl-(1,1,2-trimethyl-propyl) -silanyloxy]-13-methoxy-12-methyl-4-(3-methyl -1,2,4-oxadiazol-5-yl)-6,11-dioxo- 3,4,5,6,7,8,9,11-octahydro-1H-10,2,5- benzoxathiaazacyclotridecin-7-yl]-carbamic acid 1,1-dimethylethyl ester as an amorphous solid.

EXAMPLE 118

By operating in an analogous manner, the product of Example 118(a) was subjected to the procedure described in Example 1 to yield (4R,7S)-7-amino-15-hydroxy-13-methoxy-12-methyl-4-(3-methyl-1,2,4-oxadiazol-5-yl)-3,4,5,6,7,8,9,11-octahydro-10,2,5-benzoxathiaazacyclotridecin-6,11-dione as a white solid.

MS m/z: (M+H)$^+$=437.4

The starting material used above was prepared as follows:

(a) The product of Example 117(a) was subjected in an analogous manner to the procedure described in Example 72(b) to yield (4R,7S)-7-amino-15-[dimethyl-(1,1,2-trimethyl-propyl)-silanyloxy]-13-methoxy-12-methyl-4-(3-methyl-1,2,4-oxadiazol-5-yl)-3,4,5,6,7,8,9,11-octahydro-10,2,5-benzoxathiaazacyclotridecin -6,-dione as a white foam.

EXAMPLE 119

By operating in an analogous manner, the product of Example 119(a) was subjected to the procedure described in Example 1 to yield (4R,7S)-N-[15-hydroxy-13-methoxy-12-methyl-4-(3-methyl-1,2,4-oxadiazol-5-yl)-6,11-dioxo-3,4,5,6,7,8,9,11-octahydro-10,2,5-benzoxathiaazacyclotridecin-7-yl]-acetamide as a white solid.

MS m/z: (M+H)$^+$=479.2

The starting material used above was prepared as follows:

(a) The product of Example 118(a) was subjected in an analogous manner to the procedure described in Example 39(c) to yield (4R,7S)-N-[15-[dimethyl-(1,1,2-trimethyl-propyl)-silanyloxy]-13-methoxy-12-methyl-4-(3-methyl-1,2,4-oxadiazol-5-yl) -6,11-dioxo-3,4,5,6,7,8,9,10,11-octahydro-10,2,5-benzoxathiaazacyclotridecin-7-yl]-acetamide as an amorphous solid.

EXAMPLE 120

(4R,10S)-16-[Dimethyl-(1,1,2-trimethyl -propyl)-silanyloxy]-10-hydroxymethyl-14-methoxy-13-methyl-4-(3-methyl-1,2,4-oxadiazol-5-yl)-6-thioxo-1,3,4,5,6,7,8,9,10,12-decahydro-11,2,5 -benzoxathiaazacyclotetradecin-12-one was treated with ammonium fluoride in methanol in analogous manner to the procedure described in Example 1 to yield, after crystallization from ethyl acetate/hexane, (4R,10S)-16-hydroxy-10-hydroxymethyl-14-methoxy-13-methyl -4-(3-methyl-1,2,4-oxadiazol-5-yl)-6-thioxo-1,3,4,5,6,7,8,9,10,12-decahydro-11,2,5-benzoxathiaazacyclotetradecin-12-one as a white solid.

MS m/z: (M–H)$^-$=482.4

The starting material used above was prepared as follows:

(a) By operating in an analogous manner, the product of Example 1(g) was reacted with (R)-4-(2,2-dimethyl-1,3-dioxolan-4-yl)-butyric acid as described in Example 1(h). The resulting product was heated in 80% aqueous acetic acid to 60° C. for 30 min. The solvent was evaporated in vacuo and the residual crude 3-[dimethyl-(1,1, 2-trimethyl-propyl)-silanyloxy]-2-[(R)-2-[(R)-5,6-dihydroxyhexanoylamino]-2-(3-methyl-1,2,4-oxadiazol-5-yl)-ethylsulfanylmethyl]-5-methoxy-6-methyl-benzoic acid allyl ester was subjected in an analogous manner to a sequence of procedures described in Examples 15(b) and 1(j, k), the cyclization product was reacted in toluene with 2,4-bis-(4-methoxy-phenyl)-2,4 -dithioxo- 1,3,2,4-dithiaphosphetane in an analogous manner as described in Example 2, and the trityloxy group in the resulting product was cleaved using 4-toluene-sulfonic acid monohydrate in methanol at 60° C. as described in Example 6(c) to yield (4R,10S)-16-[dimethyl-(1,1,2-trimethyl-propyl)-silanyloxy]-10-hydroxymethyl-14 -methoxy-13-methyl-4-(3-methyl-1,2,4-oxadiazol-5-yl) -6-thioxo-1,3,4,5,6,7,8,9,10,12-decahydro-11,2,5-benzoxathiaazacyclotetradecin-12-one as an amorphous foam.

EXAMPLE 121

(S)-2-Allyloxycarbonylamino-propionic acid (4R,10S)-16-[dimethyl-(1,1,2-trimethyl-propyl)-silanyloxy]-14-methoxy -13-methyl-4-(3-methyl-1,2,4-oxadiazol-5-yl)-12-oxo-6-thioxo-1,3,4,5,6,7,8,9,10,12-decahydro-11,2,5-benzoxathiaazacyclotetradecin-10-yl ester was treated with ammonium fluoride in methanol in an analogous manner to the procedure described in Example 1. The resulting product was dissolved in ethyl acetate. Upon addition of 3N hydrochloric acid in diethyl ether, a precipitate formed which was collected to yield (S)-2-amino-propionic acid (4R,10S)-16-hydroxy-14-methoxy-13-methyl-4-(3-methyl-1,2,4-oxadiazol-5-yl)-12-oxo-6-thioxo-1,3,4,5,6,7,8,9, 10,12-decahydro-11,2,5-benzoxathiaazacyclotetradecin-10-yl ester hydrochloride as a white solid.

$^1$H-NMR (250 MHz,DMSO-d$_6$): δ inter alia 1.40(d,J=7 Hz,3H); 1.74–2.05 (m,4H) superimposed by 1.95(s,3H); 2.34(s,3H); 2.60–2.88(m,2H); 3.08 (dd,J=14 and 4 Hz,1H); 3.71(d,J=11 Hz,1H); 3.73(s,3H); 3.95 (d,J=11 Hz,1H); 4.11 (q,J=7 Hz,1H); 4.28–4.50(m,2H); 5.28(m,1H); 5.78(m,1H); 6.57(s,1H); 8.39(broad s,3H); 9,87(s,1H); 10.65(d,J=8 Hz,1H) ppm.

The starting material used above was prepared as follows:

(a) By operating in an analogous manner as described in Example 1(h), 154 mg of the product of Example 120(a) were reacted with 87 mg of N-allyloxycarbonyl-L-alanine to yield, after chromatographic purification on silica gel using ethyl acetate/hexane (1:1, v/v) as eluent, 130 mg of (S)-2-(allyloxycarbonylamino)-propionic acid (4R,10S)-16-[dimethyl-(1,1,2-trimethyl-propyl) -silanyloxy]-14-methoxy-13-methyl-4-(3-methyl -1,2,4-oxadiazol-5-yl)-12-oxo-6-thioxo-1,3,4, 5,6, 7,8,9,10,12-decahydro-11,2,5-benzoxathiaazacyclotetradecin -10-yl ester as a white foam. To a solution of this material in 2.5 ml of dichloromethane were added 118 mg of N,N-dimethyltrimethylsilylamine and 187 mg of trifluoroacetic acid trimethylsilyl ester. The solution was stirred at 20° C. for 5 min, then 12 mg of tetrakis(triphenylphosphine)palladium were added, and stirring was continued for 2 h. The mixture was evaporated in vacuo and the residue was dissolved in ethyl acetate. The solution was washed successively with saturated sodium bicarbonate solution and brine. The organic layer was dried over sodium sulfate and evaporated in vacuo and the residue was chromatographed on silica gel using ethyl acetate as eluent to yield 106 mg of (S)-2-amino-propionic acid (4R,10S)-16-[dimethyl-(1,1,2-trimethyl -propyl)-silanyloxy]-14-methoxy-13-methyl-4-(3-methyl-1,2,4-oxadiazol-5-yl)-12-oxo-6-thioxo-1,3,4,5,6, 7,8,9,10,12-decahydro-11,2,5-benzoxathiaazacyclotetradecin-10-yl ester as a white foam.

EXAMPLE 122

(4R,9R)-16-[Dimethyl-(1,1,2-trimethyl -propyl)-silanyloxy]-9-hydroxymethyl-14-methoxy-13-methyl-4-(3-methyl-1,2,4-oxadiazol-5-yl)-1,3,4,5,6,7,8,9,10,12-decahydro-11,2,5-benzoxathiaazacyclotetradecin-6,12-dione was treated with ammonium fluoride in methanol in an analogous manner to the procedure described in Example 1 to yield, after crystallization from ethyl acetate/hexane, (4R,9R)-16-hydroxy-9-hydroxymethyl-14-methoxy-13-methyl-4-(3-methyl-1,2,4-oxadiazol-5-yl)-1,3,4,5,6,7,8,9,10,12-decahydro-11,2,5-benzoxathiaazacyclotetradecin-6,12-dione as a white solid.

MS m/z: $(M+H)^+=466.4$

The starting material used above was prepared as follows:

(a) By operating in an analogous manner, 3-(2,2-dimethyl-1,3-dioxan-5-yl)-propionic acid ethyl ester was subjected to the procedure described in Example 9(d) to yield, after crystallization from dichloromethane/hexane, 3-(2,2-dimethyl-1,3-dioxolan-4-yl)-propionic acid as white crystals, m.p. 76°–77° C.

(b) By operating in an analogous manner, the product of Example 1(g) was reacted with 3-(2,2-dimethyl-1,3-dioxolan-4-yl)-propionic acid as described in Example 1(h). The resulting product was heated in 80% aqueous acetic acid to 60° C. for 30 min. The solvent was evaporated in vacuo and the residual crude 3-[dimethyl-(1,1,2-trimethyl -propyl)-silanyloxy]-2-[(R)-2-[5-hydroxy-4-hydroxymethyl -pentanoylamino]-2-(3-methyl-1,2,4-oxadiazol-5-yl) -ethylsulfanylmethyl]-5-methoxy-6-methyl-benzoic acid allyl ester was tritylated in an analogous manner as described in Example 15(b) to yield a mixture of -2-[(R)-2-[(R and S)-4-hydroxymethyl-5-trityloxy-pentanoylamino]-2-(3-methyl-1,2,4-oxadiazol-5-yl) -ethylsulfanylmethyl]-5-methoxy-3-[dimethyl-(1,1,2-trimethyl-propyl)-silanyloxy]-6-methyl -benzoic acid allyl ester. This mixture was subjected in an analogous manner to a sequence of procedures described in Examples 1(j, k) to yield, after chromatographic separation on silica gel using ethyl acetate/hexane (1:1, v/v) as eluent, (4R,9S)-16-[dimethyl -(1,1,2-trimethyl-propyl)-silanyloxy]-9-trityloxymethyl -14-methoxy-13-methyl-4-(3-methyl-1,2,4-oxadiazol-5-yl)-1,3,4,5,6,7,8,9,10,12-decahydro -11,2,5-benzoxathiaazacyclotetradecin-6,12-dione (less polar product), and (4R,9R)-16-[dimethyl-(1,1,2-trimethyl -propyl)-silanyloxy]-9-trityloxymethyl-14-methoxy-13 -methyl-4-(3-methyl-1,2,4-oxadiazol-5-yl) -1,3,4,5,6,7,8,9,10,12-decahydro-11,2,5-benzoxathiaazacyclotetradecin-6,12-dione (more polar product), as white foams.

(c) (4R,9R)-16-[Dimethyl-(1,1,2-trimethyl-propyl)-silanyloxy]-9-trityloxymethyl-14-methoxy-13-methyl-4-(3-methyl-1,2,4-oxadiazol- 5-yl)-1,3,4,5,6,7,8,9,10,12-decahydro-11,2,5-benzoxathiaazacyclotetradecin-6,12-dione was treated with 4-toluenesulfonic acid monohydrate in methanol at 20° C. for 30 min to yield (4R,9R)-16-[dimethyl-(1,1,2-trimethyl-propyl)-silanyloxy]-9-hydroxymethyl-14-methoxy-13-methyl-4-(3-methyl-1,2,4-oxadiazol-5-yl)-1,3,4,5,6,7,8,9,10,12-decahydro-11,2,5-benzoxathiaazacyclotetradecin-6,12-dione as a white foam.

EXAMPLE 123

(4R,9S)-16-[Dimethyl-(1,1,2-trimethyl -propyl)-silanyloxy]-9-hydroxymethyl-14-methoxy-13-methyl-4-(3-methyl-1,2,4-oxadiazol-5-yl)-6-thioxo-1,3,4,5,6,7,8,9,10,12-decahydro-11,2, 5-benzoxathiaazacyclotetradecin-12-one was treated with ammonium fluoride in methanol in an analogous manner to the procedure described in Example 1 to yield, after crystallization from ethyl acetate/hexane, (4R,9S)-16-hydroxy-9-hydroxymethyl-14-methoxy-13-methyl-4-(3-methyl-1,2,4-oxadiazol -5-yl)-6-thioxo-1,3,4,5,6,7,8,9,10,12-decahydro-11,2,5-benzoxathiaazacyclotetradecin-12-one as a white solid.

MS m/z: $(M+H)^+=482.3$

The starting material used above was prepared as follows:

(a) The products of Example 122(b) were treated with 2,4-bis-(4-methoxyphenyl)-2,4-dithioxo-1,3,2,4-dithiaphosphetane in toluene in an analogous manner as described in Example 2 and the resulting products were subjected in an analogous manner to the procedure described in Example 122(c) to yield, after chromatographic separation on silica gel using ethyl acetate/hexane (1:1, v/v) as eluent, (4R,9S)-16-[dimethyl-(1,1,2-trimethyl-propyl) -silanyloxy]-9-hydroxymethyl-14-methoxy-13-methyl -4-(3-methyl-1,2,4-oxadiazol-5-yl)-6-thioxo-1,3,4,5,6,7,8,9,10,12-deca-hydro-11,2,5-benzoxathiaazacyclotetradecin-12-one (less polar product) and (4R,9R)-16-[dimethyl(1,1,2-trimethylpropyl)-silanyloxy]-9-hydroxymethyl-14-methoxy-13-methyl-4-(3-methyl-1,2,4-oxadiazol-5-yl) -6-thioxo-1,3,4,5,6,7,8,9,10,12-deca-hydro-11,2,5-benzoxathiaazacyclotetradecin-12-one (more polar product), as white foams.

EXAMPLE 124

4-Aminomethyl-benzoic acid (4R,9S)-14-methoxy-13-methyl-4-( 3-methyl-1,2,4-oxadiazol-5-yl)-16-[dimethyl -(1,1,2-trimethyl-propyl)-silanyloxy]-12-oxo-6-thioxo-1,3,4,5,6,7,8,9,10,12-decahydro-11,2,5-benzoxathiaazacyclotetradecin-9-ylmethyl ester was treated with ammonium fluoride in methanol in an analogous manner to the procedure described in Example 1, and the resulting product was treated in methanol with a 3N solution of hydrochloric acid in diethyl ether to yield 4-aminomethyl-benzoic acid (4R, 9S)-16-hydroxy-14-methoxy-13-methyl-4-(3-methyl -1,2,4-oxadiazol-5-yl)-12-oxo-6-thioxo-1,3, 4,5,6,7,8,9,10,12-decahydro-11,2,5-benzoxathiaazacyclotetradecin-9-ylmethyl ester hydrochloride as white solid.

MS m/z: $(M-HCl-H)^-=613.1$

The starting material used above was prepared as follows:

(a) To a solution of 7.55 g of 4-(aminomethyl)-benzoic acid in 50 ml of 1N sodium hydroxide solution were added at 6°–8° C. over 1.5 h 6.55 g of allyl chloroformate. Stirring was continued at 0° C. for 0.5 h and the mixture was then extracted with 60 ml of diethyl ether. The organic phase was extracted with 20 ml of saturated sodium carbonate solution and the combined aqueous layers were then acidified to pH 1.8 by the addition of 12N sulfuric acid and subsequently extracted with ethyl acetate. The ethyl acetate extract was washed with brine, dried over sodium sulfate, and the solvent was evaporated in vacuo. The solid residue was crystallized from ethyl acetate/hexane to yield 7.61 g of 4-(allyloxycarbonylaminomethyl)-benzoic acid as a white solid, m.p. 175°–177° C.

(b) To a solution of 255 mg of (4R,9S)-9-hydroxymethyl-14-methoxy-16-[dimethyl-(1,1,2-trimethyl-propyl)-silanyloxy]-13-methyl-4-(3-methyl-1,2,4-oxadiazol-5-yl)-6-thioxo-1,3,4,5,6,7,8,9,10,12-decahydro-11,2,5- benzoxathiaazacyclotetradecin-12-one and 142 mg of 4-(allyloxycarbonylaminomethyl) -benzoic acid in a mixture of 3 ml of dichloromethane and 3 ml of acetonitrile were added at 0° C. 70 mg of 4-dimethylamino -pyridine and 115 mg of N-(dimethylaminopropyl)-N'-ethyl -carbodiimide hydrochloride. The mixture was stirred at 0° C. for 6 h, then diluted with 30 ml of ethyl acetate, and washed successively with 1N hydrochloric acid, water, 5% sodium bicarbonate solution, and brine. The organic layer was dried over sodium sulfate and evaporated in vacuo. The residue was chromatographed on silica gel using ethyl acetate/hexane (1:1, v/v) as eluent to yield 156 mg of an amorphous foam.

(c) To a solution of 156 mg of the material obtained in Example 124(b) in 2 ml of dichloromethane were added 140 mg of N,N-dimethyltrimethylsilylamine, 223 mg of trifloroacetic acid trimethylsilyl ester, and 68 mg of tetrakis(triphenylphosphine) palladium. The mixture was stirred at 20° C. for 6 h under an argon atmosphere, subsequently diluted with ethyl acetate and washed successively with 5% sodium bicarbonate solution and brine. The organic layer was dried over sodium sulfate and evaporated in vacuo. The residue was chromatographed on silica gel using dichloromethane/2-propanol/methanol (4:4:1, v/v/v) as ehent to yield 68 mg of 4-aminomethyl-benzoic acid (4R, 9S)-14-methoxy-13-methyl-4-(3-methyl-1,2,4-oxadiazol -5-yl)-16-[dimethyl-(1,1,2-trimethyl-propyl) -silanyloxy]-12-oxo-6-thioxo-1,3,4,5,6,7,8,9,10,12-decahydro-11,2,5-benzoxathiaazacyclotetradecin-9-ylmethyl ester as a white foam.

EXAMPLE 125

A solution of 46 mg of (4R,9R)-16-[dimethyl-(1,1,2-trimethyl-propyl)-silanyloxy]-14-methoxy -13-methyl-4-(3-methyl-[1,2,4]oxadiazol-5-yl)-9-(methylsulfonyloxymethyl)-6-thioxo-1,3,4,5,6,7,8,9,10,12-decahydro-11,2,5-benzoxathiaazacyclotetradecin-12-one in a mixture of 0.25 ml of morpholine and 0.25 ml of methanol was stirred at 20° C. for 18 h. The solution was evaporated in vacuo and the residue was treated with ammonium fluoride in methanol in an analogous manner to the procedure described in Example 1 to yield 12 mg of (4R,9S)-16-hydroxy-14-methoxy -13-methyl-4-(3-methyl-1,2,4-oxadiazol-5-yl)-9-(morpholin-4-ylmethyl)-6-thioxo-1,3,4,5,6,7,8,9,10,12-decahydro-11,2,5-benzoxathiaazacyclotetradecin-2-one as a white solid.

MS m/z: $(M-H)^-=549.0$

The starting material used above was prepared as follows:

(a) A solution of 31 mg of (4R,9S)-16-[dimethyl-(1,1,2-trimethyl-propyl)-silanyloxy]-9-hydroxymethyl-14-methoxy-13-methyl-4-(3-methyl -1,2,4-oxadiazol-5-yl)-6-thioxo-1,3,4,5,6,7,8,9, 10,12-decahydro-11,2,5-benzoxathiaazacyclotetradecin-12-one and 11.5 mg of methanesulfonyl chloride in 0.2 ml of pyridine was stirred at 20° C. for 3 h. The solution was partitioned between dichloromethane and 1M aqueous oxalic acid. The organic layer was washed with brine, dried over sodium sulfate and evaporated in vacuo to yield 46 mg of (4R,9R)-16-[dimethyl-(1,1,2-trimethyl-propyl) -silanyloxy]-14-methoxy-13-methyl-4-(3-methyl-1,2,4-oxadiazol-5-yl)-9-(methyl -sulfonyloxymethyl)-6-thioxo-1,3,4,5,6,7,8,9,10,12-decahydro-11,2,5-benzoxathiaazacyclotetradecin-12-one as an amorphous solid.

EXAMPLE 126

(4R,9R)-9-Aminomethyl-16-[dimethyl-(1,1,2-trimethyl-propyl)-silanyloxy]-14-methoxy-13-methyl-4-(3-methyl-[1,2,4]oxadiazol-5-yl)-1,3,4,5,6,7,8,9,10,12-decahydro-11,2,5-benzoxathiaazacyclotetradecin-6,12-dione was treated with ammonium fluoride in methanol in an analogous manner to the procedure described in Example 1 to yield, after crystallization from ethyl acetate/hexane, (4R,9R)-9-aminomethyl-16-hydroxy-14-methoxy-13-methyl-4-(3-methyl-1,2,4-oxadiazol-5-yl)-1,3,4,5,6,7,8,9,10,12-decahydro-11,2,5-benzoxathiaazacyclotetradecin-6,12-dione as white solid.

MS m/z: $(M+H)^+=465$

The starting material used above was prepared as follows:

(a) To a solution of 140 mg of (4R,9R)-16-[dimethyl-(1,1,2-trimethyl-propyl)-silanyloxy]-9-hydroxymethyl-14-methoxy-13-methyl-4-(3-methyl-1,2,4-oxadiazol-5-yl)-1,3,4,5,6,7,8,9,10,12-decahydro-11,2,5-benzoxathiaazacyclotetradecin-6,12-dione and 121 mg of triphenyl-phosphine in 2 ml of tetrahydrofuran were added at 0° C. 80 mg of diethyl azodicarboxylate and 127 mg of diphenylphosphoryl azide. The mixture was stirred at 0° C. for 35 min and then evaporated in vacuo. The residue was chromatographed on silica gel using ethyl acetate/hexane (1:1, v/v) as eluent, to yield (4R, 9R)-9-azidomethyl-16-[dimethyl-(1,1,2 -trimethyl-propyl)-silanyloxy]-14-methoxy-13-methyl -4-(3-methyl-1,2,4-oxadiazol-5-yl)-1,3,4,5, 6,7,8,9,10,12-decahydro-11,2,5-benzoxathiaazacyclotetradecin -6,12-dione as a foam MS m/z: $(M-H)^-=631.2$ (b) A solution of 89 mg of the product of Example 126(a), 40 mg of triphenylphosphine and 30 mg of water in 1.4 ml of tetrahydrofuran was stirred at 20° C. for 17 h. The mixture was evaporated in vacuo and the residue was chromatographed on silica gel using dichloromethane/methanol (8:1, v/v) as eluent, to yield 48 mg of (4R,9R) -9-aminomethyl-16-[dimethyl-(1,1,2-trimethyl -propyl)-silanyloxy]-14-methoxy-13-methyl-4-(3-methyl-1,2,4-oxadiazol-5-yl)-1,3,4,5,6,7,8,9,10,12-decahydro-11,2,5-benzoxathiaazacyclotetradecin-6,12-dione as a foam.

MS m/z: $(M+H)^+=607.3$

EXAMPLE 127

(4R,9R)-N-[16-[dimethyl-(1,1,2-trimethyl-propyl)-silanyloxy]-14-methoxy-13-methyl-4-(3-methyl-1,2,4-oxadiazol-5-yl)-6,12-dioxo-1,3,4,5,6,7,8,9,10,12-decahydro-11,2,5-benzoxathiaazacyclotetradecin-9-ylmethyl ]-acetamide was treated with ammonium fluoride in methanol in an analogous manner to the procedure described in Example 1 to yield, after crystallization from chloroform/hexane, (4R, 9R)-N-[16-hydroxy-14-methoxy-13-methyl-4-(3-methyl-1, 2,4-oxadiazol-5-yl)-6,12-dioxo-1,3,4,5,6,7,8,9,10,12-decahydro-11,2,5-benzoxathiaazacyclotetradecin-9-ylmethyl]-acetamide as a white solid.

MS m/z: $(M+H)^+=507.2$

The starting material used above was prepared as follows:

(a) A solution of 60 mg of the product of Example 126(b) and 20 mg of pyridine in 2 ml of acetic acid anhydride was heated to 60° C. for 1 h. The mixture was evaporated in vacuo and the residue was chromatographed on silica gel using ethyl acetate/2-propanol (9:1, v/v) as eluent to yield 41 mg of (4R,9R) -N-[16-[dimethyl-(1, 1,2-trimethyl-propyl)-silanyloxy]-14-methoxy-13-methyl-4-(3-methyl-1,2,4-oxadiazol-5-yl)-6,12-dioxo-1,3,4,5,6,7,8,9,10,12-decahydro-11,2,5-benzoxathiaazacyclotetradecin-9-ylmethyl]-acetamide as a foam.

EXAMPLE 128

(4R,9R)-9-Chloromethyl-16-[dimethyl-(1,1,2-trimethyl-propyl)silanyloxy-]-14-methoxy-13-methyl-4-(3-methyl-[1,2,4 ]oxadiazol-5-yl)-1,3,4,5,6,7,8,9,10,12-decahydro-11,2,5-benzoxathiaazacyclotetradecin-6,12-dione was treated with ammonium fluoride in methanol in an analogous manner to the procedure described in Example 1 to yield, after crystallization from ethyl acetate/hexane, (4R,9R )-9-chloromethyl-16-hydroxy-14-methoxy-13-methyl-4-(3-methyl-1,2,4-oxadiazol -5-yl)-1,3,4,5,6,7,8,9,10,12-decahydro-11,2,5-benzoxathiaazacyclotetradecin-6,12-dione as a white solid.

MS m/z: (M–H)⁻=498.0

The starting material used above was prepared as follows:

(a) A mixture of 35 mg of the product of Example 125(a) and 8 mg of lithium chloride in 0.5 ml of N,N-dimethylformamide was stirred for 17 h at 20° C. and for 6 h at 60° C. The mixture was evaporated in vacuo and the residue was chromatographed on silica gel using ethyl acetate/hexane (1:1, v/v) as eluent, to yield 19 mg of (4R,9R)-9-chloromethyl-16-[dimethyl-(1,1,2-trimethyl-propyl)-silanyloxy]-14-methoxy-13-methyl-4-(3-methyl-1,2,4-oxadiazol-5-yl)-12-thioxo-1,3,4,5,6,7,8,9,10,12-decahydro-11,2,5-benzoxathiaazacyclotetradecin-6-one as an amorphous solid.

EXAMPLE 129

(R)-4-(3-Aminomethyl-1,2,4-oxadiazol-5-yl) -16-[dimethyl-(1,1,2-trimethyl-propyl)-silanyloxy]-14-methoxy-13-methyl-1,3,4,5,6,7,8,9,10,12-decahydro-11,2,5-benzoxathiaazacyclotetradecin-6,12-dione was treated with ammonium fluoride in methanol in an analogous manner to the procedure described in Example 1. The resulting product was dissolved in ethyl acetate. Upon addition of a 3N solution of hydrochloric acid in diethyl ether, a precipitate formed which was isolated to yield (R)-4-(3-aminomethyl-1,2,4 -oxadiazol-5-yl)-16-hydroxy-14-methoxy-13-methyl-1,3,4,5,6,7,8,9,10,12-decahydro-11,2,5-benzoxathiaazacyclotetradecin-6,12-dione hydrochloride as a white solid.

MS m/z: (M+H)⁺=451.4

The starting material used above was prepared as follows:

(a) To a suspension of 110 g of aminoacetonitrile hydrochloride in 1.2 l of acetonitrile were added at 20° C. 121.5 g of triethylamine. The mixture was cooled in an acetone-ice bath and 144.7 g of allyl chloroformate were added slowly, the temperature being maintained below 20° C. Subsequently, 121.5 g of triethylamine were added at such a rate that the temperature did not rise above 20° C. The mixture was stirred at 20° C. for 2 h and then, the solids were removed by filtration. The mother liquor was concentrated in vacuo and the oily residue was partitioned between ethyl acetate and water. The organic layer was washed successively with saturated potassium hydrogen sulfate solution, saturated potassium hydrogen carbonate solution and brine, dried over magnesium sulfate and concentrated in vacuo. The residual oil was distilled in vacuo to yield 132.6 g of cyanomethyl-carbamic acid allyl ester as a colorless oil, b.p. 100° C./0.07 mbar.

(b) To a solution of 140 g of cyanomethyl-carbamic acid allyl ester in 1 l of methanol were added over 15 min a solution of 40.0 g of sodium hydroxide and 82.1 g of hydroxylamine sulfate in 200 ml of water, the reaction mixture being cooled in an ice-bath. The mixture was stirred at 20° C. for 16 h and then, the pH of the suspension was adjusted to 7.0 by the addition of concentrated hydrochloric acid. The solids were removed by filtration and the mother liquor was evaporated in vacuo. The solid residue was recrystallized from ethyl acetate to yield 143.1 g of N-hydroxycarbamimidoylmethyl-carbamic acid allyl ester as white crystals, m.p. 91°–92° C.

(c) N-hydroxycarbamimidoylmethyl-carbamic acid allyl ester was reacted with Boc-L-cystine in an analogous manner to the procedure described in Example 1(l) to yield bis-[(R)-2-(3-allyloxycarbonyl-aminomethyl-1,2,4-oxadiazol-5-yl)-2-tert-butoxy-carbonylaminoethyl] disulfide as a white solid, m.p. 118°–119° C.

(d) The product of Example 129(c) was subjected in an analogous manner to the procedure described in Example 1(m) to yield (R)-1-(3-allyloxycarbonylaminomethyl-1,2,4-oxadiazol -5-yl)-2-mercaptoethylcarbamic acid tert-butyl ester as a white solid, m.p. 55°–58° C.

(e) The product of Example 1(f) was reacted with the product of Example 129(d) in an analogous manner to the procedure described in Example 1(g) to yield (R)-2-[2-(3-allyloxycarbonylaminomethyl-1,2,4-oxadiazol-5-yl)-2-amino-ethylsulfanylmethyl]-3-[dimethyl-(1,1,2-trimethyl-propyl)-silanyloxy]-5-methoxy-6-methyl-benzoic ester as a pale yellow oil. This material was acylated with 5-trityloxypentanoic acid in an analogous manner as described in Example 1(h), and the resulting product was subjected in an analogous manner to the procedure described in Example 1(i) to yield (R)-2-[2-(3-allyloxycarbonylamino-1,2,4-oxadiazol -5-yl)-2-(5-hydroxy-pentanoylamino) -ethylsulfanylmethyl]-3-[dimethyl-(1,1,2-trimethyl -propyl)-silanyloxy]-5-methoxy-6-methyl-benzoic acid allyl ester as a colorless oil. To a solution of 3.67 g of this material in 50 ml of dichloromethane were added 2.39 g of 4-(trimethylsilyl) -morpholine and 1.98 g of acetic acid trimethylsilyl ester. The solution was stirred at 20° C. for 5 min and then, 0.115 g of tetrakis(triphenylphosphine)palladium were added. The mixture was stirred at 20° C. for 2 h under an argon atmosphere and then evaporated in vacuo. The resulting oil was dissolved in 50 ml of methanol. The solution was kept at 20° C. for 30 min and then evaporated in vacuo. The residual oil was dissolved in 50 ml of toluene and evaporated again in vacuo. The resulting oil was dissolved in 50 ml of dichloromethane. With cooling of the solution to 0° C., 0.9 g of allyl chloroformate and 1.52 g of 4-methyl-morpholine were added and stirring was continued for 2 h at 0° C. The solution was evaporated in vacuo and the residue was partitioned between 50 ml of ethyl acetate, 5 ml of ethanol and 30 ml of 1N hydrochloric acid. The organic layer was washed with brine, dried over sodium sulfate and the solvent was evaporated in vacuo. The crude (R)-2-[2-(3-allyloxycarbonylaminomethyl-1,2,4-oxadiazol-5-yl)-2-(5-hydroxy -pentanoylamino)-ethylsulfanylmethyl]-3-[dimethyl-(1,1,2-trimethyl-propyl)-silanyloxy]-5-methoxy -6-methyl-benzoic acid thus obtained was subjected in an analogous manner to the procedure described in Example 1(k) to yield, after chromatographic purification on silica gel using ethyl acetate/hexane (1:1 v/v) as eluent, 1.35 g of (R)-4-(3-allyloxycarbonylaminomethyl-1,2,4-oxadiazol-5-yl)-16 -[dimethyl-(1,1,2-trimethyl-propyl)-silanyloxy]-14-methoxy-13-methyl-1,3,4,5,6,7,8,9,10,12-decahydro-11,2,5-benzoxathiaazacyclotetradecin-6,12-dione as an amorphous foam.

(f) By operating in an analogous manner, the product of Example 129(e) was subjected to the procedure described in Example 124(c) to yield, (R)-4-(3-aminomethyl-1,2,4-oxadiazol-5-yl)-16-[dimethyl-(1,1,2-trimethyl-propyl)-silanyloxy]-14-methoxy-13-methyl-1,3,4,5,6,7,8,9,10,12-decahydro-11,2,5-benzoxathiaazacyclotetradecin-6,12-dione as an amorphous solid.

EXAMPLE 130

(R)-4-(3-Aminomethyl-1,2,4-oxadiazol-5-yl) -16-[dimethyl-(1,1,2-trimethyl-propyl)-silanyloxy]-14-methoxy-13-methyl-6-thioxo-1,3,4,5,6,7,8,9,10,12-decahydro-11,2,5-benzoxathiaazacyclotetradecin-12-one was treated with ammonium fluoride in methanol in an analogous manner to the procedure described in Example 1. The resulting product was dissolved in ethyl acetate. Upon the addition of a 3N solution of hydrochloric acid in diethyl ether, a precipitate formed which was isolated to yield (R)-4-(3-aminomethyl-1,2,4-oxadiazol-5-yl)-16-hydroxy-14-methoxy-13-methyl-6-thioxo-1,3,4,5,6,7,8,9,10,12-decahydro-11,2,5-benzoxathiaazacyclotetradecin-12-one hydrochloride as a white solid.

MS m/z: (M–H–HCl)⁻=465.2

The starting material used above was prepared as follows:

(a) By operating in an analogous manner as described in Example 2, the product of Example 129(e) was treated with 2,4-bis-(4-methoxyphenyl)- 2,4-dithioxo-1,3,2,4-dithiaphosphetane in toluene, and the resulting product was subjected in an analogous manner to the procedure described in Example 124(c) to yield (R)-4-(3-aminomethyl-1,2,4-oxadiazol-5-yl)-16-[dimethyl-(1,1,2-trimethyl-propyl)silanyloxy]-14-methoxy-13-methyl-6-thioxo-1,3,4,5,6,7,8,9,10,12-decahydro-11,2,5-benzoxathiaazacyclotetradecin-12-one as an amorphous solid.

EXAMPLE 131

By operating in an analogous manner as described in Example 1(h), the product of Example 129(f) was acylated with N,N-dimethyl-L-glycin, and the resulting product was subjected in an analogous manner to the procedure described in Example 129 to yield (R)-2-dimethylamino-N-[-5-(16-hydroxy-14-methoxy -13-methyl-6,12-dioxo-1,3,4,5,6,7,8,9,10,12-decahydro-11,2,5-benzoxathiaazacyclotetradecin-4-yl)-1,2,4-oxadiazol-3-ylmethyl]-acetamide hydrochloride as a white solid.

¹H-NMR (250 MHz,DMSO-d₆): δ 1.70–2.20(m,4H) superimposed by 1.91(s,3H); 2.30–2.50(m,2H); 2.79(s,6H); 2.87(dd,J=14 Hz and 12 Hz,1H); 3.24(dd,J=14 Hz and 4 Hz,1H); 3.70(d,J=11 Hz,1H); 3.73(s,3H); 3.87(d,J=11 Hz,1H); 3.95(s,2H; 4.10(m,1H); 4.44–4.62(m,3H); 5.20(m, 1H); 6.54(s,1H); 8.72(d,J=8 Hz,1H); 9.30(t,6 Hz,1H); 9.80(s, 2H) superimposed by 9.82(broad s,1H) ppm.

EXAMPLE 132

To a mixture of 118 mg of the product of Example 129(f), 0.22 ml of acetone, 39 mg of sodium acetate, 0.2 ml of acetic acid and 0.6 ml of water in 1 ml of tetrahydrofuran were added portionwise at 0° C. over 30 min 45 mg of sodium borohydride. Stirring was continued for 30 min and the mixture was then diluted with ethyl acetate and washed with saturated sodium carbonate solution and brine. The organic layer was dried over sodium sulfate and evaporated in vacuo. The residue was chromatographed on silica gel using ethyl acetate as eluent to yield 92 mg of (R)-4-[3-(isopropylamino)-methyl-1,2,4-oxadiazol-5-yl]-16-[dimethyl-(1,1,2-trimethyl-propyl)-silanyloxy]-14-methoxy-13-methyl-1,3,4,5,6,7,8,9,10,12-decahydro -11,2,5-benzoxathiaazacyclotetradecin-6,12-dione as a foam. This material was subjected in an analogous manner to the procedure described in Example 129 to yield (R)-16-hydroxy-4-[3-(isopropylamino)-methyl-1,2,4-oxadiazol-5-yl]-14-methoxy-13-methyl-1,3,4,5,6,7,8,9,10,12-decahydro-11,2,5-benzoxathiaazacyclotetradecin-6,12-dione hydrochloride as a white solid.

¹H-NMR (250 MHz,DMSO-d₆): δ 1.26(d,J=6 Hz,6H); 1.68–2.15(m,4H) superimposed by 1.91(s,3H); 2.33–2.65(m,2H); 2.92(dd,J=14 Hz and 12 Hz,1H); 3.20–3.40(m,1H); 3.73(d,J=11 Hz,1H) superimposed by 3.73(s,3H); 3.88(d,J=11 Hz,1H); 4.13(m,1H); 4.20(s,2H); 4.55(m,1H); 5.22(m,1H); 6.54(s,1H); 8.78(d,J=8 Hz,1H); 9.25(broad s,1H); 9.82(s,1H) ppm.

EXAMPLES 133 TO 136

By operating in an analogous manner as described in Example 132, but replacing acetone by cyclobutanone, cyclopentanone or N-ethoxycarbonyl-piperidin-4-one, respectively, the following compounds were obtained:

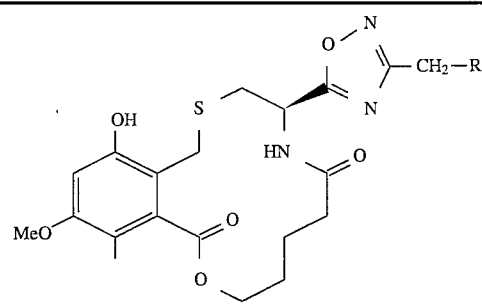

| Example No | R | ¹H-NMR (250 MHz, DMSO-d₆) δ, inter alia, ppm |
|---|---|---|
| 133 | HN—⬦ | 1.60–2.65(m, 9H) superimposed by 1.91(s, 3H); 2.75(m, 2H); 2.95(dd, 1H); 3.30(dd, 1H); 3.73(d, 1H) superimposed by 3.73(s, 3H); 3.87(d, 1H); 4.13(m, 1H); 4.34(s, 2H); 4.53(m, 1H); 5.23(m, 1H); 6.54(s, 1H); 8.76(d, 1H); 9.71(broad s, 1H); 9.81(s, 1H) |

| Example No | R | ¹H-NMR (250 MHz, DMSO-d₆) δ, inter alia, ppm |
|---|---|---|
| 134 | N—(cyclobutyl)₂ | 1.55–2.70(m, 18H) superimposed by 1.91(s, 3H); 2.95(dd, 1H); 3.31(dd, 1H); 3.74(d, 1H) superimposed by 3.73(s, 3H); 3.81(d, 1H); 4.13(m, 1H); 4.43(broad s, 2H); 4.55(m,1H); 5.24(m.1H); 6.54(s, 1H); 8.75(d, 1H); 9.80(s, 1H); 11.35(broad s, 1H) |
| 135 | HN—cyclopentyl | 1.45–2.14(m, 13H) superimposed by 1.91(s, 3H); 2.35–2.60(m, 2H); 2.92(dd, 1H); 3.29(dd, 1H); 3.62(m, 1H); 3.73(d, 1H) superimposed by 3.73(s, 3H); 3.88(d, 1H); 4.11(m.1H); 4.34(broad s, 2H); 4.55(m, 1H); 5.25(m, 1H); 6.55(s, 1H); 8.78(d, 1H); 9.58(broad s, 1H); 9.82(s, 1H) |
| 136 | HN—(piperidinyl)—N—COOEt | 1.18(t, 3H); 1.35–1.60(m, 2H); 1.65–2.20(m, 8H) superimposed by 1.91(s, 3H); 2.75(m, 2H); 2.90(dd, 1H); 3.20–3.40(m, 3H); 3.73(d, 1H) superimposed by 3.73(s, 3H); 3.92(d, 1H); 3.94(s, 3H); 3.83(d, 1H); 4.04(q, 2H); 4.38–4.68(m, 3H); 5.24(m, 1H); 6.54(s, 1H); 8.55(d, 1H); 9.68(broad s, 1H); 9.81(s, 1H) |

EXAMPLES 137–140

To a solution of 474 mg of the product of Example 128(f) in 16 ml of 75% aqueous acetic acid were added at 0° C. 276 mg of sodium nitrite. The mixture was stirred at 0° C. for 45 min, whereupon its pH was adjusted to 8 by addition of 14% aqueous sodium hydroxide solution. The mixture was extracted with ethyl acetate and the organic layer was washed with saturated sodium carbonate solution and brine, dried over sodium sulfate and evaporated in vacuo. The residue was chromatographed on silica gel using ethyl acetate/hexane (1:3, v/v) as eluent to yield, upon treatment of the individual products with ammonium fluoride in methanol in an analogous manner as described Example 1, the following compounds:

| Example No | R | Mass spectrum: m/z |
|---|---|---|
| 137 | CH₂OCOCH₃ | (M – H)⁻ = 492.2 |
| 138 | (Z) CH=N—OH | (M – H)⁻ = 463.3 |
| 139 | (E) CH=N—OH | (M – H)⁻ = 463.4 |
| 140 | CH₂OH | (M – H)⁻ = 450.3 |

EXAMPLE 141

To a solution of 30 mg of the product of Example 130(a) in 0.5 ml of dichloromethane were added at 0° C. 69 mg of methanesulfonyl chloride and 61 mg of 4-methyl-morpholine. The mixture was stirred at 0° C. for 30 min and then diluted with ethyl acetate and washed successively with 1N hydrochloric acid, 5% sodium bicarbonate solution and brine. The organic layer was dried over sodium sulfate and evaporated in vacuo. The residue was chromatographed on silica gel using ethyl acetate/hexane (1:2, v/v). as eluent to yield, upon treatment of the purified product with ammonium fluoride in methanol in an analogous manner as described Example 1, 9 mg of (R)-N-[5-(16-hydroxy-14-methoxy-13-methyl -12-oxo-6-thioxo-1,3,4,5,6,7,8,9,10,12-decahydro-11,2,5-benzoxathiaazacyclotetradecin- 4-yl)-1,2,4-oxadiazol-3-ylmethyl]-methanesulfonamide as a white solid.

MS m/z: (M+H)⁺=545.2

EXAMPLE 142

By operating in an analogous manner, the product of Example 130(a) was subjected successively to the procedures described in Example 127(a) and 1 to yield (R)-N-[5-(16-hydroxy-14-methoxy-13-methyl-12-oxo-6-thioxo-1,3,4,5,6,7,8,9,10,12-decahydro-11,2,5-benzoxathiaazacyclotetradecin-4-yl)-1,2,4-oxadiazol-3-ylmethyl]-acetamide as a white solid.

MS m/z: (M–H)⁻=507.2

EXAMPLE 143

By operating in an analogous manner, the product of Example 130(a) was acylated with N-allyloxycarbonyl-L-alanine using the procedure described in Example 1(h). The resulting product was successively subjected in an analogous manner to the procedures described in Examples 124(c) and 129 to yield (S)-2-amino-N-[5-[(R)-16-hydroxy-14-methoxy-13-methyl-12-oxo-6-thioxo-1,3,4,5,6,7,8,9,10,12-decahydro-11,2,5-benzoxathiaazacyclotetradecin-4-yl]-1,2,4-oxadiazol -3-ylmethyl]-propionamide hydrochloride as a white solid.

¹H-NMR (250 MHz,DMSO-d₆): δ 1.36(d,J=6 Hz,3H); 1.62–2.10(m,4H) superimposed by 1.91(s,3H); 2.68(m,1H); 2.88(m,1H); 3.08(dd,J=14 Hz and 12 Hz,1H); 3.72(d,J=11

Hz,1H) superimposed by 3.73(s,3H); 3.90 (d,J=11 Hz,1H); 4.11 (m,1H); 4.41–4.64(m,3H); 5.75(m,1H); 6.55(s,1H); 8.20(broad s,3H); 9.13(t,J=6 Hz,1H); 9.84(s,1H); 10.70(d, J=6 Hz,1H) ppm.

EXAMPLE 144

The pH of a suspension of 20 mg of the product of Example 130 in 3 ml of 0.05M pH7 sodium phosphate buffer was adjusted to 8.5 by the addition of 0.1N sodium hydroxide. Over 3 h, 74 mg of ethyl acetimidate hydrochloride were added in small portions, the pH of the reaction mixture being maintained at 8.5. The mixture was set to pH 7 by addition of 1N hydrochloric acid and then extracted with ethyl acetate. The aqueous phase was concentrated in vacuo and chromatographed on MCI-Gel CHP20P (Mitsubishi Chemical Industries, Ltd.) using at first 1% aqueous acetic acid and then mixtures of 1% aqueous acetic acid with acetonitrile (10:1 to 2:1, v/v). The product-containing fractions were lyophilized to yield 4 mg of (4R)-N-[5-(16-hydroxy-14-methoxy-13-methyl-12-oxo -6-thioxo-1,3,4,5,6,7,8,9,10,12-decahydro-11,2,5-benzoxathiaazacyclotetradecin-4-yl)-1,2,4-oxadiazol-3-ylmethyl]-acetimidamide hydroacetate.

MS m/z: (M–HOAc+H)$^+$=508

EXAMPLE 145

The product of Example 39(b) was treated with ammonium fluoride in methanol in an analogous manner to the procedure described in Example 1 and the resulting product was subjected in an analogous manner to the procedure described in Example 144 to yield (R)-2-[2-acetimidoylamino-2-(3-methyl-1,2,4-oxadiazol-5-yl)-ethylsulfanylmethyl]-3-hydroxy-5-methoxy-6-methyl-benzoic acid methyl ester acetate (1:1) as a white solid.

MS m/z: (M+H)$^+$=514.3

EXAMPLE 146

To a solution of 11 mg of the product of Example 33 in 0.02 ml of pyridine were added 4 mg of phosphoryl chloride. The mixture was stirred at 20° C. for 30 min, whereupon 0.2 ml of water were added and the pH was adjusted to 1.5 by the addition of 3N hydrochloric acid. Stirring was continued for 30 min and then, the mixture was extracted with ethyl acetate. The organic layer was dried over sodium sulfate and evaporated in vacuo to yield 6 mg of phosphoric acid (R)-mono-[14-methoxy-13-methyl-4-(3-methyl-1,2,4-oxadiazol-5-yl)-6,12-dioxo-1,3,4,5,6,7,8,9,10,12-decahydro-11,2,5-benzoxathiaazacyclo-tetradecin-16-yl ester as an amorphous solid.

MS m/z: (M–H)$^-$=514.3

EXAMPLE 147

By operating in an analogous manner, the product of Example 123(a) was subjected to the procedure described in Example 146 and the resulting product was treated with ammonium fluoride in methanol in an analogous manner to the procedure described in Example 1 to yield phosphoric acid (4R,9R)-mono-[16-hydroxy-14-methoxy-13-methyl-4-(3-methyl-1,2,4-oxadiazol-5-yl)-12-oxo-6-thioxo -1,3,4,5,6,7,8,9,10,12-decahydro-11,2,5-benzoxathiaazacyclo-tetradecin-9-ylmethyl] ester as an amorphous solid.

MS m/z: (M–H)$^-$=560.1

EXAMPLE 148

(R)-3-(tert-Butyl-dimethylsilanyloxy)-5-methoxy-6-methyl-2-[2-(3-methyl-1,2,4-oxadiazol-5-yl)-2-(2-oxo-pyrrolidin-1-yl)-ethylsulfanylmethyl]-benzoic acid methyl ester was subjected in an analogous manner to the procedure described in Example 1 to yield (R)-3-hydroxy-5-methoxy-6-methyl-2-[-2-(3-methyl-1,2,4-oxadiazol-5-yl)-2-(2-oxo-pyrrolidin-1-yl) -ethylsulfanylmethyl]-benzoic acid methyl ester as a white solid.

$^1$H-NMR (250 MHz,CDCl$_3$): δ 2.06(s,3H) superimposed by 2.00–2.15(m,2H); 2.41(s,3H);2.48–2.60(m,2H); 2.81–3.22(m,2H); 3,39(t,J=7 Hz,2H); 3.75–4.00 (m,2H); 3.79(s,3H); 3.93(s,3H); 5.60–5.85(m,1H); 6.51(s,1H); 7.04(s,1H) ppm.

The starting material used above was prepared as follows:
(a) To a solution of 0.30 g of the product of Example 39(b) in 3 ml of dichloromethane were added at 0° C. 0.12 g of 4-bromo-butyric acid chloride and 1 ml of saturated potassium bicarbonate solution. The mixture was stirred at 20° C. for 15 h. The pH of the mixture was adjusted to 14 by addition of 3N sodium hydroxide solution and stirring was continued for 1.5 h. Dichloromethane was evaporated and the residue was extracted with ethyl acetate. The organic phase was washed with brine, dried over magnesium sulfate and evaporated. The solid residue was purified by chromatography on silica gel using hexane/ethyl acetate (1:1, v/v) as eluent, to yield 0.075 g of (R)-3-(tert-butyl-dimethylsilanyloxy)-5-methoxy -6-methyl-2[-2-(3-methyl-1,2,4-oxadiazol-5-yl)-2-(2-oxo-pyrrolidin-1-yl) -ethylsulfanyl-benzoic acid methyl ester as a white foam.

EXAMPLE 149

(R)-3-(tert-Butyl-dimethylsilanyloxy)-5-methoxy-6-methyl-2-[2-( 3-methyl-1,2,4-oxadiazol-5-yl)-2-(2-oxo -pyrrolidin-1-yl)-ethylsulfanylmethyl]-benzoic acid methyl ester was subjected in an analogous manner to the procedure described in Example 2 to yield (R)-3-hydroxy-5-methoxy-6-methyl-2-[-2-(3-methyl-1,2,4-oxadiazol-5-yl)-2-(2-thioxo-pyrrolidin-1-yl) -ethylsulfanylmethyl]-benzoic acid methyl ester as a white solid.

$^1$H-NMR (250 MHz,CDCl$_3$): δ 2.05(s,3H); 2.06–2.219(m,2H); 2.41(s,3H); 2.94–3.30(m,4H); 3.65(t,J=7 Hz,2H); 3.76–4.00(m,2H) superimposed by 3.80(s,3H) and 3.95(s,3H); 6.26(s,1H); 6.49(s,1H); 6.65–6.76(m,1H) ppm.

EXAMPLE 150

(R)-2-[2-(5-Amino-1H-tetrazol-1-yl) -2-(3-methyl-1,2,4-oxadiazol-5-yl) -ethylsulfanylmethyl]-3-(tert-butyl-dimethyl-silanyloxy)-5-methoxy-6-methyl-benzoic acid methyl ester was subjected in an analogous manner to the procedure described in Example 1 to yield (R)-2-[2-(5-amino-1H -tetrazol-1-yl)-2-(3-methyl-1,2,4-oxadiazol-5-yl)-ethylsulfanylmethyl]-3-hydroxy -5-methoxy-6-methyl-benzoic acid methyl ester as a white solid.

$^1$H-NMR (250 MHz,CDCl$_3$): δ 2.06(s,3H); 3.20–3.55(m, 2H); 3.70–3.90(m,2H) superimposed by 3.80(s,3H); 3.94(s, 3H); 5.51(s,2H); 6.00–6.10(m,1H); 6.58 (s,1H); 7.00(s, broad,1H) ppm.

The starting material used above was prepared as follows:
(a) To a solution of 1.45 g of the product of Example 39(b) in 25 ml of dichloromethane were added with stirring 17.0 ml of saturated potassium bicarbonate solution and 0.32 g of cyanogen bromide at 20° C. The mixture was stirred at 20° C. for 15 h. The phases were separated and the organic phase was evaporated in vacuo. The residue was chromatographed on silica gel using ethyl acetate/hexane (1:1, v/v) as eluent to yield 0.85 g of (R)-3-(tert-butyl -dimethyl-silanyloxy)-2-[2-cyanoamino-2-(3-methyl-1,2,4-oxadiazol-5-yl)-ethyl-sulfanylmethyl]-5-methoxy-6-methyl-benzoic acid methylester as a white foam.

$^1$H-NMR (250 MHz,CDCl$_3$): δ 0.27(s,6H); 1.03(s,9H); 2.08(s,3H); 2.41(s,3H); 3.05(d,J=6 Hz,2H); 3.60–3.90(m, 2H) superimposed by 3.79(s,3H); 3.94(s,3H); 4.35–4.50(m, 1H); 5.01(d,J=7 Hz,1H); 6.42(s,1H) ppm.

(b) To a solution of 0.65 g of the product of Example 150(a) in 1.5 ml of ethyl acetate was added a solution of 0.12 g sodium azide in 1.5 ml water and 2.5 ml of a 2N solution of potassium hydrogen sulfate in water, and the resulting mixture was stirred at 20° C. for 15 h. The layers were separated and the organic layer was washed successively with saturated potassium bicarbonate and brine, dried over magnesium sulfate and evaporated in vacuo. The solid residue was chromatographed on silica gel using hexane/ethyl acetate (1:1, v/v) as eluent, to yield 0.25 g of (R)-2-[2-(5-amino-1H-tetrazol-1-yl)-2-(3-methyl-1,2,4-oxadiazol-5-yl)-ethylsulfanylmethyl]-3-(tert -butyl-dimethylsilanyloxy)-5-methoxy-6-methyl-benzoic acid methyl ester as white foam.

$^1$H-NMR (250 MHz,CDCl$_3$): δ 0.27(s,6H); 1.01(s,9H); 2.08(s,3H); 2.41(s,3H); 3.25–3.55(m,2H); 3.70–3.90(m,2H) superimposed by 3.79(s,3H); 3.89(s,3H); 5.24(s,2H); 5.45–5.55(m,1H); 6.41(s,1H) ppm.

EXAMPLE 151

To a solution of 100 mg of the product of Example 150(b) in 1.5 ml of dichloromethane were added 73 mg of triethylamine and 55 mg of acetyl chloride at 20° C. The mixture was stirred for 15 h and then partitioned between ethyl acetate and water. The organic layer was washed with saturated potassium bicarbonate solution and brine, dried over magnesium sulfate and evaporated in vacuo. The solid residue was chromatographed on silica gel using hexane/ethyl acetate (1:1, v/v) as eluent and the resulting product was subjected in an analogous manner to the procedure described in Example 1 to yield (R)-2-[2-(5-acetylamino-1H-tetrazol-1-yl)-2-(3-methyl-1,2,4-oxadiazol-5-yl) -ethyl-sulfanylmethyl]-3-hydroxy-5-methoxy-6-methyl-benzoic acid methyl ester as a white solid.

$^1$H-NMR (250 MHz,CDCl$_3$): δ (inter alia) 1.93(s,3H); 2.10(s,3H); 2.35(s,3H); 3.74(s,3H); 3.77(s,3H); 6.20(m,1H); 6.55(s,1H) ppm.

EXAMPLE 152

(R)-2-[2-(3-Aminomethyl-1,2,4-oxadiazol -5-yl)-2-thioacetylamino-ethylsulfanylmethyl]-6-methyl-3-[dimethyl-(1,1,2-trimethyl-propyl)-silanyloxy ]-5-methoxy-benzoic acid methyl ester was treated with ammonium fluoride in methanol in an analogous manner to the procedure described in Example 1 to yield, (R)-2-[2-(3-aminomethyl-1,2,4-oxadiazol-5-yl) -2-thioacetylamino-ethylsulfanylmethyl]-3-hydroxy-5-methoxy-6-methyl-benzoic acid methyl ester as a pale yellow foam.

MS m/z: (M+H)$^+$=441.5

The starting material used above was prepared as follows:

(a) The product of Example 1(c) was silylated in an analogous manner as described in Example 1(f) to yield 2-formyl-5-methoxy-6-methyl-3-[dimethyl-(1,1,2-trimethyl-propyl)-silanyloxy]-benzoic acid methyl ester as white crystals of m.p. 69°–70° C.

(b) 2-Formyl-5-methoxy-6-methyl-3-[dimethyl-(1,1,2-trimethyl-propyl)-silanyloxy]-benzoic acid methyl ester was reacted with the product of Example 129(d) in an analogous manner to the procedure described in Example 1(g) to yield (R)-2-[2-(3-allyloxycarbonyl-aminomethyl-1,2,4-oxadiazol-5-yl)-2-amino-ethylsulfanylmethyl]-3-[dimethyl-(1,1,2-trimethyl-propyl)-silanyloxy]-5-methoxy-6-methyl-benzoic acid methyl ester as a pale yellow oil. This material was acylated with acetic acid in an analogous manner as described in Example 1(h) and the resulting product was treated with 2,4-bis-(4-methoxyphenyl)-2,4-dithioxo-1,3,2,4 -dithiaphosphetane in toluene in an analogous manner as described in Example 2, to yield (R)-2-[2-(3-allyloxycarbonylaminomethyl-1,2,4-oxadiazol-5-yl)-2-thioacetylamino-ethylsulfanyl-methyl ]-6-methyl-3-[dimethyl-(1,1,2-trimethyl-propyl) -silanyloxy]-5-methoxy-benzoic acid methyl ester as a pale yellow foam.

MS m/z: (M+H)$^+$=667.5

(c) The product of Example 152(b) was subjected in an analogous manner to the procedures described in Example 124(c) to yield (R)-2-[2-(3-aminomethyl-1,2, 4-oxadiazol-5-yl)-2-thioacetylamino-ethylsulfanylmethyl]-3-[dimethyl-(1,1,2-trimethyl-propyl)-silanyloxy]-5-methoxy-6-methyl-benzoic acid methyl ester as an amorphous solid.

MS m/z: (M+H)$^+$=583.4

EXAMPLE 153

The product of Example 152(b) was treated with ammonium fluoride in methanol in an analogous manner to the procedure described in Example 1 to yield, (R)-2-[2-(3-allyloxycarbonyl-aminomethyl-1,2,4-oxadiazol-5-yl)-2 -thioacetylamino-ethylsulfanylmethyl]-3-hydroxy-5-methoxy-6-methyl-benzoic acid methyl ester as a pale yellow foam.

MS m/z: (M–H)$^-$=523.4

EXAMPLES 154 AND 155

By operating in an analogous manner as described in Example 1(h), the product of Example 152(c) was acylated with formic acid and with acetic acid, respectively, and the resulting products were treated with ammonium fluoride in methanol in an analogous manner to the procedure described in Example 1 to yield the following compounds:

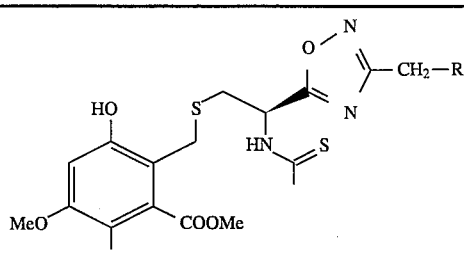

| Example No. | R | Mass spectrum: m/z |
|---|---|---|
| 154 | NHCHO | (M + H)$^+$ = 469.3 |
| 155 | NHCOCH$_3$ | (M + H)$^+$ = 483.4 |

EXAMPLE 156

A solution of 70 mg of the product of Example 152(c) and 39 mg of diethyl pyrocarbonate in 1.2 ml of dioxane was stirred at 20° C. for 15 h. The mixture was evaporated in vacuo and the residue was treated with ammonium fluoride in methanol in an analogous manner to the procedure described in Example 1 to yield, after chromatographic purification on silica gel using hexane/ethyl (1:1, v/v), (R)-2-[2-(3-ethoxycarbonylaminomethyl-1,2,4-oxadiazol-5-yl)-2-thioacetylamino -ethylsulfanylmethyl]-3-hydroxy-5-methoxy-6-methyl -benzoic acid methyl ester as a pale yellow foam.

MS m/z: (M+H)$^+$=513.4

EXAMPLES 157–159

By operating in an analogous manner, the product of Example 152(c) was subjected to the procedure described in Example 137 to yield the following compounds:

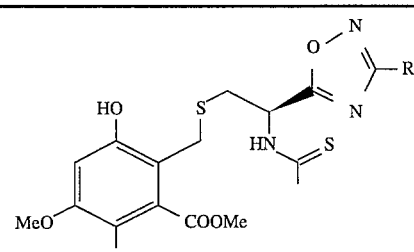

| Example No | R | Mass spectrum: m/z |
|---|---|---|
| 157 | CH$_2$OCOCH$_3$ | (M + H)$^+$ = 484.5 |
| 158 | (E) CH=N—OH | (M – H)$^-$ = 453.4 |
| 159 | CH$_2$OH | (M – H)$^-$ = 440.5 |

EXAMPLE 160

To a solution of 100 mg of (R)-3-[dimethyl-(1,1,2 -trimethyl-propyl) -silanyloxy]-5-methoxy-6-methyl-2-[2-(3-methyl-1,2,4-oxadiazol-5-yl)-2-thio-ureido -ethylsulfanylmethyl]-benzoic acid methyl ester in 3 ml of tetrahydrofuran were added 35 mg of 3-bromo-1,1,1-trifluoroacetone and the mixture was stirred at 20° C. for 16 h. The mixture was concentrated in vacuo and the residue was purified by chromatography on silica gel using hexane/ethyl acetate (2:1, v/v) as eluent. The resulting product was treated with ammonium fluoride in methanol in an analogous manner to the procedure described in Example 1 to yield 20 mg of (R)-3-hydroxy-5-methoxy-6-methyl-2-{2-[4-trifluoromethyl-thiazol-2-ylamino]-2-(3-methyl -1,2,4-oxadiazol-5-yl)-ethylsulfanylmethyl}-benzoic acid methyl ester as white foam.

MS m/z: (M–H)$^-$=517.3

The starting material used above was prepared as follows:
(a) By operating in an analogous manner, 2-formyl-5-methoxy-6-methyl-3-[dimethyl-(1,1,2-trimethyl -propyl)-silanyloxy]-benzoic acid methyl ester was subjected to the procedure described in Example 1(g) to yield (R)-2-[2-amino-2-(3-methyl-1,2,4-oxadiazol-5-yl)-ethyl-sulfanyl-methyl]-3-[dimethyl-(1,1,2-trimethyl-propyl)-silanyloxy]-5-methoxy -6-methyl-benzoic acid methyl ester as a yellow oil.
(b) (R)-2-[2-amino-2-(3-methyl-1,2,4 -oxadiazol-5-yl)-ethylsulfanylmethyl]-3-[dimethyl-(1,1,2-trimethyl-propyl)-silanyloxy]-5-methoxy-6-methyl-benzoic acid methyl ester was subjected in an analogous manner to the procedures described in Example 78(a) and 78 to yield (R)-3-[dimethyl-(1,1,2-trimethyl-propyl)-silanyloxy]-5-methoxy-6-methyl-2-[2-(3-methyl-1,2,4-oxadiazol-5-yl)-2-thioureido -ethylsulfanylmethyl]-benzoic acid methyl ester as a colorless oil.

MS m/z: (M+H)$^+$=569.1

EXAMPLE 161

By operating in an analogous manner as described in Example 160, but replacing 3-bromo-1,1,1-trifluoro-acetone by 3-bromo-2-oxo-propionic acid ethyl ester, there was obtained (R)-3-hydroxy-2-[2-[4-ethoxycarbonyl-thiazol-2-ylamino]-2-(3-methyl-1,2,4-oxadiazol-5-yl)-ethylsulfanyl-methyl]-5-methoxy-6-methyl-benzoic acid methyl ester as a white solid.

MS m/z: (M+H)$^+$=523.5

EXAMPLE 162

By operating in an analogous manner as described in Example 160, but replacing 3-bromo-1,1,1-trifluoro-acetone by 3-bromo-tetrahydro-2-furanol, there was obtained (R) -3-hydroxy-2-[2-[5-(2-hydroxy-ethyl) -thiazol-2-ylamino]-2-(3-methyl-1,2,4-oxadiazo-5-methoxy-6-methyl-benzoic acid methyl ester as a white solid.

MS m/z: (M–H)$^-$=493.2

The starting material used above was prepared as follows:

To a stirred solution of 15 ml of 2,3-dihydrofuran, 42.8 g of N-bromosuccinimide and 40 ml of water in 600 ml of dioxane were added at 0° C. dropwise over 30 min 240 ml of 1N perchloric acid. The mixture was stirred for 1 h at 0° C. followed by 4 h at 20° C. The solvent was evaporated in vacuo, the residual oil was dissolved in 200 ml of diethyl ether, and the solution was washed successively with brine, saturated sodium carbonate solution and again with brine. The organic layer was dried over sodium sulfate and evaporated in vacuo to afford 9.4 g of 3-bromo-tetrahydro-2-furanol as a colorless oil which was used without further purification.

MS m/z: (M+H)$^+$=167.0

EXAMPLE 163

To a solution of 172 mg aminoacetaldehyde diethyl acetal in 10 ml of tetrahydrofuran were added at 0° C. 420 mg of 1,1'thiocarbonyldi-2(1H)-pyridone and the mixture was stirred at this temperature for 1 h. To this mixture were then added 820 mg of (R)-2-[2-amino-2-(3-methyl-1,2,4-oxadiazol-5-yl) -ethylsulfanyl-methyl]-3-hydroxy-5-methoxy-6-methyl-benzoic acid methyl ester. Stirring was continued for 16 h while the mixture was allowed to warm to 20° C. The mixture was concentrated in vacuo and the residue was purified by chromatography on silica gel using hexane/ethyl acetate (1:2, v/v) as eluent. The resulting product was taken up in 4 ml of trifluoroacetic acid and the solution was stirred at room temperature for 2 h. The solvent was evaporated in vacuo and the residue was purified by chromatography on silica gel using dichloromethane/ethyl acetate/methanol (16:4:1, v/v/v) as eluent, to yield 225 mg of 3-hydroxy-5-methoxy-(R)-2-[(R)- and -[(S) -2-(5-methoxy-4,5-dihydro-thiazol-2-ylamino) -2-(3-methyl-1,2,4-oxadiazol-5-yl) -ethylsulfanylmethyl]-6-methyl-benzoic acid methyl ester (1:1 mixture of diastereomers) as a white foam.

MS m/z: (M–H)$^-$=481.3

The starting material used above was prepared as follows:

(a) (R)-2-[2-Amino-2-(3-methyl-1,2,4-oxadiazol-5-yl)-ethylsulfanylmethyl]-3-[dimethyl-(1,1,2-trimethyl-propyl)-silanyloxy]-5-methoxy-6-methyl-benzoic acid methyl ester was treated with ammonium fluoride in methanol in an analogous manner to the procedure described in Example 1 to yield (R)-2-[2-amino-2-(3-methyl-1,2,4-oxadiazol-5-yl)-ethylsulfanyl-methyl]-3-hydroxy-5-methoxy-6-methyl-benzoic acid methyl ester as an amorphous foam.

EXAMPLE 164

By operating in an analogous manner, the product of Example 164(a) was subjected to the procedures described in Examples 124(c) and 1, to yield (R)-2-[2-(3-aminomethyl-1,2,4-oxadiazol-5-yl)-2-(4-trifluoromethyl-thiazol-2-ylamino)-ethylsulfanylmethyl]-3-hydroxy-5-methoxy-6-methyl-benzoic acid methyl ester as a white solid.

MS m/z: (M−H)⁻=532.3

The starting material used above was prepared as follows:

(a) (R)-2-[2-(3-Allyloxycarbonylaminomethyl-1,2,4-oxadiazol-5-yl)-2-amino-ethylsulfanylmethyl]-3-[dimethyl-(1,1,2-trimethyl-propyl)-silanyloxy]-5-methoxy-6-methyl-benzoic acid methyl ester was subjected in an analogous manner to the procedures described in Examples 78(a) and 78 and the resulting product was reacted with 3-bromo-1,1,1-trifluoroacetone in an analogous manner as described in Example 160 to yield (R)-2-[2-(3-aminomethyl-1,2,4-oxadiazol-5-yl)-2-(4-trifluoromethyl-thiazol-2-ylamino)-ethylsulfanylmethyl]-3-[dimethyl-(1,1,2-trimethyl-propyl)-silanyloxy]-5-methoxy-6-methylbenzoic acid methyl ester as a foam.

EXAMPLE 165

(R)-2-Bromo-5-(tert-butyl-dimethylsilanyloxy)-3-methoxy-6-{2-(3-methyl-1,2,4-oxadiazol-5-yl)-2-[4-(4-nitro-phenyl)-thiazol-2-ylamino]-ethylsulfanylmethyl}-benzoic acid methyl ester was subjected in an analogous manner to the procedure described in Example 1 to yield (R)-2-bromo-5-hydroxy-3-methoxy-6-[2-(3-methyl-1,2,4-oxadiazol-5-yl)-2-[4-(4-nitro-phenyl)-thiazol-2-ylamino]-ethylsulfanylmethyl]-benzoic acid methyl ester as an amorphous solid.

MS m/z: (M+H)⁺=636.1/638.1

The starting material used above was prepared as follows:

(a) A solution of 20 mg of (R)-2-bromo-5-(tert-butyl-dimethyl-silanyloxy)-3-methoxy-6-[2-(3-methyl-1,2,4-oxadiazol-5-yl)-2-thioureido-ethylsulfanylmethyl]-benzoic acid methyl ester and 8 mg of 2-bromo-1-(4-nitro-phenyl)-ethanone in 3 ml of dichloromethane was stirred at 0° C. for 3 h. The solvent was evaporated in vacuo and the residue was dissolved in ethyl acetate. The solution was washed with brine, dried over sodium sulfate and evaporated in vacuo, and the crude product was chromatographed on silica gel using ethyl acetate/hexane (1:2 v/v) as eluent, to yield 23 mg of (R)-2-bromo-5-(tert-butyl-dimethylsilanyloxy)-3-methoxy-6-[2-(3-methyl-1,2,4-oxadiazol-5-yl)-2-[4-(4-nitro-phenyl)-thiazol-2-ylamino]-ethylsulfanylmethyl]-benzoic acid methyl ester as a yellow oil.

EXAMPLES 166–172

By operating in an analogous manner as described in Example 165, (R)-2-bromo-5-(tert-butyl-dimethylsilanyloxy)-3-methoxy-6-[2-(3-methyl-1,2,4-oxadiazol-5-yl)-2-thioureido-ethylsulfanylmethyl]benzoic acid methyl ester was reacted with 1-chloro-2,2-dimethoxy-ethane in acetonitrile, with 2-bromoacetic acid methyl ester, 1-bromo-3-methoxy-propan-2-one or 3-chloro-2-oxo-butyric acid tert-butyl ester in acetonitrile in the presence of diisopropylethylamine, with 2-bromoacetyl-1-hydroxy-4-methoxy-benzene in N,N-dimethylformamide in the presence of sodium bicarbonate, with 4-bromoacetyl-benzoic acid in a mixture (1:1, v/v) of dichloromethane and acetonitrile, and with 4-bromoacetyl-benzenesulfonamide in dichloromethane, respectively, and the silanyl protecting group was subsequently cleaved as described in Example 1, to yield the following compounds:

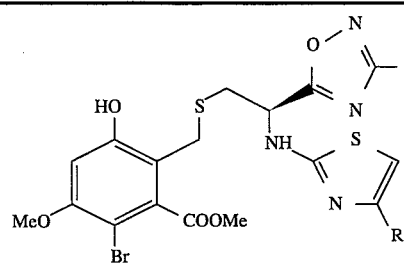

| Example No. | R | Mass spectrum: m/z |
|---|---|---|
| 166 | H | (M + H)⁺ = 515.2/517.2 |
| 167 | OH | (M − H)⁻ = 529.4/531.4 |
| 168 | −CH₂OCH₃ | (M − H)⁻ = 557.1/559.1 |
| 169 | −CH₂COOtBu | (M − H)⁻ = 627.1/629.1 |
| 170 | (phenyl with OMe and HO) | (M − H)⁻ = 635.0/637.0 |
| 171 | (phenyl with COOH) | (M + H)⁺ = 636.2/638.2 |
| 172 | (phenyl with SO₂NH₂) | (M + H)⁺ = 669.7/671.8 |

EXAMPLE 173

(a) A mixture of 15 mg of the product of Example 165(a) and 40 mg of tin dichloride dihydrate in 2 ml of tetrahydrofuran and 1 ml of 25% aqueous hydrochloric acid was stirred for 0.75 h at 0° C. and for 3 h at 20° C. The pH was adjusted to 7.5 by addition of saturated sodium bicarbonate solution and the mixture was extracted with ethyl acetate. The organic layer was dried over sodium sulfate and evaporated in vacuo and the crude product was chromatographed on silica gel using ethyl acetate/hexane (1:1 v/v) as eluent to yield 13 mg of a yellow oil which was subjected in an analogous manner to the procedure described in Example 1 to yield (R)-6-[2-[4-(4-amino-phenyl)-thiazol-2-ylamino]-2-(3-methyl-1,2,4-oxadiazol-5-yl)-ethylsulfanylmethyl]-2-bromo-5-hydroxy-3-methoxy-benzoic acid methyl ester as a white solid.

¹H-NMR (250 MHz,CDCl₃): δ 2.41(s,3H); 3.05(d,2H); 3.61(d,1H); 3.63(s,3H); 3.93(s,3H); 4.00(d,1H); 5.67(t,1H); 6.20(s,1H); 6.50(s,1H); 6.70(d,2H); 7.55(d,2H) ppm

EXAMPLE 174

A solution of 985 mg of (R)-2-[2-amino-2-(3-methyl-1, 2,4-oxadiazol-5-yl)-ethylsulfanyl -methyl]-3-[dimethyl-(1, 1,2-trimethyl-propyl) -silanyloxy]-5-methoxy-6-methyl-benzoic acid methyl ester and 237 mg of 2-fluoroimidazole hydrochloride in 5 ml of N,N-dimethylformamide were stirred under argon at 50° C. for 3 h. A second portion of 117 mg of 2-fluoroimidazole hydrochloride was added and stirring was continued for 6 h. The reaction mixture was cooled and the solvent evaporated in vacuo. The residue was purified by silica gel chromatography using methanol/dichloromethane (1:20, v/v) as eluent to yield 310 mg of (R)-3-hydroxy-2-[2-(imidazol-2-ylamino)-2-(3-methyl-1,2, 4-oxadiazol-5-yl)-ethylsulfanylmethyl]-5 -methoxy-6-methyl-benzoic acid methyl ester hydrochloride as yellow solid.

¹H-NMR (250 MHz,CDCl₃): δ 2.04(s,3H); 2.32(s,3H); 2.95(d,J=7 Hz,2H); 3.65(d,J=16 Hz,1H); 3.69(s,3H); 3.90(s, 3H); 4.14(d,J=16 Hz,1H); 5.30(m,1H); 6.39 (s,1H); 6.61(s, 1H) ppm.

EXAMPLE 175

To a solution of 270 mg of (R)-3-[dimethyl-(1,1,2 -trimethyl-propyl)-silanyloxy]-2-[2-[3-(imino-phenyl-methyl)-thioureido]-2-(3-methyl-1,2,4 -oxadiazol-5-yl)-ethylsulfanylmethyl]-5-methoxy-6-methyl-benzoic acid methyl ester in 5 ml of ethanol were added dropwise with stirring 140 mg of diethyl azodicarboxylate at 20° C. Stirring was continued for 6 h and then, the mixture was evaporated in vacuo. The residue was chromatographed on silica gel using ethyl acetate/hexane (1:2, v/v) as eluent to yield 195 mg of 3-[dimethyl-(1,1,2-trimethyl-propyl)-silanyl-protected product as a colorless oil. This material was treated with ammonium fluoride in methanol in an analogous manner to the procedure described in Example 1 to yield (R)-3-hydroxy-5-methoxy-6-methyl-2-[2-(3-methyl-1,2,4-oxadiazol-5-yl)-2-(3-phenyl-1,2,4-thiadiazol-5-ylamino)-ethylsulfanylmethyl]-benzoic acid methyl ester as a colorless oil.

¹H-NMR (250 MHz,CDCl₃): δ 2.03(s,3H); 2.39(s,3H); 3.17(q,J=16 and 7 Hz,1H); 3.23(q,J=16 and 5 Hz,1H); 3.67(s,3H); 3.75(d,J=14 Hz,1H); 3.87(d,J=14 Hz,1H); 3.95(s,3H); 5.58(m,1H); 6.35(s,1H); 6.78(s,1H); 6.80(s,1H); 7.4(m,3H); 8.11(m,2H) ppm.

The starting material used above was prepared as follows:

(a) To a stirred solution of 400 mg of (R)-2-[2 -amino-2-(3-methyl-1,2,4-oxadiazol-5-yl)-ethylsulfanyl-methyl]-3-[dimethyl-(1,1,2-trimethyl-propyl)-silanyloxy] -5-methoxy -6-methyl-benzoic acid methyl ester in 20 ml of dry dichloromethane were added slowly 186 mg of 1,1'-thiocarbonyldi-2(1H)-pyridone. The red solution was stirred for 30 min at room temperature and then cooled in an ice bath. Upon the addition of 94 mg of benzamidine (~85%), stirring was continued for 1 h at 0° C. and for 10 h at 20° C. The solution was evaporated in vacuo and the residue was chromatographed on silica gel using ethyl acetate/hexane (2:1, v/v) as eluent to afford 480 mg of (R)-3-[dimethyl-(1, 1,2-trimethyl-propyl)-silanyloxy]-2-[2-[3-(imino-phenyl-methyl)-thioureido]-2-(3-methyl-1,2,4-oxadiazol-5-yl) -ethylsulfanylmethyl]-5-methoxy-6-methyl-benzoic acid methyl ester as a colorless oil.
MS m/z: (M+H)⁺=672.4

EXAMPLE 176

To a stirred solution of 260 mg of (R)-3-[dimethyl -(1,1, 2-trimethyl-propyl)-silanyloxy]-2-[2-cyanoamino-2-(3-methyl-1,2,4-oxadiazol-5-yl) -ethylsulfanylmethyl]-5-methoxy-6-methyl-benzoic acid methyl ester in 50 ml of tetrahydrofuran were added 0.1 ml of 25% aqueous hydroxyacetone and 0.09 ml of 1N sodium hydroxide solution. The suspension was stirred for 12 h at 40° C. After cooling, the mixture was diluted with 100 ml water and subsequently extracted with 200 ml ethyl acetate. The organic layer was washed with brine, dried over sodium sulfate and evaporated in vacuo. The residue was chromatographed on silica gel using ethyl acetate/hexane (1:1, v/v) as eluent, and the purified product was treated with ammonium fluoride in methanol in an analogous manner to the procedure described in Example 1 to yield (R)-3-hydroxy-5-methoxy-6-methyl-2-[2-(3-methyl-1,2,4-oxadiazol -5-yl)-2-(4-methyl-oxazol-2-ylamino)-ethylsulfanylmethyl]-benzoic acid methyl ester as a white powder.

¹H-NMR (250 MHz,DMSO-d₆): δ 1.90(d, J=1 Hz,3H); 2.33(s,3H); 3.00 (d,J=7 Hz,2H); 3.61(d,J=16 Hz,1H); 3.63(d,J=16 Hz,1H); 3.73(s,3H); 3.77 (s,3H); 5.12(m,1H); 6.53(s,1H); 7.18 (d,J=1 Hz,1H); 7.96(d,J=8 Hz,1H) ppm.

The starting material used above was prepared as follows:

(a) (R)-2-[2-amino-2-(3-methyl-1,2,4 -oxadiazol-5-yl)-ethylsulfanylmethyl]-3-[dimethyl-(1,1,2-trimethyl-propyl)-silanyloxy]-5-methoxy-6-methyl-benzoic acid methyl ester was subjected in an analogous manner to the procedure described in Example 150(a) to yield (R)-3-[dimethyl-(1,1,2-trimethyl-propyl) -silanyloxy]-2-[2-cyanoamino-2-(3-methyl-1,2,4-oxadiazol-5-yl)-ethylsulfanylmethyl]-5-methoxy-6-methyl-benzoic acid methylester as a yellow oil.

¹H-NMR (250 MHz,CDCl₃): δ 0.29(s,3H); 0.30(s,3H); 0.93(d,J=6 Hz,6H); 0.99(s,6H); 1.78(sept,J=6 Hz); 2.08(s, 3H); 2.40(s,3H); 3.05(d,J=6 Hz,2H) 3.70(d,J=16 Hz,1H); 3.79(s,3H); 3.88(d,J=16 Hz,1H); 3.94(s,3H); 4.39(m,1H); 5.06(d,J=7 Hz,1H); 6.42(s,1H) ppm.

EXAMPLE 177

To a solution of 500 mg of (R)-2-[2-[4-(3-bromo-propyl)-thiazol-2-ylamino]-2-(3-methyl-1,2,4-oxadiazol-5-yl)-ethylsulfanylmethyl]-3-[dimethyl-(1,1,2-trimethyl-propyl)-silanyloxy]-5-methoxy-6-methyl-benzoic acid in 10 ml of dry N,N-dimethylformamide were added 233 mg of cesium carbonate. The mixture was stirred at 20° C. for 10 h. The solvent was evaporated in vacuo and the residue was chromatographed on silica gel using ethyl acetate/hexane (1:2, v/v) as eluent to yield 186 mg of a colorless foam. This material was treated with ammonium fluoride in methanol in an analogous manner to the procedure described in Example 1 to yield (R)-18-hydroxy-16-methoxy-15-methyl-4-(3-methyl-1,2,4-oxadiazol-5-yl)-3,4,5,10,11,12-hexahydro-6,9-nitrilo-1H-13,2,7,5-benzoxadithiaazacyclohexadecin-14-one as a white solid.

¹H-NMR (250 MHz,CDCl₃): δ 2.07(s,3H); 2.08(m,2H); 2.42(s,3H); 2.71 (m,2H); 3.16(d,J=7 Hz,2H); 3.79(s,3H); 3.97(d,J=15 Hz,1H); 4.14(m,1H); 4.58(d,J=15 Hz,1H); 4.75(m,1H); 5.56(m,2H); 5.88 (s,1H); 6.23(s,1H); 6.46(s, 1H) ppm.

The starting material used above was prepared as follows:

(a) To a stirred solution of 10.0 g of the product of Example 1(g) in 100 ml of dichloromethane were added dropwise at 0° C. 2.8 g of isothiocyanatoformic acid allyl ester in 30 ml of dichlormethane. The mixture was stirred for 1 h at 0° C. and for 1 h at room temperature. The solvent was evaporated in vacuo and the residue was chromatographed on silica gel using ethyl acetate/hexane (1:2, v/v) as eluent to yield 11.5 g of (R)-2-[2-(3-allyloxycarbonyl-thioureido)-2-( 3-methyl-1,2,4-oxadiazol-5-yl)-ethylsulfanylmethyl]-3-[dimethyl-( 1,1,2-trimethyl-propyl)-silanyloxy]-5-methoxy-6-methyl-benzoic acid allyl ester as a colorless oil.

MS m/z: (M+H)⁺=679.4

(b) A mixture of 10.0 g of the product of Example 177(a), 14.2 g of trifluoroacetate trimethylsilyl ester and 9.1 g of N,N-dimethyltrimethylsilylamine in 180 ml of dry dichloromethane was stirred for 10 min at 0° C. 1.70 g of tetrakis(triphenyl -phosphine)palladium were added and stirring was continued for 6 h at 0° C. and for 3 h at room temperature. The mixture was evaporated in vacuo to dryness and the residue was chromatographed two times on silica gel using methanol/dichloromethane (1:5, v/v) as eluent to afford, after crystallization from dichloromethane/hexane, 7.3 g of (R)-3 -[dimethyl-(1,1,2-trimethyl-propyl)-silanyloxy]-5-methoxy -6-methyl-2-[2-(3-methyl-1,2,4-oxadiazol-5-yl)-2-thioureidoethylsulfanylmethyl]-benzoic acid as yellow solid.

MS m/z: (M–H)⁻=553.4

(c) A solution of 500 mg of the product of Example 177(b) and of 262 mg of 1,5-dibromo-pentan-2-one in 18 ml of 1,2-epoxybutane was stirred at 0° C. for 2 h and at 20° C. for 2 h. The resulting suspension was evaporated in vacuo and the residue was chromatographed on silica gel using methanol/dichloromethane (13:87, v/v) as eluent to yield 355 mg of (R)-2-[2-[4-(3-bromo-propyl)-thiazol-2-ylamino]-2-(3-methyl-1,2,4-oxadiazol-5-yl) -ethylsulfanylmethyl]-3-[dimethyl-(1,1,2-trimethyl -propyl)silanyloxy]-5-methoxy-6-methyl-benzoic acid as a foam.

MS m/z: (M–H)⁻=699.2/701.2

EXAMPLE 178

To a cooled solution of 77 mg of 2-formyl-3-hydroxy-5-methoxy-6-methyl-benzoic acid (R)-2-[2-[1-(3-methyl-1,2,4-oxadiazol-5-yl)-2-tritylsulfanyl -ethylamino]-thiazol-4-yl]-ethyl ester in 10 ml of trifluoroacetic acid were added dropwise at 0° C. over 20 min a solution of 25 mg of triethylsilane in 2 ml of trifluoroacetic acid. The mixture was stirred under argon for 2 h at 0° C. and for 1 h at 20° C. Then, 200 ml of ethyl acetate were added and the solution was washed with brine, saturated sodium carbonate solution and again with brine. The organic layer was dried over sodium sulfate and the solvent was evaporated in vacuo. The residual oil was chromatographed on silica gel using ethyl acetate/hexane (2:1, v/v) as eluent, and the purified product was crystallized from ethyl acetate/hexane to afford 20 mg of (R)-17-hydroxy-15-methoxy-14-methyl-4-(3-methyl-1,2, 4-oxadiazol-5-yl)-3,4,5,10,11,13-hexahydro-6,9-nitrilo-1H-12,2,7,5-benzoxadithiaazacyclopentadecin-13-one as a white solid.

¹H-NMR (250 MHz,DMSO-d₆): δ 1.89(s,3H); 2.37(s, 3H); 2.89(m,2H); 3.21(d,J=6 Hz,2H); 3.65(m,2H); 3.71(s, 3H); 4.52(m,1H); 4.73(m,1H); 5.50(m,1H); 6.38(s,1H); 6.48(s,1H); 8.27(d,J=8 Hz,1H); 9.76(s,1H) ppm.

The starting material used above was prepared as follows:

(a) To a solution of 10.0 g of the product of Example 1(m) and 11.7 g triphenylmethanol in 55 ml of dichloromethane were added dropwise at 0° C. 55 ml of trifluoroacetic acid. The mixture was stirred for 16 h at 20° C. evaporated in vacuo. The residue was partitioned between water and ethyl acetate at pH 8. The organic layer was separated and washed with saturated potassium bicarbonate solution and brine. The organic phase was concentrated in vacuo and the residue was purified by chromatography on silica gel using hexane/ethyl acetate (1:1, v/v) as eluent to yield (R)-1-(3-methyl-1,2,4-oxadiazol -5-yl)-2-tritylsulfanyl-ethylamine as a pale yellow oil.

¹HNMR (250 MHz,CDCl₃): δ 2.35(s,3H); 2.60(m,2H); 3.50–3.65(m,1H); 7.2–7.50(m,15H) ppm.

(b) (R)-1-(3-methyl-1,2,4-oxadiazol-5-yl) -2-trityl-sulfanyl-ethylamine was subjected in an analogous manner to the procedures described in Example 78(a) and 78 and the resulting product was reacted with 1,4-dibromo-butan-2-one in an analogous manner to the procedure described in Example 177(c) to yield (R)-[4-(2-bromo-ethyl)-thiazol-2-yl]-[1-(3-methyl-1,2,4-oxadiazol-5-yl)-2-trityl-sulfanyl -ethyl]-amine a as a colorless oil.

MS m/z: (M+H)⁺=593.1/595.1

(c) To a solution of 600 mg of the product of Example 178(b) in 5 ml of dry acetonitrile were added 352 mg of sodium iodide. The mixture was stirred at 40° C. for 15 h under an argon atmosphere. After cooling to 20° C., the mixture was filtered and the solvent was evaporated in vacuo. The yellow, amorphous residue was dissolved in 5 ml of N,N-dimethylformamide and the solution was added dropwise to a stirred solution of 739 mg of (R)-3,4-dihydroxy-6-methoxy-7-methyl-1,3-dihydro-iso-benzofuran-1-one and 135 mg of 1,1,3,3-tetramethylguanidine in 20 ml of N,N-dimethylformamide. The solution was stirred at 50° C. for 15 h under an argon atmosphere, then evaporated in vacuo, and the residue was chromatographed on silica gel using ethyl acetate/hexane (1:1, v/v) as eluent to afford 321 mg of 2-formyl-3-hydroxy-5-methoxy-6-methyl-benzoic acid (R)-2-[2-[1-(3-methyl-1,2,4-oxadiazol-5-yl)-2-trityl-sulfanyl-ethylamino]-thiazol-4-yl]-ethyl ester as a colorless foam.

MS m/z: (M+H)⁺=721.2

EXAMPLE 179

Interlocking gelatin capsules each containing the following ingredients are made in the usual manner:

| | |
|---|---|
| (R)-N-[2-(2-cyano-6-hydroxy-4-methoxy-3-methyl-benzyl-sulfanyl]-1-(3-methyl-1,2,4-oxadiazol-5-yl)-ethyl]-acetamide | 500 mg |
| Luviskol (water-soluble polyvinylpyrrolidone) | 20 mg |
| Mannitol | 20 mg |
| Talc | 15 mg |
| Magnesium stearate | 2 mg |
| | 557 mg |

We claim:
1. A compound of the formula

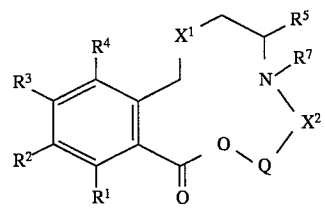

wherein $X^1$ is —S—O or —SO—;

R¹ is hydrogen, halogen or optionally substituted lower alkyl, the optional substituent being halogen;

R² is hydrogen, hydroxy, amino, lower alkylamino, di-lower alkylamino, optionally substituted lower alkoxy or a group —OP;

OP is an easily hydrolyzable group;

R³ is hydrogen, hydroxy, lower alkyl, halogen or a group —OP;

R⁴ is halogen, hydroxy or a group —OP;

R⁵ is hydrogen, cyano, optionally substituted esterified carboxy, optionally substituted amidated (thio)carboxy, optionally substituted alkyl, optionally substituted alkenyl or optionally substituted heterocycle;

R⁷ is hydrogen or lower alkyl;

X² is (thio)carbonyl;

Q is —CH(R⁸)— or —CH(R⁸)—W—;

R⁸ is hydrogen or optionally substituted lower alkyl, and

W is optionally substituted di-, tri-, tetra- or pentamethylene; or the pharmaceutically acceptable salts thereof carrying an acidic and/or basic substituent.

2. The compound of claim 1 wherein X¹ is —S—; R¹ is lower alkyl, halogen, or hydrogen; R² is lower alkoxy or hydroxy; R⁴ is hydroxy or a group —OP; X² is (thio)carbonyl; and R⁵ is cyano, optionally substituted esterified carboxy, optionally substituted amidated (thio)carboxy, or optionally substituted heterocycle.

3. The compound of claim 2 wherein W is di-, tri-, or tetramethylene and X² is (thio)carbonyl.

4. The compound of claim 3 wherein R¹ is lower alkyl or halogen.

5. The compound of claim 4 wherein R¹ is methyl.

6. The compound of claim 4 wherein R¹ is Br or Cl.

7. The compound of claim 4 wherein R² is lower alkoxy.

8. The compound of claim 7 wherein R² is methoxy.

9. The compound of claim 7 wherein R⁴ is hydroxy.

10. The compound of claim 9 wherein R⁵ is cyano, optionally substituted esterified carboxy optionally substituted amidated (thio)carboxy, or optionally substituted heterocycle.

11. The compound of claim 10 wherein optionally substituted amidated (thio)carboxy is selected from —CX²NH₂ or —CX²NR⁷Y where Y is alkyl, alkenylalkyl, alkynylalkyl, lower cycloalkyl, lower cycloalkyl-lower alkyl, lower cycloalkyl-lower alkenylalkyl, heterocycle, heterocycle-lower alkyl, heterocycle-lower alkenylalkyl, aryl, aryl-lower alkyl, or aryl-lower alkenylalkyl or wherein the residue —NR⁷Y represents a 5 to 7 membered saturated N-heterocycle optionally containing a further N, O or S atom.

12. The compound of claim 11 wherein Y is alkyl or alkenyl.

13. The compound of claim 12 wherein Y is lower alkyl or lower alkenyl.

14. The compound of claim 13 wherein R⁵ is 3-methyl-1,2,4-oxadiazol-5-yl, allylamido, or propylamido.

15. The compound of claim 10 wherein optionally substituted esterified carboxy is —COOY where Y is alkyl, alkenylalkyl, alkynylalkyl, lower cycloalkyl, lower cycloalkyl-lower alkyl, lower cycloalkyl-lower alkenylalkyl, heterocycle, heterocycle-lower alkyl, heterocycle-lower alkenylalkyl, aryl, aryl-lower alkyl, or aryl-lower alkenylalkyl.

16. The compound of claim 15 wherein Y is alkyl.

17. The compound of claim 16 wherein Y is lower alkyl.

18. The compound of claim 1 wherein R¹ is methyl, bromo or chlorine, R² is methoxy, and R⁴ is hydroxy.

19. The compound of claim 1, (4R,9S)-15-Hydroxy-9-acetoxymethyl-13-methoxy-12-methyl-11-oxo-6-thioxo-3,4,5,6, 7,8,9,11-octahydro-1H-10,2,5-benzoxathiaazacyclotridecine-4-carboxylic acid methyl ester.

20. The compound of claim 1, (4R,9S)-15-Hydroxy-9-hydroxymethyl-13-methoxy-12-methyl-11-oxo-6-thioxo-3,4,5,6,7, 8,9,11-octahydro-1H-10,2,5-benzoxathiaazacyclo-tridecine-4-carboxylic acid cyclopentylamide.

21. The compound of claim 1, (R)-16-Hydroxy-14-methoxy -13-methyl-12-oxo-6-thioxo-1,3,4,5,6,7,8,9,10,12 -decahydro-11,2,5-benzoxathiaaza-cyclotetradecine-4-carboxylic acid methyl ester.

22. The compound of claim 1, (R)-16-Hydroxy-14-methoxy -13-methyl-12-oxo-6-thioxo-1,3,4,5,6,7,8,9,10,12 -decahydro-11,2,5-benzoxathiaaza-cyclotetradecine-4-carboxylic acid propylamide.

23. The compound of claim 1, (R)-16-Hydroxy-14-methoxy -13-methyl-4-(3-methyl-1,2,4-oxadiazol-5-yl)-1,3,4,5, 6,7,8,9,10,12-decahydro-11,2,5-benzoxathiaazacyclotetradecin-6,12-dione.

24. The compound of claim 1, (R)-16-Hydroxy-14-methoxy -13-methyl-12-oxo-6-thioxo-1,3,4,5,6,7,8,9,10,12 -decahydro-11,2,5-benzoxathiaaza-cyclotetradecine-4-carboxylic acid amide.

25. The compound of claim 1, (4R,9R)-9,16-Dihydroxy-14-methoxy-13-methyl-12-oxo-6-thioxo-1,3,4,5,6,7,8,9,10, 12-decahydro-11,2,5-benzoxathiaazacyclotetradecine-4-carboxylic acid methyl ester.

26. The compound of claim 1, (4R,9S)-15-Hydroxy-9-hydroxymethyl-13-methoxy-12-methyl-4-(3-methyl-1,2, 4-oxadiazol-5-yl)-11-oxo-6-thioxo-3,4,5,6,7,8,9,11 -octahydro-1H-10,2,5-benzoxathiaazacyclotridecine.

27. The compound of claim 1, (R)-16-Hydroxy-14-methoxy -13-methyl-12-oxo-6-thioxo-1,3,4,5,6,7,8,9,10,12 -decahydro-11,2,5-benzoxathiaazacyclotetradecine-4-carboxylic acid prop-2-ynylamide.

28. The compound of claim 1, (R)-16-Hydroxy-14-methoxy -13-methyl-4-(3-methyl-1,2,4-oxadiazol-5-yl)-6-thioxo-1,3,4,5,6,7,8,9,10,12-decahydro-11,2,5-benzoxathiaazacyclotetradecin-12-one.

29. The compound of claim 1, (4R)-N-[5-(16-Hydroxy-14-methoxy-13-methyl-12-oxo-6-thioxo -1,3,4,5,6,7,8,9,10, 12-decahydro-11,2,5-benzoxathiaazacyclotetradecin-4-yl)-1,2,4-oxadiazol-3-ylmethyl]-acetamide.

30. The compound of claim 1, (4R)-4-(3-Aminomethyl-1,2,4-oxadiazol-5-yl)-16-hydroxy-14-methoxy-13-methyl-6-thioxo-1,3,4,5,6,7,8,9,10, 12-decahydro-11,2,5-benzoxathiaazacyclotetradecin-12-one hydrochloride.

31. The compound of claim 1, (4R)-16-Hydroxy-4-[3-(isopropylamino)-methyl-1,2,4-oxadiazol-5-yl]-14-methoxy-13-methyl-6-thioxo-1,3,4,5,6,7,8,9,10, 12-decahydro-11,2,5-benzoxathiaazacyclotetradecin-12-hydrochloride.

32. A pharmaceutical composition comprising an effective amount of a compound of the formula wherein X¹ is —S— or —SO—;

R¹ is hydrogen, halogen or optionally substituted lower alkyl, the optional substituent being halogen;

R² is hydrogen, hydroxy, amino, lower alkylamino, di-lower alkylamino, optionally substituted lower alkoxy or a group —OP;

OP is an easily hydrolyzable group;

R³ is hydrogen, hydroxy, lower alkyl, halogen or a group —OP;

R⁴ is halogen, hydroxy or a group —OP;

R⁵ is hydrogen, cyano, optionally substituted esterified carboxy, optionally substituted amidated (thio)carboxy, optionally substituted alkyl, optionally substituted alkenyl or optionally substituted heterocycle;

R⁷ is hydrogen or lower alkyl;

X² is (thio)carbonyl;

Q is —CH(R⁸)— or —CH(R⁸)—W—;

R⁸ is hydrogen or optionally substituted lower alkyl, and

W is optionally substituted di-, tri-, tetra- or pentamethylene; or the pharmaceutically acceptable salts thereof carrying an acidic and/or basic substituent, and a therapeutically inert carrier.

33. The composition of claim 32 which is the unit dosage form.

34. The composition of claim 33 wherein the unit dosage form is selected from tablets, coated tablets, dragees, hard gelatin capsules, soft gelatin capsules, syrups, solutions, emulsions, suspensions, suppositories, or injectable solution.

35. The composition of claim 33 wherein the compound of formula IB is present in an amount of from about 25 mg. to about 2000 mg.

36. The composition of claim 35 wherein the compound of formula IB is present in an amount of from about 100 mg. to about 1000 mg.

37. A method of treating bacterial infections in a mammal comprising administering to said mammal in need of such treatment an effective amount of a compound of the formula

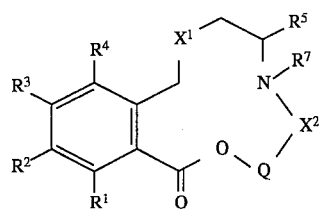

IB wherein

X¹ is —S—O or —SO—;

R¹ is hydrogen, halogen or optionally substituted lower alkyl, the optional substituent being halogen;

R² is hydrogen, hydroxy, amino, lower alkylamino, di-lower alkylamino, optionally substituted lower alkoxy or a group —OP;

OP is an easily hydrolyzable group;

R³ is hydrogen, hydroxy, lower alkyl, halogen or a group —OP;

R⁴ is halogen, hydroxy or a group —OP;

R⁵ is hydrogen, cyano, optionally substituted esterified carboxy, optionally substituted amidated (thio)carboxy, optionally substituted alkyl, optionally substituted alkenyl or optionally substituted heterocycle;

R⁷ is hydrogen or lower alkyl;

X² is (thio)carbonyl;

Q is —CH(R⁸)— or —CH(R⁸)—W—;

R⁸ is hydrogen or optionally substituted lower alkyl, and

W is optionally substituted di-, tri-, tetra- or pentamethylene; or the pharmaceutically acceptable salts thereof carrying an acidic and/or basic substituent, and a therapeutically inert carrier.

* * * * *

UNITED STATES PATENT AND TRADEMARK OFFICE
CERTIFICATE OF CORRECTION

PATENT NO. : 5,589,473
DATED : December 31, 1996
INVENTOR(S) : Jurgen Geiwiz, Erwin Gotschi, Paul Hebeisen, Helmut Link, and Thomas Lubbers It is certified that error appears in the above-indentified patent and that said Letters Patent is hereby corrected as shown below:

In claim 10, column 111, line 39, between "carboxy" and "optionally", insert therefor -- , --.

In claim 31, column 112, line 52, between "12-" and "hydrochloride", insert therefor -- one --.

In claim 37, column 114, line 11, delete "is -S-O or -SO-;" and insert therefor -- -S- or -SO-; --.

Signed and Sealed this

Twenty-seventh Day of May, 1997

Attest:

BRUCE LEHMAN

Attesting Officer        Commissioner of Patents and Trademarks